United States Patent
Dershem et al.

(10) Patent No.: US 9,278,909 B2
(45) Date of Patent: *Mar. 8, 2016

(54) AMIDE-EXTENDED CROSSLINKING COMPOUNDS AND METHODS FOR USE THEREOF

(71) Applicant: Designer Molecules, Inc., San Diego, CA (US)

(72) Inventors: Stephen M. Dershem, San Diego, CA (US); Farhad G. Mizori, San Diego, CA (US)

(73) Assignee: DESIGNER MOLECULES, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/970,523

(22) Filed: Aug. 19, 2013

(65) Prior Publication Data

US 2013/0338313 A1    Dec. 19, 2013

Related U.S. Application Data

(60) Continuation-in-part of application No. 13/058,827, filed as application No. PCT/US2009/053797 on Aug. 13, 2009, now Pat. No. 8,637,611, and a continuation-in-part of application No. 13/021,700, filed on Feb. 4, 2011, now Pat. No. 8,513,375, and a continuation-in-part of application No. 11/786,029, filed on Apr. 11, 2007, now Pat. No. 7,884,174, which is a continuation-in-part of application No. 11/642,995, filed on Dec. 19, 2006, now abandoned, which is a division of application No. 10/835,911, filed on Apr. 30, 2004, now Pat. No. 7,208,566.

(60) Provisional application No. 60/468,037, filed on May 5, 2003, provisional application No. 61/088,605, filed on Aug. 13, 2008, provisional application No. 61/358,901, filed on Jun. 26, 2010.

(51) Int. Cl.

| | | |
|---|---|---|
| C07C 233/32 | (2006.01) |
| C07D 207/40 | (2006.01) |
| C07D 207/36 | (2006.01) |
| C07C 233/45 | (2006.01) |
| C07C 233/01 | (2006.01) |
| C07D 207/34 | (2006.01) |
| C07D 207/452 | (2006.01) |
| C09J 145/00 | (2006.01) |
| C09J 147/00 | (2006.01) |
| C09J 179/08 | (2006.01) |

(52) U.S. Cl.
CPC ............ *C07C 233/32* (2013.01); *C07C 233/01* (2013.01); *C07C 233/45* (2013.01); *C07D 207/34* (2013.01); *C07D 207/36* (2013.01); *C07D 207/40* (2013.01); *C07D 207/452* (2013.01); *C09J 145/00* (2013.01); *C09J 147/00* (2013.01); *C09J 179/08* (2013.01); *C09J 179/085* (2013.01)

(58) Field of Classification Search
CPC ............... C07D 207/36; C07D 207/40; C07D 207/412; C07D 207/44; C07D 207/448; C07D 207/452; C07C 233/01; C07C 233/45; C07C 233/46; C07C 233/47; C07C 233/30; C07C 233/32; C07C 233/49; C07C 233/52
USPC .......... 525/409, 474; 548/400, 406, 520, 521, 548/523, 524, 545, 548, 550, 557; 564/123, 564/152, 155, 192, 161, 204, 215, 217
See application file for complete search history.

(56) References Cited

U.S. PATENT DOCUMENTS

| | | |
|---|---|---|
| 3,901,845 A | 8/1975 | Newbould |
| 3,905,820 A | 9/1975 | Frass |
| 4,075,167 A | 2/1978 | Takamizawa et al. |
| 4,111,879 A | 9/1978 | Mori et al. |
| 4,224,216 A | 9/1980 | Locatelli et al. |
| 4,675,379 A | 6/1987 | Mikroyannidis et al. |

(Continued)

FOREIGN PATENT DOCUMENTS

| | | |
|---|---|---|
| CN | 1187507 A | 7/1998 |
| EP | 0488066 | 6/1992 |

(Continued)

OTHER PUBLICATIONS

"Hexanamide product sheet", CAS 628-02-4, 1-2 (Sep. 11, 2012.).

(Continued)

*Primary Examiner* — Roberto Rabago
(74) *Attorney, Agent, or Firm* — The Law Office of Jane K. Babin, Professional Corporation; Jane K. Babin

(57) ABSTRACT

The invention is based on the discovery that a remarkable improvement in the performance of maleimide thermosets can be achieved by incorporating amide-extended maleimides into an adhesive formulation. Amide-extended maleimides described herein can be used to toughen bismaleimide thermosetting materials without sacrificing any thermal stability. Amide-extended maleimides are readily prepared by reacting a bismaleimide with an appropriate amine via the well-known Michael addition reaction. Acylation of the resulting secondary amines provides the amide-extended maleimide. The acylating agent can also be used to introduce polymerizable functional groups into the backbones of these thermoset monomers. Amide-extended acrylate and methacrylate monomers can also be prepared.

1 Claim, 2 Drawing Sheets

(56) References Cited

U.S. PATENT DOCUMENTS

| | | |
|---|---|---|
| 4,775,740 A | 10/1988 | Beggs et al. |
| 4,925,915 A | 5/1990 | Mueller |
| 4,931,540 A | 6/1990 | Mueller et al. |
| 4,968,738 A | 11/1990 | Dershem |
| 5,003,017 A | 3/1991 | Eisenbarth et al. |
| 5,045,127 A | 9/1991 | Dershem et al. |
| 5,064,480 A | 11/1991 | Dershem et al. |
| 5,086,139 A | 2/1992 | Corley |
| 5,128,444 A | 7/1992 | Inoue et al. |
| 5,155,177 A | 10/1992 | Frihart |
| 5,189,116 A | 2/1993 | Boyd et al. |
| 5,229,485 A | 7/1993 | Kramer et al. |
| 5,232,962 A | 8/1993 | Dershem et al. |
| 5,284,959 A | 2/1994 | Marien et al. |
| 5,306,333 A | 4/1994 | Dershem et al. |
| 5,315,011 A | 5/1994 | Benicewicz et al. |
| 5,358,992 A | 10/1994 | Dershem et al. |
| 5,393,887 A | 2/1995 | Petit |
| 5,403,389 A | 4/1995 | Dershem |
| 5,447,988 A | 9/1995 | Dershem et al. |
| 5,489,641 A | 2/1996 | Dershem |
| 5,554,769 A | 9/1996 | Sheppard et al. |
| 5,602,205 A | 2/1997 | Singh et al. |
| 5,616,666 A | 4/1997 | Morton et al. |
| 5,646,241 A | 7/1997 | Dershem et al. |
| 5,717,034 A | 2/1998 | Dershem et al. |
| 5,718,941 A | 2/1998 | Dershem et al. |
| 5,753,748 A | 5/1998 | Dershem et al. |
| 5,760,165 A | 6/1998 | Dao et al. |
| 5,770,681 A | 6/1998 | Corley |
| 5,861,111 A | 1/1999 | Dershem et al. |
| 5,891,566 A | 4/1999 | Sakumoto et al. |
| 5,969,036 A | 10/1999 | Dershem |
| 5,973,166 A | 10/1999 | Mizori et al. |
| 6,034,194 A | 3/2000 | Dershem |
| 6,034,195 A | 3/2000 | Dershem |
| 6,063,828 A | 5/2000 | Ma et al. |
| 6,121,358 A | 9/2000 | Dershem et al. |
| 6,187,886 B1 | 2/2001 | Husson, Jr. et al. |
| 6,211,320 B1 | 4/2001 | Dershem et al. |
| 6,214,923 B1 | 4/2001 | Goto et al. |
| 6,265,530 B1 | 7/2001 | Herr et al. |
| 6,281,314 B1 | 8/2001 | Tong et al. |
| 6,300,456 B1 | 10/2001 | Musa |
| 6,303,743 B1 | 10/2001 | You et al. |
| 6,316,566 B1 | 11/2001 | Ma et al. |
| 6,355,750 B1 | 3/2002 | Herr |
| 6,369,124 B1 | 4/2002 | Hoyle et al. |
| 6,423,780 B1 | 7/2002 | Dershem et al. |
| 6,429,281 B1 | 8/2002 | Dershem et al. |
| 6,521,731 B2 | 2/2003 | Dershem et al. |
| 6,620,946 B2 | 9/2003 | Dershem et al. |
| 6,699,929 B2 | 3/2004 | Musa et al. |
| 6,730,763 B1 | 5/2004 | Okazaki et al. |
| 6,743,852 B2 | 6/2004 | Dershem et al. |
| 6,790,597 B2 | 9/2004 | Dershem |
| 6,825,245 B2 | 11/2004 | Dershem |
| 6,831,132 B2 | 12/2004 | Liu et al. |
| 6,852,814 B2 | 2/2005 | Dershem et al. |
| 6,855,745 B2 | 2/2005 | Hoyle et al. |
| 6,881,820 B1 | 4/2005 | Meador et al. |
| 6,908,957 B2 | 6/2005 | Musa et al. |
| 6,916,856 B2 | 7/2005 | Dershem |
| 6,946,523 B2 | 9/2005 | Dershem et al. |
| 6,960,636 B2 | 11/2005 | Dershem et al. |
| 6,963,001 B2 | 11/2005 | Dershem et al. |
| 6,977,057 B2 | 12/2005 | Reitz et al. |
| 7,102,015 B2 | 9/2006 | Dershem et al. |
| 7,157,587 B2 | 1/2007 | Mizori et al. |
| 7,176,044 B2 | 2/2007 | Forray et al. |
| 7,199,249 B2 | 4/2007 | Liu et al. |
| 7,208,566 B2 | 4/2007 | Mizori et al. |
| 7,230,055 B2 | 6/2007 | Musa |
| 7,285,613 B2 | 10/2007 | Dershem et al. |
| 7,309,724 B2 | 12/2007 | Dershem et al. |
| 7,517,925 B2 | 4/2009 | Dershem et al. |
| 7,678,879 B2 | 3/2010 | Dershem |
| 7,777,064 B2 | 8/2010 | Mizori |
| 7,786,234 B2 | 8/2010 | Dershem et al. |
| 7,786,248 B2 | 8/2010 | Dershem |
| 7,795,362 B2 | 9/2010 | Dershem |
| 7,825,188 B2 | 11/2010 | Dershem |
| 7,863,346 B2 | 1/2011 | Dershem et al. |
| 7,868,113 B2 | 1/2011 | Dershem |
| 7,875,688 B2 | 1/2011 | Dershem et al. |
| 7,884,174 B2 | 2/2011 | Mizori et al. |
| 7,928,153 B2 | 4/2011 | Dershem |
| 8,008,419 B2 | 8/2011 | Dershem |
| 8,013,104 B2 | 9/2011 | Dershem |
| 8,039,663 B2 | 10/2011 | Dershem |
| 8,043,534 B2 | 10/2011 | Dershem |
| 8,063,161 B2 | 11/2011 | Dershem |
| 8,158,748 B2 | 4/2012 | Dershem et al. |
| 8,217,120 B2 | 7/2012 | Dershem |
| 8,287,686 B2 | 10/2012 | Dershem |
| 8,288,591 B2 | 10/2012 | Dershem |
| 8,308,892 B2 | 11/2012 | Dershem |
| 8,344,076 B2 | 1/2013 | Dershem |
| 8,378,017 B2 | 2/2013 | Dershem et al. |
| 8,398,898 B2 | 3/2013 | Dershem |
| 8,415,812 B2 | 4/2013 | Dershem et al. |
| 8,431,655 B2 | 4/2013 | Dershem |
| 8,513,375 B2 | 8/2013 | Mizori et al. |
| 8,530,573 B2 | 9/2013 | Dershem |
| 8,541,531 B2 | 9/2013 | Dershem |
| 8,637,611 B2 | 1/2014 | Dershem |
| 2002/0007042 A1 | 1/2002 | Herr et al. |
| 2002/0010281 A1 | 1/2002 | Musa et al. |
| 2002/0062923 A1 | 5/2002 | Forray |
| 2002/0099168 A1 | 7/2002 | Dershem et al. |
| 2002/0188137 A1 | 12/2002 | Dershem et al. |
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |
| 2003/0060531 A1 | 3/2003 | Dershem et al. |
| 2003/0083436 A1 | 5/2003 | Deitch |
| 2003/0087999 A1 | 5/2003 | Dershem et al. |
| 2003/0109666 A1 | 6/2003 | Dershem et al. |
| 2003/0125551 A1 | 7/2003 | Dershem et al. |
| 2003/0129438 A1 | 7/2003 | Becker et al. |
| 2003/0199638 A1 | 10/2003 | Liu et al. |
| 2003/0208016 A1 | 11/2003 | Dershem et al. |
| 2004/0006166 A1 | 1/2004 | Liu et al. |
| 2004/0019224 A1 | 1/2004 | Dershem et al. |
| 2004/0077798 A1 | 4/2004 | Dershem et al. |
| 2004/0082724 A1 | 4/2004 | Dershem et al. |
| 2004/0102566 A1 | 5/2004 | Forray et al. |
| 2004/0123948 A1 | 7/2004 | Dershem et al. |
| 2004/0225026 A1* | 11/2004 | Mizori et al. .................. 522/99 |
| 2004/0225045 A1 | 11/2004 | Forray |
| 2004/0225059 A1* | 11/2004 | Mizori et al. ................. 524/811 |
| 2005/0107542 A1 | 5/2005 | Liu et al. |
| 2005/0136620 A1 | 6/2005 | Dershem et al. |
| 2005/0137277 A1 | 6/2005 | Dershem et al. |
| 2005/0267254 A1 | 12/2005 | Mizori et al. |
| 2005/0272888 A1 | 12/2005 | Dershem et al. |
| 2006/0009578 A1 | 1/2006 | Dershem |
| 2006/0025542 A1 | 2/2006 | Musa |
| 2006/0063014 A1 | 3/2006 | Forray |
| 2006/0069232 A1 | 3/2006 | Dershem |
| 2006/0122306 A1 | 6/2006 | Stafford et al. |
| 2006/0142517 A1 | 6/2006 | Dershem |
| 2006/0284141 A1 | 12/2006 | Musa et al. |
| 2007/0060683 A1 | 3/2007 | Musa et al. |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |

(56) References Cited

U.S. PATENT DOCUMENTS

| | | |
|---|---|---|
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dershem |
| 2008/0257493 A1 | 10/2008 | Dershem |
| 2008/0262191 A1 | 10/2008 | Mizori |
| 2009/0020319 A1 | 1/2009 | Yamada |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041823 A1 | 2/2010 | Dershem |
| 2010/0041832 A1 | 2/2010 | Dershem |
| 2010/0041845 A1 | 2/2010 | Dershem et al. |
| 2010/0056671 A1 | 3/2010 | Dershem |
| 2010/0063184 A1 | 3/2010 | Dershem |
| 2010/0113643 A1 | 5/2010 | Dershem |
| 2010/0144977 A1 | 6/2010 | Dershem |
| 2010/0249276 A1 | 9/2010 | Dershem |
| 2011/0017400 A1 | 1/2011 | Dershem |
| 2011/0049731 A1 | 3/2011 | Dershem et al. |
| 2011/0130485 A1 | 6/2011 | Mizori et al. |
| 2011/0152466 A1 | 6/2011 | Dershem |
| 2012/0049106 A1 | 3/2012 | Dershem |
| 2012/0065336 A1 | 3/2012 | Mizori et al. |
| 2013/0012620 A1 | 1/2013 | Dershem |
| 2013/0187095 A1 | 7/2013 | Dershem et al. |
| 2013/0199724 A1 | 8/2013 | Dershem |
| 2013/0203895 A1 | 8/2013 | Dershem |
| 2013/0228901 A1 | 9/2013 | Dershem et al. |
| 2013/0299747 A1 | 11/2013 | Dershem |
| 2013/0313489 A1 | 11/2013 | Dershem |
| 2013/0338313 A1 | 12/2013 | Dershem et al. |
| 2014/0020827 A1 | 1/2014 | Dershem |

FOREIGN PATENT DOCUMENTS

| | | |
|---|---|---|
| EP | 1156036 | 11/2001 |
| JP | 62-212390 | 9/1987 |
| JP | 01135765 | 5/1989 |
| JP | 01-167332 | 7/1989 |
| JP | H02-639 | 1/1990 |
| JP | H02-124940 | 5/1990 |
| JP | H03-502941 | 7/1991 |
| JP | H04-351634 | 12/1992 |
| JP | H05-506255 | 9/1993 |
| JP | H10-505599 | 6/1998 |
| JP | 11246759 | 9/1999 |
| JP | 2001-100215 | 4/2001 |
| WO | 8604073 | 7/1986 |
| WO | 9003405 | 4/1990 |
| WO | 9011317 | 10/1990 |
| WO | 9607691 A2 | 3/1996 |
| WO | 9607691 A3 | 3/1996 |
| WO | 2004099331 A2 | 11/2004 |
| WO | 2004099331 A3 | 11/2004 |
| WO | 2005121190 A2 | 12/2005 |
| WO | 2005121190 A3 | 12/2005 |
| WO | 2007100329 | 9/2007 |
| WO | 2008077140 A2 | 6/2008 |
| WO | 2008077140 A3 | 6/2008 |
| WO | 2008077141 | 6/2008 |
| WO | 2008092168 | 7/2008 |
| WO | 2008124797 | 10/2008 |
| WO | 2008128209 | 10/2008 |
| WO | 2008130894 | 10/2008 |
| WO | 2009117729 A2 | 9/2009 |
| WO | 2009117729 A3 | 9/2009 |
| WO | 2010019832 A2 | 2/2010 |
| WO | 2010019832 A3 | 2/2010 |
| WO | 2011116050 A2 | 9/2011 |
| WO | 2011116050 A3 | 9/2011 |

OTHER PUBLICATIONS

"Hexanamine product sheet", CAS 111-26-2, 1-2 (Sep. 11, 2012).
"N-isopropyl-2-methylene-5-hexeneamide Product Sheet", 1-3 (Sep. 11, 2012).
Adamson, "Review of CSP and Flip Chip Underfill Processes and When to Use the Right Dispensing Tools for Efficient Manufacturing", Paper Presented at GlobalTRONICS Technology Conference,Singapore , 1-6 (2002).
Kohli, et al., "Co-Polymerization of Maleimides and Vinyl Ethers: A Structural Study", Macromolecules 31:5681-5689 (1998).
Andersson, et al., "Initiator-Free Photopolymerization of an Aliphatic Vinyl Ether-Maleimide Monomer", J Coatings Tech 69:91-95 (1997).
Fouassier, "Photoinitiation, Photopolymerization, and Photocuring", Hanser/Gardner, 276-283 (1995).
Chen, et al., "Interfacial Properties of Metal/Polyimide Layered Structures", in Micro Electronic Packaging Technology—Materials and Processes (Shieh ed; ASM International, Metals Park, Ohio), 345-350 (1989).

* cited by examiner

AMIDE-EXTENDED CROSSLINKING COMPOUNDS AND METHODS FOR USE THEREOF

RELATED APPLICATIONS

This application is a Continuation-in-Part of U.S. application Ser. No. 13/058,827, filed Feb. 11, 2011 now U.S. Pat. No. 8,637,611, which is a U.S. National Phase of PCT/US09/53797, filed Aug. 13, 2009, which claims the benefit of priority under 35 USC §119 of U.S. Provisional Applications No. 61/088,605 filed Aug. 13, 2008. This application is also a Continuation-in-Part of U.S. application Ser. No. 13/021,700, filed Feb. 4, 2011 now U.S. Pat. No. 8,513,375, which claims the benefit of priority under 35 USC §119 of U.S. Provisional Application No. 61/358,901, filed Jun. 26, 2010, and which is also a Continuation-in-Part of U.S. application Ser. No. 11/786,029, filed Apr. 11, 2007 (now U.S. Pat. No. 7,884,174; issued Feb. 8, 2011), which is a Continuation-in-Part of U.S. application Ser. No. 11/642,995, filed Dec. 19, 2006, which is a Divisional of U.S. application Ser. No. 10/835,911, filed Apr. 30, 2004 (now U.S. Pat. No. 7,208,566; issued Apr. 24, 2007), which claims the benefit of priority under 35 USC §119 of U.S. Provisional Application No. 60/468,037, filed May 5, 2003. The entire disclosure of each of the aforementioned applications is incorporated herein by reference.

FIELD OF THE INVENTION

The present invention relates to thermosetting adhesive compositions, methods of preparation and uses therefor. In particular, the present invention relates to amide-extended compounds and thermosetting compositions comprised thereof, as well as thermosetting compounds and compositions containing imide-extended mono-, bis-, and polymaleimide compounds.

BACKGROUND OF THE INVENTION

Adhesive compositions, particularly conductive adhesives, are used for a variety of purposes in the fabrication and assembly of semiconductor packages and microelectronic devices. The more prominent uses include bonding of electronic elements such as integrated circuit chips to lead frames or other substrates, and bonding of circuit packages or assemblies to printed wire boards. Adhesives useful for electronic packaging applications typically exhibit properties such as good mechanical strength, curing properties that do not affect the component or the carrier, and thixotropic properties compatible with application to microelectronic and semiconductor components.

A few methods have been described in the art to decrease the brittleness of bismaleimide thermosets. The well-known Michael addition reaction, using aromatic or aliphatic diamines is one of these methods. Michael addition has been used to reduce the cross-link density and therefore to improve the toughness of these thermosets. The Michael addition approach to toughen BMI resins, however, has at least one significant limitation. Michael addition is thermally reversible and the amine extended bismaleimides will revert to the starting materials in the vicinity of 300° C. This thermal reversion or retro-Michael addition is unacceptable for any adhesive end-use that requires thermal resistance.

The bismaleimides represent one useful class of thermoset compounds that have been used in the microelectronic packaging industry. Bismaleimides are curable, meaning that they are capable of polymerization to yield cross-linked resins. In addition, bismaleimides may be homocured in the presence of free radicals or photoinitiators, or combined with other free-radical curing monomers (e.g., acrylates, methacrylates, syrenics, vinyl ethers, vinyl esters, allyl monomers, olefins, and the like). They may also be cured in the presence of comonomers via, Diels-Alder, -ene, and Michael addition mechanisms.

Commercially available bismaleimide thermoset compositions are noted for their high modulus, and excellent resistance to thermal degradation. However, these thermoset compositions are also well known for brittleness. The utility of the bismaleimide class of thermosets could be vastly improved if less brittle formulations could be achieved that retain the desirable thermal and elastic properties.

A few methods have been described in the art to decrease the brittleness of bismaleimide thermosets. The well-known Michael addition reaction, using aromatic or aliphatic diamines is one of these methods. Michael addition has been used to reduce the cross-link density and therefore to improve the toughness of these thermosets. The Michael addition approach to toughen BMI resins, however, has at least one significant limitation. Michael addition is thermally reversible and the amine extended bismaleimides will revert to the starting materials in the vicinity of 300° C. This thermal reversion or retro-Michael addition is unacceptable for any adhesive end-use that requires thermal resistance.

The imide-extended polymaleimides of this invention are contemplated for use in a wide variety of applications. They can be used, for example, as matrix resins and adhesives for aerospace, marine, automotive, wind turbine, and sports equipment composite products. They can be used in the fabrication of printed wiring boards and flexible circuits. The compounds of this invention can be used in die attach adhesives, underfill and mold compound resins for electronic packaging. They can be used to make thermally resistant films and film adhesives. They may also be used in the fabrication of anisotropic conductive adhesive films and pastes.

SUMMARY OF THE INVENTION

The present invention provides methods for amide-extending an ethylenically unsaturated monomer, oligomer or polymer, the method comprising: reacting an ethylenically unsaturated monomer, oligomer or polymer with a primary amine via a Michael addition reaction to form an amine-terminated intermediate; acylating the amine-terminated intermediate to form an amide-extended monomer, oligomer or polymer, where the amide-terminated monomer, oligomer or polymer has thermal resistance that is higher than the thermal resistance of the amine-terminated intermediate, thereby amide-extending the ethylenically unsaturated monomer, oligomer or polymer. The thermal resistances of each of the amide-terminated monomer, oligomer or polymer and of the amine-terminated intermediate can be characterized, for example, by the respective decomposition onsets via thermogravimetric analysis, and the decomposition onset of the amide-terminated monomer, oligomer or polymer is at least about 100° C. higher than the decomposition onset of the amine-terminated intermediate. In some embodiments, the decomposition onset of the amide-terminated monomer, oligomer or polymer is at least about 110° C. higher than the decomposition onset of the amine-terminated intermediate. In other the decomposition onset of the amide-terminated monomer, oligomer or polymer is at least about 120° C. higher than the decomposition onset of the amine-terminated intermediate.

The ethylenically unsaturated monomer, oligomer or polymer can be a maleimide bismaleimide, an acrylate, a diacrylate, a methacrylate or a dimethacrylate. In certain embodiments, the ethylenically unsaturated monomer, oligomer or polymer is present in a stoichiometric excess over the primary amine. The primary amine can be, e.g., a mono-amine or a diamine.

In certain embodiments, acylating includes contacting the amine-terminated intermediate with an acylating agent selected from selected from the group consisting of an acid anhydride, an acid chloride, and a free acid. In other embodiments, acylating includes contacting the amine-terminated intermediate with an acylating agent selected from the group consisting of methacrylic anhydride, acryloyl chloride maleimidocaproyl chloride and cinnamyl chloride, whereby a reactive functional group is added to the ethylenically unsaturated monomer, oligomer or polymer.

Also provided by the invention are amide-extended monomers, oligomers or polymers prepared according the methods described herein. Certain compounds according to the invention are represented by the formula I or formula II:

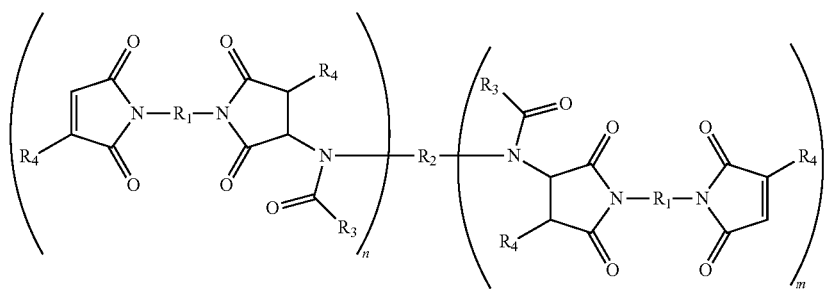

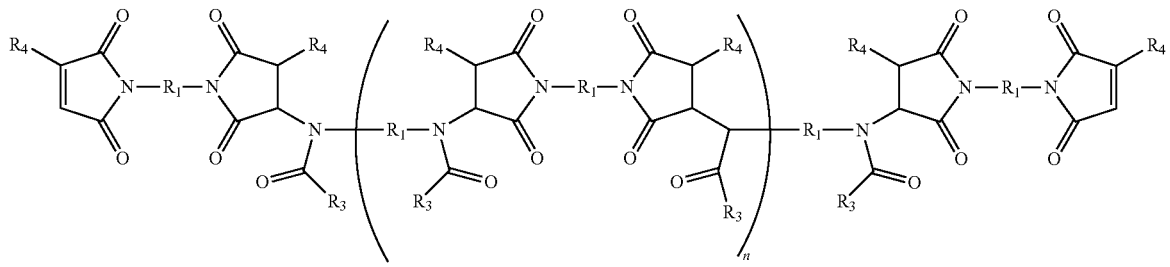

where each of $R_1$ and $R_2$ is independently selected from the group consisting of an unsubstituted or a substituted aliphatic, cycloaliphatic, alkenyl, aryl, heteroaryl, a polydimethylsiloxanemoiety, a poly(butadiene-co-acrylonitrile) moiety, and a poly(alkylene oxide)-derived moiety; $R_3$ is selected from the group consisting of H, an unsubstituted or a substituted $C_1$ to about $C_{10}$ alkyl, and an unsubstituted or a substituted $C_2$ to about $C_{10}$ alkenyl; $R_4$ is selected from the group consisting of H and methyl; and each of n and m is an integer independently having the value between 0 and about 10, with the proviso that the sum m+n has the value between 1 and about 10.

In one embodiment, there are provided imide-extended bismaleimide compounds having the structure:

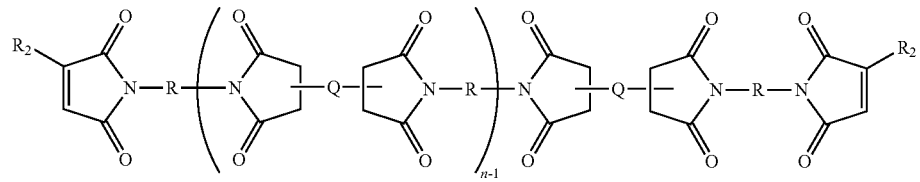

where each of R and Q is independently a substituted or an unsubstituted aliphatic, alkenyl, aromatic, heteroaromatic, or siloxane moiety; $R_2$ is H or methyl; and n is an integer having the value between 1 and about 10, with the proviso that the imide-extended bismaleimide is not:

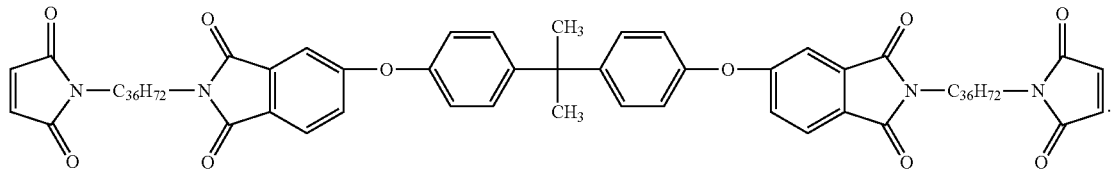

In some aspects, $R_1$ is aryl and $R_2$ is an unsubstituted or a substituted aliphatic or cycloaliphatic moiety. In other aspects each of $R_1$, and $R_2$ is, independently, a substituted or an unsubstituted aliphatic moiety. In yet further aspects, each of $R_1$, and $R_2$ is, independently, a $C_2$ to about a $C_{500}$ substituted or unsubstituted alkenyl, aliphatic, or cycloaliphatic moiety. $R_1$, and $R_2$ can also be, independently, a $C_6$ to about a $C_{50}$ substituted or unsubstituted alkenyl, aliphatic, or cycloaliphatic moiety. In other embodiments, each of $R_1$, and $R_2$ is, independently, a $C_6$ to about a $C_{40}$ substituted or unsubstituted alkenyl, aliphatic, or cycloaliphatic moiety. In yet further embodiments, at least one of $R_1$, and $R_2$ is, independently, a $C_{36}$ substituted or unsubstituted alkenyl, aliphatic, or cycloaliphatic moiety. In still other embodiments, each of $R_1$, and $R_2$ is a $C_{36}$ substituted or unsubstituted alkenyl, aliphatic, or cycloaliphatic moiety. In some aspects at least one of $R_1$, and $R_2$ is, independently, a $C_{36}$ moiety having the structure:

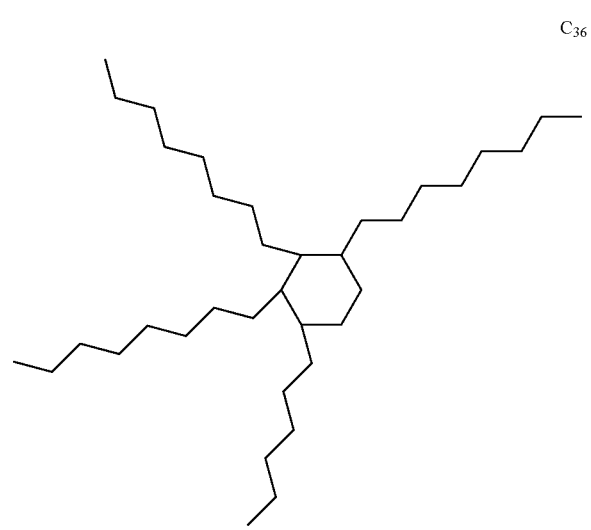 [SMILES: CCCCCCCCC1CCC(CCCCCC)C(CCCCCCCC)C1CCCCCCCC]

$C_{36}$

In various embodiments of the invention, each of $R_1$, and $R_2$ is, independently, a substituted or an unsubstituted cycloalkyl having from 5 to about 20 carbon atoms, 5 to about 12 carbon atoms, or 6 to about 14 carbon atoms.

Each of $R_1$, and $R_2$ can independently be selected from substituted and unsubstituted cyclopentyl, cyclohexyl, norbornyl, tricyclodecyl, cyclododecyl, dicyclopentadienyl, phenyl and naphthyl.

$R_3$ according to the invention, can be selected from an unsubstituted or a substituted methyl, ethyl, propyl, iso-propyl, butyl, sec-butyl, iso-butyl, tert-butyl, a pentyl, propenyl, a butenyl, and cinnamyl. In other embodiments, $R_3$ is substituted and the substitutent comprises a moiety selected from the group consisting of 1-substituted ethylene and 1-substituted 1-methylethylene.

Exemplary compounds are also provided by the invention as indicated herein below (Compounds 1-42).

The present invention also provides compositions comprising at least one amide-terminated compound of the invention. The invention composition can be, for example, an adhesive composition. Adhesive compositions of the invention can be cured or uncured, and in certain embodiments can include at least one curing initiator (such as a free-radical initiator), co-monomer, co-curing compound, coupling agent, or filler. Exemplary co-curing compound suitable for use in the compositions of the invention include acrylates, methacrylates, maleimides, vinyl ethers, vinyl esters, styrenics and allyl functional compound.

The present invention also provides methods for increasing the adhesiveness of a monomer-containing composition, comprising replacing all or a portion of the monomer in the composition with a compound of the invention. The monomer in this method can be, for example, a bismaleimide. In certain aspects, replacing all or a portion of the bismaleimide in the composition increases the adhesiveness of the composition by at least about 50%.

The present invention also provides methods for increasing the toughness and/or thermal stability of a monomer-containing composition, comprising replacing all or a portion of the monomer in the composition with a compound of the invention. The monomer in this method can be, for example, a bismaleimide.

BRIEF DESCRIPTION OF THE DRAWINGS

FIG. 3A shows a polymaleimide structure with succinimide connecting groups pendant from the maleimide polymer or oligomer. FIG. 3B shows a polymaleimide structure where the succinimide connecting groups are part of the main-chain maleimide polymer or oligomer.

DETAILED DESCRIPTION OF THE INVENTION

Figure 1:
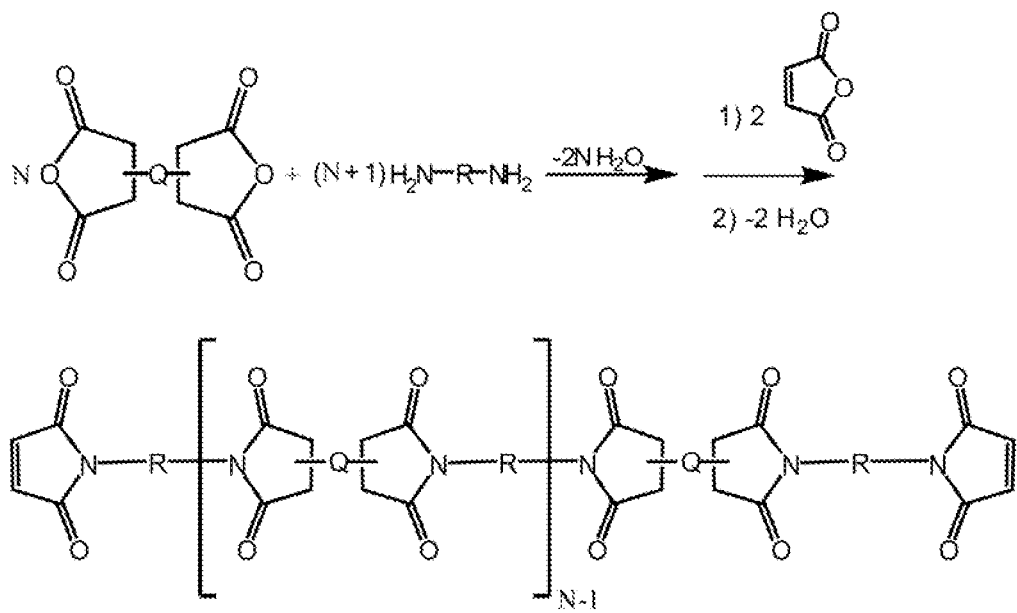
FIGS. 1 and 2 illustrate an exemplary preparation of an imide-extended compound of the invention.
Figure 2:
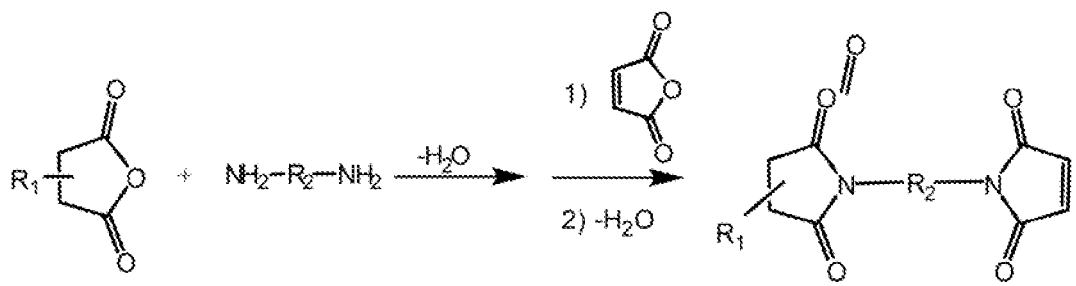

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art, such as those set forth in "IUPAC Compendium of Chemical Terminology: IUPAC Recommendations (The Gold Book)" (McNaught ed.; International Union of Pure and Applied Chemistry, $2^{nd}$ Ed., 1997) and "Compendium of Polymer Terminology and Nomenclature: IUPAC Recommendations 2008" (Jones et al., eds; International Union of Pure and Applied Chemistry, 2009). Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

DEFINITIONS

"About" as used herein means that a number referred to as "about" comprises the recited number plus or minus 1-10% of that recited number. For example, "about" 100 degrees can mean 95-105 degrees or as few as 99-101 degrees depending on the situation. Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms (although the term "alkyl" also includes instances where no numerical range of carbon atoms is designated).

As used herein, the term "amide-extended" means that the compound contains at least one amide moiety in a non-terminal position of the molecule.

"Imide-extended" means that the compound contains at least one imide moiety in a non-terminal position of the molecule.

The "Michael reaction" or "Michael addition" is the nucleophilic addition of a carbanion to an α,β-unsaturated carbonyl compound. It belongs to the larger class of conjugate additions and is one of the most useful methods for mild formation of C—C bonds. The general scheme for Michael addition reactions is shown below:

Michael Addition Reaction Scheme

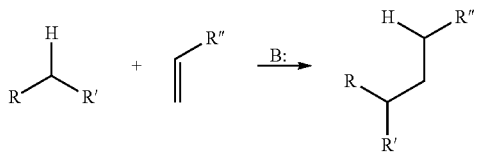

In this scheme, the R and R' substituents on the nucleophile ("Michael donor") are electron-withdrawing groups such as acyl and cyano making the methylene hydrogen acidic forming the carbanion on reaction with base B. Non-limiting examples of substituents on the activated alkene ("Michael acceptor") include a keto-acyl, sulfone, sulfoxide, and nitro groups. The nucleophilic addition of amines or thiols to activated olefins are considered to be Michael-type reactions which result in the formation of carbon-nitrogen bonds and carbon-sulfur bonds, respectively. Amine compounds suitable for this Michael-type reaction include primary and secondary amines. Amines are generally sufficiently basic in nature that no additional base catalyst is usually required for this addition to occur.

"Adhesive" or "adhesive compound" as used herein, refers to any substance that can adhere or bond two items together. Implicit in the definition of an "adhesive composition" or "adhesive formulation" is the fact that the composition or formulation is a combination or mixture of more than one species, component or compound, which can include adhesive monomers, oligomers, and/or polymers along with other materials, whereas an "adhesive compound" refers to a single species, such as an adhesive polymer or oligomer.

More specifically, adhesive composition refers to un-cured mixtures in which the individual components in the mixture retain the chemical and physical characteristics of the original individual components of which the mixture is made. Adhesive compositions are typically malleable and may be liquids, paste, gel or another form that can be applied to an item so that it can be bonded to another item.

"Cured adhesive," "cured adhesive composition" or "cured adhesive compound" refers to adhesives components and mixtures obtained from reactive curable original compound(s) or mixture(s) thereof which have undergone a chemical and/or physical changes such that the original compound(s) or mixture(s) is (are) transformed into a solid, substantially non-flowing material. A typical curing process may involve crosslinking.

"Curable" means that an original compound(s) or composition material(s) can be transformed into a solid, substantially non-flowing material by means of chemical reaction, crosslinking, radiation crosslinking, or the like. Thus, adhesive compositions of the invention are curable, but unless otherwise specified, the original compound(s) or composition material(s) is (are) not cured.

"Thermoplastic," as used herein, refers to the ability of a compound, composition or other material (e.g. a plastic) to dissolve in a suitable solvent or to melt to a liquid when heated and freeze to a solid state when cooled sufficiently.

"Thermoset," as used herein, refers to the ability of a compound, composition or other material to irreversibly "cure" resulting in a single tridimensional network that has greater strength and less solubility compared to the non-cured product. Thermoset materials are typically polymers that may be cured, for example, through heat (e.g. above 200° C.), via a chemical reaction (e.g. epoxy ring-opening, free-radical polymerization, etc or through irradiation (e.g. visible light, UV light, electron beam radiation, ion-beam radiation, or X-ray irradiation).

Thermoset materials, such as thermoset polymers or resins, are typically liquid or malleable forms prior to curing, and therefore may be molded or shaped into their final form, and/or used as adhesives. Curing transforms the thermoset resin into a rigid infusible and insoluble solid or rubber by a cross-linking process. Thus, energy and/or catalysts are typically added that cause the molecular chains to react at chemically active sites (unsaturated or epoxy sites, for example), linking the polymer chains into a rigid, 3-D structure. The cross-linking process forms molecules with a higher molecular weight and resultant higher melting point. During the reaction, when the molecular weight of the polymer has increased to a point such that the melting point is higher than the surrounding ambient temperature, the polymer becomes a solid material.

"Cross-linking," as used herein, refers to the attachment of two or more oligomer or longer polymer chains by bridges of an element, a molecular group, a compound, or another oligomer or polymer. Crosslinking may take place upon heating or exposure to light; some crosslinking processes may also occur at room temperature or a lower temperature. As crosslinking density is increased, the properties of a material can be changed from thermoplastic to thermosetting.

As used herein, "B-stageable" refers to the properties of an adhesive having a first solid phase followed by a tacky rubbery stage at elevated temperature, followed by yet another solid phase at an even higher temperature. The transition from the tacky rubbery stage to the second solid phase is thermosetting. However, prior to thermosetting, the material behaves similarly to a thermoplastic material. Thus, such adhesives allow for low lamination temperatures while providing high thermal stability. A "die" or "semiconductor die" as used herein, refers to a small block of semiconducting material, on which a functional circuit is fabricated.

A "flip-chip" semiconductor device is one in which a semiconductor die is directly mounted to a wiring substrate, such as a ceramic or an organic printed circuit board. Conductive terminals on the semiconductor die, usually in the form of solder bumps, are directly physically and electrically connected to the wiring pattern on the substrate without use of wire bonds, tape-automated bonding (TAB), or the like. Because the conductive solder bumps making connections to the substrate are on the active surface of the die or chip, the die is mounted in a face-down manner, thus the name "flip-chip."

The term "monomer" refers to a molecule that can undergo polymerization or copolymerization thereby contributing constitutional units to the essential structure of a macromolecule (a polymer).

"Underfill," "underfill composition" and "underfill material" are used interchangeably to refer to a material, typically polymeric compositions, used to fill gaps between a semiconductor component, such as a semiconductor die, and a substrate. "Underfilling" refers to the process of applying an underfill composition to a semiconductor component-substrate interface, thereby filling the gaps between the component and the substrate.

"Polymer" and "polymer compound" are used interchangeably herein, to refer generally to the combined the products of a single chemical polymerization reaction. Polymers are produced by combining monomer subunits into a covalently bonded chain. Polymers that contain only a single type of monomer are known as "homopolymers," while polymers containing a mixture of monomers are known as "copolymers."

The term "copolymers" is inclusive of products that are obtained by copolymerization of two monomer species, those obtained from three monomers species (terpolymers), those obtained from four monomers species (quaterpolymers), etc. It is well known in the art that copolymers synthesized by chemical methods include, but are not limited to, molecules with the following types of monomer arrangements:

alternating copolymers, which contain regularly alternating monomer residues;

periodic copolymers, which have monomer residue types arranged in a repeating sequence;

random copolymers, which have a random sequence of monomer residue types;

statistical copolymers, which have monomer residues arranged according to a known statistical rule;

block copolymers, which have two or more homopolymer subunits linked by covalent bonds. The blocks of homopolymer within block copolymers, for example, can be of any length and can be blocks of uniform or variable length. Block copolymers with two or three distinct blocks are called diblock copolymers and triblock copolymers, respectively; and star copolymers, which have chains of monomer residues having different constitutional or configurational features that are linked through a central moiety.

The skilled artisan will appreciate that a single copolymer molecule may have different regions along its length that can be characterized as an alternating, periodic, random, etc. A copolymer product of a chemical polymerization reaction may contain individual polymeric fragments that each differ in the arrangement of monomer units. The skilled artisan will further be knowledgeable in methods for synthesizing each of these types of copolymers, and for varying reaction conditions to favor one type over another.

Furthermore, the length of a polymer chain according to the present invention, will typically vary over a range or average size produced by a particular reaction. The skilled artisan will be aware, for example, of methods for controlling the average length of a polymer chain produced in a given reaction and also of methods for size-selecting polymers after they have been synthesized.

Unless a more restrictive term is used, polymer is intended to encompass homopolymers, and copolymers having any arrangement of monomer subunits as well as copolymers containing individual molecules having more than one arrangement. With respect to length, unless otherwise indicated, any length limitations recited for the polymers described herein are to be considered averages of the lengths of the individual molecules in polymer.

"Thermoplastic elastomer" or "TPE", as used herein refers to a class of copolymers that consist of materials with both thermoplastic and elastomeric properties.

"Hard blocks" or "hard segments" as used herein refer to a block of a copolymer (typically a thermoplastic elastomer) that is hard at room temperature by virtue of a high melting point ($T_m$) or $T_g$. By contrast, "soft blocks" or "soft segments" have a $T_g$ below room temperature.

As used herein, "oligomer" or "oligomeric" refers to a polymer having a finite and moderate number of repeating monomers structural units. Oligomers of the invention typically have 2 to about 100 repeating monomer units; frequently 2 to about 30 repeating monomer units; and often 2 to about 10 repeating monomer units; and usually have a molecular weight up to about 3,000.

The skilled artisan will appreciate that oligomers and polymers may, depending on the availability of polymerizable groups or side chains, subsequently be incorporated as monomers in further polymerization or crosslinking reactions.

As used herein, "aliphatic" refers to any alkyl, alkenyl, cycloalkyl, or cycloalkenyl moiety.

"Aromatic hydrocarbon" or "aromatic" as used herein, refers to compounds having one or more benzene rings.

"Alkane," as used herein, refers to saturated straight-chain, branched or cyclic hydrocarbons having only single bonds. Alkanes have general formula $C_nH_{2n+2}$.

"Cycloalkane," refers to an alkane having one or more rings in its structure.

As used herein, "alkyl" refers to straight or branched chain hydrocarbyl groups having from 1 up to about 500 carbon atoms. "Lower alkyl" refers generally to alkyl groups having 1 to 6 carbon atoms. The terms "alkyl" and "substituted alkyl" include, respectively, substituted and unsubstituted $C_1$-$C_{500}$ straight chain saturated aliphatic hydrocarbon groups, substituted and unsubstituted $C_2$-$C_{200}$ straight chain unsaturated aliphatic hydrocarbon groups, substituted and unsubstituted $C_4$-$C_{100}$ branched saturated aliphatic hydrocarbon groups, substituted and unsubstituted $C_1$-$C_{500}$ branched unsaturated aliphatic hydrocarbon groups.

For example, the definition of "alkyl" includes but is not limited to: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, tricyclodecyl, adamantyl, norbornyl and the like.

"Substituted alkyl" refers to alkyl moieties bearing substituents that include but are not limited to alkyl, alkenyl, alkynyl, hydroxy, oxo, alkoxy, mercapto, cycloalkyl, substituted cycloalkyl, heterocyclic, substituted heterocyclic, aryl, substituted aryl (e.g., aryl$C_{1-10}$alkyl or aryl$C_{1-10}$alkyloxy), heteroaryl, substituted heteroaryl (e.g., heteroaryl $C_{1-10}$alkyl), aryloxy, substituted aryloxy, halogen, haloalkyl (e.g., trihalomethyl), cyano, nitro, nitrone, amino, amido, carbamoyl, =O, =CH—, —C(O)H, —C(O)O—, —C(O)—, —S—, —S(O)$_2$, —OC(O)—O—, —NR—C(O), —NR—C(O)—NR, —OC(O)—NR, where R is H or lower alkyl, acyl, oxyacyl, carboxyl, carbamate, sulfonyl, sulfonamide, sulfuryl, $C_{1-10}$alkylthio, aryl$C_{1-10}$alkylthio, $C_{1-10}$alkylamino, aryl$C_{1-10}$alkylamino, N-aryl-N—$C_{1-10}$alkylamino, $C_{1-10}$alkyl carbonyl, aryl$C_{1-10}$alkylcarbonyl, $C_{1-10}$alkylcarboxy, aryl $C_{1-10}$alkylcarboxy, $C_{1-10}$alkyl carbonylamino, aryl $C_{1-10}$alkylcarbonylamino, tetrahydrofuryl, morpholinyl, piperazinyl, and hydroxypyronyl.

In addition, as used herein "$C_{36}$" refers to all possible structural isomers of a 36 carbon aliphatic moiety, including branched isomers and cyclic isomers with up to three carbon-carbon double bonds in the backbone. One non-limiting example of a moiety that the definition of "$C_{36}$" refers to is the moiety comprising a cyclohexane-based core and four long "arms" attached to the core, as demonstrated by the following structure:

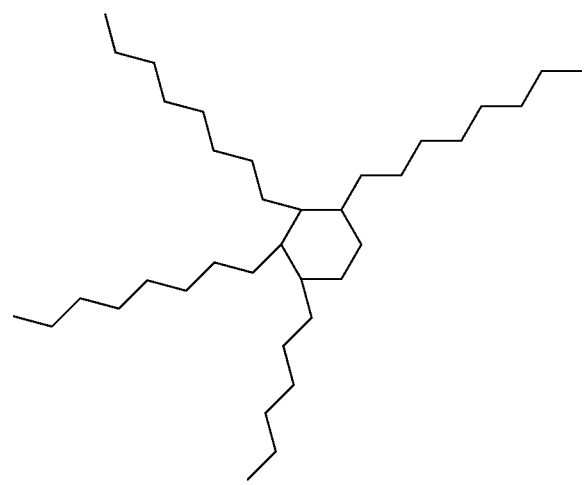

$C_{36}$

As used herein, "cycloalkyl" refers to cyclic ring-containing groups containing in the range of about 3 up to about 20 carbon atoms, typically 3 to about 15 carbon atoms. In certain embodiments, cycloalkyl groups have in the range of about 4 up to about 12 carbon atoms, and in yet further embodiments, cycloalkyl groups have in the range of about 5 up to about 8 carbon atoms. and "substituted cycloalkyl" refers to cycloalkyl groups further bearing one or more substituents as set forth below.

As used herein, "alkenyl," "alkene" or "olefin" refers to straight or branched chain unsaturated hydrocarbyl groups having at least one carbon-carbon double bond, and having in the range of about 2 up to 500 carbon atoms. In certain embodiments, alkenyl groups have in the range of about 5 up to about 250 carbon atoms, 5 up to about 100 carbon atoms, 5 up to about 50 carbon atoms or 5 up to about 25 carbon atoms. In other embodiments, alkenyl groups have in the range of about 6 up to about 500 carbon atoms, 8 up to about 500 carbon atoms, 10 up to about 500 carbon atoms or 20 up to about 500 carbon atoms or 50 up to about 500 carbon atoms. In yet further embodiments, alkenyl groups have in the range of about 6 up to about 100 carbon atoms, 10 up to about 100 carbon atoms, 20 up to about 100 carbon atoms or 50 up to about 100 carbon atoms, while in other embodiments, alkenyl groups have in the range of about 6 up to about 50 carbon atoms, 6 up to about 25 carbon atoms, 10 up to about 50 carbon atoms, or 10 up to about 25 carbon atoms. "Substituted alkenyl" refers to alkenyl groups further bearing one or more substituents as set forth above.

As used herein, "alkynyl" refers to straight or branched chain hydrocarbyl groups having at least one carbon-carbon triple bond, and having in the range of 2 up to about 100 carbon atoms, typically about 4 to about 50 carbon atoms, and frequently about 8 to about 25 carbon atoms. "Substituted alkynyl" refers to alkynyl groups further bearing one or more substituents as set forth below.

As used herein, "alkylene" refers to a divalent alkyl moiety, and "oxyalkylene" refers to an alkylene moiety containing at least one oxygen atom instead of a methylene ($CH_2$) unit. "Substituted alkylene" and "substituted oxyalkylene" refer to alkylene and oxyalkylene groups further bearing one or more substituents as set forth above.

As used herein, "alkynyl" refers to straight or branched chain hydrocarbyl groups having at least one carbon-carbon triple bond, and having in the range of 2 up to about 100 carbon atoms, typically about 4 to about 50 carbon atoms, and frequently about 8 to about 25 carbon atoms. "Substituted alkynyl" refers to alkynyl groups further bearing one or more substituents as set forth below.

As used herein, the term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from the group consisting of halo, —OH, —SH, —CN, —NO$_2$, trihalomethyl, hydroxypyronyl, $C_{1-10}$alkyl, aryl$C_{1-10}$alkyl, $C_{1-10}$alkyloxy$C_{1-10}$alkyl, aryl$C_{1-10}$alkyloxy$C_{1-10}$alkyl, $C_{1-10}$alkylthio$C_{1-10}$alkyl, aryl$C_{1-10}$alkylthio$C_{1-10}$alkyl, $C_{1-10}$alkylamino$C_{1-10}$alkyl, aryl$C_{1-10}$alkylamino$C_{1-10}$alkyl, N-aryl-N—$C_{1-10}$alkylamino$C_{1-10}$alkyl, $C_{1-10}$alkylcarbonyl$C_{1-10}$alkyl, aryl $C_{1-10}$alkylcarbonyl $C_{1-10}$alkyl, $C_{1-10}$alkylcarboxy$C_{1-10}$alkyl, aryl$C_{1-10}$alkylcarboxy$C_{1-10}$alkyl, $C_{1-10}$alkylcarbonylamino$C_{1-10}$alkyl, and aryl$C_{1-10}$alkylcarbonylamino$C_{1-10}$alkyl.

Some specific examples of moieties encompassed by the definition of "aryl" include but are not limited to phenyl, biphenyl, naphthyl, dihydronaphthyl, tetrahydronaphthyl, indenyl, indanyl, azulenyl, anthryl, phenanthryl, fluorenyl, pyrenyl and the like. "Substituted aryl" refers to aryl groups further bearing one or more substituents as set forth below.

As used herein, "arylene" refers to a divalent aryl moiety. "Substituted arylene" refers to arylene moieties bearing one or more substituents as set forth above.

As used herein, "alkylaryl" refers to alkyl-substituted aryl groups and "substituted alkylaryl" refers to alkylaryl groups further bearing one or more substituents as set forth below.

As used herein, "arylalkyl" refers to aryl-substituted alkyl groups and "substituted arylalkyl" refers to arylalkyl groups further bearing one or more substituents as set forth below. Some examples of included but are not limited to (4-hydroxyphenyl)ethyl, or (2-aminonaphthyl) hexenyl.

As used herein, "arylalkenyl" refers to aryl-substituted alkenyl groups and "substituted arylalkenyl" refers to arylalkenyl groups further bearing one or more substituents as set forth below.

As used herein, "arylalkynyl" refers to aryl-substituted alkynyl groups and "substituted arylalkynyl" refers to arylalkynyl groups further bearing one or more substituents as set forth below.

As used herein, "aroyl" refers to aryl-carbonyl species such as benzoyl and "substituted aroyl" refers to aroyl groups further bearing one or more substituents as set forth below.

As used herein, "hetero" refers to groups or moieties containing one or more heteroatoms such as N, O, Si and S. Thus, for example "heterocyclic" refers to cyclic (i.e., ring-containing) groups having e.g. N, O, Si or S as part of the ring structure, and having in the range of 3 up to 14 carbon atoms. "Heteroaryl" and "heteroalkyl" moieties are aryl and alkyl groups, respectively, containing e.g. N, O, Si or S as part of their structure. The terms "heteroaryl", "heterocycle" or "heterocyclic" refer to a monovalent unsaturated group having a single ring or multiple condensed rings, from 1 to 8 carbon atoms and from 1 to 4 hetero atoms selected from nitrogen, sulfur or oxygen within the ring.

The definition of heteroaryl includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl. 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5] tetrazinanyl-3,6-dione, dihydro-pyrimidinyl-2,4-dione, pyrimidinyl-2,4,6-trione, 1H-pyrimidinyl-2,4-dione, 5-iodo-1H-pyrimidinyl-2,4-dione, 5-chloro-1H-pyrimidinyl-2,4-dione, 5-methyl-1H-pyrimidinyl-2,4-dione, 5-isopropyl-1H-pyrimidinyl-2,4-dione, 5-propynyl-1H-pyrimidinyl-2,4-dione, 5-trifluoromethyl-1H-pyrimidinyl-2,4-dione, 6-amino-9H-purinyl, 2-amino-9H-purinyl, 4-amino-1H-pyrimidinyl-2-one, 4-amino-5-fluoro-1H-pyrimidinyl-2-one, 4-amino-5-methyl-1H-pyrimidinyl-2-one, 2-amino-1,9-dihydro-purinyl-6-one, 1,9-dihydro-purinyl-6-one, 1H-[1,2,4] triazolyl-3-carboxylic acid amide, 2,6-diamino-N.sub.6-cyclopropyl-9H-purinyl, 2-amino-6-(4-methoxyphenylsulfanyl)-9H-purinyl, 5,6-dichloro-1H-benzoimidazolyl, 2-isopropylamino-5,6-dichloro-1H-benzoimidazolyl, 2-bromo-5,6-dichloro-1H-benzoimidazolyl, and the like. Furthermore, the term "saturated heterocyclic" represents an unsubstituted, mono-, di- or trisubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl and the like).

Hetero-containing groups may also be substituted. For example, "substituted heterocyclic" refers to a ring-containing group having in the range of 3 up to 14 carbon atoms that contains one or more heteroatoms and also bears one or more substituents, as set forth above. Examples of substituents include, but are not limited to halo, —OH, —SH, —CN, —NO$_2$, trihalomethyl, hydroxypyronyl, $C_{1-10}$alkyl, aryl$C_{1-10}$alkyl, $C_{1-10}$alkyloxy$C_{1-10}$alkyl, aryl$C_{1-10}$alkyloxy $C_{1-10}$alkyl, $C_{1-10}$alkylthio$C_{1-10}$alkyl, aryl$C_{1-10}$alkylthio $C_{1-10}$alkyl, $C_{1-10}$alkylamino$C_{1-10}$alkyl, aryl$C_{1-10}$alkylamino $C_{1-10}$alkyl, N-aryl-N—$C_{1-10}$alkylamino$C_{1-10}$alkyl, $C_{1-10}$alkylcarbonyl$C_{1-10}$alkyl, aryl$C_{1-10}$alkylcarbonyl $C_{1-10}$alkyl, $C_{1-10}$alkylcarboxy$C_{1-10}$alkyl, aryl$C_{1-10}$alkylcarboxy$C_{1-10}$alkyl $C_{1-10}$alkylcarbonylamino$C_{1-10}$alkyl, and aryl$C_{1-10}$alkylcarbonylamino $C_{1-10}$alkyl.

As used herein, the term "phenol" includes compounds having one or more phenolic functions per molecule. The terms aliphatic, cycloaliphatic and aromatic, when used to describe phenols, refers to phenols to which aliphatic, cycloaliphatic and aromatic residues or combinations of these backbones are attached by direct bonding or ring fusion.

As used herein, "acyl" refers to alkyl-carbonyl species.

As used herein, the terms "halogen," "halide," or "halo" include fluorine, chlorine, bromine, and iodine.

"Allyl" as used herein, refers to refers to a compound bearing at least one moiety having the structure:

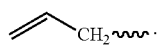

"Imide" as used herein, refers to a functional group having two carbonyl groups bound to a primary amine or ammonia. The general formula of an imide of the invention is:

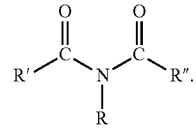

"Polyimides" are polymers of imide-containing monomers. Polyimides are typically linear or cyclic. Non-limiting examples of linear and cyclic (e.g. an aromatic heterocyclic polyimide) polyimides are shown below for illustrative purposes.

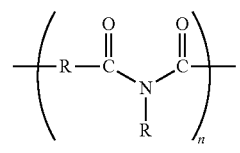

Linear Polyimide

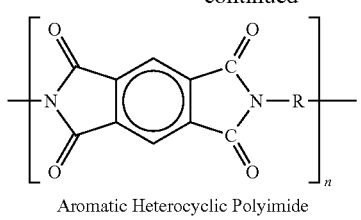

Aromatic Heterocyclic Polyimide

"Maleimide," as used herein, refers to an N-substituted maleimide having the formula as shown below:

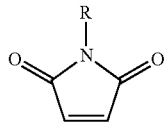

where R is an aromatic, herteroaromatic, aliphatic, or polymeric moiety.

"Bismaleimide" or "BMI", as used herein, refers to compound in which two imide moieties are linked by a bridge, i.e. a compound a polyimide compound in which two imide moieties are linked by a bridge, i.e., a compound having the general structure shown below:

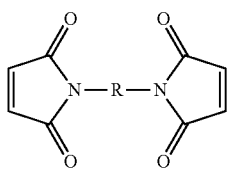

BMIs can cure through an addition rather than a condensation reaction, thus avoiding problems resulting from the formation of volatiles. BMIs can be cured by a vinyl-type polymerization of a pre-polymer terminated with two maleimide groups.

As used herein, the term "acrylate" refers to a compound bearing at least one moiety having the structure:

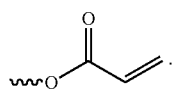

As used herein, the term "acrylamide" refers to a compound bearing at least one moiety having the structure:

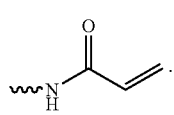

As used herein, the term "methacrylate" refers to a compound bearing at least one moiety having the structure:

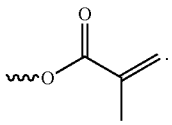

As used herein, the term "methacrylamide" refers to a compound bearing at least one moiety having the structure:

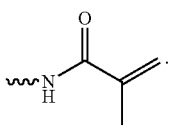

As used herein, "maleate" refers to a compound bearing at least one moiety having the structure:

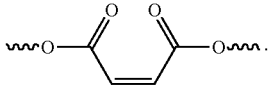

As used herein, the term "acyloxy benzoate" or "phenyl ester" refers to a compound bearing at least one moiety having the structure:

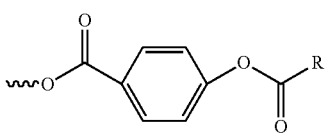

wherein R=H, lower alkyl, or aryl.

As used herein, the term "citraconimide" refers to a compound bearing at least one moiety having the structure:

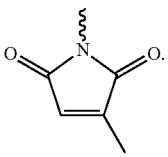

"Itaconate," as used herein refers to a compound bearing at least one moiety having the structure:

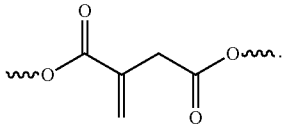

As used herein, "siloxane" refers to any compound containing a Si—O moiety. Siloxanes may be either linear or cyclic. In certain embodiments, siloxanes of the invention include 2 or more repeating units of Si—O. Exemplary cyclic siloxanes include hexamethylcyclotrisiloxane, octamethylcyclotetrasiloxane, decamethylcyclopentasiloxane, dodecamethylcyclohexasiloxane and the like.

As used herein, "oxiranylene" or "epoxy" refers to divalent moieties having the structure:

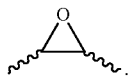

The term "epoxy" also refers to thermosetting epoxide polymers that cure by polymerization and crosslinking when mixed with a catalyzing agent or "hardener," also referred to as a "curing agent" or "curative." Epoxies of the present invention include, but are not limited to aliphatic, cycloaliphatic, glycidyl ether, glycidyl ester, glycidyl amine epoxies, and the like, and combinations thereof.

As used herein, the term "oxetane" refers to a compound bearing at least one moiety having the structure:

As used herein, the term "vinyl ether" refers to a compound bearing at least one moiety having the structure:

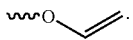

As used herein, the term "vinyl ester" refers to a compound bearing at least one moiety having the structure:

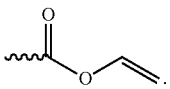

As used herein, "styrenic" refers to a compound bearing at least one moiety having the structure:

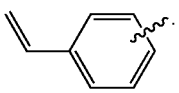

"Oxazoline" as used herein, refers to a compound bearing at least one moiety having the structure:

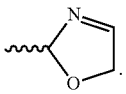

"Benzoxazine" as used herein, refers to a compound bearing at least one moiety having the structure:

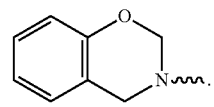

"Fumarate" as used herein, refers to a compound bearing at least one moiety having the structure:

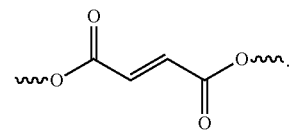

"Propargyl" as used herein, refers to a compound bearing at least one moiety having the structure:

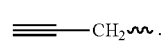

"Cyanate" as used herein, refers to a compound bearing at least one moiety having the structure:

As used herein, "norbornyl" refers to a compound bearing at least one moiety having the structure:

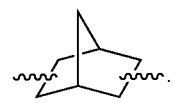

As used herein, a "primary amine terminated difunctional siloxane bridging group" refers to a moiety having the structural formula:

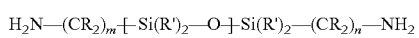

$$H_2N-(CR_2)_m-[Si(R')_2-O]-Si(R')_2-(CR_2)_n-NH_2$$

where each R is H or Me, each R' is independently H, lower alkyl, or aryl; each of m and n is an integer having the value between 1 to about 10, and q is an integer having the value between 1 and 100.

As used herein a "primary amine terminated polypropylene oxide" refers to a moiety having the structural formula:

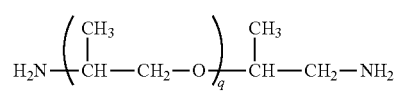

wherein q is 4 to about 50.

As used herein a "primary amine terminated butadiene acrylonitrile copolymer" refers to a moiety having the structural formula:

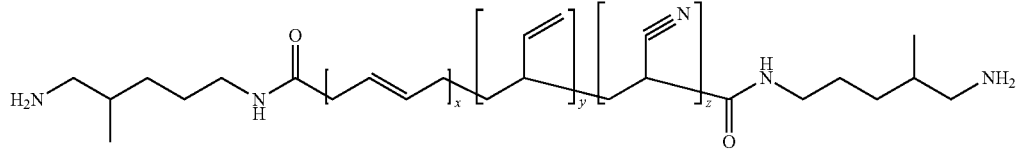

where each x and y are independently 0 to about 20; x plus y is about 10 to about 20, and z is about 1 to 5.

As used herein, the term "free radical initiator" refers to any chemical species which, upon exposure to sufficient energy (e.g., light, heat, or the like), decomposes into parts which are uncharged, but every one of such part possesses at least one unpaired electron.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

"Diamine," as used herein, refers generally to a compound or mixture of compounds, where each species has 2 amine groups.

A "diol" according to the present invention, is a compound containing two hydroxyl groups (—OH groups); while "polyol" refers to alcohols containing multiple hydroxyl groups.

The term "solvent," as used herein, refers to a liquid that dissolves a solid, liquid, or gaseous solute, resulting in a solution. "Co-solvent" refers to a second, third, etc. solvent used with a primary solvent.

As used herein, "polar protic solvents" are ones that contain an O—H or N—H bond, while "polar aprotic solvents" do not contain an O—H or N—H bond.

As used herein, "alcohol catalyst" refers to an alcohol or combination of alcohols that, when added to a chemical reaction, has the effect of accelerating, increasing the rate or yield of the reaction without being consumed by the overall reaction. Typically, an alcohol catalyst will contain a single alcohol, but mixtures comprising two or more alcohols are contemplated for use in the present invention. As used herein, "acid catalyst" refers to any acidic substance or compound that, when added to a chemical reaction, has the effect of accelerating, increasing the rate or yield of the reaction without being consumed by the overall reaction. Typically, an acid catalyst will contain a single acid, but mixtures comprising two or more acids are contemplated for use in the present invention. Acid catalysts of the invention can be soluble or insoluble. For example, polymer-bound acid catalysts may conveniently be used in the methods of the invention and then easily removed e.g. by gravity filtration.

"Friedel-Crafts alkylation" is an electrophilic aromatic substitution that involves the alkylation of an aromatic ring with an alkyl halide using a strong Lewis acid catalyst. A typical reaction scheme for alkylation of a benzene ring is shown below:

Friedel Crafts Alkylation Scheme

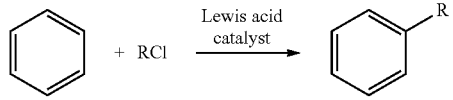

"Prilezhaev reaction" is a method for synthesizing epoxy compounds are by reacting olefins with peroxides; the later provide an oxygen atom that becomes a part of the resulting epoxy compound. Some peroxide reagents that may be used include hydrogen peroxide, peroxycarboxylic acids, and alkyl hydroperoxides. The Prilezhaev reaction may be schematically illustrated by the following reaction scheme demonstrating the formation of an epoxy compound from styrene:

Prilezhaev Reaction Scheme

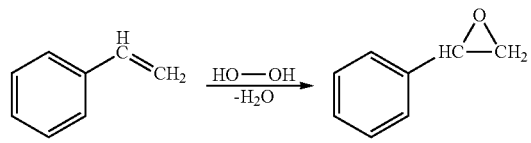

"Glass transition temperature" or "$T_g$": is used herein to refer to the temperature at which an amorphous solid, such as a polymer, becomes brittle on cooling, or soft on heating. More specifically, it defines a pseudo second order phase transition in which a supercooled melt yields, on cooling, a glassy structure and properties similar to those of crystalline materials e.g. of an isotropic solid material.

"Modulus" or "Young's modulus" as used herein, is a measure of the stiffness of a material. Within the limits of elasticity, modulus is the ratio of the linear stress to the linear strain which can be determined from the slope of a stress-strain curve created during tensile testing.

The "Coefficient of Thermal Expansion" or "CTE" is a term of art describing a thermodynamic property of a substance. The CTE relates a change in temperature to the change in a material's linear dimensions. As used herein "$\alpha_1$ CTE" or "$\alpha_1$" refers to the CTE before the $T_g$, while "$\alpha_2$ CTE" refers to the CTE after the $T_g$.

"Thixotropy" as used herein, refers to the property of a material which enables it to stiffen or thicken in a relatively short time upon standing, but upon agitation or manipulation to change to low-viscosity fluid; the longer the fluid undergoes shear stress, the lower its viscosity. Thixotropic materials are therefore gel-like at rest but fluid when agitated and have high static shear strength and low dynamic shear strength, at the same time.

"Glass transition temperature" or "$T_g$" is used herein to refer to the temperature at which an amorphous solid, such as a polymer, becomes brittle on cooling, or soft on heating. More specifically, it defines a pseudo second order phase transition in which a supercooled melt yields, on cooling, a glassy structure and properties similar to those of crystalline materials e.g. of an isotropic solid material.

"Thermogravimetric analysis" or "TGA" refers to a method of testing and analyzing a material to determine changes in weight of a sample that is being heated in relation to change in temperature. "Decomposition onset" refers to a temperature when the loss of weight in response to the increase of the temperature indicates that the sample is beginning to degrade.

"Coefficient of Thermal Expansion" or "CTE" is a term of art describing a thermodynamic property of a substance. The CTE relates a change in temperature to the change in a material's linear dimensions. As used herein "$\alpha_1$ CTE" or "$\alpha_1$" refers to the CTE before the $T_g$, while "$\alpha_2$ CTE" refers to the CTE after the $T_g$.

The present invention is based on the discovery that a remarkable improvement in the performance of maleimide thermosets can be achieved through the incorporation of imide-extended mono-, bis-, or polymaleimide compounds. In one embodiment, there are provided imide-extended bismaleimide compounds having the structure:

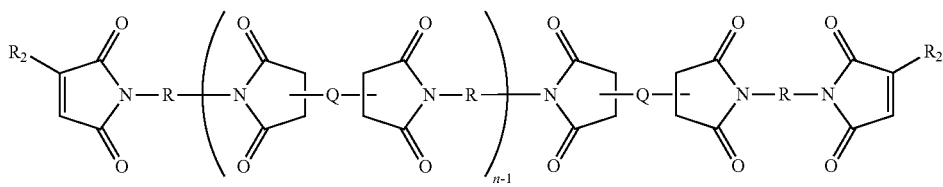

wherein each of R and Q is independently a substituted or an unsubstituted aliphatic, alkenyl, aromatic, heteroaromatic, or siloxane moiety; $R_2$ is H or methyl; and n is an integer having the value between 1 and about 10, with the proviso that the imide-extended bismaleimide is not polymerizable moiety. In some embodiments, the polymerizable moiety is vinyl ether, vinyl ester, acrylate, methacrylate, epoxy, oxetane, oxazoline, benzoxazine, prorpargyl ether, urethane, norbornyl, maleimide, or nadimide. In some embodiments the curative is phenol, phenyl ester and the like.

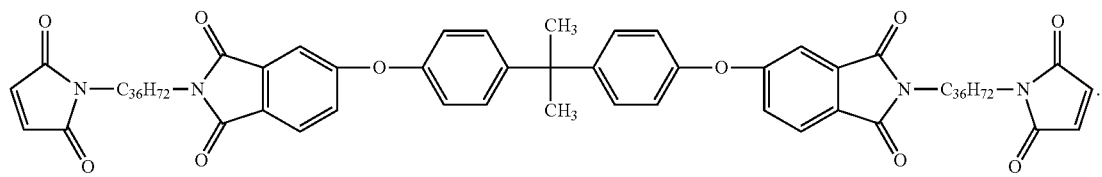

In certain embodiments, R and Q are each independently substituted or unsubstituted linear, branched, or cyclic aliphatic or alkenyl moieties having from 2 to about 500 carbon atoms. In other embodiments, R and Q are each independently substituted or unsubstituted aromatic or heteroaromatic moieties having from 6 to about 20 carbon atoms.

In other embodiments, R and Q are each independently substituted or unsubstituted siloxane moieties having from 2 to about 1000 silicon atoms. In some embodiments, R and Q are each independently polysiloxane moieties, such as, for example, dimethylsiloxane, methylphenylsiloxane, diphenylsiloxane, methylhydrosiloxane, or combinations thereof.

When R and Q include substituted aliphatic, aromatic, heteroaromatic, or siloxane moieties, such substituents include alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—, —S—, —S(O)$_2$—, —OC(O)—O—, —NR—C(O)—, —NR—C(O)—NR—, —OC(O)—NR—, wherein R is H or lower alkyl, acyl, oxyacyl, carboxyl, carbamate, sulfonyl, sulfonamide, sulfuryl, and the like.

In another embodiment, there are provided compounds having the structure:

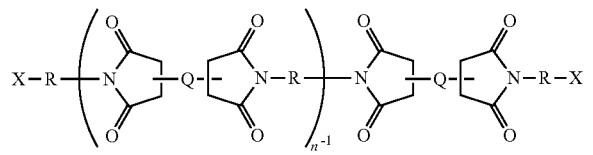

where R and Q are each independently substituted or unsubstituted aliphatic, aromatic, heteroaromatic, siloxane, unsaturated hydrocarbon, polyester, polyamide, or polyurethane moieties; and X is a polymerizable or curative moiety.

In some embodiments, the polymerizable moiety is a cationic polymerizable moiety, an anionic polymerizable moiety, a ring-opening polymerizable moiety, or a free radical Referring to FIG. 1, imide-extended bismaleimide compounds are readily prepared by a two-step, single-pot synthesis. The first step involves the condensation of a dianhydride with a dimer diamine to form an amine-terminated polyimide. The diamine should be present in at least a slight excess of that necessary to form the imide-linked diamine intermediate.

A wide variety of diamines are contemplated for use in the practice of the invention, such as for example, 1,10-diaminodecane; 1,12-diaminododecane; dimer diamine; 1,2-diamino-2-methylpropane; 1,2-diaminocyclohexane; 1,2-diaminopropane; 1,3-diaminopropane; 1,4-diaminobutane; 1,5-diaminopentane; 1,7-diaminoheptane; 1,8-diaminomenthane; 1,8-diaminooctane; 1,9-diaminononane; 3,3'-diamino-N-methyldipropylamine; diaminomaleonitrile; 1,3-diaminopentane; 9,10-diaminophenanthrene; 4,4'-diaminooctafluorobiphenyl; 3,5-diaminobenzoic acid; 3,7-diamino-2-methoxyfluorene; 4,4'-diaminobenzophenone; 3,4-diaminobenzophenone; 3,4-diaminotoluene; 2,6-diaminoanthroquinone; 2,6-diaminotoluene; 2,3-diaminotoluene; 1,8-diaminonaphthalene; 2,4-diaminotoluene; 2,5-diaminotoluene; 1,4-diaminoanthroquinone; 1,5-diaminoanthroquinone; 1,5-diaminonaphthalene; 1,2-diaminoanthroquinone; 2,4-cumenediamine; 1,3-bisaminomethylbenzene; 1,3-bisaminomethylcyclohexane; 2-chloro-1,4-diaminobenzene; 1,4-diamino-2,5-dichlorobenzne; 1,4-diamino-2,5-dimethylbenzene; 4,4'-diamino-2,2'-bistrifluoromethylbiphenyl; bis(amino-3-chlorophenyl)ethane; bis(4-amino-3,5-dimethylphenyl)methane; bis(4-amino-3,5-diethylphenyl) methane; bis(4-amino-3-ethyl diaminofluorene; diaminobenzoic acid; 2,3-diaminonaphthalene; 2,3-diaminophenol; -5-methylphenyl)methane; bis(4-amino-3-methylphenyl)methane; bis(4-amino-3-ethylphenyl)methane; 4,4'-diaminophenylsulfone; 3,3'-diaminophenylsulfone; 2,2-bis(4-(4-aminophenoxy)phenyl)sulfone; 2,2-bis(4-(3-aminophenoxy)phenyl)sulfone; 4,4'-oxydianiline; 4,4'-diaminodiphenyl sulfide; 3,4'-oxydianiline; 2,2-bis(4-(4-aminophenoxy)phenyl)propane; 1,3-bis(4-aminophenoxy)benzene; 4,4'-bis(4-aminophenoxy)biphenyl; 4,4'-diamino-3,3'-dihydroxybiphenyl; 4,4'-diamino-3,3'-dimethylbiphenyl; 4,4'-diamino-3,3'-dimethoxybiphenyl; Bisaniline M; Bisaniline P; 9,9-bis(4-aminophenyl)fluorene;

o-tolidine sulfone; methylene bis(anthranilic acid); 1,3-bis(4-aminophenoxy)-2,2-dimethylpropane; 1,3-bis(4-aminophenoxy)propane; 1,4-bis(4-aminophenoxy)butane; 1,5-bis(4-aminophenoxy)butane; 2,3,5,6-tetramethyl-1,4-phenylenediamine; 3,3',5,5'-tetramethylbenzidine; 4,4'-diaminobenzanilide; 2,2-bis(4-aminophenyl)hexafluoropropane; polyoxyalkylenediamines (e.g. Huntsman's Jeffamine D-230, D400, D-2000, and D-4000 products); 1,3-cyclohexanebis(methylamine); m-xylylenediamine; p-xylylenediamine; bis(4-amino-3-methylcyclohexyl)methane; 1,2-bis(2-aminoethoxy)ethane; 3(4),8(9)-bis(aminomethyl)tricyclo(5.2.1.0$^{2,6}$)decane; and the like.

The second step of the reaction involves the condensation of the remaining amine residues with a slight excess of maleic anhydride to form the maleimide moieties. This second step can be accomplished employing techniques well known to those of skill in the art. The most straightforward preparation of maleimides entails formation of the maleamic acid via reaction of the primary amine with maleic anhydride, followed by dehydrative closure of the maleamic acid with acetic anhydride. A major complication is that some or all of the closure is not to the maleimide, but to the isomaleimide. Essentially the isomaleimide is the dominant or even exclusive kinetic product, whereas the desired maleimide is the thermodynamic product. Conversion of the isomaleimide to the maleimide is effectively the slow step and, particularly in the case of aliphatic amines, may require forcing conditions which can lower the yield. Of course, a variety of other approaches can also be employed.

For example, dicyclohexylcarbodiimide (DCC) closes maleamic acids much more readily than does acetic anhydride. With DCC, the product is exclusively isomaleimide. However, in the presence of suitable isomerizing agents, such as 1-hydroxybenzotriazole (HOBt), the product is solely the maleimide. The function of the HOBt could be to allow the closure to proceed via the HOBt ester of the maleamic acid (formed via the agency of DCC) which presumably closes preferentially to the maleimide. Likely, isomerizing agents such as HOBt add to the isoimide to yield the amic acid ester. If this exhibits any tendency whatsoever to close to the imide, much less a strong bias for doing so, a route for interconverting isoimide and imide is thereby established and the thermodynamic product, imide, should ultimately prevail. Thus if the initial closure of ester formed in the DCC reaction yields any isoimide, or if any isoimide is produced by direct closure of the acid, the situation will be subsequently "corrected" via conversion of the isoimide to the imide by the action of the active ester alcohol as an isomerizing agent. An alternative method for affecting the cyclodehydration of maleamic acids is set forth in U.S. Pat. No. 5,973,166, the entire contents of which are incorporated herein by reference. This method utilizes amine salts that can be successfully used to replace the polar, aprotic solvents that have been used for the cyclodehydration of maleamic acids. The use of these salts provides competitive reaction times and product yields relative to results obtained with polar, aprotic solvents. These salts have the advantage of having no vapor pressure and, therefore, have no possibility to co-distill with the water produced by the cyclodehydration reaction. Furthermore, such salts can be tailored to have desirable solubility characteristics (i.e., soluble in the refluxing azeotropic solvent, but insoluble at room temperature) that permit their easy removal from the reaction product. Such salts are not destroyed during the cyclodehydration reaction and, therefore, can be efficiently recycled again and again.

A wide variety of anhydrides are contemplated for use in the practice of the invention, such as, for example, polybutadiene-graft-maleic anhydride; polyethylene-graft-maleic anhydride; polyethylene-alt-maleic anhydride; polymaleic anhydride-alt-1-octadecene; polypropylene-graft-maleic anhydride; poly(styrene-co-maleic anhydride); pyromellitic dianhydride; maleic anhydride, succinic anhydride; 1,2,3,4-cyclobutanetetracarboxylic dianhydride; 1,4,5,8-naphthalenetetracarboxylic dianhydride; 3,4,9,10-perylenentetracarboxylic dianhydride; bicyclo(2.2.2)oct-7-ene-2,3,5,6-tetracarboxylic dianhydride; diethylenetriaminepentaacetic dianhydride; ethylenediaminetetraacetic dianhydride; 3,3',4,4'-benzophenone tetracarboxylic dianhydride; 3,3',4,4'-biphenyl tetracarboxylic dianhydride; 4,4'-oxydiphthalic anhydride; 3,3',4,4'-diphenylsulfone tetracarboxylic dianhydride; 2,2'-bis(3,4-dicarboxyphenyl)hexafluoropropane dianhydride; 4,4'-bisphenol A diphthalic anhydride; 5-(2,5-dioxytetrahydro)-3-methyl-3-cyclohexene-1,2-dicarboxylic anhydride; ethylene glycol bis(trimellitic anhydride); hydroquinone diphthalic anhydride; allyl nadic anhydride; 2-octen-1-ylsuccinic anhydride; phthalic anhydride; 1,2,3,6-tetrahydrophthalic anhydride; 3,4,5,6-tetrahydrophthalic anhydride; 1,8-naphthalic anhydride; glutaric anhydride; dodecenylsuccinic anhydride; hexadecenylsuccinic anhydride; hexahydrophthalic anhydride; methylhexahydrophthalic anhydride; tetradecenylsuccinic anhydride; and the like.

Additional anhydrides contemplated for use include, but are not limited to:

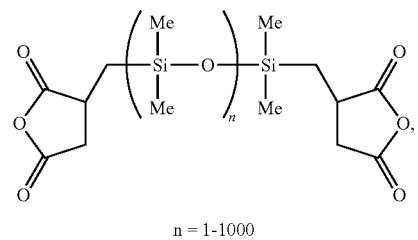

n = 1-1000

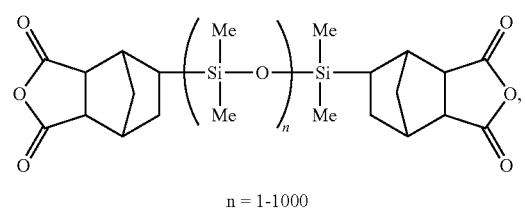

n = 1-1000

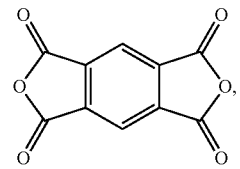

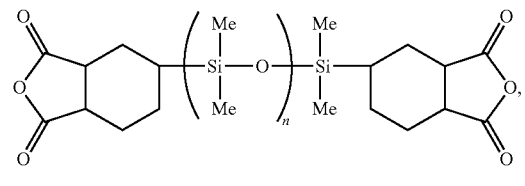

n = 1-1000

25
-continued

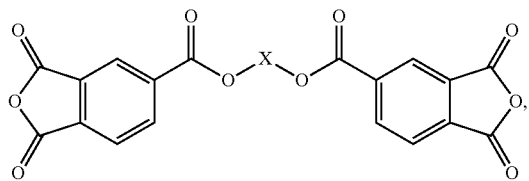

where X is saturated or unsaturated straight or branched alkyl, polyester, polyamide, polyether, polysiloxane, or polyurethane,

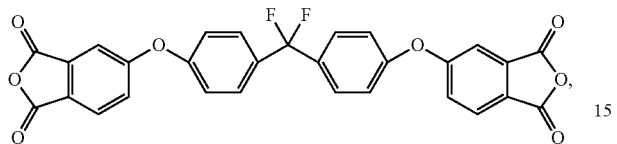

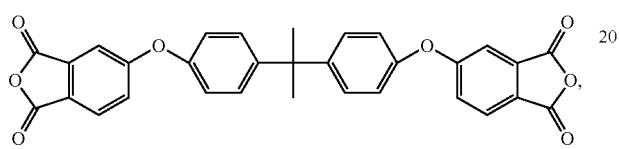

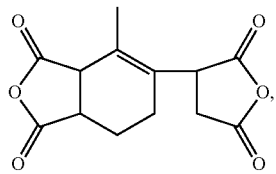

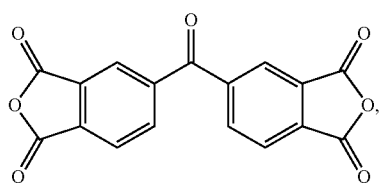

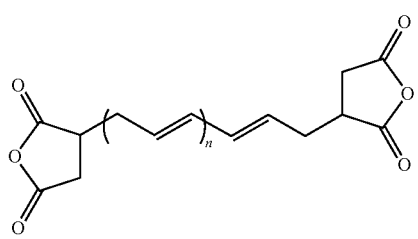

n = 1-10

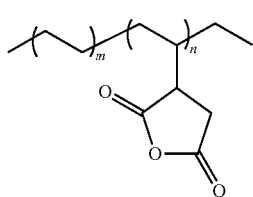

Polyethylene-graft-
Maleic anhydride

26
-continued

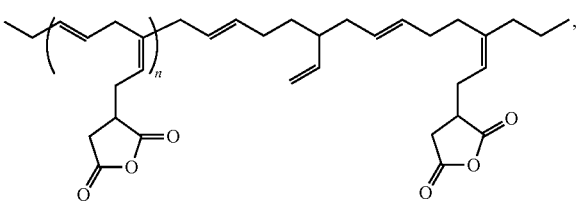

Maleated Ricon

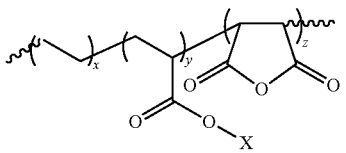

Poly(ethylene-co-x-acrylate-co-maleic anhydride)

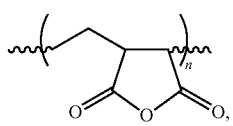

Polyethylene-alt-
maleic anhydride

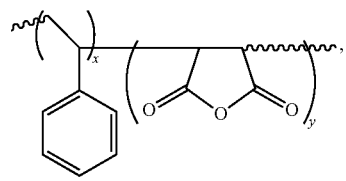

Poly(styrene-co-maleic anhydride)

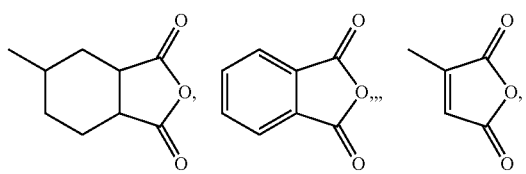

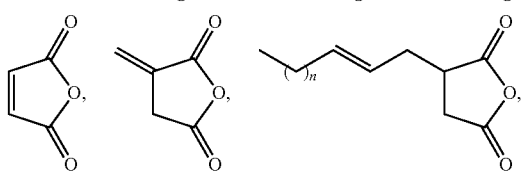

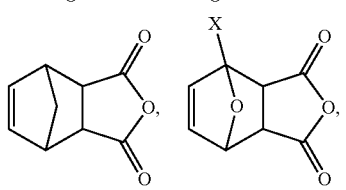

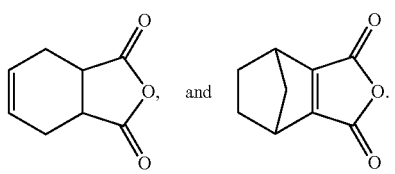

All of the following compounds are also contemplated for use in the practice of the invention:

Maleimides, Citraconimides, and Itaconimides
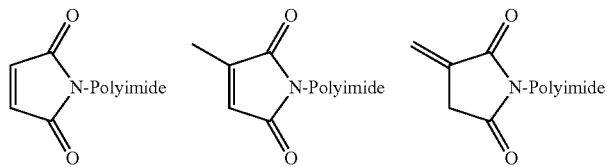
Other Alkene End Groups
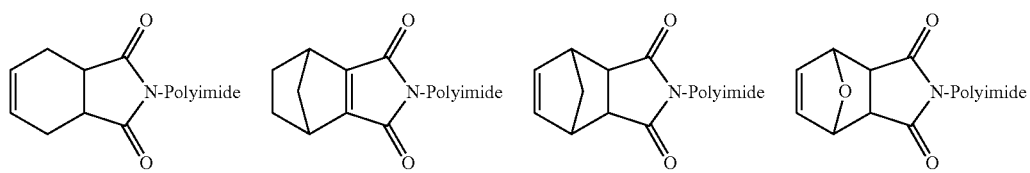
Cycloaliphatic Epoxies
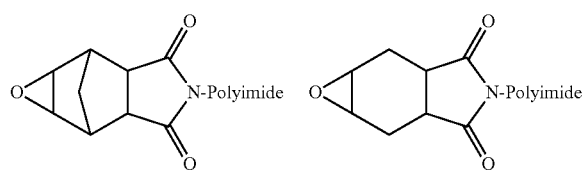
Amines, Alcohols, Carboxylic acids, Phenols, thiols.
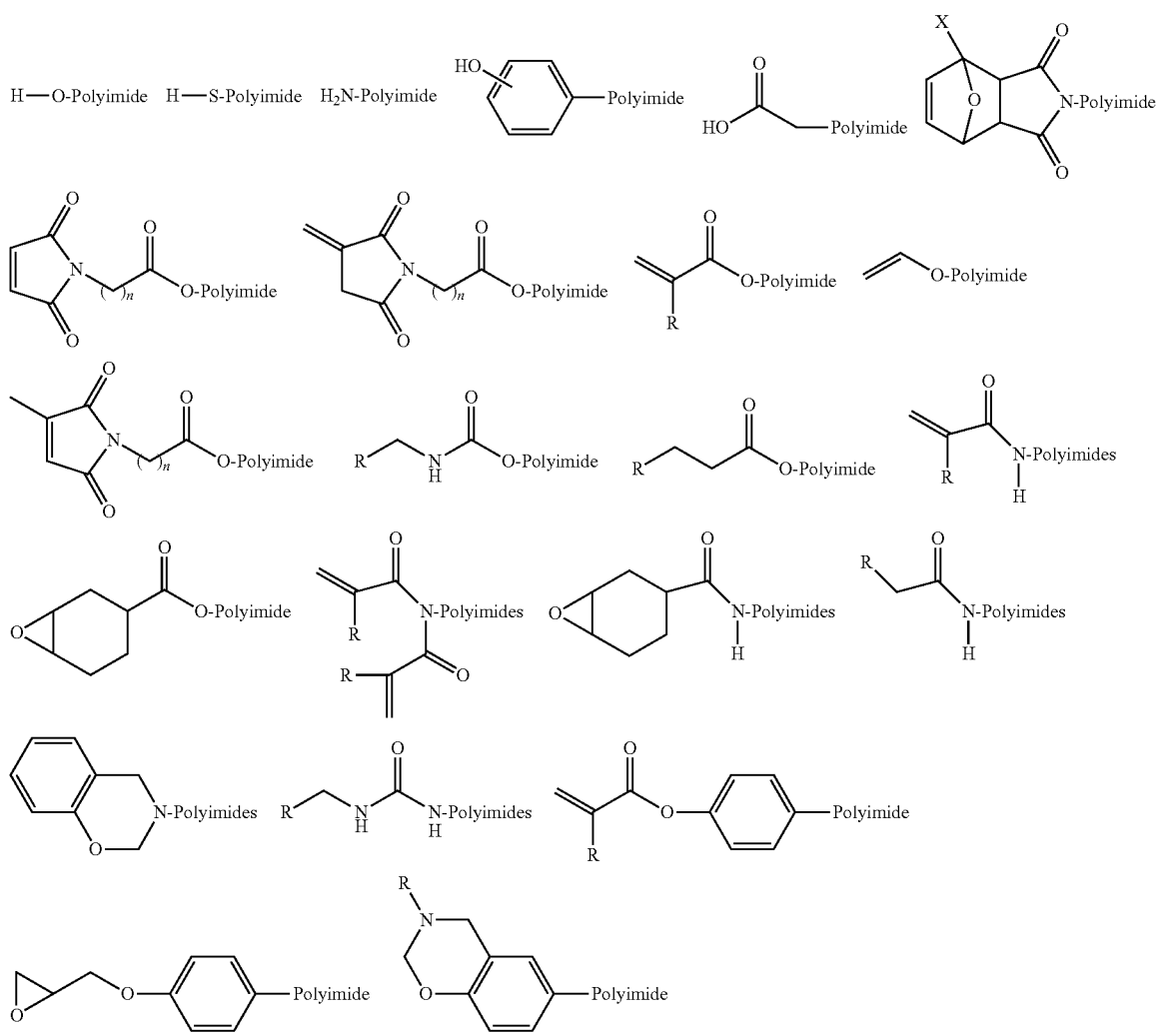

-continued
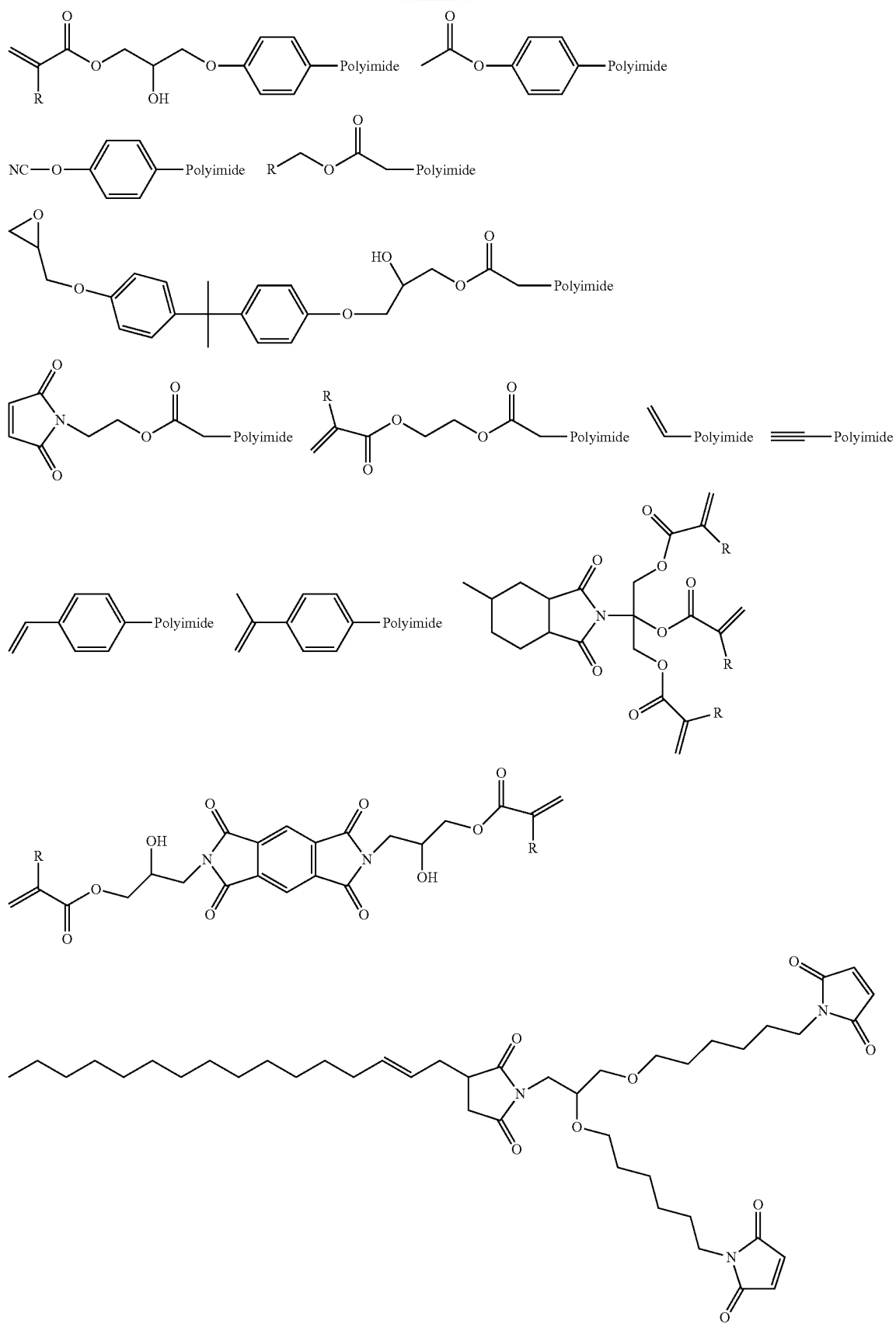

As set forth in the Examples herein, imide-extended maleimide compounds remain flexible at room temperature and are tougher than currently available maleimide-terminated rubbers. Thus, they may be used alone in adhesive compositions or added to available resins as a toughening agent. The maleimides of the invention will be present in the curable adhesive compositions in an amount from 0.05 to 98 weight percent (wt %) based on the organic components present (excluding any fillers).

In another embodiment, there are provided monomaleimides having the formula:

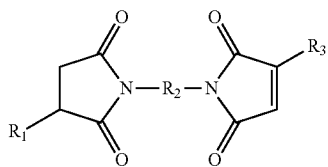

wherein $R_1$ is a substituted or an unsubstituted aliphatic, alkenyl, or aromatic moiety; and $R_2$ is a substituted or an unsubstituted aliphatic, alkenyl, aromatic, or siloxane moiety; and $R_3$ is H or methyl.

In some embodiments, each of $R_1$ and $R_2$ is independently a substituted or an unsubstituted linear, branched, or cyclic aliphatic or alkenyl moieties having from 2 to about 500 carbon atoms. In other embodiments, $R_1$ is a substituted or an unsubstituted aromatic or heteroaromatic moiety having from 6 to about 14 carbon atoms.

In certain other embodiments, $R_2$ is a substituted or an unsubstituted siloxane moiety having from 2 to about 1000 silicon atoms. In some embodiments, $R_2$ is a polysiloxane moiety, such as, for example, dimethylsiloxane, methylphenylsiloxane, diphenylsiloxane, or combinations thereof.

When $R_1$ and $R_2$ are substituted, the substituents present are those as set forth above.

In another embodiment of the invention, there are provided polymaleimides including polymers having a plurality of pendant repeating units having the structure:

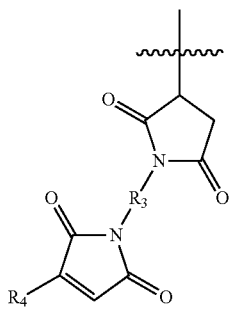

wherein $R_3$ is a substituted or an unsubstituted aliphatic, alkenyl, aromatic, heteroaromatic, or siloxane moiety; and $R_4$ is H or methyl As used herein, the term "pendant" means that the structure set forth above is attached to a polymer main chain through at least one covalent bond.

In some embodiments, $R_3$ is a substituted or an unsubstituted linear, branched, or cyclic aliphatic or alkenyl moiety having from 2 to about 500 carbon atoms. In other embodiments, $R_3$ is a substituted or an unsubstituted aromatic or heteroaromatic moiety having from 6 to about 14 carbon atoms. In other embodiments, $R_3$ is a substituted or an unsubstituted siloxane moiety having from 2 to about 1000 silicon atoms. $R_3$ can also be a polysiloxane, such as, for example, dimethylsiloxane, methylphenylsiloxane, diphenylsiloxane, or combinations thereof. When $R_3$ is substituted, the substituents are as set forth above.

In a further embodiment, there are provided polymaleimide polymers including a plurality of repeating units having the structure:

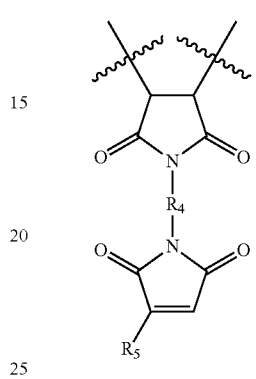

wherein $R_4$ is a substituted or an unsubstituted linear, branched, or cyclic aliphatic or alkenyl moiety having from 2 to about 500 carbon atoms, or an aromatic moiety; and $R_5$ is H or methyl.

In some embodiments, $R_4$ is a substituted or an unsubstituted linear, branched, or cyclic aliphatic or alkenyl moiety having from 2 to about 500 carbon atoms. In other embodiments, $R_4$ is a substituted or an unsubstituted aromatic or heteroaromatic moiety having from 6 to about 14 carbon atoms. In other embodiments, $R_4$ is a substituted or an unsubstituted siloxane moiety having from 2 to about 1000 silicon atoms. $R_4$ can also be a polysiloxane, such as, for example, dimethylsiloxane, methylphenylsiloxane, diphenylsiloxane, methylhydrosiloxane, or combinations thereof. When $R_4$ is substituted, the substituents are as set forth above.

Figure 3:
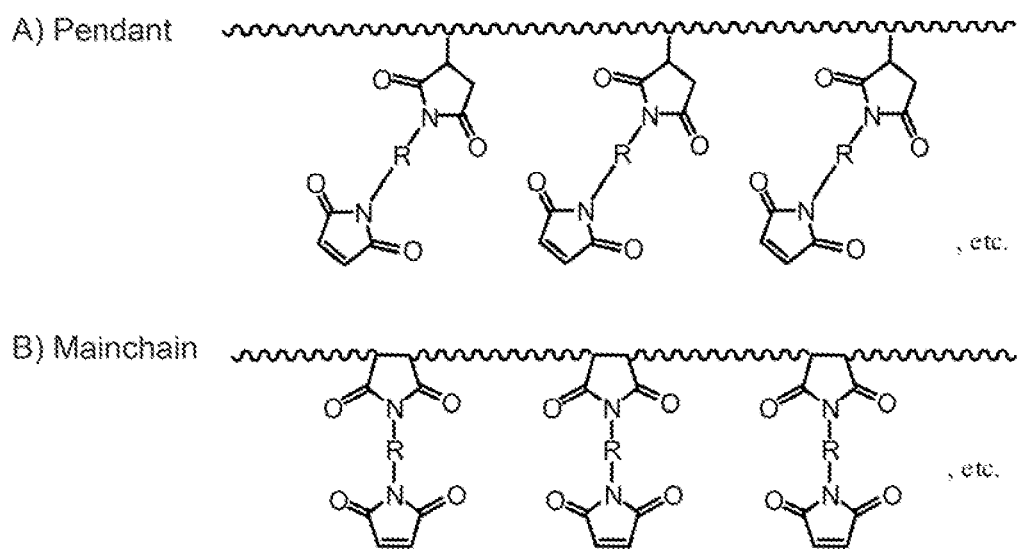
FIG. 3 shows the generic structure of exemplary polymaleimides of the invention.

Examples of such polymaleimides are shown in FIG. 3. The precursor polymers or oligomers with pendant or main-chain succinic anhydride functional groups are known in the art. Examples of such materials include polyolefins (e.g., polyethylene, polypropylene, and the like) grafted with succinic anhydride residues, polybutadiene grafted with succinic anhydride residues, alternating or random copolymers of maleic anhydride with styrene or -olefins, and the like. In order to prepare the polymaleimides of the invention, a large excess of diamine is typically used in order to suppress undesirable cross-linking reactions.

The imide-extended mono-, bis, and polymaleimides of the invention may be used independently in adhesive compositions, or may be combined with other adhesive compounds and resins. In one embodiment, the bismaleimide monomer of the invention may be used as the sole thermoset monomer of the adhesive composition. In another embodiment, the bismaleimide monomer of the invention may be with other thermoset monomers to make a fully formulated adhesive.

In one embodiment, there is provided an adhesive composition including an imide-extended bismaleimide compound and at least one curing initiator.

In some embodiments, the imide-extended bismaleimide compound is present in the composition from 0.05 weight percent to about 98 weight percent (wt %) based on total weight of the composition. In other embodiments, there is at least one co-monomer typically is present in the composition from 10 wt % to about 90 wt % based on total weight of the composition. Such comonomers include, for example, acrylates, methacrylates, maleimides, vinyl ethers, vinyl esters, styrenic compounds, allyl functional compounds, epoxy, oxetane, phenols, phenyl esters, and the like.

Amide Extended Maleimides

According to embodiments of the present invention, an improvement in the performance of maleimide thermosets can be achieved by incorporating amide-extended maleimides into an adhesive formulation. Amide-extended maleimides described herein can be used to toughen bismaleimide thermosetting materials without sacrificing thermal stability. Amide-extended maleimides are readily prepared by reacting a bismaleimide with an appropriate primary amine via the well-known Michael addition reaction.

Acylation of the resulting secondary amines provides the amide-extended maleimide. Indeed the thermal stability of Michael-extended BMI resins is improved when the residual amine residues are acylated and thus converted to pendant amides. These amide-extended bismaleimides have the same beneficial impact on the toughness as the Michael addition extended compounds, but have superior thermal stability. The improvement in thermal stability, as reflected in the increase in the decomposition onset via thermogravimetric analysis, is generally equal to, or greater than 100° C., as described in more detail below. The amide extended bismaleimides of the present invention can therefore be used in applications where the requirement for thermal resistance would preclude the use of simple Michael addition BMI adducts.

The amide extension strategy of the present invention can be applied to (meth)acrylate monomers as well. A difunctional acrylate monomer, for example, can be chain-extended through a Michael addition reaction with a sub-stoichiometric amount of a difunctional primary amine. The resulting secondary amine residues are then acylated with an acid anhydride, acid chloride, or free acid to the corresponding amides. The resulting amide-extended bis-acrylate can then be polymerized to yield tough, thermally stable thermoset resins. The acrylate equivalent weight of the amide-extended compounds according to this method of the invention depends solely on the stoichiometric ratio of the original diacrylate and primary diamine. Thus, a wide variety of polymerizable (meth)acrylate functional oligomers and polymers are provided by the invention. The cross-link density and modulus of the compounds of this invention can thus be tailored to suit the specific performance requirements of an application. The conversion of the initial Michael addition products to amide-extended compounds prevents the retro-Michael addition from occurring in these compounds. Therefore, these amide-extended (meth)acrylate oligomers are suitable for use in applications where thermal resistance is required.

The amide extension points may, themselves, be synthesized to bear polymerizable functionality. Thus, in certain embodiments of the invention, the residual secondary amine functional groups can be converted to amides bearing polymerizable ethylenic unsaturation. These reactive amide species can be prepared, for example, by the condensation of acrylic, methacrylic, cinnamic, mono-O-alkylfumaric, mono-O-alkylmaleic, and maleimidoalkylcarboxylic acids, or their anhydride or acid chloride equivalents with the Michael addition intermediates. One advantageous feature of these polymerizable amide graft points is their improved hydrolytic resistance.

Accordingly, in one aspect of the invention, an amide-extended diacrylates is prepared such that the amide extension points are, for example, tertiary methacrylamide residues. Resulting in methacrylamide residues in the backbone of compound and compositions of the invention that are more resistant to hydrolysis than the terminal acrylate functional groups in the amide-extended diacrylate compound. The overall performance of such acrylate-methacrylamide hybrid monomer benefits from both the high cure speed of the acrylate as well as the hydrolytic resistance of the methacrylamide.

The thermal resistance of the amide-terminated or amide-extended monomer, oligomer or polymer of the present invention may be characterized by its decomposition onset via thermogravimetric analysis and can be compared with decomposition onset or weight loss profile via thermogravimetric analysis of the corresponding amine-terminated or amine-extended monomer, oligomer or polymer According to embodiments of the present invention, the amide-terminated or amide-extended monomer, oligomer or polymer has the thermal resistance that is higher than the thermal resistance of the amine-terminated or amide-extended of the corresponding amine-terminated monomer, oligomer or polymer. More specifically, decomposition onset via thermogravimetric analysis of the amide-terminated or amide-extended monomer, oligomer or polymer of the present invention is at least about 100° C. higher than the decomposition onset of the intermediate. In some embodiments, the decomposition onset of the amide-terminated or amide-extended monomer, oligomer or polymer is at least about 110° C. higher. In other embodiments, it is at least about 120° C. higher.

A further point should be borne in mind with respect to the hydrolytic resistance of the amide extensions present in the backbones of the compounds of the invention. The acylation of the secondary amine residues in the Michael addition intermediates results in amide linkages that fundamentally differ from the traditional amide linkages found in traditional polyamide materials.

This point is illustrated by Scheme A below.

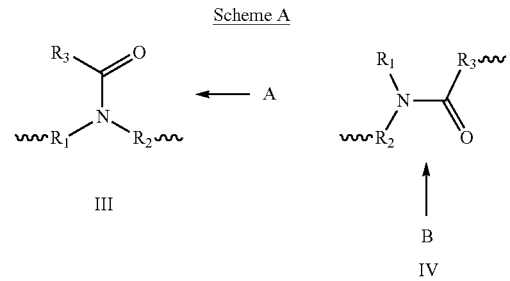

Scheme A presents a comparison of amide linkages of the present invention (represented by structural formula III) with the traditional amide linkage found in most polyamides (represented by structural formula IV). Both sides of the chain extension of the type I amide linkage pass through the nitrogen atom. Hydrolysis of the nitrogen-carbonyl bond at point A on Scheme A (formula III amides) does not result in scission of the core polymerized backbone. In contrast, hydrolysis of the nitrogen-carbonyl bond in the traditional type amide-extended polymer (formula IV) at point B results in main chain scission and therefore produces a significant degradation of the physical properties of the cured thermosets network.

Those skilled in the art will recognize that the amines used for the initial Michael extension, according to this invention, are typically primary amines. A secondary amine can be also used for the Michael addition reaction, if desired, but the resulting extension product would include tertiary amine residues that are not amenable to further conversion to amides. The tertiary amine-containing reaction products would thus be subject to retro-Michael addition at high temperatures. Some level of tertiary amine moieties in the backbone of the oligomer may be acceptable for certain applications, but are generally not desirable.

In some embodiments of the invention, either the reactive double bond, the primary amine, or both, is sterically hindered. Steric crowding around the Michael addition reaction site dramatically reduces any further addition of reactive double bonds to the initially-formed secondary amine. If the reaction site is not sufficiently hindered, the secondary amine that forms in a first Michael addition step may add to another reactive double bond to yield a tertiary amine center. This may result in weak links in the backbone of the oligomer and provide an adhesive with relatively poor thermal resistance.

In another embodiment of the invention the amide extension technique is used to introduce other ethylenically unsatured thermoset monomers to the resin. It will be appreciated that this approach requires unsaturation that is sufficiently reactive with the amine to permit the initial Michael addition. Unsaturated compounds that are suitable for use in such methods of the invention have adjacent electron withdrawing groups including, for example, maleimides, citraconimides, itaconimides, acrylates, methacrylates, acrylamides, methacrylamides, itaconates, maleates, fumarates benzoquinones, naphthoquinones, vinyl ketones, acrylonitrile, methacrylonitrile, and vinylsulfone compounds. One or more of these compounds can be used to generate the Michael addition secondary amine intermediates.

The general reaction scheme is presented on Scheme B shown below.

Scheme B

Step 1 - Michael Addition Reaction

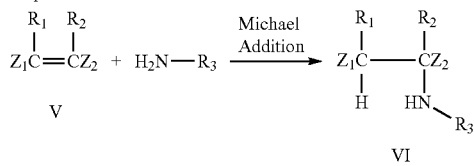

Step 2 - Acylation Reaction

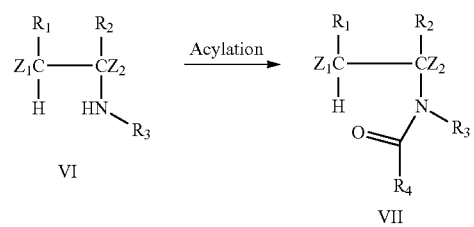

According to Scheme B, an unsaturated reactive compound is represented by structural formula V. This olefinically unsaturated compound is rendered electron deficient by the presence of $Z_1$ and/or $Z_2$ which are electron withdrawing groups. It is worth mentioning that in acrylates, methacrylates, acrylamides, methacrylamides, acrylonitrile, methacrylonitrile, itaconates, itaconimides, vinyl ketones and vinyl sulfones only one Z group is directly adjacent the carbon-carbon double bond, while in the case of, maleimides, citraconimides, maleates, fumarates, benzoquinones, and naphthoquinones both Z electron withdrawing groups are directly adjacent to the carbon-carbon double bond. The presence of electron withdrawing groups directly attached to the carbon-carbon double bond activates it toward nucleophilic (Michael) addition of a primary amine to create the secondary amine intermediate (structural formula VI). This addition is rendered substantially thermally irreversible through the acylatation of VI, thereby converting it to an amide (structural formula VII).

The acylation reaction can also be used to introduce reactive functional groups to resins. If, for example, methacrylic anhydride, acryloyl chloride, maleimidocaproyl chloride or cinnamyl chloride are used to acylate secondary amine residues on, the resulting oligomers will have additional polymerizable reactive sites which may be cured through these residues via heat or light (optionally in the presence of suitable initiators). Thus, the substituent $R_4"$ on Scheme B, will become a free radically polymerizable moiety. It is also possible, and in some cases desirable, to have both terminal polymerizable moieties as well as polymerizable functionality at the amide extension points.

In one embodiment of the present invention provides compounds having the structure of formula I:

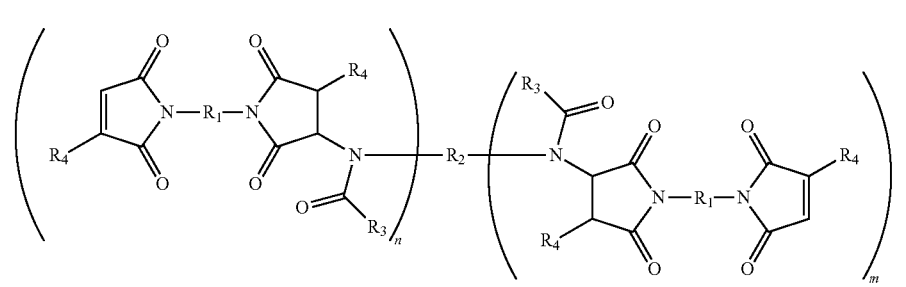

In the compounds having the structure of formula I each of $R_1$ and $R_2$ is, independently, a substituted or an unsubstituted aliphatic, cycloaliphatic, alkenyl, aryl, heteroaryl, an organosilicon moiety, or a polyalkylene oxide-derived moiety; $R_3$ is H, an unsubstituted or a substituted $C_1$ to about $C_{10}$ alkyl, or an unsubstituted or a substituted $C_2$ to about $C_{10}$ alkenyl; $R_4$ is H or methyl; and each of n and m is an integer independently having the value between 0 and about 10, with the proviso that the sum m+n has the value between 1 and about 10. In some exemplary embodiments, the sum m+n=1; in other exemplary embodiments, the sum m+n=2. In some other exemplary embodiments, m=0 and n=1, and in yet other exemplary embodiments, m=0 and n=2.

In some embodiments, $R_1$ is aryl and $R_2$ is an unsubstituted or a substituted aliphatic or cycloaliphatic moiety. In other embodiments, each of $R_1$, and $R_2$ is, independently, a substituted or an unsubstituted aliphatic or cycloaliphatic moiety. In some embodiments, each of $R_1$, and $R_2$ is, independently, a $C_2$ to about a $C_{500}$ substituted or unsubstituted alkenyl, aliphatic, or cycloaliphatic moiety, such as a $C_6$ to about a $C_{50}$ substituted or unsubstituted alkenyl, aliphatic, or cycloaliphatic moiety, for example, a $C_6$ to about a $C_{40}$ substituted or unsubstituted alkenyl, aliphatic, or cycloaliphatic moiety.

In still other embodiments, at least one of $R_1$, and $R_2$ is, independently, a $C_{36}$ substituted or unsubstituted alkenyl, aliphatic, or cycloaliphatic moiety. In other embodiments, each of $R_1$, and $R_2$ is a $C_{36}$ substituted or unsubstituted alkenyl, aliphatic, or cycloaliphatic moiety. A variety of structures may represent a $C_{36}$ substituted or unsubstituted alkenyl, aliphatic, or cycloaliphatic moiety. In some embodiments utilizing such a $C_{36}$ substituted or unsubstituted alkenyl, aliphatic, or cycloaliphatic moiety, the $C_{36}$ moiety has the structure:

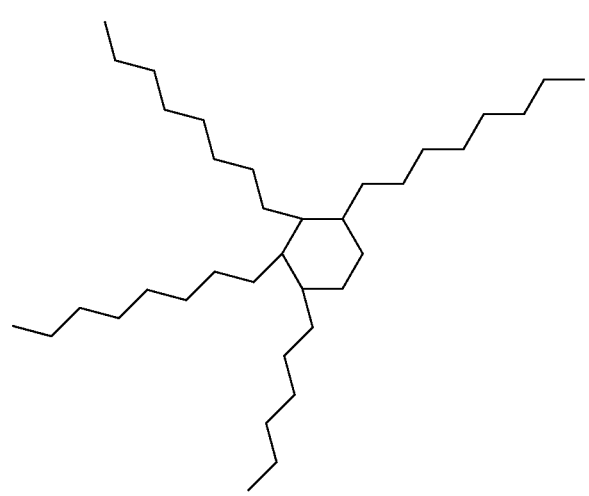

$C_{36}$

In other embodiments of the invention, each of $R_1$, and $R_2$ is, independently, a substituted or an unsubstituted cycloalkyl having from 5 to about 20 carbon atoms. In other embodiments, each of $R_1$, and $R_2$ is, independently, a substituted or an unsubstituted cycloalkyl having from 5 to about 12 carbon atoms. In yet other embodiments, each of $R_1$, and $R_2$ is, independently, a substituted or an unsubstituted aryl or heteroaryl having from 6 to about 14 carbon atoms. Non-limiting examples of specific substituents $R_1$ and $R_2$ that may be used include an unsubstituted or a substituted cyclopentyl, cyclohexyl, norbornyl, tricyclodecyl, cyclododecyl, dicyclopentadienyl, phenyl, and naphthyl.

Non-limiting examples of specific substitutent $R_3$ include an unsubstituted or a substituted methyl, ethyl, propyl, isopropyl, butyl, sec-butyl, iso-butyl, tert-butyl, a pentyl, propenyl, a butenyl, and cinnamyl. If a substituted $R_3$ is used, the substitutent on $R_3$ may include an acrylic or a methacrylic moiety.

The maleimide functional compounds of the invention can be readily prepared in a two-step, single-pot process. First, a primary mono-amine, diamine, or polyfunctional amine is reacted with a stoichiometric excess of a bismaleimide via the Michael addition reaction. Second, any resulting secondary amines are then acylated to form the amide moiety, thereby providing amide-extended bismaleimides.

A typical synthesis is outlined on Scheme C.

Scheme C

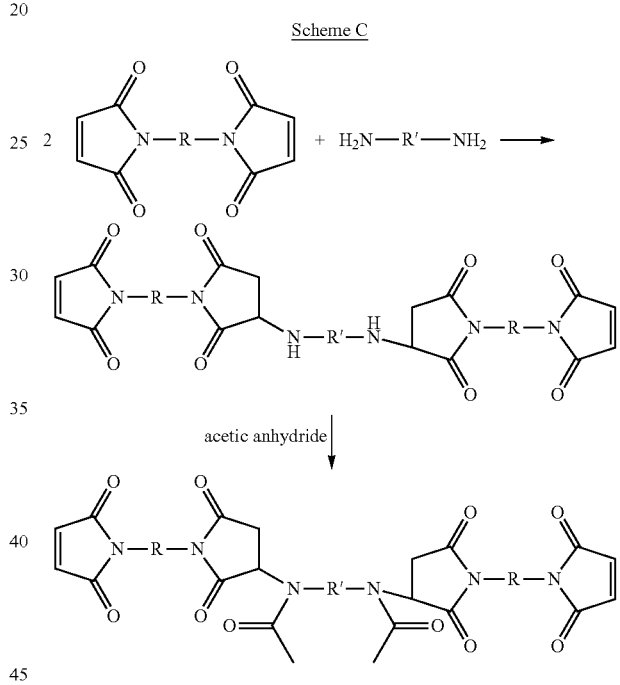

In Scheme C, acetic anhydride is illustrated as the acylating agent, but it is to be understood that any anhydride, indeed, any acylating agent is contemplated for use in the practice of the invention. Acylation of the secondary amine residues could also be accomplished directly from an acid in the presence of a suitable dehydrating agent. It will be well understood by those familiar with the art that the acylation step must be conducted under relatively mild conditions when the acid also contains an electron deficient carbon-carbon double bond. This is because the secondary amine produced in the initial Michael addition could also add a second time across the activated ethylenic unsaturation. One preferred mild dehydrating agent that can be used to accomplish the direct condensation of both saturated and active unsaturated carboxylic acids with the secondary amine residues is N,N'-dicyclohexylcarbodiimide. It is also to be understood that any suitable, ethylenically unsaturated, monomer may be substituted for the bismaleimide.

Exemplary amide-extended maleimides of the invention are set forth below. In each compound below having the "$C_{36}$" bridge, "$C_{36}$" stands for the structure as shown above.

Compound 1
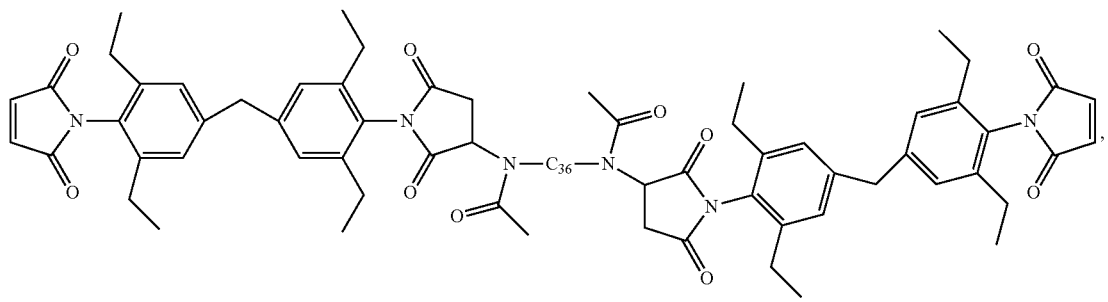
Compound 2
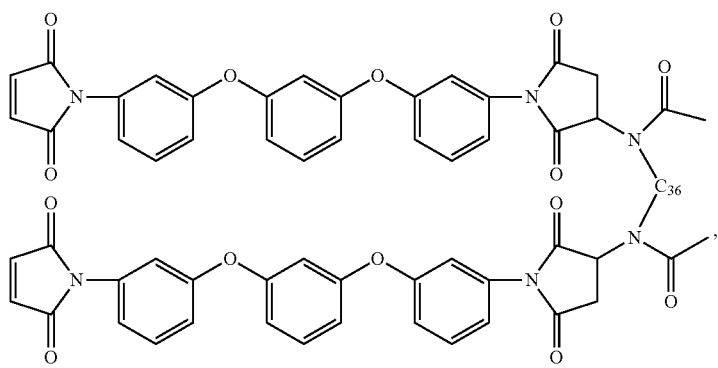
Compound 3
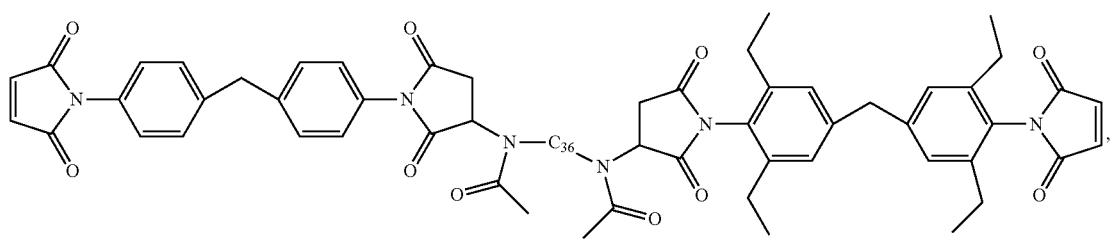
Compound 4
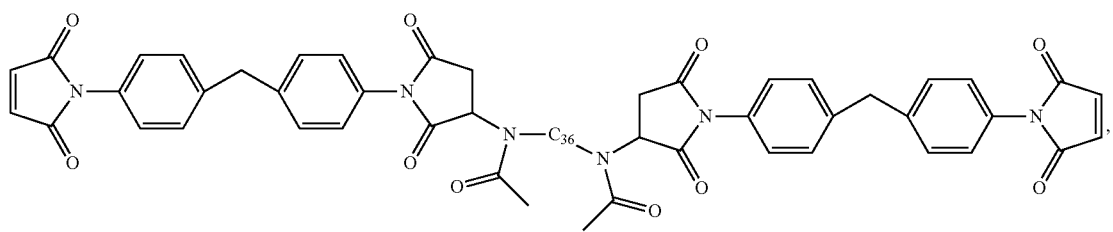

Compound 5
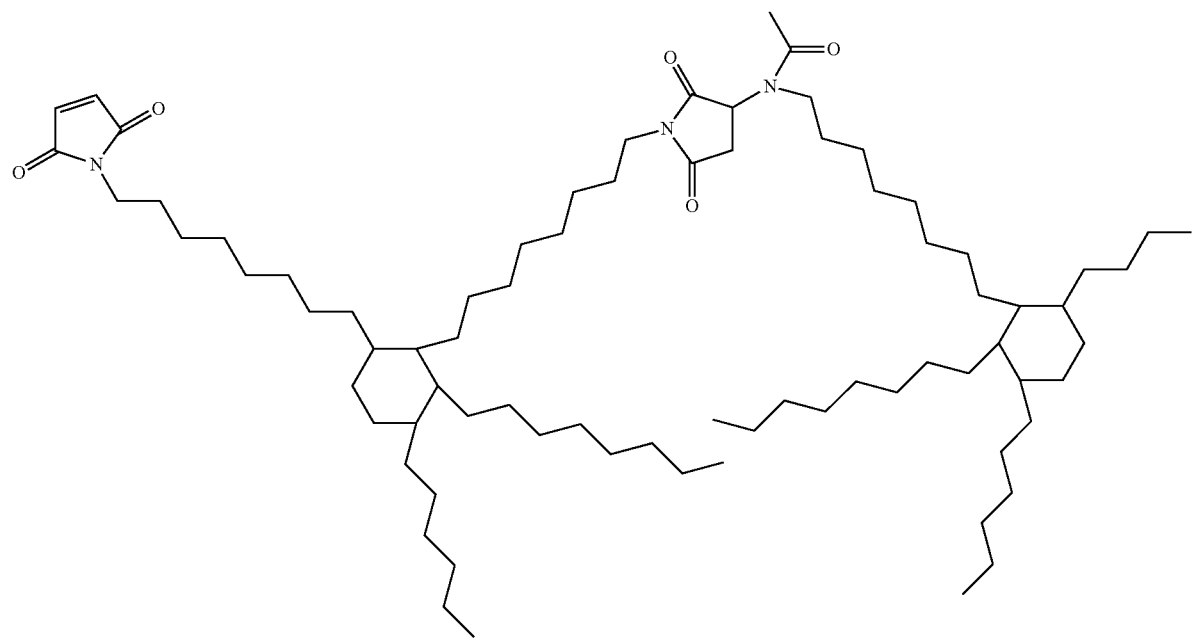
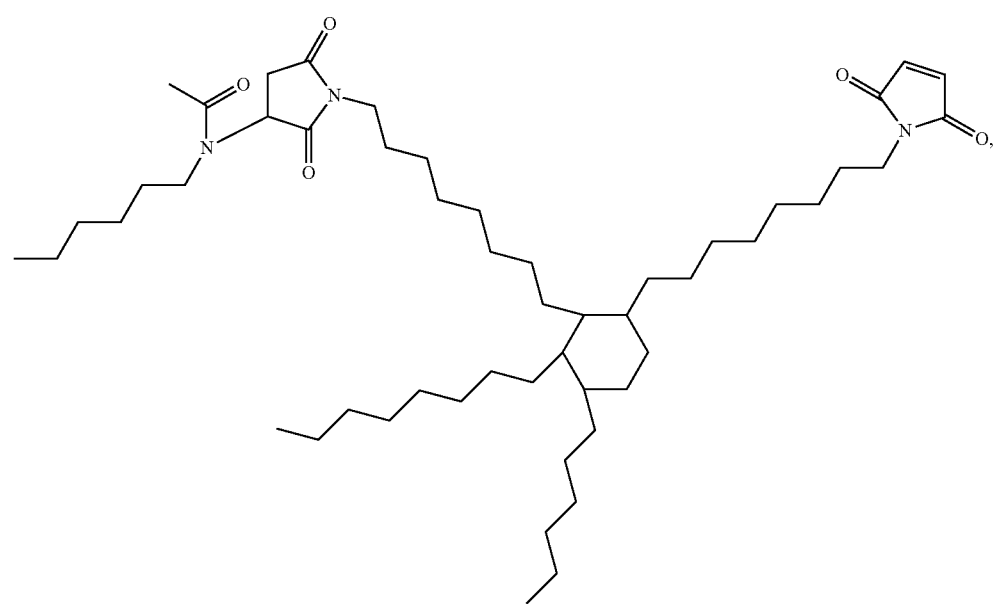

Compound 6
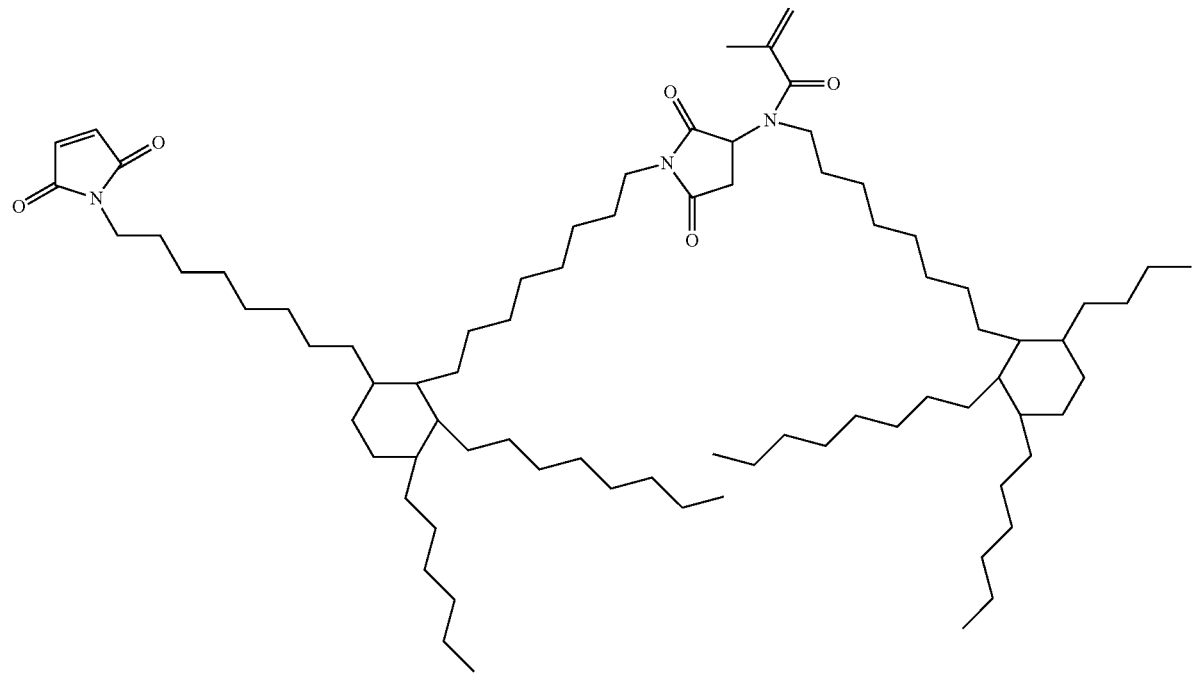
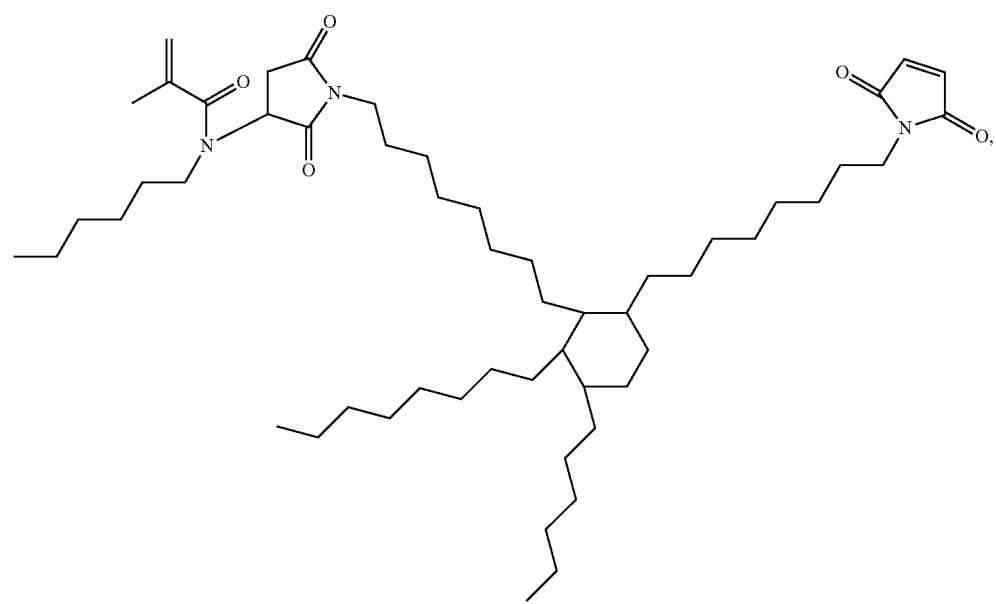

-continued
Compound 7
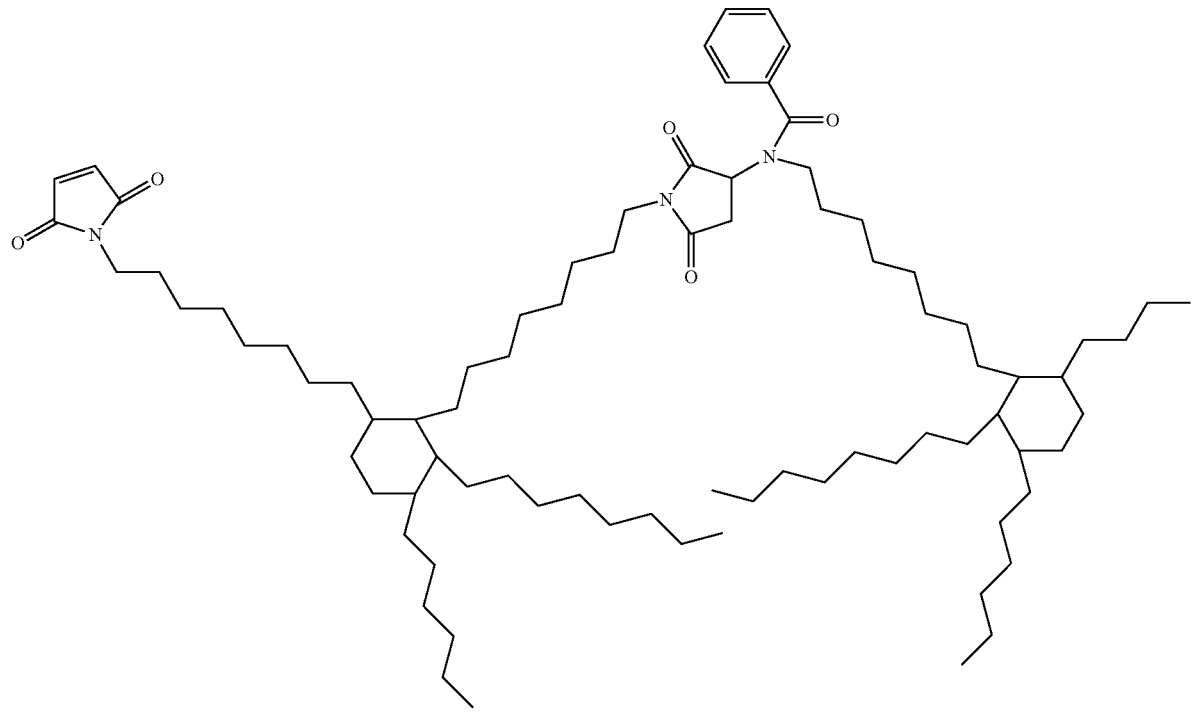
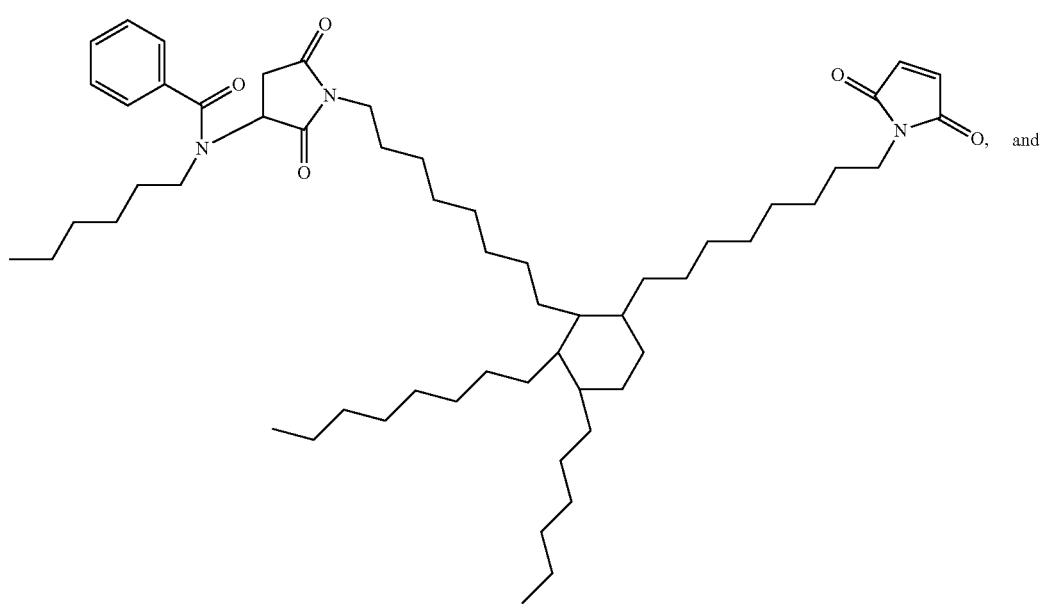 and

-continued
Compound 8
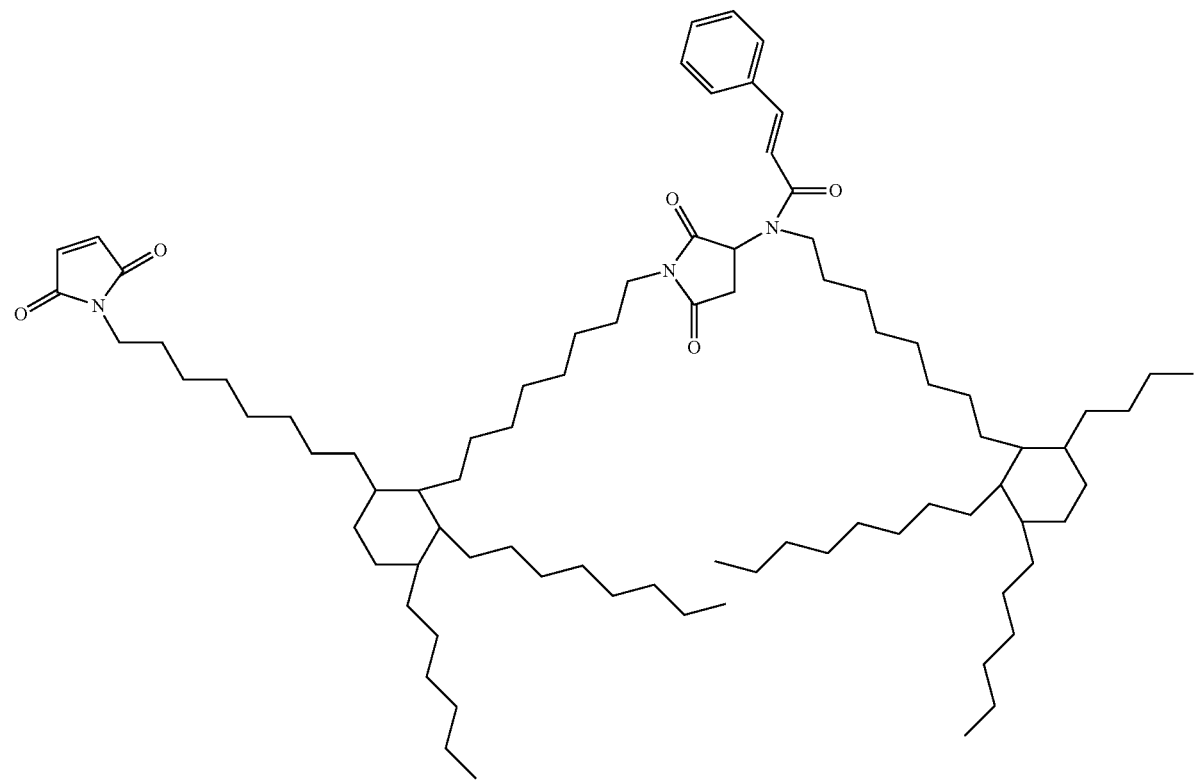
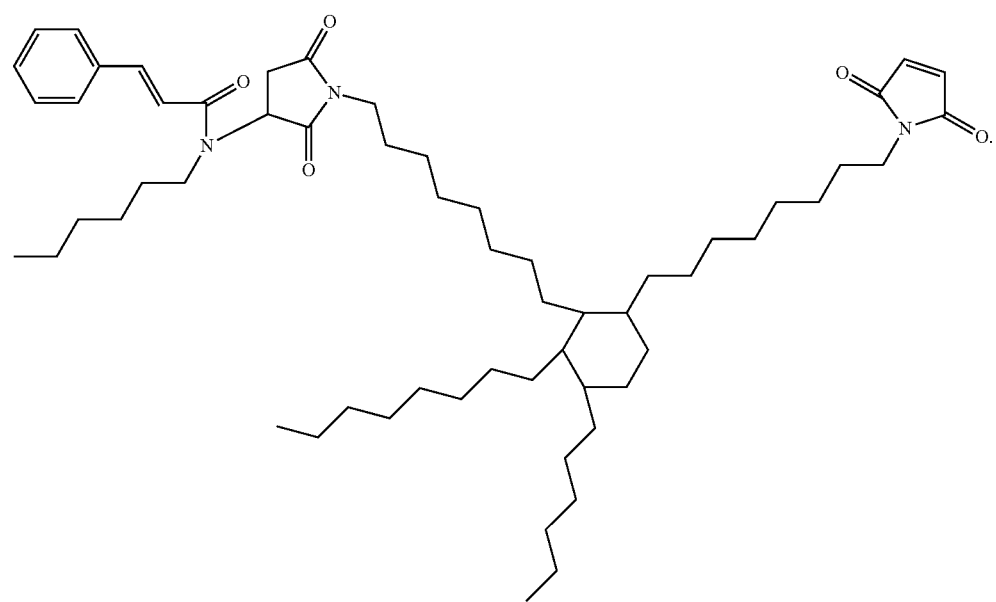

In another embodiment the present invention provides compounds having the structure represented by formula II:

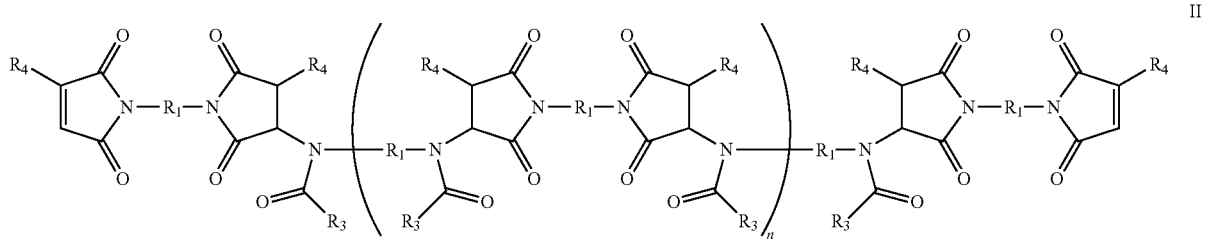

where each $R_1$ is an independently substituted or unsubstituted aliphatic, alkenyl, aryl, heteroaryl, a silicone-derived moiety, or a polyalkylene oxide-derived moiety; $R_3$ is H, a $C_1$ to $C_{10}$ alkyl or a $C_2$ to $C_{10}$ alkenyl; $R_4$ is H or methyl; and n is an integer having the value between 1 and about 10. In some exemplary embodiments, n=1; in other exemplary embodiments, n=2.

In some embodiments, each $R_1$ is independently substituted or unsubstituted alkenyl or aliphatic. In certain aspects of the invention, each $R_1$ is independently $C_5$ to about $C_{500}$ alkenyl or aliphatic. In other embodiments, each $R_1$ is independently $C_5$ to about $C_{250}$ alkenyl or aliphatic. In still further embodiments, each $R_1$ is independently $C_5$ to about $C_{100}$ alkenyl or aliphatic. In other embodiments of the invention, each $R_1$ is independently $C_5$ to about $C_{50}$ alkenyl or aliphatic. In another embodiment, each $R_1$ is independently $C_{36}$ alkenyl or aliphatic.

In additional embodiments of the invention, each $R_1$ is an independently substituted or unsubstituted cycloalkyl having from 5 to about 20 carbon atoms. In other embodiments, each $R_1$ is an independently substituted or unsubstituted cycloalkyl having from 5 to about 12 carbon atoms. In still further embodiments of the invention, each $R_1$ is an independently substituted or unsubstituted cyclopentyl, cyclohexyl, norbornyl, cyclododecyl, or dicyclopentadienyl.

Non-limiting examples of compounds according to formula II of the invention include some of the compounds 9-37 shown below, and in each of these compounds below having the "$C_{36}$" bridge, "$C_{36}$" stands for:

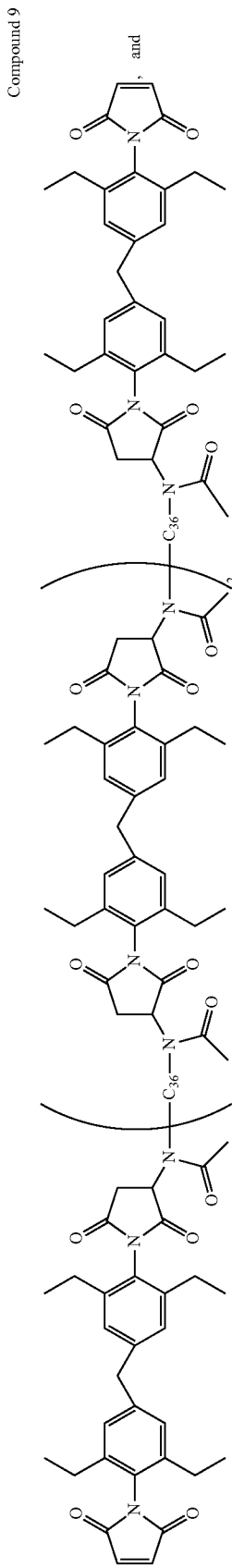
Compound 9
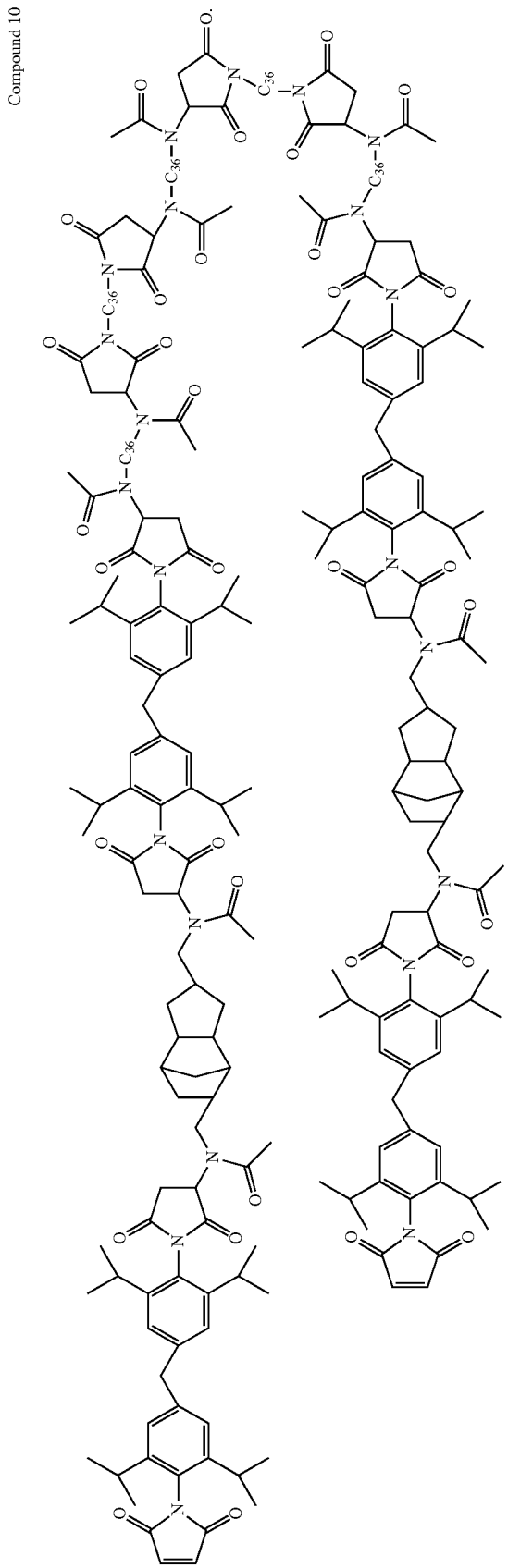
Compound 10

Amide-extensions may also be incorporated into acrylate resins, such as in the exemplary invention compounds illustrated below:
Compound 11
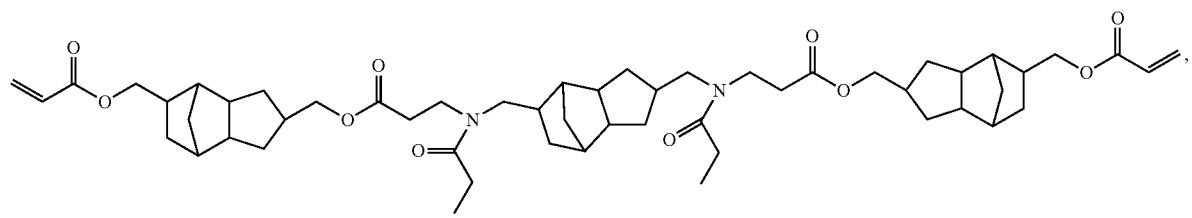
Compound 12
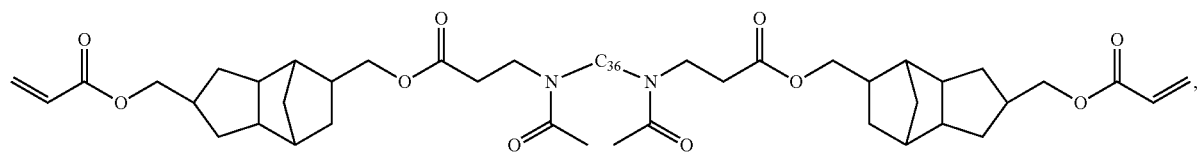
Compound 13
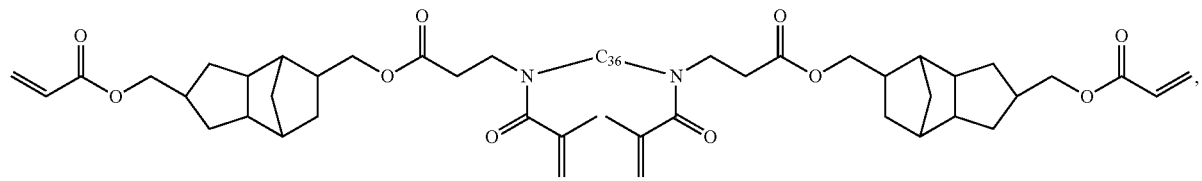
Compound 14
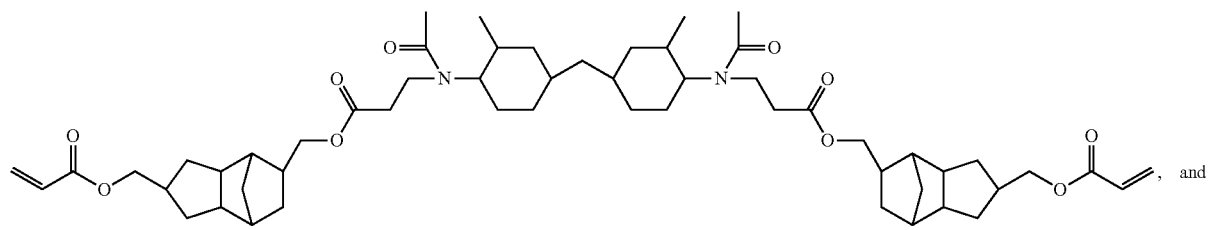
, and
Compound 15
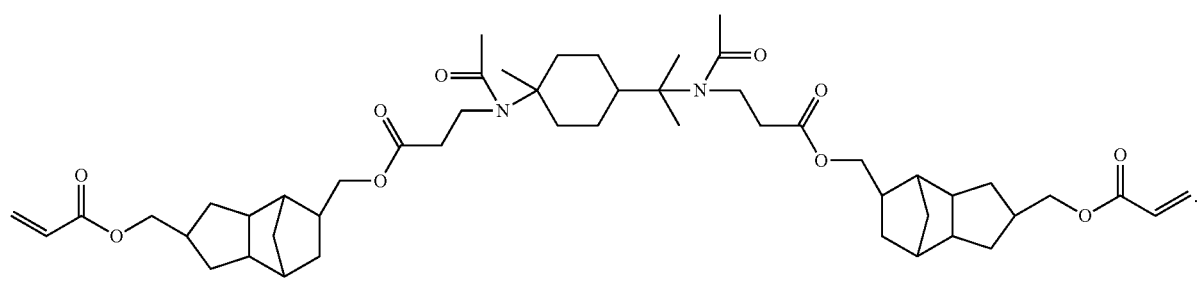
.
Further exemplary compounds according to the invention include:
Compound 16
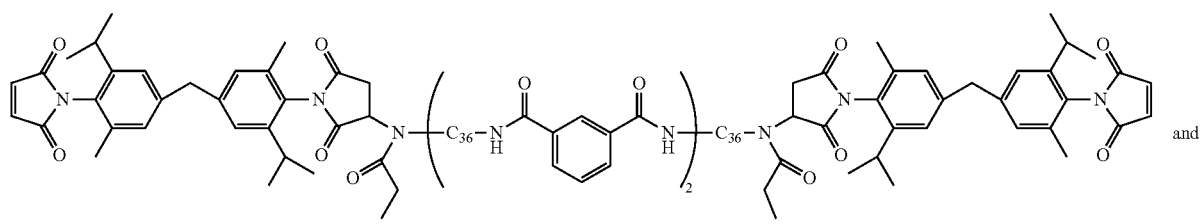
and Compound 17
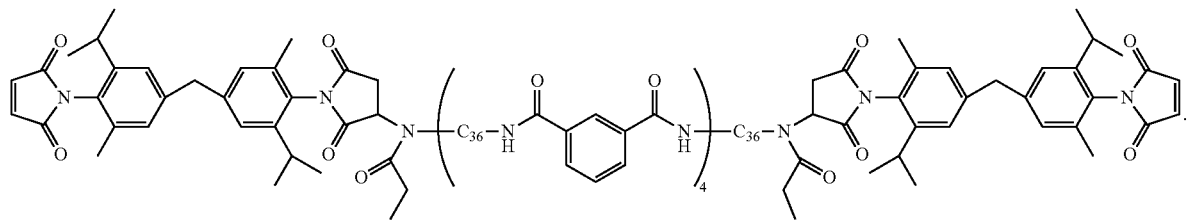
The acylating agent can also be used to introduce ethylenic unsaturation to essentially any resin that contains a secondary amine as illustrated in the exemplary compounds set forth below:
Compound 18
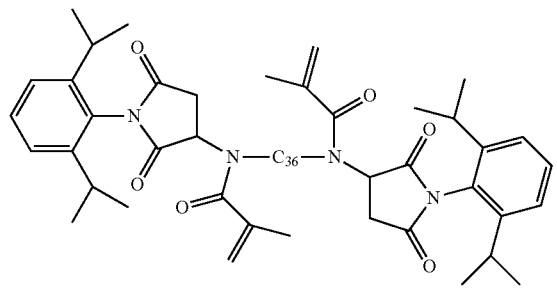
Compound 19
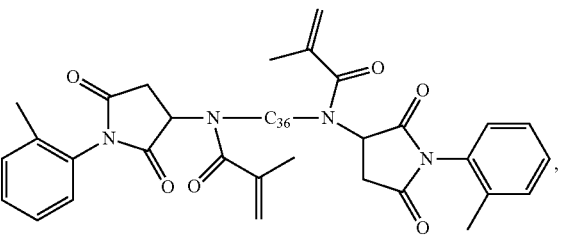
Compound 20
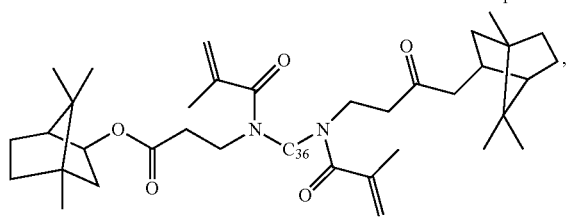
Compound 21
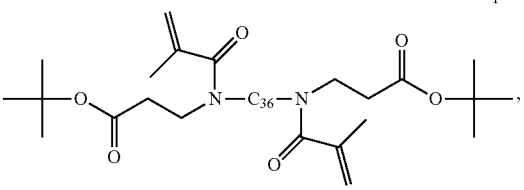
Compound 22
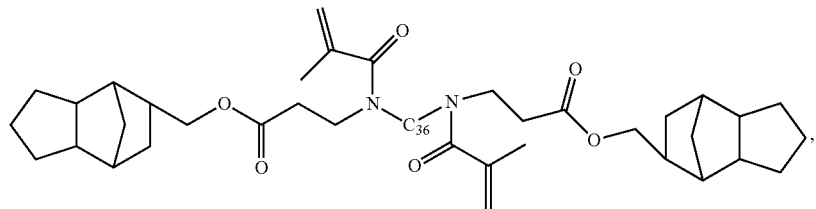
Compound 23
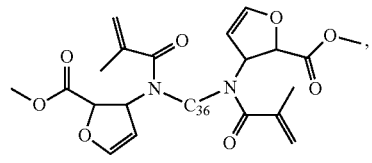
Compound 24
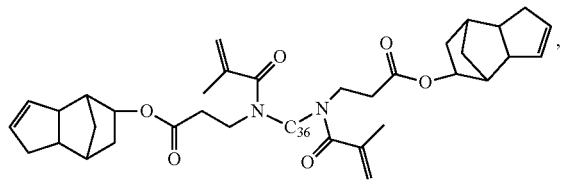

Compound 25
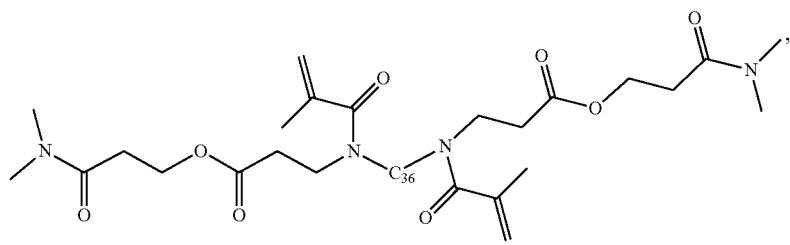
Compound 26
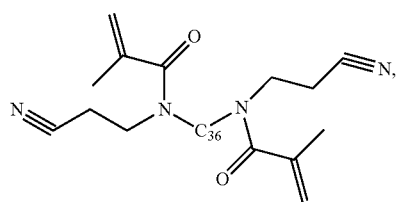
Compound 27
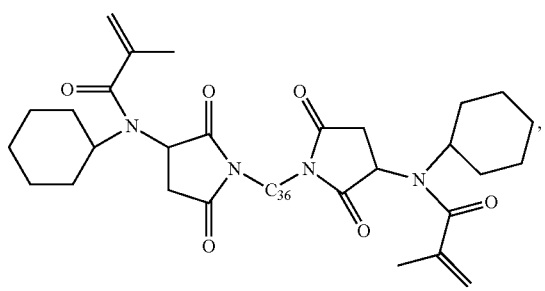
Compound 28
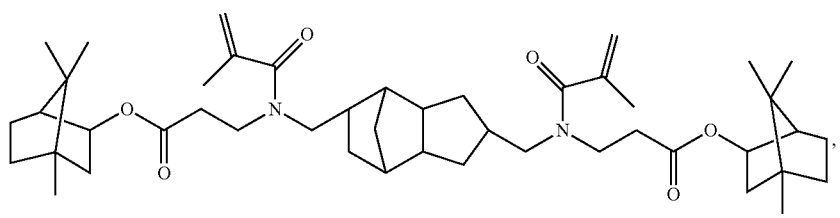
Compound 29
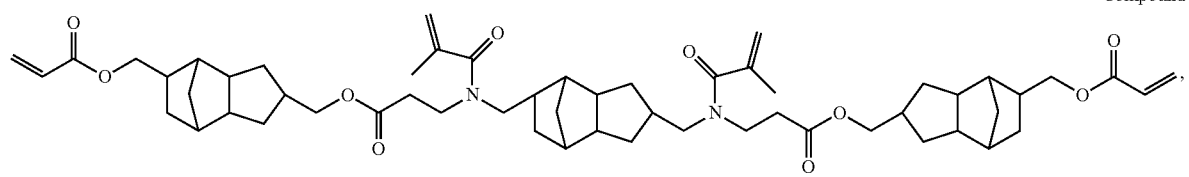
Compound 30
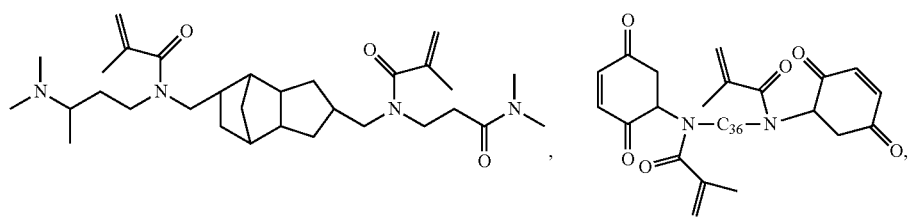
Compound 31
Compound 32
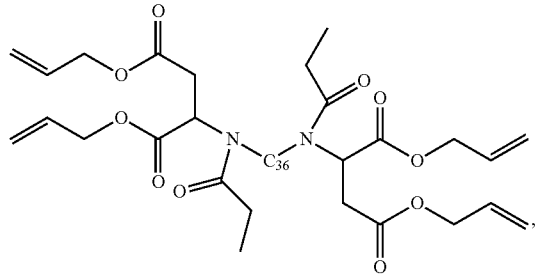

Compound 33
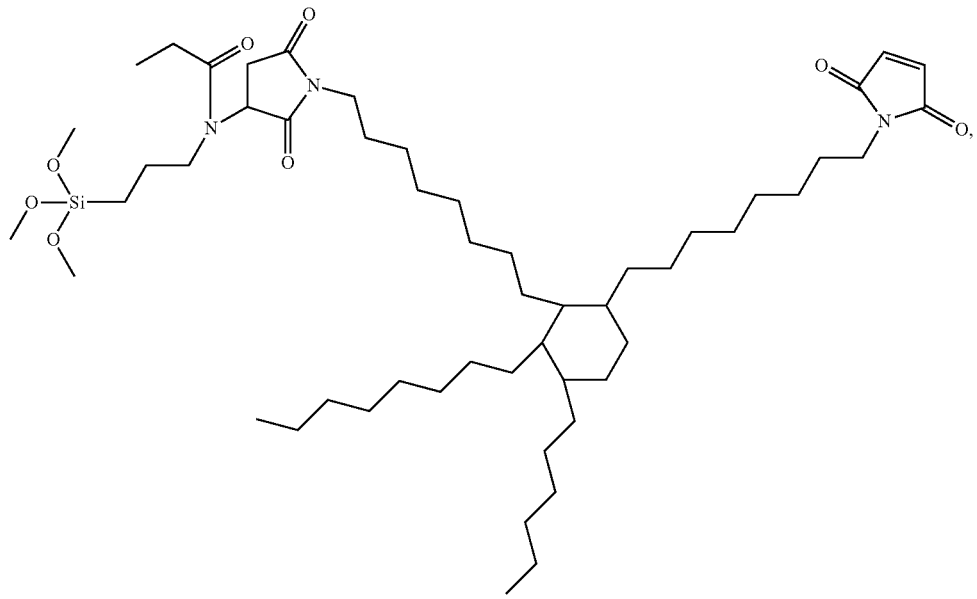
Compound 34
Compound 35
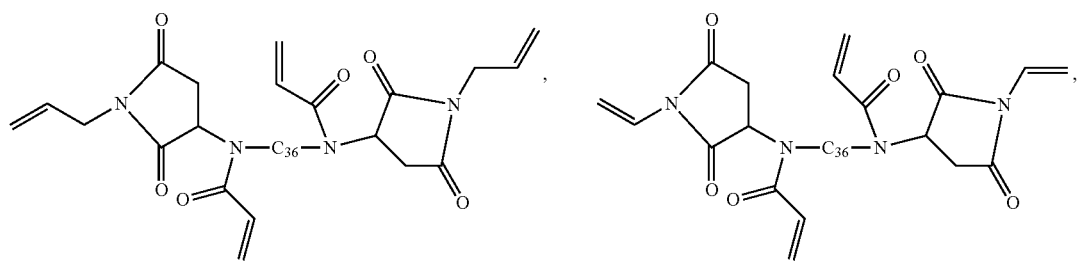
Compound 36
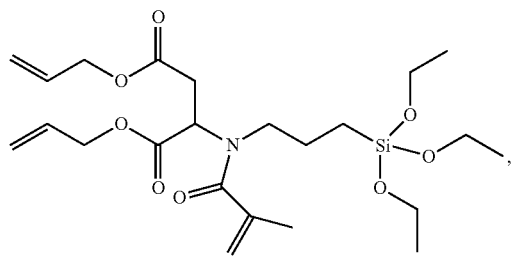
Compound 37
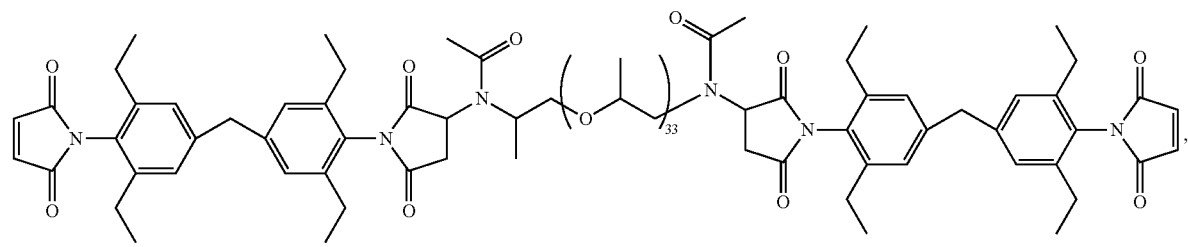

-continued
Compound 38
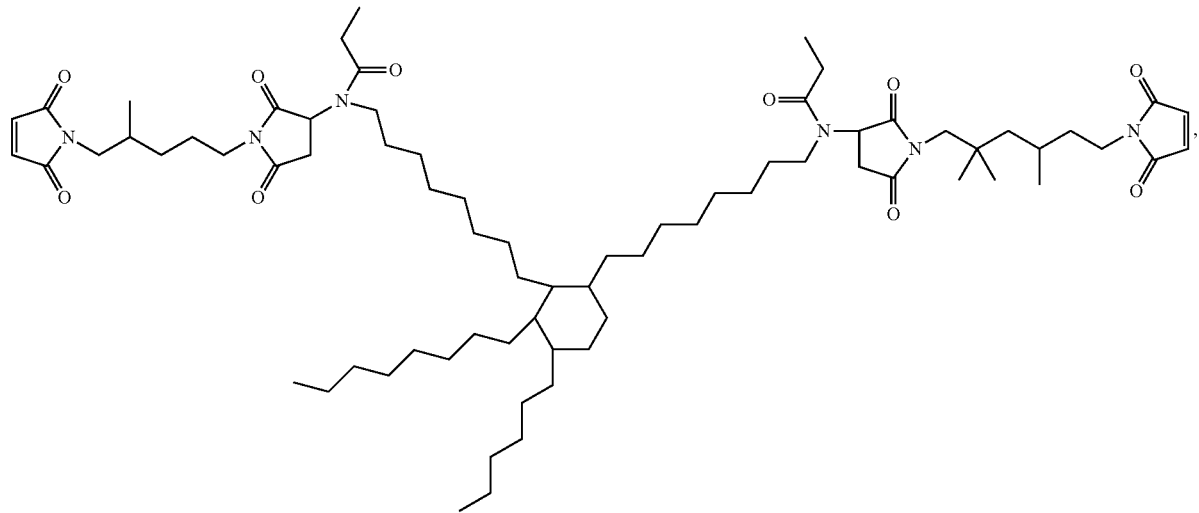
Compound 39
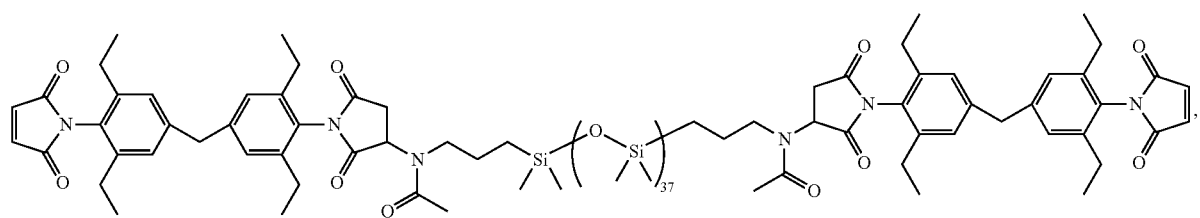
Compound 40
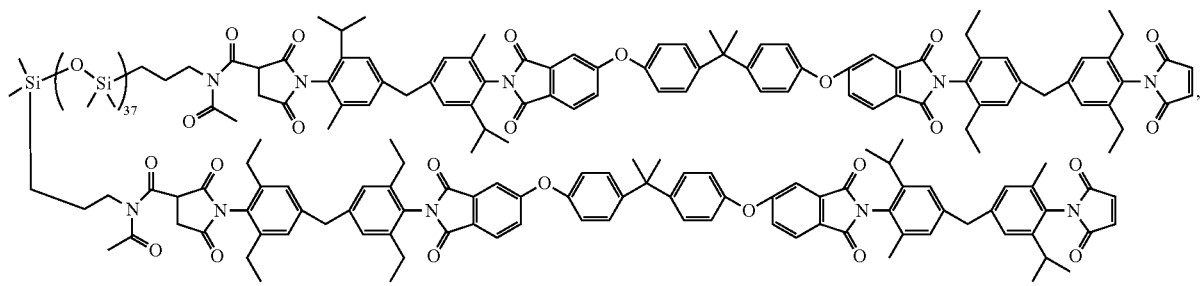
Compound 41
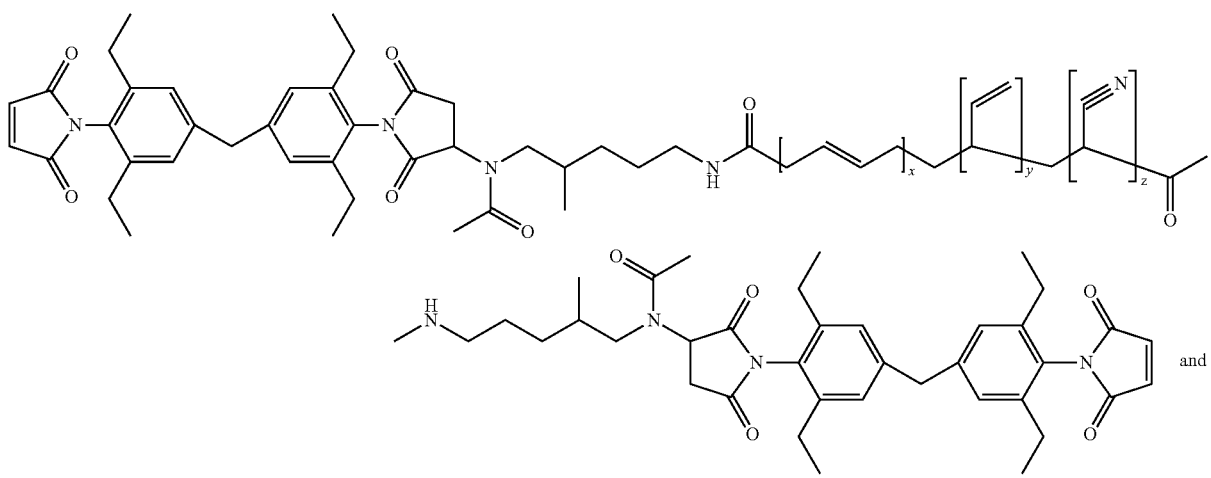

-continued

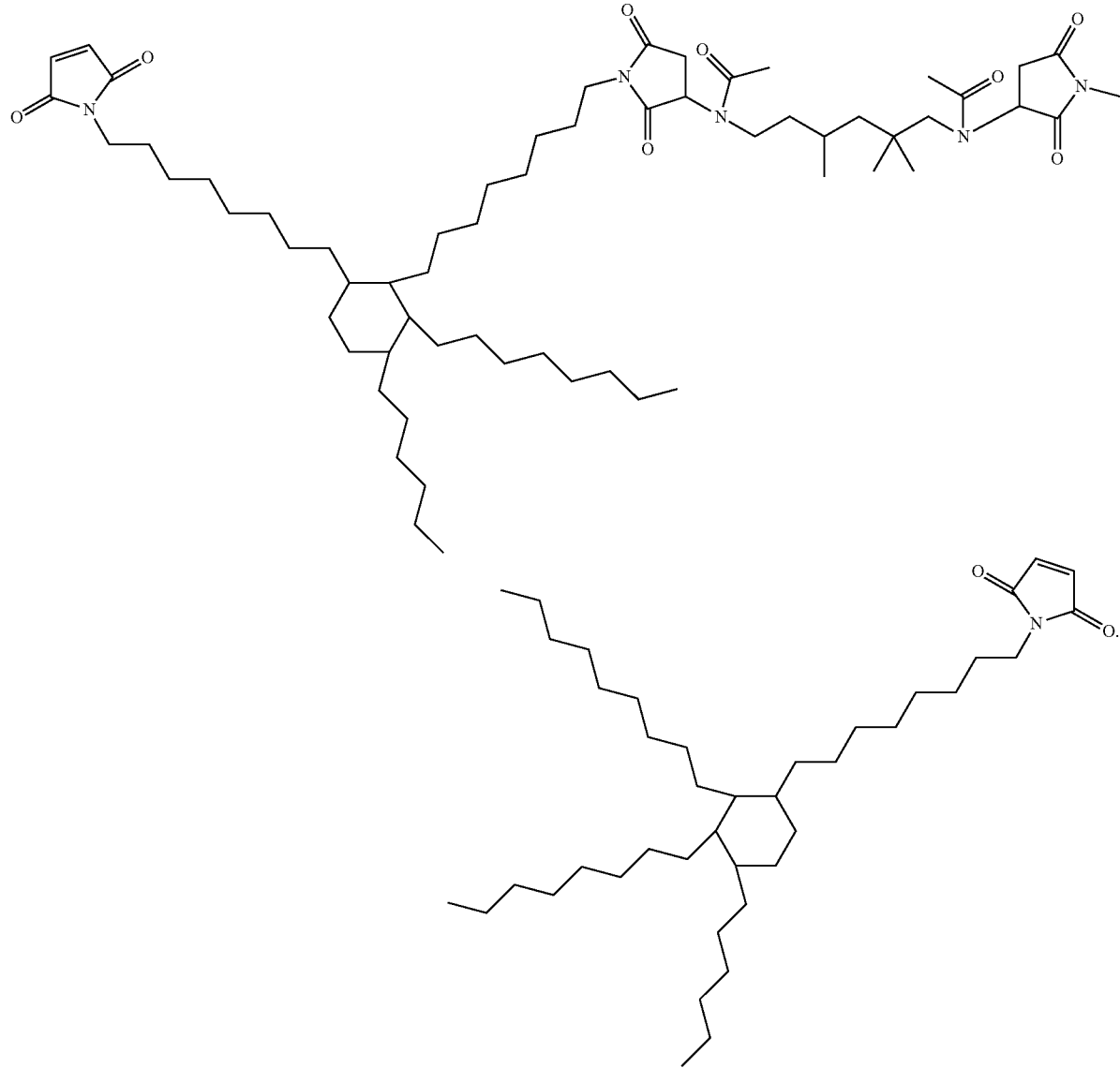

Compound 42

Compositions Containing Amide Extended Compounds

The present invention provides compositions containing at least one compound according to formula I or II, above. For example, the amide-extended compound of the invention may be used independently as the monomer in a polymeric composition, such as an adhesive composition, or may be combined with other materials and reagents to prepare compositions. In certain embodiments, the amide-extended compounds may be combined with other adhesives and/or resins to prepare adhesive compositions. In certain embodiments, an amide-extended compound of the invention may be used as the sole monomer of a thermoset adhesive composition of the invention. In other embodiments, the amide-extended compound of the invention may be combined with other adhesive monomers, such as thermoset monomers, to make a fully formulated adhesive composition.

In certain embodiments of the invention, the compound according to formula I or II is present in a composition, such as an adhesive composition, in an amount from 0.5 weight percent (wt %) to about 98 wt %, based on the total weight of the composition. Typically, the composition will contain an amount of the compound of formula I or II equal to at least about 5 wt %, often at least about 10 wt %, frequently at least about 20 wt %, and in some embodiments at least about 40 wt % based on the total weight of the composition.

In other embodiments of the invention, the composition containing the compound of formula I and/or II includes at least one co-monomer, which is typically present in an amount from 10 wt % to about 90 wt %, based on the total weight of the composition. In some aspects of the invention, the composition will contain an amount of the co-monomer equal to at least about 15 wt %, often at least about 20 wt %, frequently at least about 25 wt %, and in some embodiments at least about 30 wt % based on the total weight of the composition. Co-monomers suitable for use in the amide-extended compound-containing compositions according to the invention include, but are not limited to, acrylates, acrylamides, methacrylates, methacrylamides, maleimides, vinyl ethers, vinyl esters, styrenic compounds, allyl functional compounds, olefins and the like.

Curing Initiators.

In certain embodiments, the present invention provides compositions, such as adhesive compositions, including at least one compound of formula I and/or II and at least one curing initiator. The curing initiator is typically present in the composition from 0.1 wt % to about 5 wt % based on total weight of the composition, and is typically a free-radical initiator. As used herein, the term "free radical initiator" refers to any chemical species which, upon exposure to sufficient energy (e.g., light, heat, or the like), decomposes into two parts which are uncharged, but which each possess at least one unpaired electron. In some embodiments, the curing initiator is present at least about 0.5 wt %, often at least about 1 wt %, frequently at least about 2 wt %, at in some embodiments at least about 3 wt %, based on total weight of the composition.

Some free radical initiators contemplated for use in the practice of the present invention are compounds which decompose (i.e., have a half life in the range of about 10 hours) at temperatures in the range of about 70° C. up to 180° C. Exemplary free radical initiators contemplated for use in the practice of the present invention include peroxides (e.g. dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-azobis(cyclohexanecarbonitrile)). Other free-radical initiators that will be well-known in the art may also be suitable for use in the compositions of the present invention.

Photoinitiators.

The term "free radical initiator" also includes photoinitiators. For example, for invention adhesive compositions that contain a photoinitiator, the curing process can be initiated by UV radiation. In one embodiment, the photoinitiator is present at a concentration of 0.1 wt % to 5 wt % based on the total weight of the organic compounds in the composition (excluding any filler). In a one embodiment, the photoinitiator comprises 0.1 wt % to 3.0 wt %, based on the total weight of the organic compounds in the composition. In other embodiments, the photoinitiator is present at least about 0.5 wt %, often at least about 1 wt %, frequently at least about 2 wt %, and in some embodiments at least about 3 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive compositions of the invention.

Anionic Catalysts.

In other embodiments the initiator is an anionic catalyst. Examples of anionic initiators include Lewis bases such as tertiary amines and imidazoles. Specific examples include benzyldimethlamine, triethylamine, tripropylamine, pyridine, dimethylaminopyridine, dimethylethanolamine, diethylethanolamine, tributylamine, 2-methylimidazole, 2-undecylimidazole, 1-benzyl-2-methylimidazole, 1-cyanoethyl-2-methylimidazole, 1-cyanoethyl-2-phenylimidazole, 1-cyanoethyl-2-undecylimidazole, 1-cyanoethyl-2-ethyl-4-methylimidazole, 1-cyanoethyl-2-isopropylimidazole, 1-cyanoethyl-2-methylimidazole-trimellitate, 1-cyanoethyl-2-phenylimidazole-trimellitate, 1-cyanoethyl-2-ethyl-4-methylimidazole-trimellitate, 1-cyanoethyl-2-undecylimidazole-trimellitate, 2,4-diamino-6-(2'methylimidazolyl-(1')) ethyl-s-triazine, 2,4-diamino-6-(2'-ethyl-4'-methyl-imidazolyl-(1'))ethyl-s-triazine, 2,4-diamino-6-(2'-undecylimidazolyl-(1'))ethyl-s-triazine, 2-phenyl-4-methyl-5-hydroxymethylimidazole, 2-phenyl-4,5-dihydroxymethylimidazole, 1-cyanoethyl-2-phenyl-4,5-di(cyanoethoxymethyl)imidazole, 2-methylimidazole-isocyanuric acid addition compound, 2-phenylimidazole-isocyanuric acid addition compound, 2,4-diamino-6[2'-methylimidazolyl-(1)']ethyl-s-triazine isocyanurate adduct, 4,4'-methylene-bis-(2-ethyl-5-methylimidazole), and the like.

Cationic Catalysts.

In other embodiments the initiator is a cationic catalyst. Specific examples include onium compounds. Specific examples include bis[4-(diphenylsulphonio)-phenyl]sulphide bis-hexafluorophosphate, bis[4-(di(2-hydroxyethyl) phenyl)sulphonio-phenyl]sulphide bis-hexafluorophosphate, bis[4-(di(4-(2-hydroxyethyl)phenyl)sulphonio) phenyl]sulphide bis-hexafluoroantimonate, ($\eta^5$-2,4-(cyclopentadienyl) [(1,2,3,4,5,6-$\eta$)-(methylethyl)-benzene]-iron(II) hexafluorophosphate, triarylsulphonium hexafluorophosphate, (tolylcumyl) iodonium tetrakis (pentafluorophenyl) borate, diaryl iodonium hexafluoroantimonate, and the like. In certain embodiments, the invention provides adhesive compositions including 0.5 wt % to about 98 wt % of at least one described herein, based on total weight of the composition; optionally, 10 wt % to about 90 wt % of at least one co-monomer selected from acrylates, methacrylates, maleimides, vinyl ethers, vinyl esters, styrenic compounds, allyl functional compounds, and olefins, based on total weight of the composition; 0 to about 90 wt % of a conductive filler; 0.1 wt % to about 5 wt % of at least one curing initiator, based on total weight of the composition; and 0.1 wt % to about 4 wt %, of at least one coupling agent, based on total weight of the composition.

Co-Curing Compounds

Additional Co-Curing Compounds.

In certain aspects, the compositions, such as adhesive compositions of the invention include at least one additional compound that can co-cure with the compound of formula I and/or II. The additional compound is typically present in an adhesive composition from about 10 wt % to about 90 wt % based on total weight of the composition. In such aspects, the composition will typically contain an amount of the co-curing compound equal to at least about 20 wt %, often at least about 30 wt %, frequently at least about 40 wt %, and in some embodiments at least about 50 wt % based on the total weight of the composition.

Exemplary co-curing compounds can be selected from an epoxy, an acrylate, a methacrylate, a maleimide, a poly-phenol compound, an anhydride, a dianhydride, a polyanhydride, an imide, a carboxylic acid, a dithiol, a polythiol, a phenol functional mono-maleimide, a bismaleimide, a polymaleimide, a mono-itaconate, a mono-maleate, a mono-fumarate, acrylic acid, methacrylic acid, a cyanate ester, a vinyl ether, a vinyl ester, a phenol functional ester, a urea, an amide, a polyolefin, a cyanoacrylate, an allyl functional compound, and a styrenic.

In other embodiments, the co-curing compound is an epoxy of a glydicyl ether of an alcohol, an epoxy of a glydicyl ether of a phenol, an epoxy of a glydicyl ether of a bisphenol, an epoxy of a glydicyl ether of an oligomeric phenolic, an epoxy of a glydicyl ether of a phenolic novolac, an epoxy of a glydicyl ether of a cresolic novolac, a styrene-maleic anhydride co-polymer, an amine functional polyolefin, a carboxylic acid functional polyolefin, a hydroxy functional polyolefin, an epoxy functional polyolefin, an epoxy functional siloxane, a phenolic functional siloxane, a carboxylic acid functional siloxane, or thiol functional siloxane.

Such compounds include, for example, epoxies (e.g. epoxies based on glydicyl ethers of alcohols, phenols, bisphenols, oligomeric phenolics, phenolic novolacs, cresolic novolacs, acrylates, methacrylates, maleimides, poly-phenol compounds (e.g. poly(4-hydroxystyrene)), anhydrides, dianhydrides, polyanhydrides such as styrene-maleic anhydride co-polymers, imides, carboxylic acids, dithiols, polythiols, phenol functional mono-maleimides, bismaleimides, polymaleimides, mono-itaconates, mono-maleates, mono-fumarates, acrylic acid, methacrylic acid, cyanate esters, vinyl ethers, vinyl esters, or phenol functional esters, ureas, amides, polyolefins (e.g. amine, carboxylic acid, hydroxy, and epoxy functional) siloxanes (e.g. epoxy, phenolic, carboxylic acid, or thiol functional), cyanoacrylates, allyl functional compounds and styrenic, as well as combinations thereof. In yet further embodiments, the invention provides cured adhesives prepared from compositions that include at least one compound according to formula I or II.

Coupling Agents.

In certain aspects, the adhesive compositions of the invention include at least one additional coupling agent. Exemplary coupling agents contemplated for use in the practice of the present invention include silicate esters, metal acrylate salts (e.g., aluminum methacrylate), titanates (e.g., titanium methacryloxyethylacetoacetate triisopropoxide), zirconates, or compounds that contain a copolymerizable group and a chelating ligand (e.g., phosphine, mercaptan, acetoacetate, and the like). In some embodiments, the coupling agent contains both a co-polymerizable function (e.g., vinyl, acrylate, methacrylate, epoxy, thiol, anhydride, isocyanate, and phenol moieties) and a silicate ester function. The silicate ester portion of the coupling agent is capable of condensing with metal hydroxides present on the mineral surface of substrate, while the co-polymerizable function is capable of co-polymerizing with the other reactive components of invention adhesive compositions, such as die-attach pastes. In certain embodiments coupling agents contemplated for use in the practice of the invention are oligomeric silicate coupling agents such as poly(methoxyvinylsiloxane).

Adhesive Paste Compositions Containing Amide-Extended Compounds

In certain embodiments, the present invention provides adhesive compositions that are of various consistencies including, liquids, gels, pastes and solids. In one embodiment, the adhesive composition is a paste suitable for attaching an electronics die to a substrate (i.e., die-attach pastes). Die attach pastes of the invention are optimized for long-term reliability, rapid inline curing, long pot-life, viscosity and thixotropic control for fast automated dispensing and manufacturing.

In one embodiment, the present invention provides an adhesive composition that include 0.5 wt % to about 98 wt % based on total weight of the composition, of a compound represented by structural formula I and/or II; 0 to about 90 wt % of a filler, based on total weight of the composition; 0.1 wt % to about 5 wt % of at least one curing initiator, based on total weight of the composition; and 0.1 wt % to about 4 wt %, of at least one coupling agent, based on total weight of the composition.

In another embodiment of the invention, there are provided die-attach pastes including 0.05 weight percent to about 98 weight percent (wt %) of at least one imide-extended mono-, bis-, or polymaleimide compound described herein, or combinations thereof, based on total weight of the composition; optionally, 10 wt % to about 90 wt % of at least one co-monomer selected from the group consisting of acrylates, methacrylates, maleimides, vinyl ethers, vinyl esters, styrenic compounds, and allyl functional compounds, epoxies, oxetanes, phenols, phenyl esters, and the like, based on total weight of the composition; 0 to about 90 wt % of a filler; 0.1 wt % to about 5 wt % of at least one curing initiator, based on total weight of the composition; and 0.1 wt % to about 4 wt %, of at least one coupling agent, based on total weight of the composition.

In one embodiment, there is provided die-attach paste comprising:

a) 0.05 weight percent to about 98 weight percent (wt %) based on total weight of the composition, an imide-extended bismaleimide having the structure:

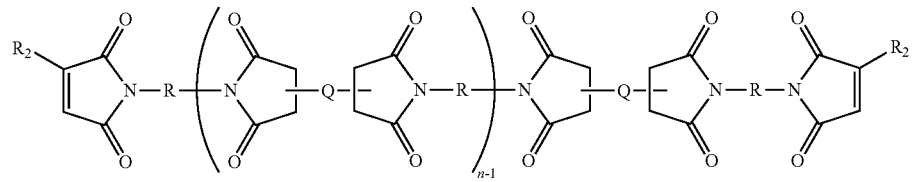

wherein each of R and Q is independently a substituted or an unsubstituted aliphatic, alkenyl, aromatic, heteroaromatic, or siloxane moiety; $R_2$ is H or methyl; and n is an integer having the value between 1 and about 10, with the proviso that the imide-extended bismaleimide is not

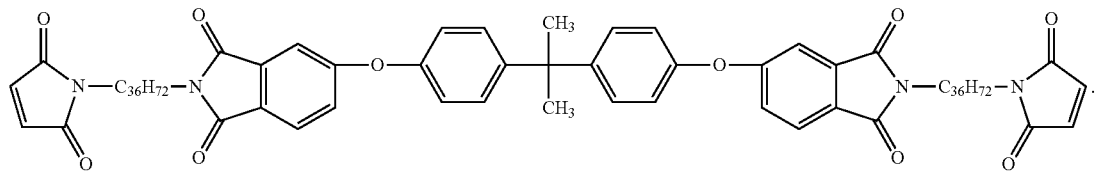

b) 0 to about 90 wt % of a filler;
d) 0.1 wt % to about 5 wt % of at least one curing initiator, based on total weight of the composition;
e) 0.1 wt % to about 4 wt %, of at least one coupling agent, based on total weight of the composition.

Advantageously, the imide-linked mono-, bis-, and polymaleimide compounds and compositions of the present invention can be designed to remain as stable and flexible thermoplastic materials at room temperature. These thermoplastic imide-linked maleimides can be compounded with fillers, catalysts, inhibitors, and coupling agents to make a fully formulated adhesive package. Since the matrix of these compositions is thermoplastic, no settling will occur during shipping or storage. These characteristics therefore also permit packaging, shipment and storage without refrigeration. These properties also facilitate forming adhesives of the invention into various shapes and sizes for ease of use and application to electronic components and/or substrates. Thus, one aspect of the invention is a method for forming an adhesive rope that may be applied directly to a substrate for bonding electronic components thereto. According to this method, an imide-linked maleimide compound or adhesive composition is extruded in a rope shape. Unit lengths of the adhesive rope can then be dispensed into a packaging container. The length of adhesive rope dispensed can conveniently be selected by the desired use, application or unit of sale. Thus, a short rope may be packaged for a single-use application while a longer length can be dispensed for bulk sale. In one embodiment of this method, the rope adhesive is a circular, square, or rectangular shape (across the short axis) of about two to 15 millimeters in diameter. One useful shape for the rope adhesive is where the material is extruded in the shape (in cross section) of a four lobbed clover or starfish. The invention also contemplates that other shapes may be manufactured by extrusion or molding, such as ribbons, dots, spheres, and the like. For example, the adhesive may be formed into single-use dots of suitable volume to bond a single electronic component to a substrate. Individual dots may be packaged on a disposable paper or film support and peeled off for use. The dot of adhesive may also be applied in advance to a suitable electronic device substrate (e.g. a lead frame, or ball grid array). Typically, the dots are in the range of 0.5 mm to 10 mm in diameter. A multiple number of dots may also be applied across the bond area of a substrate to accommodate larger devices. The dots may have the form of hemispherical or "Hershey's Kiss-like" shapes.

The present invention also provides methods for bonding an electronic component to a substrate using formed adhesive manufactures such as ropes, ribbons and dots. According to this method, the adhesive manufacture is dispensed directly onto the substrate in an amount sufficient to bond the desired electronic component. For example, a rope can be contacted with the substrate and the desired quantity can be cut from the end, thereby delivering a controlled amount of adhesive to the precise point of desired bonding. Optionally, the substrate can be heated to facilitate delivery of the adhesive by melting. When the amount of adhesive that will be required for a single application can be predetermined at the time of manufacture, individual aliquots of the adhesive can be premeasured, dispensed, and subsequently transferred to the substrate at the time of use, for example as individual dots. Once the adhesive is positioned onto the substrate, the electronic component is then contacted with the dispensed adhesive and the adhesive cured to bond the electronic component to the substrate. This method reduces waste, in that use of excess adhesive is avoided. Furthermore, this method facilitates precise positioning of adhesive and eliminates unwanted adhesive contamination of the substrate and surrounding work area. The thermoplastic nature of these adhesives offers other significant advantages for commercial applications compared to the traditional paste adhesives used for die attach. The materials described here don't require the −40° C. refrigerated storage conditions traditionally used for the paste adhesives. A fully formulated thermoplastic adhesive mixture that contains sufficient inhibitors can be kept for several months at or just below room temperature without any loss of performance. The thermoplastic nature of this adhesive furthermore prevents any settling of the filler from the resin matrix during such storage.

Conveniently, the adhesive compositions of the invention can be packaged into kits for consumption by the end-user. Included in each kit is a package containing a sufficient amount of a curable imide-linked maleimide adhesive composition to bond at least one electronic component to a substrate and instructions for using said adhesive to bond an electronic component to a substrate. The adhesive supplied in the kit may be, for example, in bulk, rope or dot form, depending of the intended end-use. The instructions are contemplated to include directions for preparation of the elements that will be bonded (e.g., electronic components and substrates) application of the adhesive, suggested quantities for various applications, and conditions required to cure the adhesive. The kit format will be particularly useful for maleimide adhesives of the invention with characteristics that may not be well known in the art. For example, techniques for application and curing of adhesive manufactures (e.g., ropes and dots) can be described and illustrated.

B-Stageable Adhesives

In certain embodiments, the adhesive compositions and die attach pastes of the invention are B-stageable. As used herein, "B-stageable" refers to the properties of an adhesive having a first solid phase followed by a tacky rubbery stage at elevated temperature, followed by yet another solid phase at an even higher temperature. The transition from the rubbery stage to the second solid phase is thermosetting. However, prior to that, the thermosetting material behaves similarly to a thermoplastic material. Thus, such adhesives allow for low lamination temperatures while providing high thermal stability.

The B-stageable adhesive can be dispensed onto a die or a substrate by a variety of methods well known to those skilled in the art. In some embodiments, the adhesive is cast from solution using techniques such as spin coating, spray coating, stencil printing, screen printing, and the like. This dual stage cure is especially attractive for applications were it is desirable to apply an adhesive in liquid form, cure the material to a non-tacky thermoplastic state, and then cure this B-staged adhesive in a final heating step to bond two or more parts together. Thus, this dual stage cure method of the invention is particularly advantageous for silicon wafer back coatings. The original adhesive mixture can be spin coated onto the back of a silicon wafer. The coating can then be B-staged with heat or light. The coated wafers can then be diced to yield individual microelectronic components, which may be thermally attached directly to a substrate, and/or stacked together. The thermal "tacking step" re-liquifies the adhesive coating and provides a thermoplastic bond between the parts. The final bonding step involves a thermal (or in some cases light-based) cure to cross-link the B-staged adhesive composition. This method of assembly is highly desirable because it is easier to manufacture (especially for stacked die) than a traditional liquid adhesive assembly, and is much less expensive and wasteful compared to film-based adhesive technology.

In certain embodiments, a solvent may be employed in the practice of the invention. For example, when the B-stageable adhesive is spin-coated onto a circular wafer, it is desirable to have an even coating throughout the entire wafer, i.e., the solvent or solvent system should have the ability to deliver the same amount of adhesive to each point on the wafer. Thus, the adhesive will be evenly coated throughout, i.e., there will be the same amount of material at the center of the wafer as at the edges. Ideally, the adhesive is "Newtonian", with a thixotropic slope of 1.0. In certain embodiments, the solvent or solvent systems used to dispense the B-stageable adhesive have slopes ranging from 1.0 to about 1.2.

In some instances, the B-stageable adhesive is dispensed onto the backside of a die that has been coated with a polyimide. Thus, the solvent or solvent system used to dispense the B-stageable adhesive should not have any deleterious effects on the polyimide coating. To achieve this goal, in certain embodiments, the solvent system will include a polar solvent in combination with a nonpolar solvent. Typically, the polar solvent is suitable for use with the amide-extended compounds described herein in B-stageable adhesives, and the nonpolar solvent is a non-solvent for the amide-extended compound. In addition, the polar solvent typically has a lower boiling point than the non-polar solvent. Without wishing to be to be limited to a particular theory, it is believed that when the adhesive is dispensed and then B-staged, the lower boiling polar solvent escapes first, leaving behind only the nonpolar non-solvent, essentially precipitating the oligomer uniformly and leaving the polyimide film undamaged.

In some embodiments, the solvent or solvent system has a boiling point ranging from about 150° C. up to about 300° C. In some embodiments, the solvent system is a combination of dimethyl phthalate (DMP), NOPAR 13, and terpineol. In other embodiments, the solvent system is a 1:1 (by volume) ratio of terpineol and NOPAR 13.

In general, adhesive compositions such as die-attach pastes and B-stageable adhesive compositions of the invention, will cure within a temperature range of 80-220° C., and curing will be effected within a length of time of less than 1 minute up to about 60 minutes. The B-stageable adhesive composition may be pre-applied onto either a semiconductor die or onto a substrate. As will be understood by those skilled in the art, the time and temperature curing profile for each adhesive composition will vary, and different compositions can be designed to provide the curing profile that will be suited to a particular industrial manufacturing process.

Additional Compounds.

In certain embodiments, the compositions of the invention, such as adhesives (including die-attach paste adhesives), may contain modifiers that lend additional flexibility and toughness to the resultant cured adhesive. Such modifiers may be any thermoset or thermoplastic material having a $T_g$ of 50° C. or less, and typically will be a polymeric material characterized by free rotation about the chemical bonds, the presence of ether groups, and the absence of ring structures. Suitable such modifiers include polyacrylates, poly(butadiene), poly-THF (polymerized tetrahydrofuran, also known as poly(1,4-butanediol)), CTBN (carboxy-terminated butadiene-acrylonitrile) rubber, and polypropylene glycol. When present, toughening compounds may be present in an amount up to about 15 percent by weight of compound according formula I and/or II and any other monomer in the adhesive.

Inhibitors for free-radical cure may also be added to the adhesive compositions and die-attach pastes described herein to extend the useful shelf life. Examples of free-radical inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants such as derivatives of p-phenylenediamine and diphenylamine. It is also well know in the art that hydrogen-donating antioxidants may be synergistically combined with quinones and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

The adhesive compositions, such as die-attach paste adhesives, described herein will generally perform within the commercially acceptable ranges for die attach adhesives. Commercially acceptable values for die shear for the adhesives on a 80×80 mil$^2$ silicon die are in the range of greater than or equal to 1 kg at room temperature, and greater than or equal to 0.5 kg at 260° C. Acceptable values for warpage for a 500×500 mil$^2$ die are in the range of less than or equal to 70 Nm at room temperature.

Fillers.

In some embodiments, fillers are contemplated for use in the practice of the present invention, which can be electrically conductive and/or thermally conductive, and/or fillers which act primarily to modify the rheology of the resulting composition. Examples of suitable electrically conductive fillers that can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers that can be employed in the practice of the present invention include graphite, aluminum nitride, silicon carbide, boron nitride, diamond dust, zinc oxide, alumina, and the like. Compounds which act primarily to modify rheology include polysiloxanes (such as polydimethyl siloxanes), silica, fumed silica, fumed alumina, fumed titanium dioxide, calcium carbonate and the like.

Underfill Compositions

During its normal service life, an electronic assembly is subjected to repeated cycles of widely varying temperature. Due to the differences in the coefficient of thermal expansion between the electronic component, the solder, and the substrate, thermal cycling can stress the components of the assembly and cause it to fail. To prevent the failure, the gap between the component and the substrate is filled with an underfill material to reinforce the solder material and to absorb some of the stress of the thermal cycling.

In practice, the underfill material is typically dispensed into the gap between and electronic component (such as a flip-chip) and the substrate by injecting the underfill along two or more sides of the component, with the underfill material flowing, usually by capillary action, to fill the gap. Alternatively, underfilling can be accomplished by backfilling the gap between the electronic component and the substrate through a hole in the substrate beneath the chip. In either method, the underfill material must be sufficiently fluid to permit filling very small gaps.

The requirements and preferences for underfills are well known in the art. Specifically, monomers for use in underfills should have high $T_g$ and low $\alpha_1$ CTE, important properties. A high $T_g$, preferably in the range of at least about 100-135° C., and a low modulus or $\alpha_1$, preferably lower than about 60-65 ppm/° C., are optimal for underfill compositions.

The siloxanes compounds of the invention are particularly suited as monomers or co-monomers in underfill composition. Thus, the present invention provides underfill compositions including at least one compound according to formula I or formula II. Optionally, the underfill will also contain a fluxing agent and/or a filler.

Two prominent uses for underfill technology are in packages known in the industry as flip-chip, in which a chip is attached to a lead frame, and ball grid array, in which a package of one or more chips is attached to a printed wire board.

The underfill encapsulation may take place after the reflow of the metallic or polymeric interconnect, or it may take place simultaneously with the reflow. If underfill encapsulation takes place after reflow of the interconnect, a measured amount of underfill encapsulant material will be dispensed along one or more peripheral sides of the electronic assembly and capillary action within the component-to-substrate gap draws the material inward. The substrate may be preheated if needed to achieve the desired level of encapsulant viscosity for the optimum capillary action. After the gap is filled, additional underfill encapsulant may be dispensed along the complete assembly periphery to help reduce stress concentrations and prolong the fatigue life of the assembled structure. The underfill encapsulant is subsequently cured to reach its optimized final properties.

If underfill encapsulation is to take place simultaneously with reflow of the solder or polymeric interconnects, the underfill encapsulant, which can include a fluxing agent if solder is the interconnect material, first is applied to either the substrate or the component; then terminals on the component and substrate are aligned and contacted and the assembly heated to reflow the metallic or polymeric interconnect material. During this heating process, curing of the underfill encapsulant occurs simultaneously with reflow of the metallic or polymeric interconnect material.

A wide variety of acids are contemplated for use as the acidic fluxing agent. Typically, the acidic fluxing agent is a carboxylic acid such as, for example, 3-cyclohexene-1-carboxylic acid, 2-hexeneoic acid, 3-hexeneoic acid, 4-hexeneoic acid, acrylic acid, methacrylic acid, crotonic acid, vinyl acetic acid, tiglic acid, 3,3-dimethylacrylic acid, trans-2-pentenoic acid, 4-pentenoic acid, trans-2-methyl-2-pentenoic acid, 2,2-dimethyl-4-pentenoic acid, trans-2-hexenoic acid, trans-3-hexenoic acid, 2-ethyl-2-hexenoic acid, 6-heptenoic acid, 2-octenoic acid, (+/−)-citronellic acid, (R)-(+)-citronellic acid, (S)-(−)-citronellic acid, undecylenic acid, myristolic acid, palmitoleic acid, oleic acid, elaidic acid, cis-11-eicosenoic acid, erucic acid, nervonic acid, cis-3-chloroacrylic acid, trans-3-chloroacrylic acid, 2-bromoacrylic acid, 2-(trifluoromethyl)acrylic acid, 2-(bromomethyl)acrylic acid, 2-cyclopentene-1-acetic acid, (1R-trans)-2-(bromomethyl)-2-methyl-3-methylenecyclopentaneacetic acid, 2-acetamidoacrylic acid, 5-norbornene-2-carboxylic acid, 3-(phenylthio)acrylic acid, trans-styrylacetic acid, trans-cinnamic acid, alpha-methylcinnamic acid, alpha-phenylcinnamic acid, 2-(trifluoromethyl)cinnamic acid, 2-chlorocinnamic acid, 2-methoxycinnamic acid, cis-2-methoxycinnamic acid, 3-methoxycinnamic acid, 4-methylcinnamic acid, 4-methoxycinnamic acid, 2,5-dimethoxycinnamic acid, 3,4-(methylenedioxy)cinnamic acid, 2,4,5-trimethoxycinnamic acid, 3-methylindene-2-carboxylic acid, and trans-3-(4-methylbenzoyl)acrylic acid, oxalic acid, malonic acid, methylmalonic acid, ethylmalonic acid, butylmalonic acid, dimethylmalonic acid, diethylmalonic acid, succinic acid, methylsuccinic acid, 2,2-dimethylsuccinic acid, 2-ethyl-2-methylsuccinic acid, 2,3-dimethylsuccinic acid, meso-2,3-dimethylsuccinic acid, glutaric acid, (+/−)-2-methylglutaric acid, 3-methylglutaric acid, 2,2-dimethylglutaric acid, 2,4-dimethylglutaric acid, 3,3-dimethylglutaric acid, adipic acid, 3-methyladipic acid, (R)-(+)-3-methyladipic acid, 2,2,5,5-tetramethylhexanedioic acid, pimelic acid, suberic acid, azelaic acid, 1,10-decanedicarboxylic acid, sebacic acid, 1,11-undecanedicarboxylic acid, undecanedioic acid, 1,12-dodecanedicarboxylic acid, hexadecanedioic acid, docosanedioic acid, tetracosanedioic acid, tricarballylic acid, beta-methyltricarballylic acid, 1,2,3,4-butanetetracarboxylic acid, itaconic acid, maleic acid, fumaric acid, citraconic acid, mesaconic acid, trans-glutatonic acid, trans-beta-hydromuconic acid, trans-traumatic acid, trans, trans-muconic acid, cis-aconitic acid, trans aconitic acid, (+/−)-chlorosuccinic acid, (+/−)-bromosuccinic acid, meso-2,3-dibromosuccinic acid, hexa fluoroglutaric acid, perfluoroadipic acid hydrate, dibromo-maleic acid, DL-malic acid, D-malic acid, L-malic acid, (R)-(−)-citramalic acid, (S)-(+)-citramalic acid, (+/−)-2-isopropylmalic acid, 3-hydroxy-3-methylglutaric acid, ketomalonic acid monohydrate, DL-tartaric acid, L-tartaric acid, D-tartaric acid, mucic acid, citric acid, citric acid monohydrate, dihydroflumaric acid hydrate, tetrahydrofuran-2,3,4,5-tetracarboxylic acid, mercaptosuccinic acid, meso-2,3-dimercaptosuccinic acid, thiodiglycolic acid, 3,3'-thiodipropionic acid, 3,3'-dithiodipropionic acid, 3-carboxypropyl disulfide, (+/−)-2-(carboxymethylthio) succinic acid, 2,2',2'',2'''-[1,2-ethanediylidenetetrakis(thio)]-tetrakisacetic acid, nitromethanetrispropionic acid, oxalacetic acid, 2-ketoglutaric acid, 2-oxoadipic acid hydrate, 1,3-acetonedicarboxylic acid, 3-oxoadipic acid, 4-ketopimelic acid, 5-oxoazelaic acid, chelidonic acid, 1,1-cyclopropanedicarboxylic acid, 1,1-cyclobutanedicarboxylic acid, (+/−)-trans-1,2-cyclobutanedicarboxylic acid, trans-DL-1,2-cyclopentanedicarboxylic acid, 3,3-tetramethyleneglutaric acid, (1R,3S)-(+)-camphoric acid, (1S,3R)-(−)-camphoric acid, (+/−)-cyclohexylsuccinic acid, 1,1-cyclohexanediacetic acid, (+/−)-trans-1,2-cyclohexanedicarboxylic acid, (+/−)-1,3-cyclohexanedicarboxylic acid, trans-1,2-cyclohexanedicarboxylic acid, 1,4-cyclohexanedicarboxylic acid, 1,3-adamantanedicarboxylic acid, 3-methylenecyclopropane-trans-1,2-dicarboxylic acid, cis-5-norbornene-endo-2,3-dicarboxylic acid, 1,3,5-cyclohexanetricarboxylic acid, 1,3,5-cyclohexanetricarboxylic acid, kemp's triacid, (1alpha.3alpha.5beta)-1,3,5-trimethyl-1,3,5-cyclohexanetricarboxylic acid, 1,2,3,4-cyclobutanetetracarboxylic acid, and 1,2,3,4,5,6-cyclo-hexanehexacarboxylic acid monohydrate, phenylmalonic acid, benzylmalonic acid, phenylsuccinic acid, 3-phenylglutaric acid, 1,2-phenylenediacetic acid, homophthalic acid, 1,3-phenylenediacetic acid, 4-carboxyphenoxyacetic acid, 1,4-phenylenediacetic acid, 2,5-dihydroxy-1,4-benzenediacetic acid, 1,4-phenylenediacrylic acid, phthalic acid, isophthalic acid, 1,2,3-benzenetricarboxylic acid hydrate, terephthalic acid, 1,2,4-benzenetricarboxylic acid, 1,2,4,5-benzenetetracarboxylic acid, mellitic acid, 3-(carboxymethylaminomethyl)-4-hydroxybenzoic acid, 4-methylphthalic acid, 2-bromoterephthalic acid, 4-bromoisophthalic acid, 4-hydroxyisophthalic acid, 4-nitrophthalic acid, nitrophthalic acid, 1,4-phenylenedipropionic acid, 5-tert-butylisophthalic acid, 5-hydroxyisophthalic acid, 5-nitroisophthalic acid, 5-(4-carboxy-2-nitrophenoxy)-isophthalic acid, diphenic acid, 4,4'-biphenyldicarboxylic acid, 5,5'dithiobis(2-nitrobenzoic acid), 4-[4-(2-carboxybenozoyl)phenyl]-butyric acid, pamoic acid, 1,4-naphthalenedicarboxylic acid, 2,3-naphthalenedicarboxylic acid, 2,6-naphthalenedicarboxylic acid, 1,4,5,8-naphthalene-tetracarboxylic acid hydrate, 2,7-di-tert-butyl-9,9-dimethyl-4,5-xanthenedicarboxylic acid, and the like.

A particularly useful carboxylic acid for the preparation of the latent fluxing agents of the present invention is DIACID 1550®, a monocyclic $C_{21}$ dicarboxylic acid product derived from tall oil fatty acids, commercially available from Westvaco Corporation.

Mold Compounds and Compositions

In the electronics industry, a semiconductor chip or die mounted to a "package" substrate may be overmolded with a mold compound to provide a level of protection from environmental effects such as moisture and contaminants.

In terms of reliability performance, various properties of mold compositions materials are generally considered important. The properties desirable for mold compositions are known in the art. See, for example, U.S. Pat. Nos. 7,294,915, 6,512,031, and 6,429,238. These include low CTE, low modulus, adhesion, and high fracture toughness of the cured resin. A high $T_g$, preferably in the range of at least about 100-135° C., and a low modulus or $\alpha_1$, preferably lower than about 60-65 ppm/° C., are optimal for mold compositions. See, for example, U.S. Pat. Nos. 6,512,031 and 5,834,848. A typical overmolding process places a solid or semi-solid molding compound over the chip using a mold press. The package is then transferred through a heated mold that causes the molding compound to flow and encapsulate the chip.

Mold compositions are highly filled compositions. They are typically filled with silica. This high filler loading is critical to their performance in terms of CTE (coefficient of thermal expansion), flame retardance, and thermal conductivity.

The compounds of the present invention were found to have properties desirable of mold compounds. Specifically, the amide-extended compounds of the invention have a high $T_g$ and certain compounds have a low modulus as well. A high $T_g$, preferably in the range of at least about 100-135° C., and a low modulus or $\alpha_1$, preferably lower than about 60-65 ppm/° C., are optimal for mold compositions. Thus, the present invention provides mold compositions containing at least one compound according to formula I or II.

Assemblies

The present invention also provides assemblies of components adhered together by the above-described adhesive compositions (e.g., B-stageable adhesives and die-attach pastes) of the invention. Thus, for example, assemblies comprising a first article adhered to a second article by a cured aliquot of an adhesive composition containing at least one compound of formula I and/or II are provided. Articles contemplated for assembly employing invention compositions include electronic components such as dies, memory devices (e.g. as flash memory devices), ASIC devices, microprocessors, and other microelectronic components. Assemblies also include microelectronic devices, such as copper lead frames, Alloy 42 lead frames, silicon dice, gallium arsenide dice, and germanium dice, that are adhered to a substrate by a cured aliquot of the above-described adhesive compositions Additional embodiments of the invention include adhesively bonded structures containing at least amide-extended compound described herein. Non-limiting examples of the adhesively bonded structures include electronic components bonded to a substrate, and circuit components bonded to printed wire boards. In other embodiments of the invention, articles of manufactures can be comprised substantially of a cured amount of the composition described herein, such as an industrial, marine, automotive, airline, aerospace, sporting goods, medical or dental article. Such articles of manufacture can also include fillers, extenders, pigments and/or reinforcing materials along with the compositions disclosed herein.

Conditions suitable to cure invention die attach paste adhesives include subjecting the above-described assembly to a temperature of less than about 200° C. for about 0.5 up to 2 minutes. This rapid, short duration heating can be accomplished in a variety of ways, e.g., with an in-line heated rail, a belt furnace, or the like. Optionally, the material can be oven cured at 150-220° C.

In other embodiments the invention provides methods for attaching a semiconductor die to a substrate. Such methods can be performed, for example, by (a) applying a die-attach adhesive composition described herein to the substrate and/or the semiconductor die, (b) bringing the substrate and the die into contact to form an assembly, such that the substrate and the die are separated only by the die-attach adhesive composition applied in step (a), and (c) subjecting the assembly to conditions sufficient to cure the die-attach paste, thereby attaching the semiconductor die to the substrate.

In yet another embodiment of the invention, there are provided assemblies of components adhered together employing the above-described adhesive compositions and/or die attach pastes. Thus, for example, assemblies comprising a first article permanently adhered to a second article by a cured aliquot of the above-described adhesive composition are provided. Articles contemplated for assembly employing invention compositions include memory devices, ASIC devices, microprocessors, flash memory devices, and the like.

Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

In accordance with still another embodiment of the present invention, there are provided methods for adhesively attaching two component parts to produce the above-described assemblies. Thus, for example, a first article can be adhesively attached to a second article, employing a method including:

(a) applying the above-described adhesive composition to the first article, (b) bringing the first and second article into intimate contact to form an assembly wherein the first article and the second article are separated only by the adhesive composition applied in (a), and thereafter, (c) subjecting the assembly to conditions suitable to cure the adhesive composition.

Similarly, a microelectronic device can be adhesively attached to a substrate, employing a method including the steps of:

(a) applying the above-described die attach paste to the substrate and/or the microelectronic device, (b) bringing the substrate and the device into intimate contact to form an assembly wherein the substrate and the device are separated only by the die attach composition applied in (a), and thereafter, (c) subjecting the assembly to conditions suitable to cure the die attach composition.

Conditions suitable to cure invention die attach pastes include subjecting the above-described assembly to a temperature of less than about 400° C. for about 0.5 up to 2 minutes. This rapid, short duration heating can be accomplished in a variety of ways, e.g., with an in-line heated rail, a belt furnace, or the like. Optionally, the material can be oven cured at 80-400° C.

Methods of Using Amide Extended Compounds and Adhesive Compositions

According to the present invention, methods for adhesively attaching a first article to a second article are provided. Such methods can be performed, for example, by a) applying an adhesive composition of the invention to the first article, the second article or both the first and second articles; b) contacting the first article and the second article, where the first article and the second article are separated only by the adhesive composition applied in step a); and c) curing the adhesive composition applied in step a), thereby adhesively attaching the first article to the second article.

In one aspect of this method, the first and second articles are a semiconductor die and a substrate, respectively. Typically, according to this aspect the adhesive is a die attach paste. The method can include the steps of applying the adhesive composition (e.g. die attach paste) to the substrate, the semiconductor die, or both the substrate and the semiconductor die; b) melting the adhesive composition applied in step a); c) contacting the semiconductor device and the substrate, where the die and substrate are separated only by the adhesive composition applied in step a); and d) curing the adhesive composition applied in step a), thereby adhesively attaching the semiconductor device to the substrate. Applying the adhesive composition can include spin-coating, spray coating, stencil printing, screen printing and other methods well known in the art.

It will be understood those of skill in the art that using the compounds and methods of the present invention, it is possible to prepare adhesives having a wide range of cross-link density by the judicious choice and amount of a compound having a structure represented by formula I or II. The greater proportion of polyfunctional compounds reacted, the greater the cross-link density. If thermoplastic properties are desired, the adhesive compositions can be prepared from (or at least contain a higher percentage of) mono-functional compounds to limit the cross-link density. A minor amount of poly-functional compounds can be added to provide some cross-linking and strength to the composition, provided the amount of poly-functional compounds is limited to an amount that does not diminish the desired thermoplastic properties. Within these parameters, the strength and elasticity of individual adhesives can be tailored to a particular end-use application.

Properties of Adhesives Containing Compounds of the Invention

Advantageously, the compounds of the invention can impart many properties that are desirable in an adhesive. Historically, the large majority of integrated circuits have been mounted on printed circuit boards using lead-based soldering. However, the demand for lead-free materials is increasing year by year, and electrically conductive adhesives are seen as an environmentally-friendly alternative.

Adhesiveness.

To fully replace lead-based solders, adhesives in the microelectronic industry, adhesives must address the need for signal and power distribution, heat dissipation (i.e., cooling) while at the same time having and maintaining high adhesiveness. Conductive adhesives, for example, typically have conductive fillers dispersed in a polymer matrix. The polymer matrix, when cured, provides the mechanical adhesion, but can interfere with conductivity and increase electrical resistance.

Compounds of the present invention can be used to increase adhesiveness of polymer compositions. Amide-extended compounds of the invention increased adhesiveness by 50% over the same composition containing only X-BMI, in some tests, and by greater than 8 fold in other tests as described below in the EXAMPLES.

Thus the present invention provides methods for increasing the adhesiveness of an adhesive composition by replacing all or a portion of a monomer (such as an acrylate or maleimide monomer) in the composition, with an amide-extended compound of the invention. In one embodiment, the amide-extended compound can be represented by structural formula I. In other embodiments the amide-extended compound can be represented by structural formula II.

The following examples are intended only to illustrate the present invention and should in no way be construed as limiting the subject invention.

EXAMPLES

Example 1

The Synthesis of Imide-Extended Mono-, Bis-, and Polymaleimides

A 500 ml round bottom flask equipped with a Teflon coated stir bar was charged with 250 ml of toluene. Triethylamine, 35 g (0.35 mole) was added to the flask, followed by the slow addition of 35 g (0.36 mole) of anhydrous methanesulphonic acid to form a salt. The mixture was allowed to stir for approximately 10 minutes, followed by the addition of 57 g (0.11 mole) of Versamine 552 (dimer diamine, Cognis Corporation). Pyromellitic dianhydride (10.9 g, 0.05 mole) was slowly added to the stirred mixture. A Dean-Stark trap and condenser were attached to the flask, and the mixture was heated to reflux for 2 hours to form an amine-terminated diimide. The theoretical quantity of water from this condensation had been collected by this time. The reaction mixture was cooled down to room temperature and 12.8 g (0.13 mole) of maleic anhydride was added to the flask, followed by the of 5 g of anhydrous methanesulphonic acid. The mixture was brought to reflux for an additional 12 hours to obtain the expected amount of water. An additional 100 ml of toluene was added to the flask after it had been cooled down to room temperature, and the mixture was then allowed to settle. The solution was decanted, and the salt was rinsed with additional toluene (2×100 ml). The extracts were combined and then again allowed to settle overnight in order to provide sufficient time for additional salt and acid to separate. The solution was filtered through a glass-fritted funnel tightly packed with 30 g of silica gel. The solvent was removed under vacuum to produce 60 g (84% yield) of a dark waxy resin.

Example 2

Similar to the method outlined in the previous example, a salt was formed by mixing 38 g (0.38 mole) of triethylamine with 38 g (0.39 mole) of anhydrous methanesulphonic acid in 250 ml of toluene. Versamine 552, 59 g (0.11 mole) was added to the flask, followed by the slow addition of 16.1 g (0.05 mole) of 3,3',4,4'-benzophenone tetracarboxylic dianhydride. About two of hours of reflux were required for the azeotropic removal of the water to form the amine-terminated diimide. The mixture was cooled down to room temperature, followed by the addition of 12.5 g (0.13 mole) of maleic anhydride and 5 g of methanesulphonic acid. The mixture was refluxed again for 12 hours to form the bismaleimide. The product was worked-up according to the procedure described in the previous example. A dark amber colored resin (65 g, 82% yield) was collected after the complete removal of the solvent.

Example 3

A salt was made by mixing 10 g (0.10 mole) of triethylamine with 11 g (0.11 mole) of methanesulphonic acid in 200 ml of toluene. Verasmine 552, 32 g (0.06 mole) was added to the mixture, followed by the slow addition of 13.5 g (0.03 mole) of 1,1,3,3-tetramethyl-1,3-bis(norbornyldicarboxylic anhydride)disiloxane. The amine-terminated diimide was formed after the azeotropic distillation of the water, which required approximately 1 hour of reflux. The mixture was cooled down, followed by the addition of 10 g (0.10 mole) of maleic anhydride along with 3 g of methanesulphonic acid. The mixture was refluxed for 18 hours to collect the required amount of water in the Dean-Stark trap. The work-up of the product was conducted as outlined in the previous examples. The final material (35 g, 73% yield) was obtained as a dark-amber colored resin after the removal of the solvent.

Example 4

A salt was prepared by mixing 40 g (0.40 mole) triethylamine with 40 g (0.42 mole) methanesulphonic acid in 200 ml of toluene. This was followed by the sequential addition of 57 g (0.11 mol) of Versamine 552 and 17 g (0.05 mole) of 2,8-decadiene-1,10-disuccinic anhydride. The mixture was refluxed for 12 hours with azeotropic removal of the water to produce the amine-terminated diimide. The mixture was then cooled down to room temperature and 12.8 g (0.13 mol) of maleic anhydride and 5 g. of methanesulphonic acid were then added to the flask. The mixture was again heated to reflux overnight with azeotropic removal of the water. Work-up of the product gave 65 g (82% yield) of an amber-colored resin.

Example 5

A salt was formed by mixing 35 g. (0.35 mole) of triethylamine with 36 g. (0.37 mole) of methanesulphonic acid in 250 ml of toluene (inside a 500 ml flask). Verasmine 552, 90 g (0.17 mole) was added to the flask, followed by the slow addition of 24 g. (0.11 mole) of pyromellitic dianhydride. About two of hours of reflux were required for the complete azeotropic removal of the water to form the amine-terminated diimide. The mixture was then cooled down to room temperature and 13 g (0.13 mole) of maleic anhydride and 10 g of methanesulphonic acid were then added. The mixture was refluxed again for 12 hours to form the imide-linked bismaleimide. The product was worked up according to the procedure described in the previous example. A dark amber colored resin (100 g, 82% yield) was collected after the complete removal of the solvent.

Example 6

A salt was formed by mixing 50 g (0.50 mole) of triethylamine with 50 g (0.52 mole) of anhydrous methanesulphonic acid in 400 mL of toluene (inside a one liter flask). Bis (aminomethyl)tricyclo[5.2.1.2,6]decane, 33 g. (0.17 mole) was added to the flask, followed by the slow addition of 42 g (0.08 mole) 4,4'-bisphenol-A dianhydride. A couple of hours of reflux were required for the azeotropic removal of the water to form the amine-terminated diimide. The mixture was cooled down to room temperature, followed by the addition of 22 g (0.22 mole) of maleic anhydride and 8 g of methanesulphonic acid. The mixture was refluxed again for 16 hours to form the imide-linked bismaleimide. The product was worked up according to the procedure described in the previous example. The solvent was removed to obtain 80 g (94% yield) of a glassy, light yellow, solid.

Example 7

A salt was formed by mixing 35 g (0.35 mole) of triethylamine with 36 g (0.38 mole) of anhydrous methanesulphonic acid in 400 ml of toluene (inside a 1000 ml flask). Forty-two grams (0.10 mole) of 2,2'-Bis[4-(4-aminophenoxy)phenyl] propane was added to the flask, followed by the slow addition of 11 g (0.05 mole) of pyromellitic dianhydride. About two hours of reflux were required for the azeotropic removal of the water to form the desired amine-terminated diimide. The mixture was cooled down to room temperature, followed by the addition of 8 g (0.08 mole) of maleic anhydride and 8 g of methanesulphonic acid. The mixture was refluxed again for 6 hours to form the bismaleimide. The work-up of the product consisted of removal of the solvent under vacuum, followed by washing the solid on a Buchner funnel with water to remove the salt and acid. A final rinse with acetone was used to remove most of the water. The product was laid out in a shallow pan and dried in a oven overnight at approximately 100° C. A fine yellow powder (44 g, 86% yield) was obtained after drying.

Example 8

A salt was formed by mixing 35 g (0.35 mole) of triethylamine with 36 g (0.38 mole) of anhydrous methanesulphonic acid and 400 ml of toluene (inside a 1000 ml round-bottom flask). Bisphenol-A dianhydride (32 g, 0.06 mole) of was then added to the flask, followed by the addition of 16 g. (0.03 mole) of Versamine 552. The mixture was stirred at room temperature for an hour, followed by the addition of 24 g (0.06 mole) of 2,2'-Bis[4-(4-aminophenoxy)phenyl]propane to the flask. Azeotropic removal of the water was conducted over approximately 20 hours to form the desired amine-terminated imide. The mixture was then cooled down to room temperature, followed by the addition of 10 g (0.10 mol) of maleic anhydride and 5 g of methanesulphonic acid. The mixture was refluxed again for 18 hours to form the imide-extended bismaleimide. The product was worked up according to the procedure described in the previous example. After removal of the solvent, 60 g (82% yield) of a yellow, friable, glassy solid was obtained.

Example 9

A 500 ml round bottom flask equipped with a teflon coated stir bar was charged with 24 g (0.40 mole) of ethylenediamine along with 100 ml of toluene. This was followed by the slow addition of 100 g of polybutadiene grafted with 8% by weight maleic anhydride (RI130MA8, Sartomer). The azeotropic removal of the water and excess ethylenediamine was conducted over a twelve-hour reflux period. The removal of the excess ethylene diamine was aided by the addition of steam into the reaction vessel. The salt (25 g) of triethylamine-methanesulphonic acid was then added to the solution, along with an additional 3 g of methanesulphonic acid and 12 g (0.12 mole) of maleic anhydride. The azeotropic removal of the water was conducted over 12 hours to form the polymaleimide. The work-up of the product was conducted according to the previous examples to obtain 100 g of an amber colored viscous liquid resin.

Example 10

Toluene (350 ml) was added to a one liter round bottom flask equipped with a Teflon coated stir bar. Triethylamine, 50 g (~0.50 mole) was added to the flask followed by the slow addition of 50 g (0.52 mole) of anhydrous methanesulphonic acid. The mixture was allowed to stir at room temperature approximately 10 minutes, followed by the addition of 90 g (0.17 mole) of Versamine 552 (dimer diamine, Cognis Corporation). To the mixture was added 41 g (0.08 mole) of BPADA (4,4'-bisphenol-A dianhydride, GE Plastics). A Dean-Stark trap and condenser were attached to the flask, and the mixture was heated to reflux. After approximately two hours the expected amount of water was collected corresponding to the complete conversion to the amine terminated diimide. The mixture was allowed to cool down to below 40° C., and 22 g (0.23 mole, ~20% excess) of crushed maleic anhydride was added to the flask, followed by the addition of an extra 10 g of anhydrous methanesulphonic acid. The mixture was again slowly heated to reflux. Approximately 18 hours of reflux were required to collect the expected amount of water in the Dean-Stark trap. After cooling down to room temperature an extra 200 ml of toluene was added to the flask; the stirring was stopped at this point and the mixture was allowed to separate. The upper (toluene solution) fraction was carefully decanted into a 2 liter Erlenmeyer flask. The salt was washed with toluene (2×500 ml) the rinses were also decanted and combined. The amber solution was allowed to settle overnight to allow sufficient time for more salt and acid to separate from the combined toluene solution. The solution was then filtered through a glass-fritted funnel tightly packed with 65 g of silica gel. Following filtration the silica gel was washed with an extra 100 ml of toluene. The toluene was removed under reduced pressure to provide 120 g (~85% yield) of a dark amber colored resin.

Example 11

Tensile adhesion testing was done on some of the products from the preceding examples. The only component added to the test resin was 2% by weight of dicumyl peroxide initiator. The catalyzed resin mix was then used to affix aluminum studs to copper slugs. The aluminum posts had a contact head diameter of 290 mils. The copper slugs had dimensions of 1000×400×150 mils. Ten of these test assemblies were constructed for each of the catalyzed resin mixtures. The parts were cured for thirty minutes in an oven at 200° C. The parts were then allowed to cool to room temperature and the adhesive strength was determined using a Sebastian III tensile tester. A control composition was also run along side the test mixtures. The control mix used was the bismaleimide derived from the dimer diamine (i.e. Versamine 552) also catalyzed with 2% dicumyl peroxide.

TABLE 1

Tensile Adhesion Test Results

| Part | Stud Pull Value (pounds force) | |
|---|---|---|
| | Example 10 | Control |
| 1 | 66 | 23 |
| 2 | 54 | 16 |
| 3 | 57 | 15 |
| 4 | 75 | 12 |
| 5 | 47 | 19 |
| 6 | 71 | 9 |
| 7 | 52 | 22 |
| 8 | 70 | 18 |
| 9 | 63 | 8 |
| 10 | 77 | 6 |
| Average | 63 | 15 |
| Fn-1 | 10 | 6 |

TABLE 2

Tensile Adhesion Test Results

| Part | Stud Pull Value (pounds force) | | | |
|---|---|---|---|---|
| | Example 1 | Example 2 | Example 5 | Control |
| 1 | 73 | 97 | 95 | 30 |
| 2 | 59 | 69 | 145 | 15 |
| 3 | 91 | 68 | 103 | 23 |
| 4 | 96 | 77 | 113 | 7 |
| 5 | 98 | 88 | 143 | 21 |
| 6 | 97 | 79 | 156 | 16 |
| 7 | 102 | 81 | 127 | 28 |
| 8 | 60 | 93 | 126 | 24 |
| 9 | 101 | 81 | 113 | 25 |
| 10 | 61 | 71 | 126 | 25 |
| Average | 84 | 80 | 125 | 21 |
| Fn-1 | 18 | 9.9 | 19 | 6.9 |

The adhesion results for all of the examples shown in Tables 1 and 2 were clearly superior to the control test composition. While not wishing to be bound by theory, it is believed that the improvement seen here is a direct result of the reduced cross-link density and/or reduced cure shrinkage of the invention composition versus the BMI derived solely from the dimer diamine.

Example 12A

SMA EF60 Poly(Isophrone Maleimide), Method 1

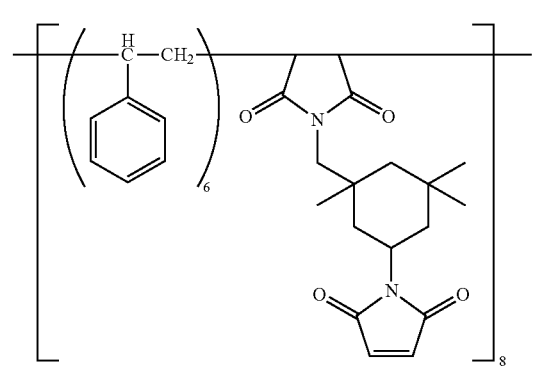

Triethylamine (20 g, 198 mmol), methanesulfonic acid (25 g, 260 mmol), toluene (200 ml), and a stir bar were added to a 1-neck, 1 L flask. A trap and condenser were attached to the flask. This mixture was refluxed for an hour to remove residual water. Cumene end-capped styrene maleic anhydride (72.5 g, 100 meq, "SMA EF60" available from Sartomer) was dissolved into the stirred mixture while it was still warm. The solution was cooled to room temperature. Isophorone diamine (20.4 g, 120 mmol) was then dripped in slowly to the stirred solution. Solids separated from the solution during this addition. The solution had to be manually swirled towards the end of the diamine addition. Once the diamine addition was complete, maleic anhydride (17.7 g, 180 mmol) was added and the flask was manually swirled until the anhydride was completely dissolved. The addition of the anhydride transformed the solution to a bright yellow color. Butylated hydroxytoluene (BHT, 75 mg) was added to the flask. A Dean-Stark trap and condenser were attached to the flask and the mix was then stirred and refluxed for 69 hours to collect 3.7 ml of water from the condensation of the amic acid residues. Toluene (200 ml) was stirred into the cooled mixture. The mix was allowed to settle and the upper toluene phase was decanted. Additional portions of toluene (4×50 ml) were used to extract the product from the lower phase. The combined toluene extracts were allowed to settle overnight and then decanted once again into a clean flask. The toluene phase was passed over a bed of 30 g of silica gel in a fritted funnel. The toluene was removed via rotary evaporation followed by air sparge. The recovered solids were dissolved in acetone (300 ml) and precipitated into deionized water (2 L). 56.0 grams of an off-white solid was collected. A portion of this product was catalyzed with 2% by weight dicumyl peroxide and then subjected to thermogravimetric analysis (TGA). The retained weight at 300° C. (TGA ramp rate=10° C./min., air purge) was 97.7% and the decomposition onset was at 381° C. A DSC (differential scanning calorimeter) run was conducted (ramp rate=10° C./min., air purge) on the compound (again catalyzed with 2% by weight dicumyl peroxide). A cure exotherm was observed to occur with an onset of 156.8° C., cure maxima at 172.6° C. and cure energy of 31.3 J/g. An infrared spectrum of the neat material included absorptions at 2926, 1855, 1779, 1709, 1601, 1493, 1453, 1360, 1220, 1154, 1078, 1030, 920, 829, 759, and 699 wavenumbers. Thermomechanical analysis (TMA) was conducted on a cured slug of this compound. The cured resin was found to have an $\alpha_1$=56.7 ppm/° C., an $\alpha_2$=225.0 ppm/° C. and a $T_g$=148.6° C.

Example 12B

SMA EF60 Poly(Isophrone Maleimide), Method 2

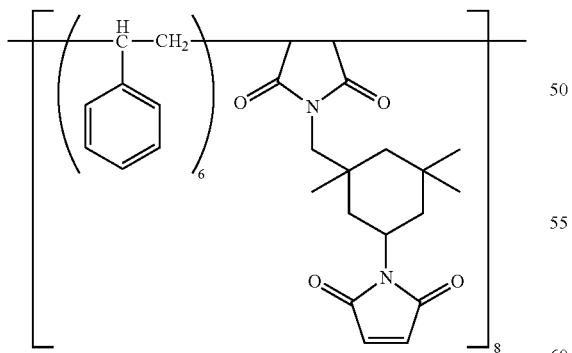

The same molecule as shown in Example 1a was made using a different method. The styrene maleic anhydride copolymer (72.5 g, 100 meq, "SMA EF60" available from Sartomer) was dissolved in toluene (250 ml) in a 1 L flask. N-methyl-2-pyrrolidone (60 ml) and a stir bar were added to the flask. A trap and condenser were then attached to the flask. This mixture was refluxed for 45 minutes to remove all residual water. This toluene-NMP solution was then dripped into a solution of isophorone diamine (20.4 g, 120 mmol) dissolved in toluene (100 ml). Halfway through the addition of NMP, the solution became too thick to stir. It had to be manually swirled as the toluene-NMP solution continued to drip in. Additional NMP (30 ml) was added. Methanesulfonic acid (5.0 g) and maleic anhydride (17.7 g, 180 mmol) were then also added to the flask. The mix was, at this point, a very viscous, gelatinous mass. The flask was rotated in a water bath for 2 hours in a 75° C. bath to complete the dissolution of the maleic anhydride. The flask was then fitted with a trap and condenser. The solution was stirred and refluxed for 50 hours. A total of 4.9 ml of water was collected. Toluene (100 ml) was added to the flask. The solution was neutralized with sodium bicarbonate (15 g) and water (5 g). It was then dried with magnesium sulfate (15 g) and passed over silica gel (35 g). The toluene was removed via rotary evaporation and air sparge. The solids were dissolved in acetone (300 ml) and precipitated into deionized water (2 L). A total of 95.1 grams of a beige solid was recovered after the collected solids had been dried. A sample of this compound was catalyzed with 2% by weight dicumyl peroxide and subjected to thermogravimetric analysis (TGA). The retained weight at 300° C. (TGA ramp rate=10° C./min., air purge) was 97.0% and the decomposition onset was at 396° C. A DSC (differential scanning calorimeter) run was conducted (ramp rate=10° C./min., air purge) on a sample of this material that was catalyzed with 2% by weight dicumyl peroxide. A cure exotherm was observed to occur with an onset of 141.7° C., cure maxima at 164.9° C. and cure energy of 74.7 J/g. Infrared spectrum included absorptions at 2922, 1778, 1710, 1601, 1494, 1453, 1404, 1359, 1220, 1148, 1090, 918, 829, 759, and 697 wavenumbers. A TMA was conducted on a cured slug of this compound. The cured resin was found to have an $\alpha_1$=58.9 ppm/° C., an $\alpha_2$=185.0 ppm/° C. and a $T_g$=146.0° C.

Example 13

SMA EF60 Poly(2,6,2',6'-methylenedianiline maleimide)

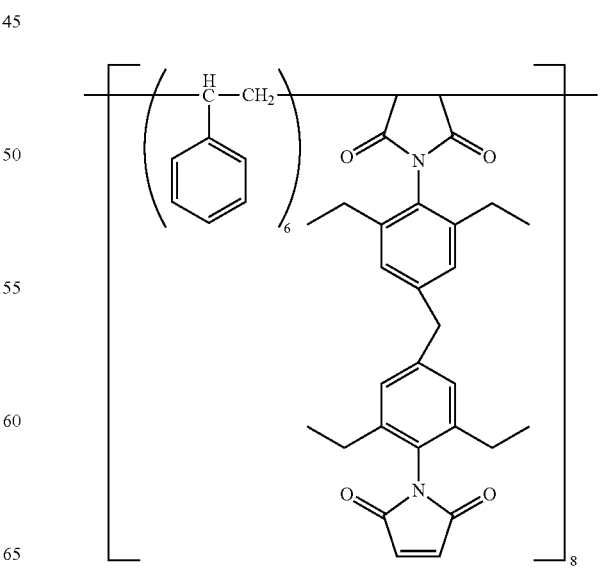

4,4'-Methylenebis(2,6-diethylaniline) (20.2 g, 65 mmol) was dissolved in NMP (10 ml) and toluene (160 ml). The solution was refluxed to azeotrope off any residual water. Once the solution had been cooled to room temperature, maleic anhydride (9.8 g, 100 mmol) was dissolved in, turning the solution a cherry red. Cumene end-capped styrene maleic anhydride (21.8 g, 30 meq, "SMA EF60" available from Sartomer) was dissolved in next. The addition of the "SMA EF60" did not result in any further change in color or viscosity. The solution, however, became a purplish red after the addition of methanesulfonic acid (3.0 g). The solution was refluxed for 2.75 hours and 2.4 ml of water was collected. Toluene (100 ml) was added to the flask. The solution was then subjected to repeated brine extractions (6×25 ml). The toluene phase was dried with magnesium sulfate (20 g) and passed over silica gel (30 g). The toluene was removed via rotary evaporation and air sparge. The residue was dissolved in acetone (150 ml) and precipitated into ice-cold deionized water (1.5 L). A total of 95.1 grams of an amber, glassy, powdered solid was recovered. A portion of this compound was catalyzed with 2% by weight dicumyl peroxide and subjected to thermogravimetric analysis (TGA). The retained weight at 300° C. (TGA ramp rate=10° C./min., air purge) was 96.5% and the decomposition onset was at 409° C. A DSC (differential scanning calorimeter) run was conducted (ramp rate=10° C./min., air purge) on a sample of this material that was catalyzed with 2% by weight dicumyl peroxide. A cure exotherm was observed to occur with an onset of 153.2° C., cure maxima at 186.4° C. and cure energy of 82.6 J/g. Infrared spectrum included absorptions at 2967, 1778, 1712, 1601, 1453, 1376, 1220, 1151, 1060, 952, 828, 759, and 700 wavenumbers. Thermomechanical analysis (TMA) was performed on a cured slug of this polymaleimide compound. The cured resin was found to have an $\alpha_1$=60.0 ppm/° C., an $\alpha_2$=187.6 ppm/° C. and a $T_g$=119.1° C.

Example 14

SMA 2000P Poly(Isophrone Maleimide)

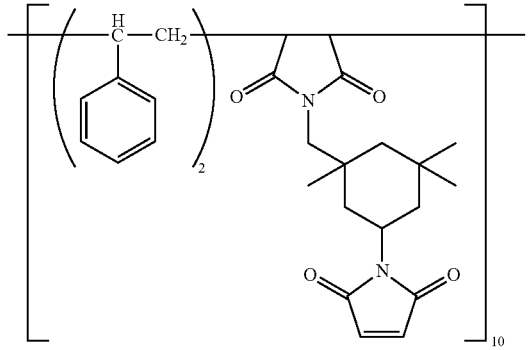

Cumene-capped styrene maleic anhydride resin (30.6 g, 100 meq, "SMA 2000P" available from Sartomer) was dissolved in heated N-methyl-2-pyrrolidone (60 ml). The solution was allowed to cool to room temperature and was then dripped into isophorone diamine (20.4 g, 120 mmol) dissolved in toluene (180 ml). The mixture stirred for an additional ten minutes. Methanesulfonic acid (5.0 g) was then added. The solution was refluxed for half an hour to remove residual water. Once the solution had cooled, maleic anhydride (15.7 g, 160 mmol) and BHT (108 mg) were added. As the components mixed into the solution, it became a fairly thick slurry. The slurry solids dissolved and the mixture transformed into a clear solution upon reflux. The solution was refluxed for 34 hours. A total of 4.5 ml of water was collected in the trap at the end of this period. Toluene (200 ml) was added. The solution was neutralized with sodium bicarbonate (10 g) and water (5 g). It was dried with magnesium sulfate (10 g), and then passed over silica gel (25 g). The toluene was removed via rotary evaporation followed by air sparge. The residue was dissolved in acetone (250 ml) and precipitated into deionized water (1.5 L). The solids were filtered and dried and then re-dissolved in acetone (300 ml). The acetone solution was then precipitated again in deionized water (2 L). The solids were filtered and dried overnight in a 75° C. oven. A total of 55.1 grams (90.8% theory) of a fine, buff, powder was collected. A portion of this compound was catalyzed with 2% by weight dicumyl peroxide and subjected to thermogravimetric analysis (TGA). The retained weight at 300° C. (TGA ramp rate=10° C./min., air purge) was 93.7% and the decomposition onset was at 364° C. A DSC (differential scanning calorimeter) run was also conducted (ramp rate=10° C./min., air purge) on a sample of this material (again, catalyzed with 2% by weight dicumyl peroxide). A cure exotherm was observed to occur with an onset of 156.2° C., a cure maxima at 168.0° C., and a cure energy of 86.5 J/g. An infrared spectrum on this compound revealed prominent absorptions at 2927, 1778, 1704, 1601, 1371, 1220, 1146, 920, 829, 762, and 696 wavenumbers. A TMA test was performed on a cured slug of this compound. The cured resin was found to have an $\alpha_1$=48.7 ppm/° C., an $\alpha_2$=88.1 ppm/° C. and a $T_g$=183.6° C.

Example 15

SMA EF30 Poly(Isophrone Maleimide)

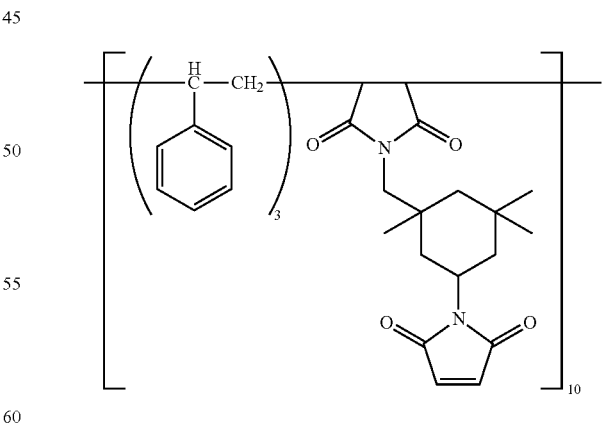

Cumene end-capped styrene maleic anhydride resin (41.0 g, 100 meq, "SMA EF30" available from Sartomer) was not soluble in warm N-methyl-2-pyrrolidone (60 ml), so heated toluene (60 ml) was added to dissolve the resin. This solution was dripped into isophorone diamine (20.4 g, 120 mmol) in toluene (120 ml). The mixture became a slurry, but was still fluid enough to be stirred magnetically for an hour at room temperature. As the mixture continued stirring at room temperature, it did become thicker, so additional toluene (50 ml) was added. The mixture was then stirred in a 60° C. water bath for an hour. Methanesulfonic acid (5.0 g) and maleic anhydride (17.7 g, 180 mmol) were added and to the flask. A trap and condenser were attached and the mixture was then refluxed for 48 hours. A total of 4.9 ml of water was collected. The solution was then diluted with toluene (200 ml), and neutralized with sodium bicarbonate (15 g) and water (5 g). The solution was dried with magnesium sulfate (15 g) and passed over silica (30 g). The toluene was removed via rotary evaporation followed by air sparge. The residue was dissolved in acetone (250 ml) and precipitated into deionized water (1.6 L). The precipitate was filtered and dried in a 75° C. oven. A total of 69.6 grams (97.9% theory) of a buff colored powder was collected. A portion of this compound was catalyzed with 2% by weight of dicumyl peroxide and subjected to TGA (10° C. per minute ramp, air purge). The retained weight at 300° C. (TGA ramp rate=10° C./min., air purge) was 96.1% and the decomposition onset was at 407° C. A DSC (differential scanning calorimeter) run was conducted (ramp rate=10° C./min., air purge) on a sample of this material (again catalyzed with 2% by weight dicumyl peroxide). A cure exotherm was observed to occur with an onset of 150.0° C., cure maxima at 161.1° C. and cure energy of 111.3 J/g. Prominent infrared spectrum absorptions included 1777, 1695, 1601, 1453, 1404, 1363, 1220, 1146, 921, 829, 761, and 697 wavenumbers. A TMA was conducted on a cured slug of the cured compound from this example. The cured resin was found to have an $\alpha_1$=53.0 ppm/° C., an $\alpha_2$=119.1 ppm/° C. and a $T_g$=198.1° C.

Example 16

SMA EF40 Poly(Isophrone Maleimide)

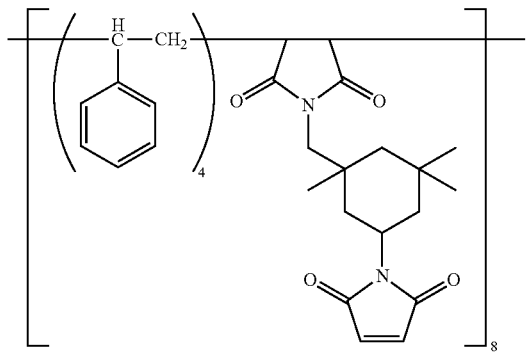

Cumene end-capped styrene maleic anhydride resin (51.7 g, 100 meq, "SMA EF40" available from Sartomer) was dissolved in a mixture of N-methyl-2-pyrrolidone (60 ml) and toluene (150 ml). This solution was refluxed (with a trap and condenser attached) to remove any residual water. When cool, this dried solution was dripped into a solution of isophorone diamine (20.4 g, 120 mmol) dissolved in toluene (100 ml). The mixture became too thick to stir magnetically, so it had to be swirled manually during the final stage of the addition. Methanesulfonic acid (5.0 g) and maleic anhydride (17.7 g, 180 mmol) were then added to the flask. The mix was swirled for 25 minutes. BHT (75 mg) was added. A trap and condenser were again attached to the flask and reflux of this stirred mixture was conducted for 56 hours. A total of 4.4 ml of water was collected. The cooled solution was diluted with toluene (200 ml) and then neutralized with sodium bicarbonate (15 g) and water (5 g). The solution was dried with magnesium sulfate (15 g) and then passed over silica (30 g). The toluene was removed via rotary evaporation followed air sparge. The residue was dissolved in acetone (250 ml) and precipitated into deionized water (1.6 L). The precipitate was filtered and dried in a 75° C. oven. A total of 79.2 grams (97% theory) of buff colored powder was collected. A portion of this compound was catalyzed with 2% by weight dicumyl peroxide and subjected to a TGA. The retained weight at 300° C. (TGA ramp rate=10° C./min., air purge) was 96.3% and the decomposition onset was at 414° C. A DSC (differential scanning calorimeter) run was conducted (ramp rate=10° C./min, air purge) on a sample of the compound (again catalyzed with 2% by weight dicumyl peroxide). A cure exotherm was observed to occur with an onset of 151.7° C., cure maxima at 168.2° C., with a energy of 160.4 J/g. Significant infrared spectrum absorptions included 2925, 1778, 1704, 1494, 1377, 1220, 1146, 921, 829, 760, and 697 wavenumbers. The cured resin was found to have an $\alpha_1$=52.0 ppm/° C., an $\alpha_2$=125.4 ppm/° C. and a $T_g$=153.2° C.

Example 17

Imide-Extended Hindered BMI

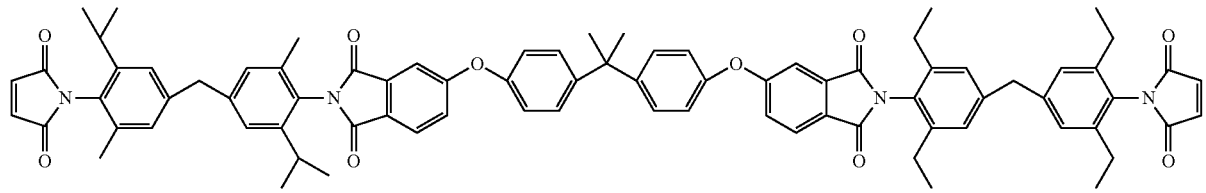 [SMILES: CCc1cc(Cc2cc(CC)c(N3C(=O)c4ccc(Oc5ccc(C(C)(C)c6ccc(Oc7ccc8c(c7)C(=O)N(c7c(C)cc(Cc9cc(C)c(N%10C(=O)C=CC%10=O)c(C(C)C)c9)cc7C(C)C)C8=O)cc6)cc5)cc4C3=O)c(CC)c2)cc(CC)c1N1C(=O)C=CC1=O]

A 500 ml, 1-neck flask was charged with 26.0 g (0.050 mmole) Bisphenol A dianhydride (GE Plastics), 9.8 g (0.10 mole) maleic anhydride, and 200 ml toluene. This mixture was stirred magnetically and heated to 75° C. to form a solution/slurry. A solution consisting of Lonzacure M-DEA and Lonzacure M-MIPA (15.53 g, 0.050 mole, each) dissolved in 50 ml toluene was added to the hot solution. A gooey, purple solid precipitated out of solution during this addition, but this did not interfere with the stirring. Methanesulfonic acid (2.0 g) was added to the flask. A Dean-Stark trap and condenser were attached to the flask the mixture was refluxed for 4 hours to collect 3.6 ml (equal to theory) water. The toluene solution was a homogeneous, clear amber liquid at the end of the reflux period. The solution was cooled, diluted with toluene (100 ml) and then neutralized with sodium bicarbonate (10 g) and water (3 g). The solution was dried with magnesium sulfate (8 g) and then passed over silica (15 g). The bulk of the toluene was removed via rotary evaporation followed air sparge. The product became too viscous to remove the last traces of toluene using a water bath, so the final air sparge was conducted using an oil bath to heat the flask to 120° C. A total of 58.76 g (92.9% of theory) of a clear, amber, glassy solid was recovered. A TGA was run on the neat compound which revealed a retained weight at 300° C. (TGA ramp rate=10° C./min., air purge) was 98.9% and a decomposition onset at 501.8° C. Significant infrared spectrum absorptions for this compound included 2966, 1776, 1710, 1600, 1475, 1372, 1233, 1153, 1103, 829, and 691 wavenumbers.

Example 18

Imide-Extended Hindered BMI

Bisphenol A dianhydride (26 g, 50 mmol, available from Sabic Innovative Plastics) was dissolved in toluene (100 ml) in a 3-neck, 500 ml flask. A stir bar was added to the flask. One neck was equipped with a temperature controller probe. Another neck was equipped with a Dean-Stark trap and condenser. The third neck was equipped with an addition funnel. The temperature was set to 75° C. Versamine 552 (13.4 g, 25 mmol, Cognis Corporation) was diluted in toluene (50 ml). This solution was dripped into the stirred mixture via the addition funnel. Afterwards, 4,4'-methylenebis(2,6-diethylaniline) (15.5 g, 50 mmol, available from Lonza Group of Switzerland) was dissolved in toluene (50 ml) and dripped into the solution. The mixture refluxed for 2.5 hours. 1.8 ml $H_2O$ (equivalent to theoretical) was collected. The mixture was cooled and maleic anhydride (5.4 g, 55 mmol) plus methanesulfonic acid (2 g) were added to the flask. The solution was refluxed for 4 hrs and another 1.0 ml of water was collected. The solution was washed with sodium bicarbonate, treated with $MgSO_4$ and then passed over $SiO_2$. Removal of toluene by rotary evaporation followed by heating the product in a vacuum oven at 100° C. afforded the corresponding bismaleimide in 86% yield. The product was a clear, amber, glassy solid. The neat BMI compound was subjected to thermogravimetric analysis (TGA). The retained weight at 400° C. (TGA ramp rate=10° C./min., air purge) was 98.4% and the decomposition onset was at 479° C. Infrared spectrum included absorptions at 3026, 2968, 2922, 2856, 1774, 1711, 1600, 1472, 1370, 1234, 1105, 1015, 832, and 693 wavenumbers.

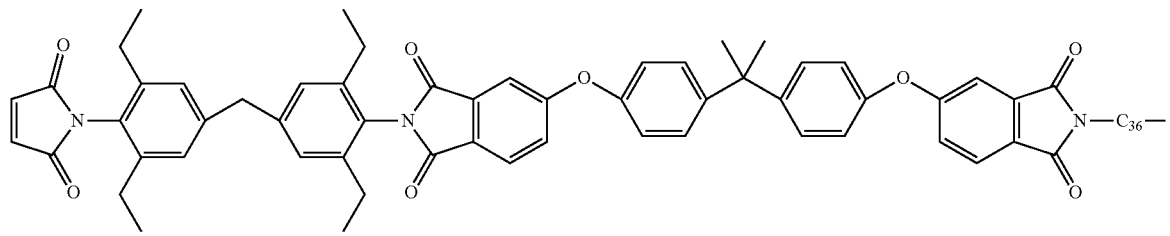

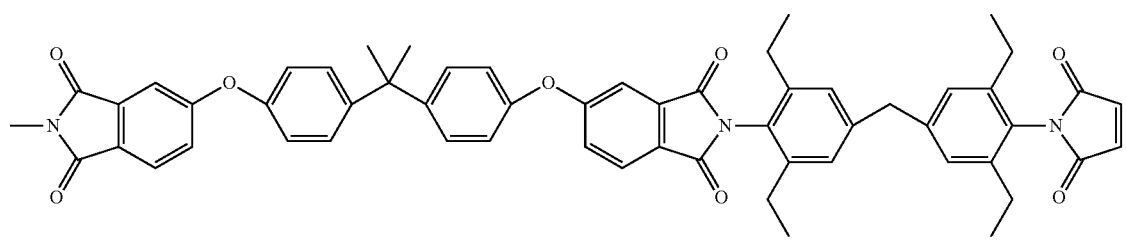

Example 19

Imide-Extended Hindered BMI

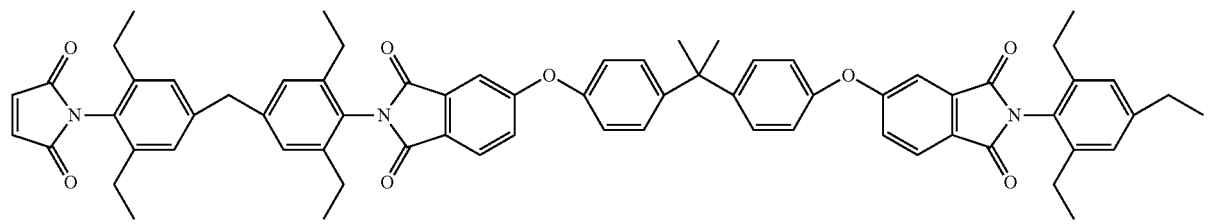

Bisphenol A dianhydride (26 g, 50 mmol) was dissolved in toluene (100 ml) in a 3-neck, 500 ml flask. A stir bar was added to the flask. One neck was equipped with a temperature controller probe. Another neck was equipped with a Dean-Stark trap and condenser. The third neck was equipped with an addition funnel. The temperature was set to 75° C. 4,4'-Methylenebis(2,6-diethylaniline) (23.3 g, 100 mmol) was dissolved in toluene (100 ml) and dripped into the stirred solution of dianhydride. The mixture refluxed for 3.3 hours and 1.9 ml of water (theoretical was 1.8 ml) was collected. The mixture was cooled and maleic anhydride (10.8 g, 110 mmol) plus methanesulfonic acid (2.5 g) were added to the flask. The solution refluxed for 49 hrs and 1.1 ml of water was collected in the trap. The solution was neutralized with sodium bicarbonate (10 g+3 g H$_2$O), then dried with MgSO$_4$ (8 g), and finally passed over SiO$_2$ (20 g). The toluene was removed via rotary evaporation and air sparge. Residual toluene was removed in a vacuum oven (set at approximately 160° C.). The product was a clear, amber solid that weighed 48.2 g. The BMI compound was subjected to thermogravimetric analysis (TGA). The retained weight at 400° C. (TGA ramp rate=10° C./min., air purge) was 99.9% and the decomposition onset was at 521° C. Infrared spectrum included absorptions at 3029, 2969, 2874, 1775, 1710, 1601, 1476, 1369, 1236, 1101, 1014, 827, and 694 wavenumbers.

Example 20

Imide-Extended TMH-BMI

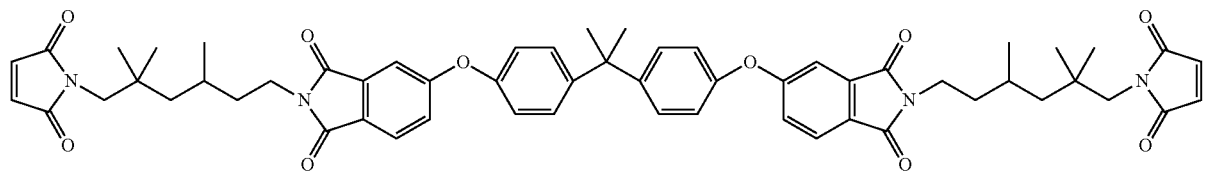 [SMILES: CC(CCN1C(=O)c2ccc(Oc3ccc(C(C)(C)c4ccc(Oc5ccc6c(c5)C(=O)N(CCC(C)CC(C)(C)CN5C(=O)C=CC5=O)C6=O)cc4)cc3)cc2C1=O)CC(C)(C)CN1C(=O)C=CC1=O]

Triethylamine (20 g), methanesulfonic acid (25 g), and toluene (200 ml) were added to a 1-neck, one-liter flask. The mix was refluxed to remove any residual water. When cool, bisphenol A dianhydride (52 g, 100 mmol) and maleic anhydride (19.6 g, 200 mmol) were added to the flask. When the solids had completely dissolved, 2,2,4-trimethyl-1,6-hexanediamine (31.7 g, 200 mmol) was dripped in. The mix was refluxed for 24 hours to collect 7.1 ml of water (theoretical was 7.2 ml). Toluene (100 ml) and water (25 ml) were added to the cooled solution. Toluene extractions (4×50 ml) were used to extract the toluene soluble product from the inorganic phase. The collected toluene fractions were dried with magnesium sulfate (15 g) and passed over a bed of silica gel (2×25 g). The toluene was removed via rotary evaporation and air sparge. Residual toluene was removed in a vacuum oven (oven temperature was ~125° C.). The product was an amber, friable, glassy solid that weighed 58.8 g. The BMI compound was subjected to thermogravimetric analysis (TGA). The retained weight at 400° C. (TGA ramp rate=10° C./min., air purge) was 97.1% and the decomposition onset was at 469° C. Infrared spectrum included absorptions at 3459, 3095, 2962, 1769, 1709, 1601, 1504, 1443, 1367, 1266, 1230, 1172, 1014, 888 and 695 wavenumbers.

Example 21

Imide-Extended Liquid BMI

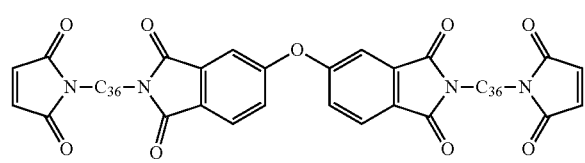

Triethylamine (20 g), methanesulfonic acid (25 g), and toluene (200 ml) were added to a 1-neck, 1 L flask. The mix was refluxed to remove any residual water. Oxydiphthalic anhydride (15.5 g, 50 mmol, available from Sabic Innovative Plastics) was added to the salt mix. The anhydride did not dissolve completely, even with warming Versamine 552 (53.6 g, 100 mmol) was added over the course of 10 minutes (which resulted in an exotherm). The mixture was refluxed for 14.5 hrs and 1.9 ml of water (theoretical=1.8 ml) was collected. When the solution cooled, maleic anhydride (10.8 g, 110 mmol) was dissolved in. The solution was then refluxed for 27 hours and 1.7 ml of water (theoretical=1.8 ml) was collected. Toluene (6×100 ml) was used to extract the product from the triethylamine-methanesulfonic acid phase. The collected toluene phase was passed over silica gel (30 g). The toluene was removed via rotary evaporation followed by a sparge with clean, dry air. The product was a clear, red, viscous liquid. The BMI compound was subjected to thermogravimetric analysis (TGA). The retained weight at 400° C. (TGA ramp rate=10° C./min., air purge) was 99.4% and the decomposition onset was at 474° C. Infrared spectrum included absorptions at 2922, 2851, 1771, 1708, 1609, 1441, 1393, 1366, 1272, 1233, 826, 747, and 696 wavenumbers.

Example 22

Maleimide-Capped Poly(Amide-Imides)

Poly(amide-imide) bismaleimides are a new class of thermoset resins that are similar to the imide-linked maleimides, with one exception in that they also have an amide linker in the molecule. This amide linker is produced via the reaction of a carboxylic acid with an isocyanate. When cured these materials should offer the advantage of giving a tougher plastic in certain circumstances and they also tend to be more soluble in a wider variety of organic solvents than many of the imide-linked maleimides.

The synthesis of these materials is conducted in a one-pot procedure in a polar aprotic solvent along with acid catalyst. The first part of the reaction is to produce an anhydride-capped polyimide. The reaction of a diamine with excess dianhydride coupled with azeotropic distillation of the water co-product produces this intermediate.

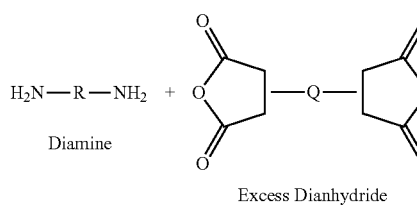

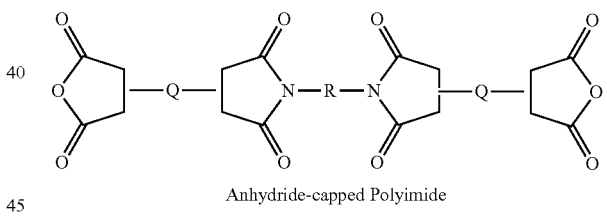

Anhydride-capped Polyimide

The anhydride-capped polyimide is then reacted with two equivalents of an amino acid to give a carboxyl-capped polyimide after further azeotropic distillation of the water co-product.

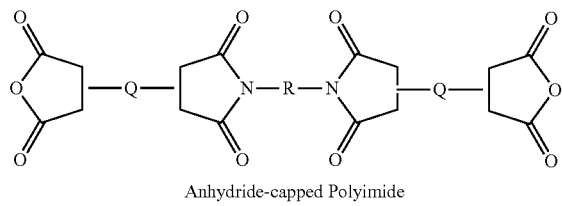

Anhydride-capped Polyimide

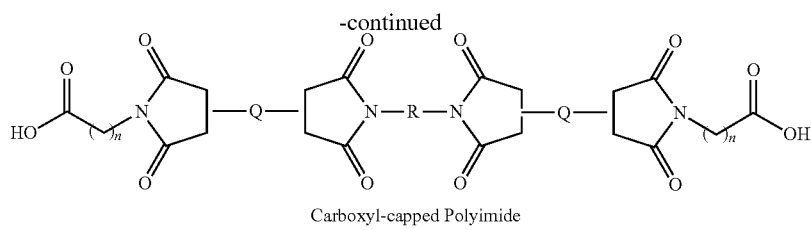

Carboxyl-capped Polyimide

The carboxyl-capped polyimide is then reacted with excess diisocyanate. This is a classic reaction that is known to produce amide and give off carbon dioxide gas as a byproduct. The reaction at this point has produced an isocyante-capped poly(amide-imide).

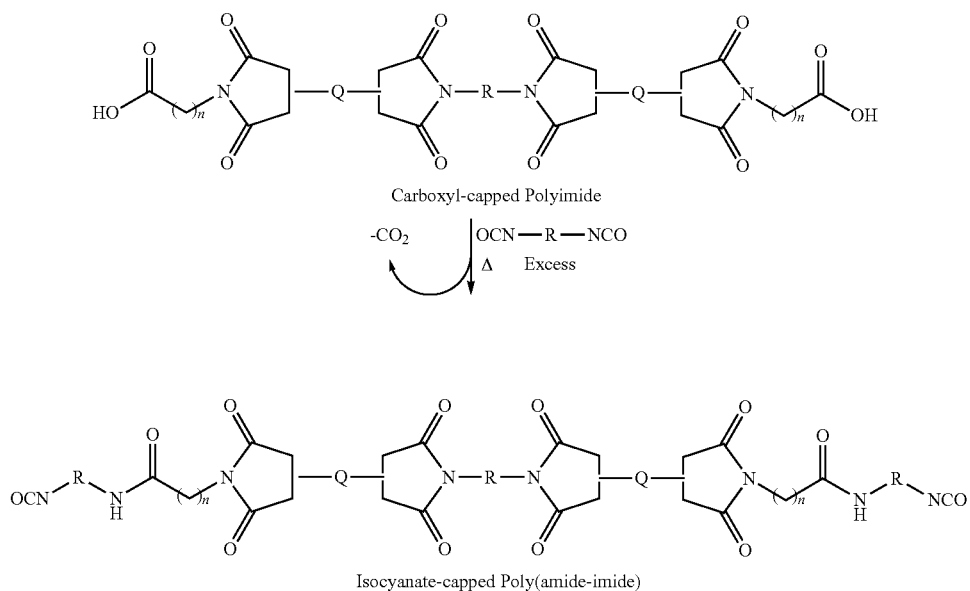

Reacting the isocyante-capped poly(amide-imide) with a functionalized carboxylic acid such as a maleimido-acid produces the final product, along with further evolution of carbon dioxide. The finished product, which is a maleimide-capped poly(amide-imide), is isolated by precipitation in an appropriate solvent such as acetone or methanol to remove the NMP and any residual acid contaminants

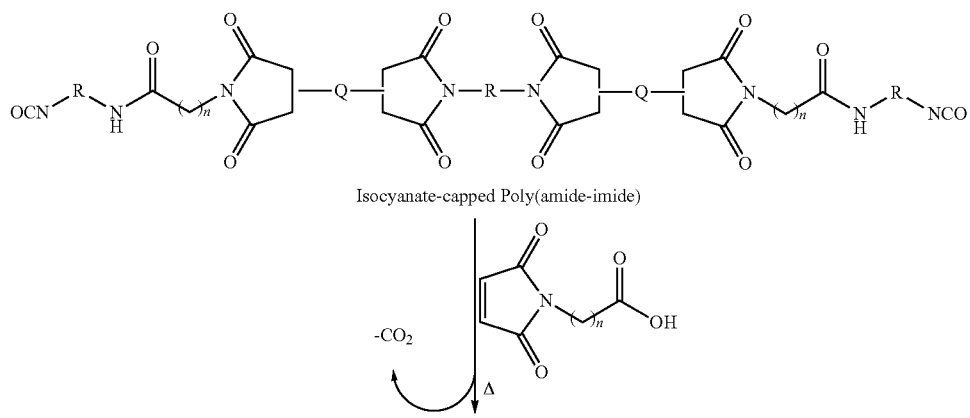

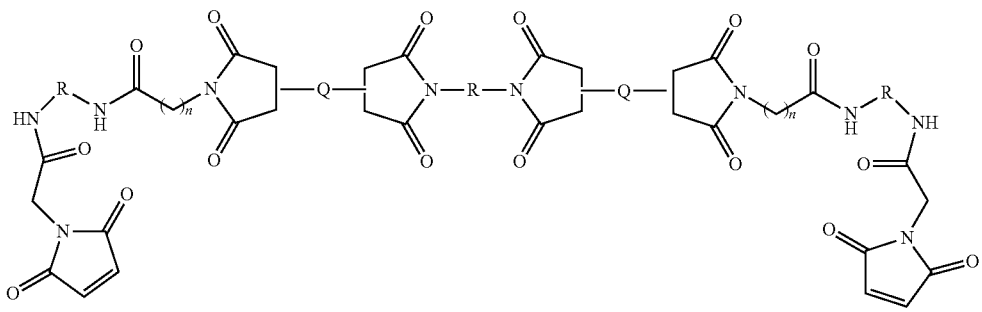

Maleimide-capped poly(amide-imide)

A specific example of a maleimide-capped poly(amide-imide) is the following. In this case a combination of two different dianhydrides was used to produce a lower melting molecule. The polyimide portion was synthesized using four equivalents of dianhydride and three equivalents of diamine. Subsequently, the polyimide was reacted with two equivalents of 6-aminocaproic acid, followed by the reaction with 2-equivalents of a diisocyanate (TMDI). The final step was the addition of 6-maleimidocaproic acid to produce the final product.

A representative structure for the targeted poly(amide-imide) BMI compound is shown below.

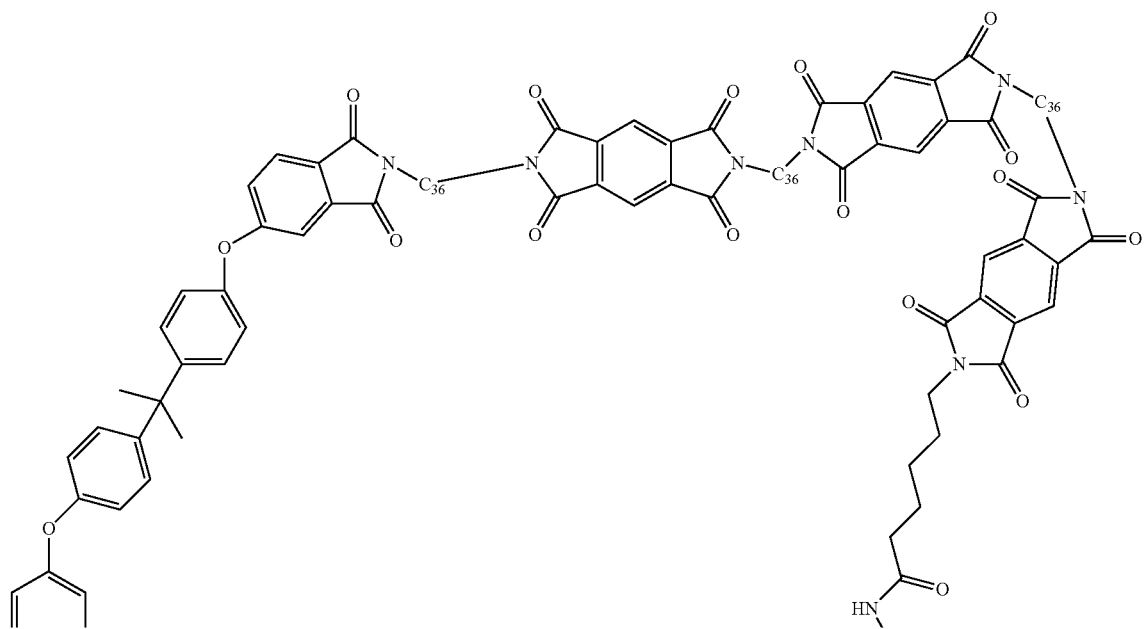

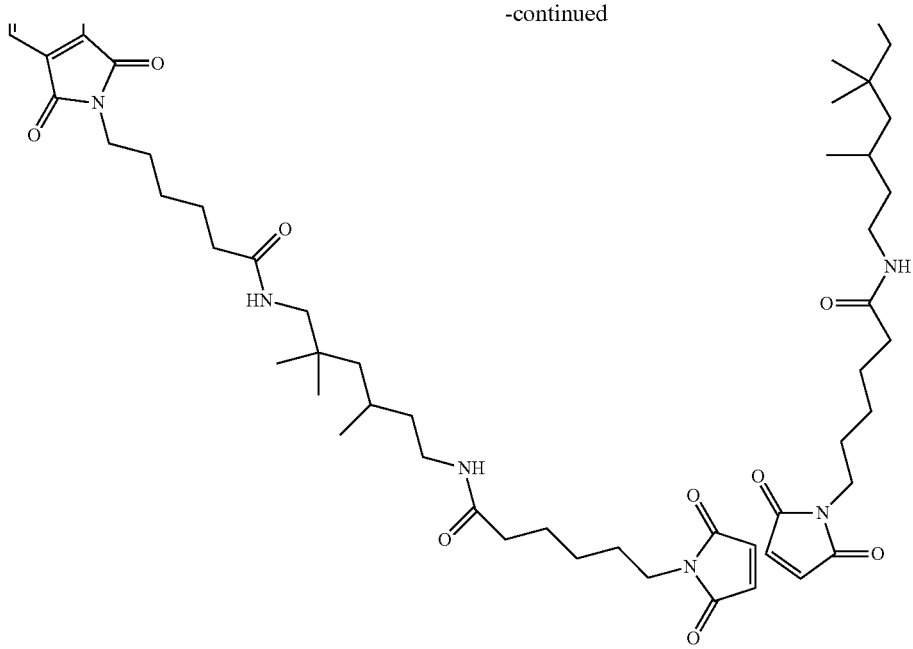

-continued

Procedure:

A 2-L reaction flask, equipped with a Teflon-coated stir bar, and reflux condenser was assembled. To the flask was added 300 mmol (65.4 g) of pyromellitic dianhydride along with 100 mmol (52.0 g) of bisphenol-A dianhydride. A solvent mixture was added to the flask composed of 500 g of NMP and 150 g of toluene. The mixture was stirred until the solids were completely dissolved. This was followed by the addition of 50 g of anhydrous methanesulfonic acid. Slowly, 300 mmol (160.8 g) of Versamine-552 was added to the stirred mixture using a dropping funnel over 30 minutes to form the polyamic acid. A Dean-Stark trap was attached to the flask and the material was heated to reflux to remove the water that is condensed in the reaction. After 3 hours of reflux the solution was cooled down and 200 mmol (26.2 g) of 6-aminocaproic acid was added to the flask. The solution was heated again to reflux for 3 hours to azeotrope the water from the imidization reaction. Once the water stops coming off, the heat is turned off and the solution is cooled down below boiling. At this point 200 mmol (42.0 g) of TMDI is added to the solution, and heated to reflux. The $CO_2$ generated in the reaction is observed by attaching an oil bubbler to the reflux condenser. After several hours of reflux, the $CO_2$ stops being generated signaling the end of the reaction. The solution is cooled once again and 250 mmol (52.7 g) of 6-maleimidocaproic acid is added to the solution. The solution was then heated to reflux overnight to complete the amide formation. The cooled solution was transferred to a dropping funnel and slowly added to 2 gallons of stirred acetone to precipitate the solid product. The solid was filtered through a Buchner funnel and washed with acetone to wash out any remaining NMP and acid. The solid was then placed in an oven at 40° C. to dry the product. Approximately 300 g of product was isolated, which was about an 84% yield.

Example 23

Polypropylene and Polyethylene Compounds with Pendent Maleimides

Westlake Chemical Corporation and other companies offer several different maleated polyethylene and maleated polypropylene compounds. These are relatively low molecular weight polymers that may have branching to help solubility and also have different amounts of maleic anhydride reacted with them to give the maleated product. These maleated polyolefins can be used as very hydrophobic, low modulus substrates to produce compounds with pendent maleimide groups.

Figure 4:
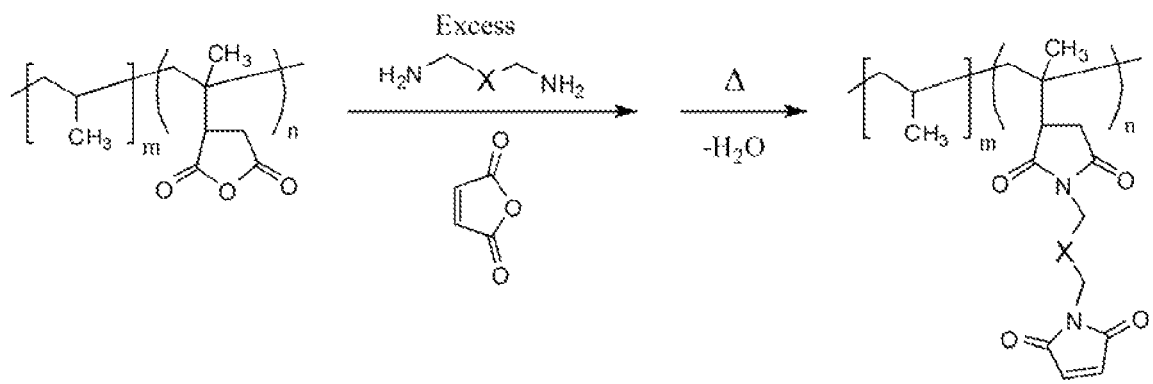
FIG. 4 illustrates the synthesis of polymaleimide of polypropylene-graft-maleic anhydride.

In one specific case a polypropylene-graft-maleic anhydride was used that was purchased from Aldrich. This material has an average molecular weight $M_W$ of approximately 9100, and is approximately 10% maleated. The material, which is supplied in pellet form, was dissolved in a mixture of toluene and NMP and was converted to the maleimide (FIG. 4) according to the following procedure.

Procedure:

A 1-L reaction flask equipped with a Teflon-coated stir bar, Dean-Stark trap and condenser was assembled. To the flask was added 50 g of the polypropylene-graft-maleic anhydride along with 400 mL of toluene and 100 mL of NMP. The mixture was heated to 50-60° C. and stirred on a hot plate to completely dissolve the polymer. Once the polymer was dissolved, 100 mmol of Versamine-552 (53.6 g, which was a large excess based on the number of equivalents anhydride present) was added to the flask and stirred to form the polyamic acid. The solution was heated to reflux for two hours to remove the small amount of water produced in the reaction (<1 mL). The solution was cooled down below 50° C. and 200 mmol (19.6 g) of maleic anhydride was added to the flask along with 10 g of anhydrous methanesulfonic acid. The solution was heated to reflux overnight to complete the conversion to the maleimide. After 16 hours of reflux, approximately 4 mL of additional water and NMP was collected in the Dean-Stark trap. The solution was cooled down, and transferred to a dropping funnel. The solution was slowly added to 2-L of stirred acetone to precipitate the product. The mixture was filtered through a Buchner funnel and the solid was continually washed with acetone to remove all impurities. Approximately 52 g of a white powder was collected after drying in the oven at 50° C. overnight.

Figure 5:
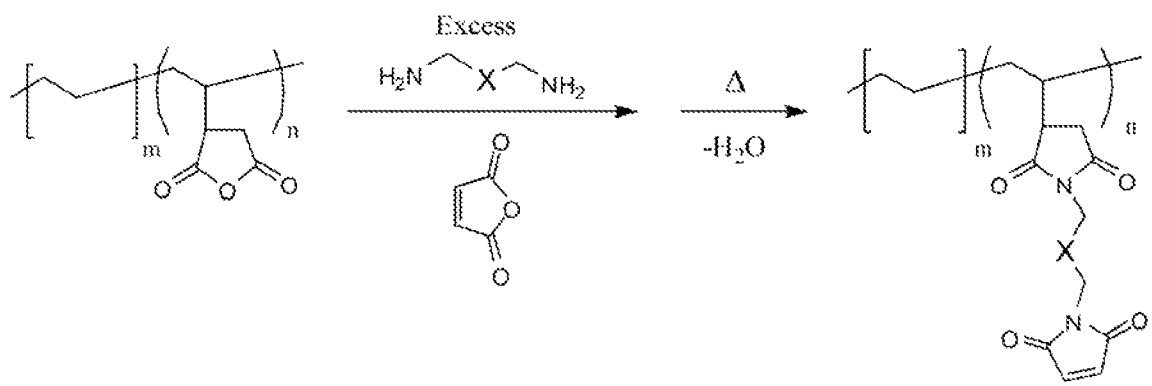
FIG. 5 illustrates the synthesis of polymaleimide of polyethylene-graft-maleic anhydride.

The Epolene®Polymers from Westlake Chemical Corporation were used for some polyethylene derivatives. The compound used was Epolene®C-19, which is a medium molecular weight highly branched polyethylene-grafted-maleic anhydride. The average molecular weight of the C-19 resin $M_W$ is approximately 13000, and the material has an acid number of 5. The material was converted to the maleimide derivative (FIG. 5) according to the following procedure.

Procedure:

Epolene®C-19 (50 g) was dissolved in 400 mL of toluene and 100 mL of NMP in a 1-L reaction flask equipped with a Teflon-coated stir bar, a Dean-Stark trap and a condenser. To the flask was added 50 mmol (26.8 g, again a large excess) of Versamine-552. The solution was heated to reflux for 2 hours to remove the small amount of water formed during the imidization process (<0.5 mL). The solution was cooled down below 50° C. and 100 mmol (9.8 g) of maleic anhydride was added to the flask along with 10 g of anhydrous methanesulfonic acid. The solution was again heated to reflux overnight to complete the maleimide synthesis. After 16 hours of reflux approximately 2 mL of water had been collected in the Dean-Stark trap. The solution was allowed to cool down and then was transferred to a dropping funnel. The solution was slowly added to 2-L of stirred acetone to precipitate the product. The mixture was filtered through a Buchner funnel and the solid was washed several times with acetone to remove any impurities. The solid was then dried in an oven at 50° C. overnight. Approximately 48 g of a white powder was recovered after drying.

The following EXAMPLES show the synthetic procedures that were used to prepare certain compounds of the present invention. It will be understood by those skilled in the art that the Michael addition extension of a di-functional ethylenically unsaturated compound with a diamine will generate a statistical distribution of products. The structure shown for each of these cases is a representative molecule that may be obtained as part of that distribution. The structures shown for EXAMPLES 24-37, 40, 50, and 54-58 are all model compound representations of compounds that may be found within the statistical distribution. Compounds that are produced by the reaction of one equivalent of a mono-functional ethylenically unsaturated compound with one equivalent of a diamine or the reaction of one equivalent of a di-functional ethylenically unsaturated compound with one equivalent of a mono-amine will not generate a distribution of compounds, but only a discreet, single compound (or isomers thereof). The structures shown for EXAMPLES 38, 39, 41-49, 51, and 52 are representations of the exact molecule generated (or an isomer thereof). The reaction of a large excess of a di-functional ethylenically unsaturated compound with a monoamine will generate a distribution of three possible molecules. The predominant species for the one EXAMPLE of this (EXAMPLE 53) is shown.

Example 24

Synthesis of Compound 1

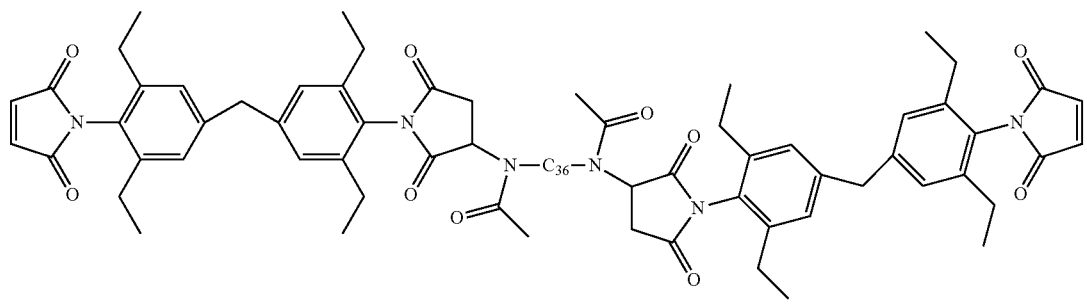

Maleic anhydride (21.6 g, 220 mmol) was dissolved in toluene (150 ml). To this solution was added methylene-1,1-bis(2,6-diethylaniline) (Lonzacure®, 31 g, 100 mmol available from Lonza Group of Switzerland) over a 10 minute period. The solution appeared orange immediately, then changed to a cherry red as the diamine continued to be added. The solution then became bi-phasic with the lower phase becoming a thick amber liquid and then setting up to a purple-gray solid. Methanesulfonic acid (2.5 g) was added. The solution was refluxed for about 90 minutes and 3.6 ml water was collected in a Dean-Stark trap. The reaction solution at this point appeared yellow-orange. The solution was washed with sodium bicarbonate, then treated with $MgSO_4$ and passed over $SiO_2$. Removal of toluene by rotary evaporation afforded the corresponding bismaleimide in 96% yield. The BMI compound was subjected to thermogravimetric analysis (TGA). The retained weight at 300° C. (TGA ramp rate=10° C./min., air purge) was 98.1% and the decomposition onset was at 525° C. Infrared spectrum included absorptions at 3472, 3098, 2968, 1708, 1600, 1475, 1375, 1150, 1060, 826, and 691 wavenumbers.

The bismaleimide obtained as described above (18.8 g, 40 mmol) and toluene (50 ml) were placed in a 250 ml flask and heated to about 85° C. The mixture was bi-phasic. Versamine® 552 available from Cognis Corp. of Cincinnati, Ohio (10.7 g, 20 mmol) was added dropwise and the solution was stirred for one hour at 75° C. The solution appeared light pink, but was clear and homogeneous. Acetic anhydride (5.1 g, 50 mmol) was added and the solution was stirred at 75° C. for 0.5 hours.

Toluene was removed by rotary evaporation followed by air sparge at 90° C. The reaction product was then dried in an oven at 100° C. for three days. The retained weight via TGA at 300° C. (TGA ramp rate=10° C./min, air purge) was 99.2%, and the decomposition onset was at 437.3° C. Fourier Transform Infrared Spectroscopy (FTIR) was performed on the final compound and it was found to have major absorptions at 2926, 1711, 1648, 1475, 1376, 1153, 829, and 692 wavenumbers.

Example 25

Synthesis of Compound 2

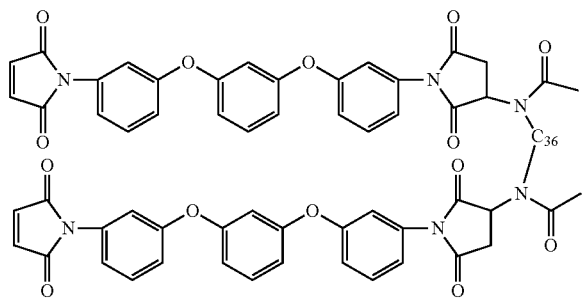

The bismaleimide 1,3-bis(3-maleimidophenoxy)benzene (available from Mitsui Corp. of Japan, 22.6 g, 50 mmol) was dissolved in toluene (50 ml). Versamine® 552 (13.4, 25 mmol) was added over a 15 minute period and the solution was refluxed for one hour. Acetic anhydride (5.1, 50 mmol) was added and the mixture was refluxed for an additional hour. The toluene was removed by rotary evaporation and sparging and the product was then dried in an oven for 4 days at 80° C. The retained weight via TGA at 300° C. (TGA ramp rate=10° C./min, air purge) was 98.9%, and the decomposition onset was at 426° C. An FTIR was run on the final compound and it was found to have major absorptions at 2925, 2853, 1717, 1590, 1479, 1381, 1241, 1150, 827, and 698 wavenumbers.

Example 26

Synthesis of Compound 3

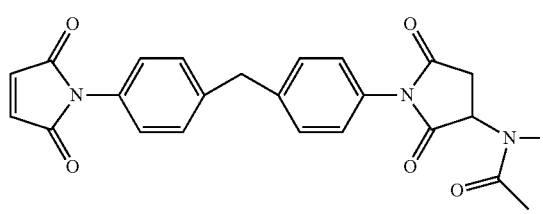

The bismaleimide described in EXAMPLE 1 (11.8 g, 25 mmol) and methylene-1,1-bisphenylmaleimide (8.9 g, 25 mmol; Sigma-Aldrich, St Louis) were dissolved in refluxing toluene (100 ml). The mixture was cooled to 50° C. and Versamine® 552 (13.4 g, 25 mmol) was added over a 10 minute period. The mixture was refluxed for one hour. Acetic anhydride (5.1 g, 50 mmol) was added and the mixture was refluxed for an additional hour. The toluene was removed by rotary evaporation and sparging and the product was dried for 4 days at 80° C. The decomposition onset C (TGA, ramp rate=10° C./min, air purge) was at 429.3° C. An FTIR was run on the final compound and it was found to have major absorptions at 2923, 1713, 1623, 1377, 1153, 828, and 692 wavenumbers.

Example 27

Synthesis of Compound 4

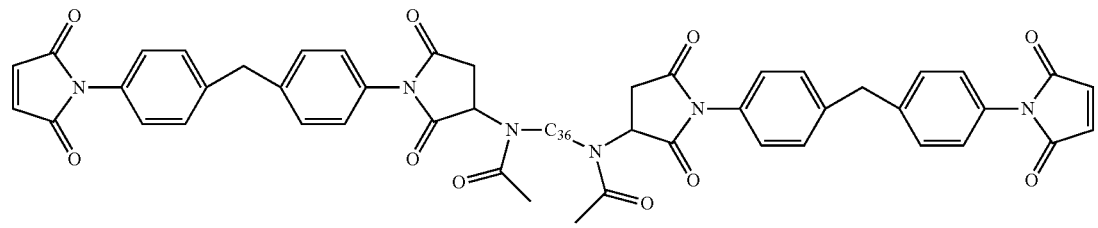

Methylene-1,1-bisphenylmaleimide (17.9 g, 50 mmol) was dissolved in toluene (100 ml). To this solution was added Versamine® 552 (13.4 g, 25 mmol) over a 15 minute period. The mixture was refluxed for one hour, followed by addition of acetic anhydride (5.1 g, 50 mmol). This new mixture was refluxed for one hour. Toluene and acetic acid were removed by rotary evaporation followed by air sparge. The viscous reaction product was transferred to a bowl and dried in an oven at 80° C. for three days. The final product appeared as a yellow glassy solid. The retained weight via TGA at 300° C. (TGA ramp rate=10° C./min., air purge) was 97.8%, and the decomposition onset was at 416.2° C. An FTIR was run on the final compound and it was found to have major absorptions at 3282, 2923, 2854, 1712, 1606, 1513, 1393, 1148, 828, and 691 wavenumbers.

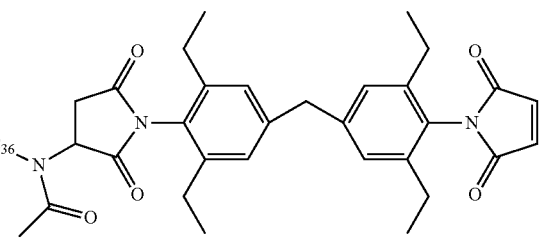

Example 28

Synthesis of Compound 5

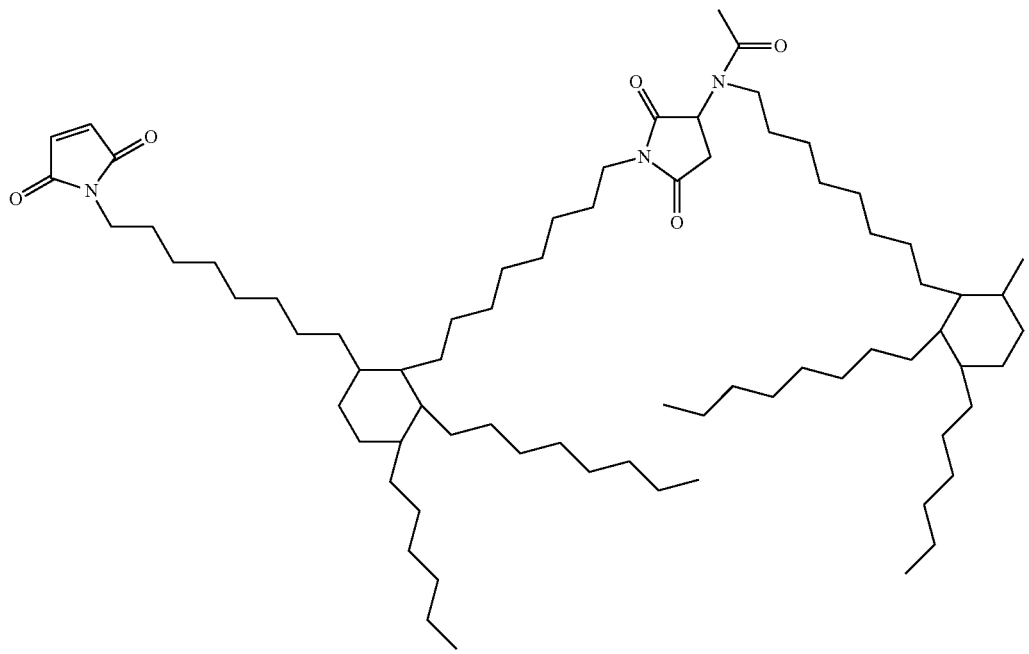

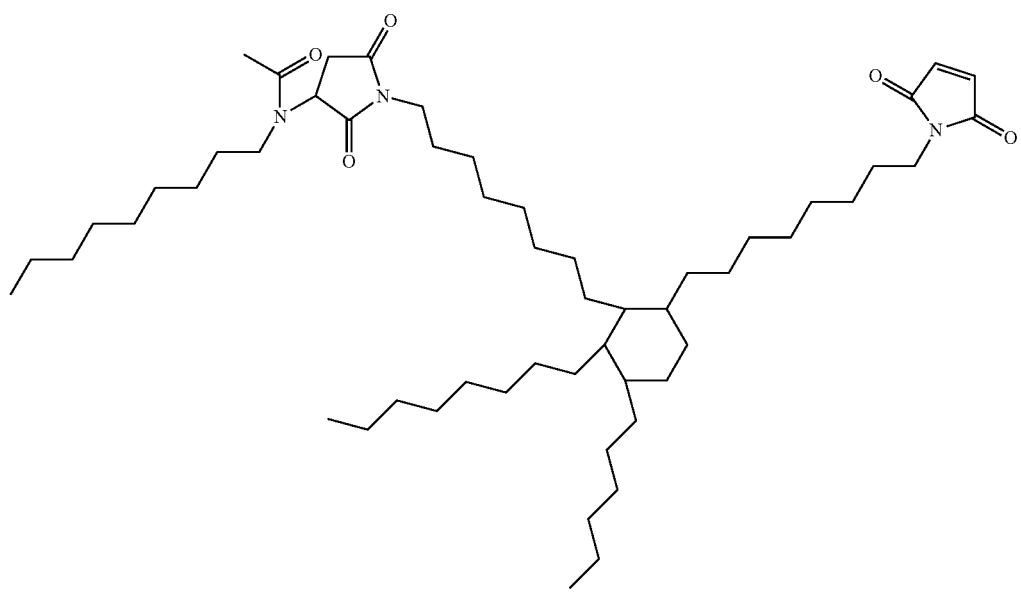

A 250 ml, 1-neck flask was charged with 34.75 g (50 mmol) of the dimer diamine bismaleimide monomer (also known as X-BMI—see EXAMPLE 36) and 25 ml toluene. This mixture was stirred at room temperature and 13.4 g (25 mmol) Versamine® 552 was dripped in over about 15 minutes. A slight exotherm was noted (the solution temperature rose by 9° C.). Another 25 ml toluene was added and this mixture was allowed to stir at room temperature overnight (13.5 hours). The flask was then charged with 5.1 g (50 mmol) acetic anhydride (another exotherm was noted), and this new mixture was stirred for another 4.5 hours at room temperature. The toluene and acetic acid co-product were then removed via rotary evaporation followed by an air sparge to yield 50.12 g (99.8% of theory) of a very viscous, tacky, clear amber liquid. The retained weight for the neat monomer via TGA at 300° C. (TGA ramp rate=10° C./min., air purge) was 100.0%, and the decomposition onset was at 451.8° C. A DSC (differential scanning calorimeter) run was conducted (ramp rate=10° C./min., air purge) on a sample of this material that was catalyzed with 2% by weight dicumyl peroxide. A cure exotherm was observed to occur with an onset of 135.4° C., a cure maxima at 152.5° C. and a cure energy of 74.2 J/g An FTIR was run on the final compound and it was found to have major absorptions at 2926, 2856, 1706, 1649, 1440, 1366, 1139, 827, and 696 wavenumbers.

Example 29

Synthesis of Compound 6

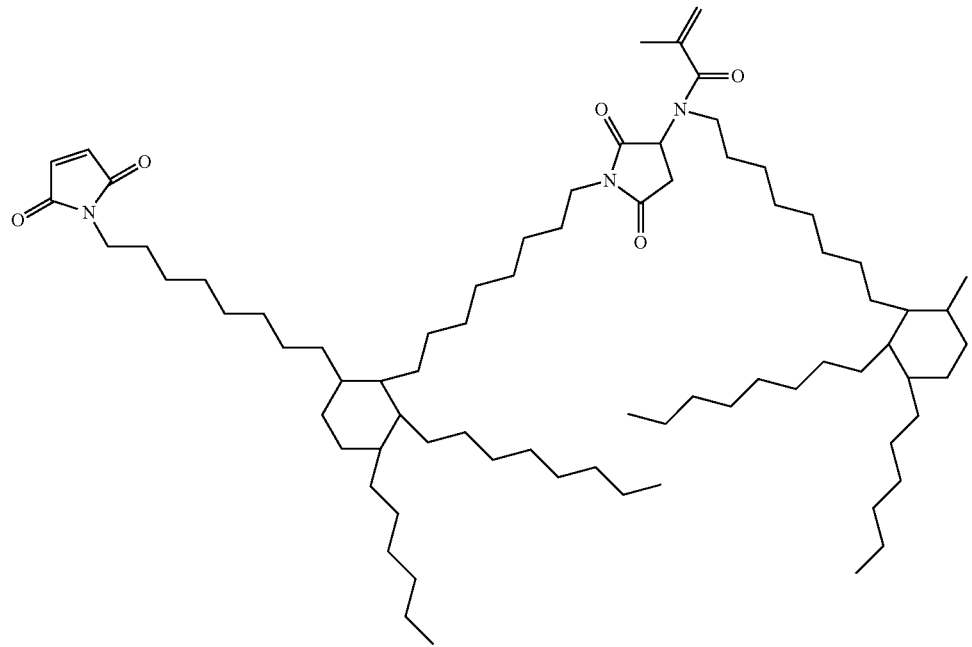

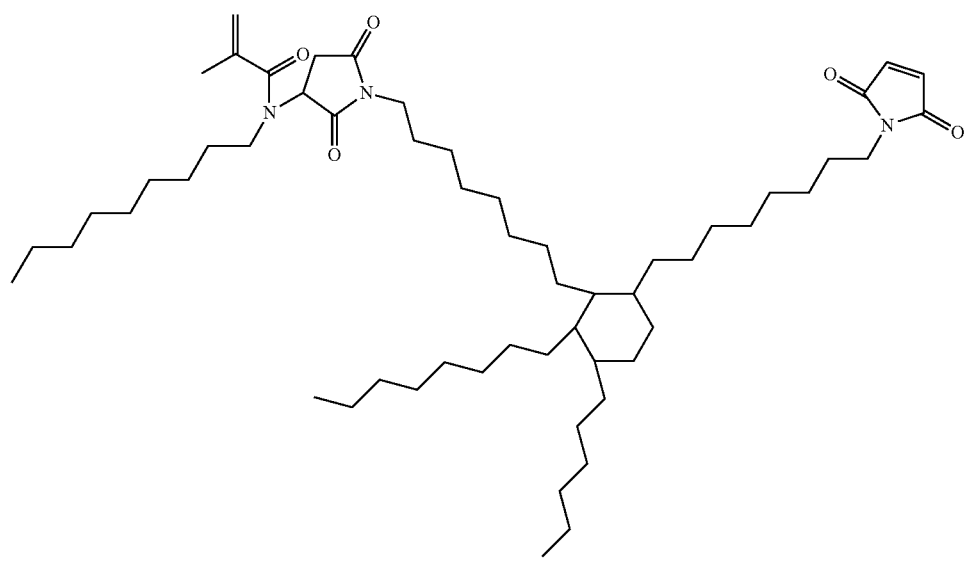

A 250 ml, 1-neck flask was charged with 34.75 g (50 mmol) of the dimer diamine bismaleimide monomer and 25 ml toluene. This mixture was stirred at room temperature and 13.4 g (25 mmol) Versamine® 552 was dripped in over about 15 minutes. Another 25 ml toluene was added and this mixture was allowed to stir at room temperature overnight (15.5 hours). The flask was then charged with 7.7 g (50 mmol) methacrylic anhydride (a mild exotherm was noted), and this new mixture was stirred for another 6 hours at room temperature. The toluene and methacrylic acid co-product were then removed via rotary evaporation and sparging to yield 51.31 g (99.6% of theory) of a very viscous, tacky, clear amber liquid. The retained weight for the neat monomer via TGA at 300° C. (TGA ramp rate=10° C./min, air purge) was 97.5%, and the decomposition onset was at 455.0° C. A DSC was conducted (ramp rate=10° C./min., air purge) on a sample of this material catalyzed with 2% by weight dicumyl peroxide. A cure exotherm was observed to occur with an onset of 136.3° C., a cure maxima at 153.0° C. and a cure energy of 98.3 J/g An FTIR was run on the final compound and it was found to have major absorptions at 2923, 2854, 1709, 1625, 1440, 1405, 1366, 1134, 826, and 696 wavenumbers.

Example 30

Synthesis of Compound 7

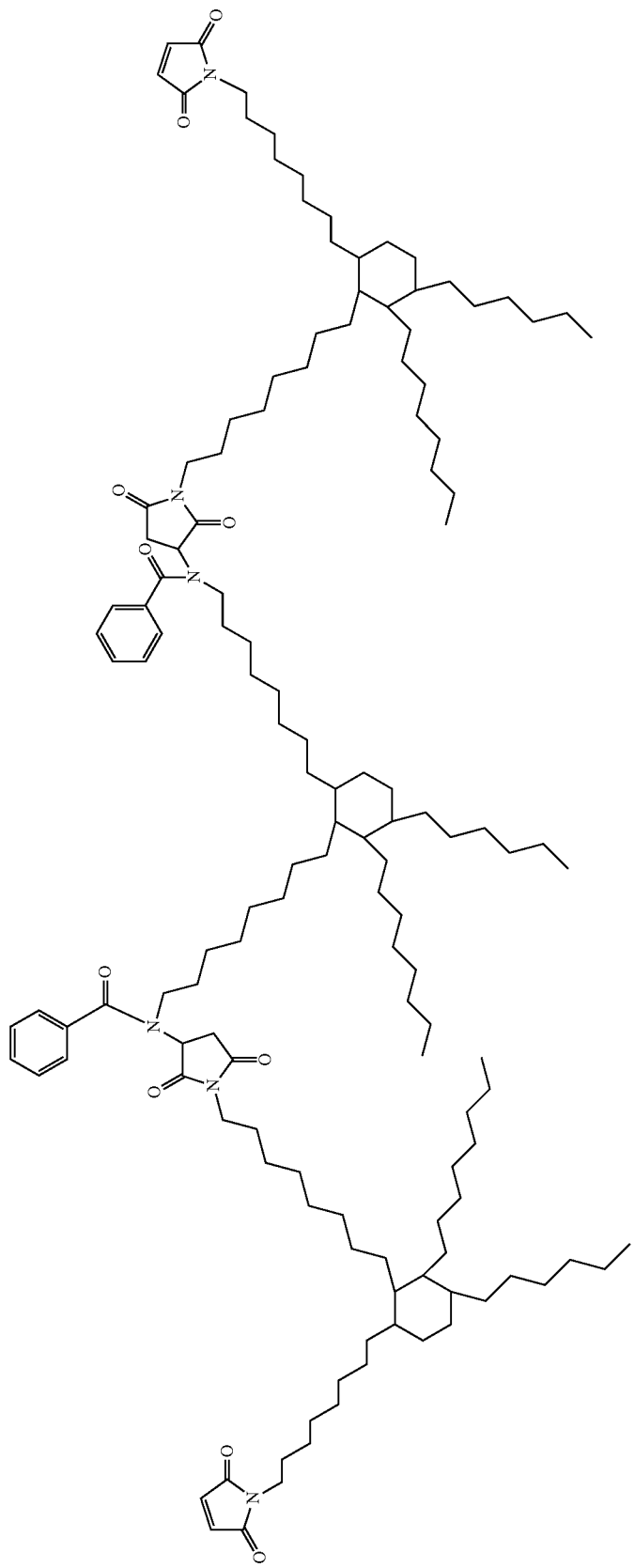

A 500 ml, 1-neck flask was charged with 34.75 g (50 mmol) of the dimer diamine bismaleimide monomer and 25 ml toluene. This mixture was stirred at room temperature and 13.4 g (25 mmol) Versamine® 552 was dripped in over about 15 minutes. Another 25 ml toluene was added and this mixture was allowed to stir at room temperature overnight (14 hours). The flask was then charged with 5.9 g (55 mmol) 2,6-lutidine along with another 125 ml toluene. The mixture was stirred while benzoyl chloride (7.03 g, 50 mmol) was dripped in over a 15 minutes. The mixture was stirred at room temperature for another 3.5 hours. The toluene phase was then extracted with 3×25 ml deionized water and 2×25 ml brine. The filtrate was dried with 10 g $MgSO_4$ and then passed over a bed of 20 g silica gel. The toluene then removed via rotary evaporation followed by an air sparge to yield 48.34 g (90.6% of theory) of a viscous, clear amber liquid. The retained weight for the neat monomer via TGA at 300° C. (TGA ramp rate=10° C./min., air purge) was 98.7%, and the decomposition onset was at 467.9° C. A DSC was conducted (ramp rate=10° C./min., air purge) on a sample of this material that was catalyzed with 2% by weight dicumyl peroxide. A cure exotherm was observed to occur with an onset of 135.5° C., a cure maxima at 151.3° C. and a cure energy of 79.6 J/g An FTIR was run on the final compound and it was found to have major absorptions at 2924, 2855, 1704, 1634, 1440, 1406, 1372, 1137, 827, and 696 wavenumbers.

Example 31

Synthesis of Compound 9 (SD13-86)

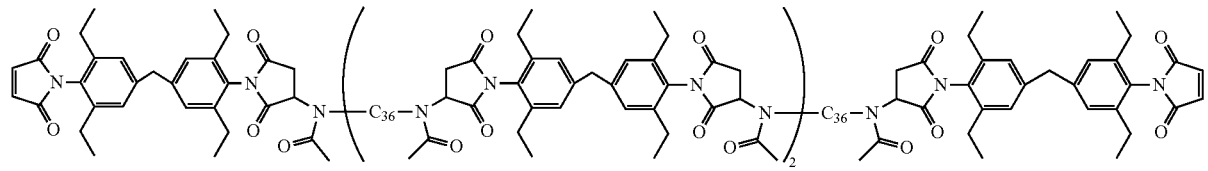

The bismaleimide described in EXAMPLE 1 (18.8 g, 40 mmol) was dissolved in toluene (100 ml) and Versamine® 552 (16 g, 30 mmol) was added over a 15 minute period. The mixture was refluxed for one hour. The mixture was cooled to 80° C. and acetic anhydride (6.1 g, 60 mmol) was added, followed by reflux for an additional hour. Toluene and acetic acid were removed by rotary evaporation and sparging. The viscous reaction product was transferred to a bowl and dried in an oven at 80° C. for three days. The final product was a friable glass at room temperature. The retained weight via TGA at 200° C. (TGA ramp rate=10° C./min, air purge) was 97.5%, and the decomposition onset was at 414.1° C. An FTIR was run on the final compound and it was found to have major absorptions at 2923, 2853, 1713, 1649, 1467, 1376, 1190, 829, and 693 wavenumbers.

Example 32

Synthesis of Compound 10

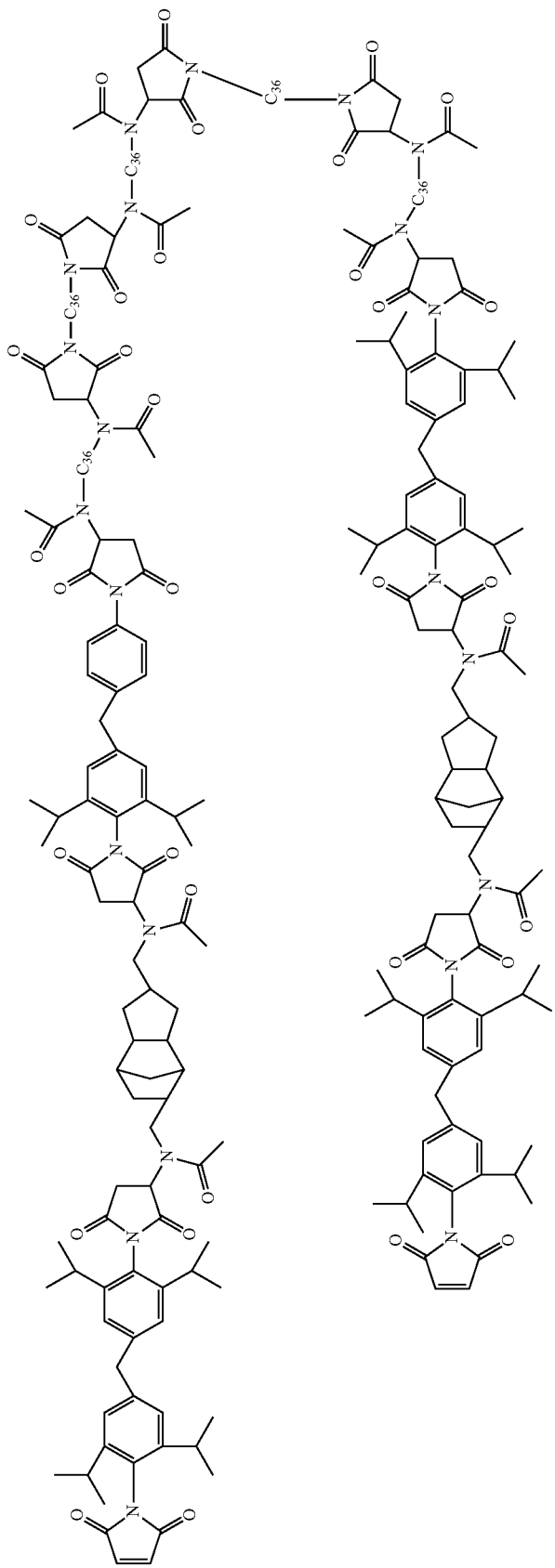

Maleic anhydride (21.6 g, 220 mmol) was dissolved in toluene (150 ml). To this solution was added methylene-1,1-bis(2,6-diethylaniline) (Lonzacure®, 36.7 g, 100 mmol) over a 10 minute period. Methanesulfonic acid (2.5 g) was added and the solution was refluxed for about 3 hours while the expected 3.6 ml water was collected in a Dean-Stark trap. The reaction solution at this point appeared amber. The solution was washed with sodium bicarbonate, then treated with MgSO$_4$ and passed over SiO$_2$. Removal of toluene by rotary evaporation followed by oven drying at 85° C. afforded the corresponding bismaleimide (51.1 g) in 97% yield. The retained weight via TGA at 200° C. (TGA ramp rate=10° C./min, air purge) was 99.3%, and the decomposition onset was at 488.9° C. An FTIR was run on this bismaleimide and it was found to have major absorptions at 3473, 2964, 1710, 1602, 1473, 1392, 1152, 829, 731 and 691 wavenumbers.

Versamine® 552 (16.1 g, 30 mmol) and the bismaleimide of dimerdiamine (13.9 g, 20 mmol) were each dissolved in toluene (25 ml each). The dimer diamine bismaleimide solution was added to the Versamine® solution dropwise at ambient temperature over a 15 minute period. Next, the bismaleimide obtained as described above in this EXAMPLE (21 g, 40 mmol) was dissolved in toluene and added to a toluene solution of TCD diamine (available from Celanese Corporation of Dallas, Tex., 3.9 g, 20 mmol). This mixture was allowed to stir at ambient temperature for one hour. The Versamine® solution was then combined with the bismaleimide solution, and this new mixture was stirred with slight warming for 45 minutes. Acetic anhydride (10.2 g, 100 mmol) was added and the reaction was allowed to stir overnight. Some solids had separated so the solution was filtered, the toluene and acetic acid removed by rotary evaporation. The red, rubbery product was dried in an oven at 80° C. for three days. The retained weight via TGA at 300° C. (TGA ramp rate=10° C./min., air purge) was 99.4%, and the decomposition onset was at 413.8° C. An FTIR was run on the final compound and it was found to have major absorptions at 2923, 2854, 1706, 1650, 828, 728 and 696 wavenumbers.

Example 33

Synthesis of Compound 11

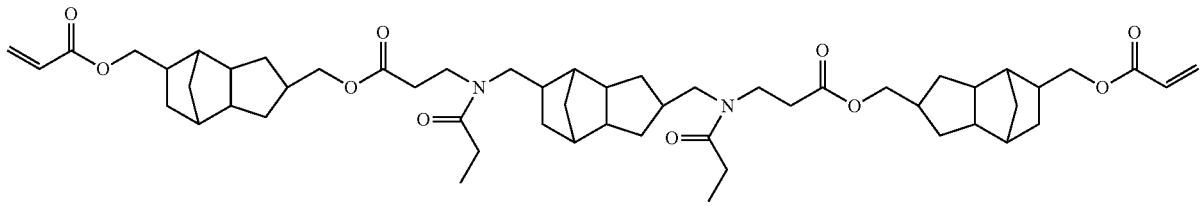 [SMILES: C=CC(=O)OCC1CC2CC1C1CC(COC(=O)CCN(CC3CC4C5CC(CN(CCC(=O)OCC6CC7C8CC(COC(=O)C=C)C(C8)C7C6)C(=O)CC)C(C5)C4C3)C(=O)CC)CC21]

The diacrylate of tricyclodecane dimethanol (SR833S available from Sartomer Company, Inc. of Exton, Pa., 30.4 g, 100 mmol) was placed in a 125 ml flask and stirred in an oil bath at about 85° C. for 10 minutes. Tricyclodecyl diamine (9.7 g, 50 mmol) was added dropwise over a 10 minute period. The solution was then stirred at about 85° C. for one hour. The mixture was cooled and propionic anhydride (13 g, 100 mmol) was added in portions. The mixture was then sparged at 70° C. for two hours, affording the product as a viscous, colorless liquid. The retained weight for the neat compound via TGA at 300° C. (TGA ramp rate=10° C./min., air purge) was 96.2%, and the decomposition onset was at 403.1° C. An FTIR was run on the final amide extended acrylate monomer and it was found to have major absorptions at 2943, 1721, 1641, 1407, 1266, 1179, 1051, 982, and 810 wavenumbers.

Example 34

Synthesis of Compound 12

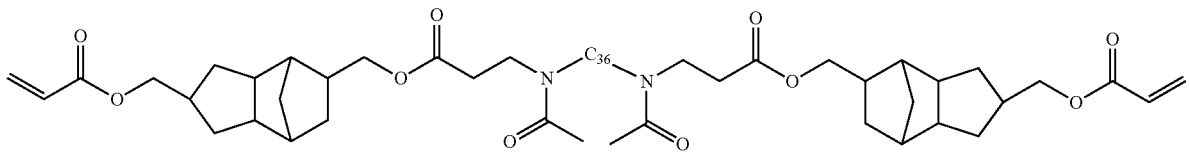

Sartomer's SR 833S (30.4 g, 100 mmol) was placed in a 250 ml flask. To the flask was added Versamine® 552 (26.8 g, 50 mmol) in a small amount of toluene. This mixture was then placed on a rotary evaporator at 65° C. for 30 minutes. Acetic anhydride (10.2 g, 100 mmol) was added and the mixture remained on the rotary evaporator for an additional 90 minutes 70-75° C. Residual toluene and acetic acid were removed by sparging, affording the product as a viscous, colorless liquid. The retained weight for this amide-extended diacrylate compound via TGA at 300° C. (TGA ramp rate=10° C./min., air purge) was 98.1%, and the decomposition onset was at 422° C. An FTIR was run on this monomer and it was found to have major absorptions at 2924, 2854, 1726, 1650, 1461, 1406, 1266, 1183, 1054, 983, and 810 wavenumbers.

Example 35

Synthesis of Compound 13

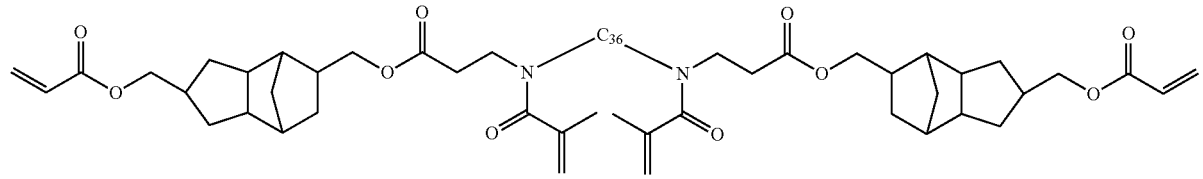

A 250 ml flask was charged with Sartomer's SR 833S (30.4 g, 100 mmol). To the flask was added Versamine® 552 (26.8 g, 50 mmol) in a small amount of toluene. This mixture was then placed on a rotary evaporator at 80° C. for 150 minutes. Methacrylic anhydride (15.4 g, 100 mmol) was added (a mild exotherm was noted) and the mixture was kept on the rotary evaporator and rotated for an additional 120 minutes at 65° C. Toluene (100 ml) was added and the solution was then charged with 15 g $NaHCO_3$ and 3 g $H_2O$. This mixture was stirred until $CO_2$ evolution ceased. The flask was then charged with 8 g $MgSO_4$ and stirred for another half hour. The mixture was then passed over a bed of 20 g silica gel, and the solids were rinsed with additional toluene. The toluene was then removed by rotary evaporation followed by sparging. The product was recovered as a clear, light yellow, viscous, liquid. The compound weighed 58.1 grams (91% of theory). The retained weight for this methacrylamide-extended diacrylate compound via TGA at 300° C. (TGA ramp rate=10° C./min., air purge) was 98.4%, and the decomposition onset was at 441° C. An FTIR was run on this monomer and it was found to have major absorptions at 2921, 1726, 1625, 1464, 1268, 1187, 1054, 983, 910, and 810 wavenumbers.

Example 36

Synthesis of Compound 16

Maleic anhydride (21.6 g, 220 mmol) was dissolved in toluene (150 ml). To this solution was added methylene-1,1-bis(2,2'-dimethyl-6,6'-diisopropylaniline) (Lonzacure®, 31.0 g, 100 mmol) dropwise over a 10 minute period. The solution appeared red and then bi-phasic. Methanesulfonic acid (2.5 g) was added and the solution was refluxed for about 3 hours while the expected 3.6 ml water was collected in a Dean-Stark trap. The reaction solution now appeared amber. The solution was washed with sodium bicarbonate, then treated with $MgSO_4$ and passed over $SiO_2$. Removal of toluene by rotary evaporation followed by oven drying at 85° C. afforded the corresponding bismaleimide (51.1 g) as yellow-white crystals in 94% yield. The retained weight for this bismaleimide via TGA at 300° C. (TGA ramp rate=10° C./min, air purge) was 98.3%, and the decomposition onset was at 515.7° C. An FTIR was run on this monomer and it was found to have major absorptions at 3472, 3101, 2964, 1711, 1601, 1482, 1376, 1153, 828, 726, and 691 wavenumbers.

Versamine® 552 (40 g, 75 mmol) and n-dibutyl isophthalate (13.9 g, 50 mmol) were placed in a 250 ml flask and heated with stirring to 160-175° C. Toluene (100 ml) and the bismaleimide obtained as described above in this EXAMPLE (23.5 g, 50 mmol) were added to the flask and the mixture was allowed to reflux for one hour. Propionic anhydride (6.5 g, 50 mmol) was added and the mixture was refluxed for an additional 1.25 hours. The mixture appeared as an intensely red, clear solution. Removal of toluene by rotary evaporation and sparging followed by oven drying afforded the product as a red-brown taffylike material. The retained weight for this amide-extended bismaleimide compound via TGA at 300° C. (TGA ramp rate=10° C./min, air purge) was 96.9%, and the decomposition onset was at 450.5° C. An FTIR was run on this monomer and it was found to have major absorptions at 3349, 2921, 2853, 1712, 1645, 1462, 1376, 1153, 827, 727, and 692 wavenumbers.

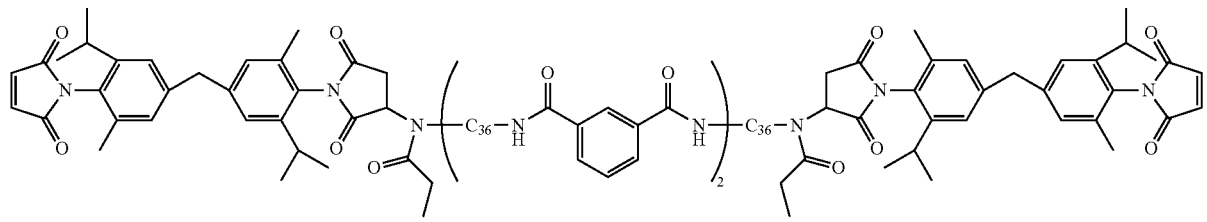

Example 37

Synthesis of Compound 17

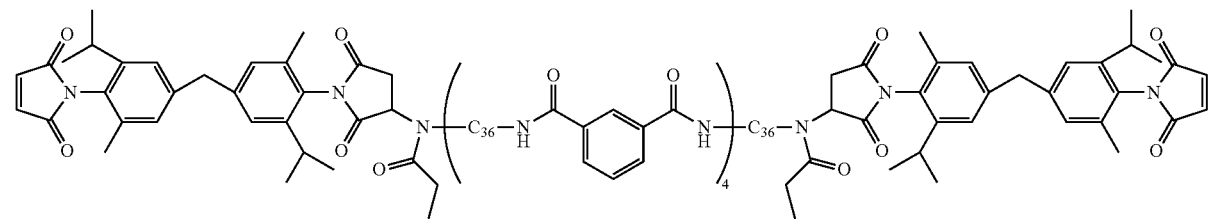

Versamine® 552 (53.6 g, 100 mmol), n-dibutyl isophthalate (22.3 g, 80 mmol), and DMAP (0.25 g) were placed in a 500 ml flask and heated with stirring to 210° C. for 24 hours under an argon purge. Butanol was evolved. The material was quite viscous but could be stirred at 210° C. The mixture was cooled and toluene (100 ml) was added. The bismaleimide obtained as described in EXAMPLE 13 (18.8 g, 40 mmol) was added along with additional toluene (100 ml). This mixture was refluxed for one hour. Propionic anhydride (5.2 g, 40 mmol) was added and the mixture was refluxed for an additional 90 minutes. The solution appeared deep red. Removal of toluene by rotary evaporation and sparging followed by oven drying afforded the product.

Example 38

Synthesis of Compound 18

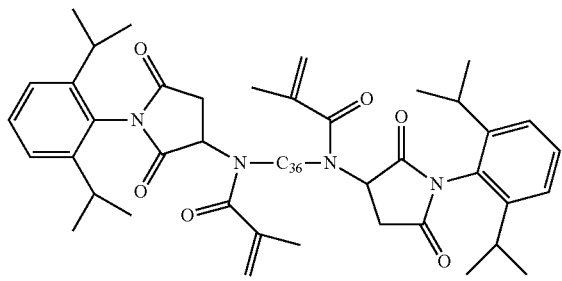

Versamine® 552 (26.8 g, 50 mmol) and toluene (50 ml) were placed in a 250 ml flask. N-2,6-diisopropylphenylmaleimide (25.6 g, 100 mmol) was added over a 10 minute period. The mixture was then refluxed for 19.5 hours. Methacrylic anhydride (15.5 g, 100 mmol) was added and the mixture was refluxed for one hour. The solution was washed with sodium bicarbonate, then treated with $MgSO_4$ and passed over $SiO_2$. Removal of toluene by rotary evaporation followed by oven drying at 85° C. afforded a red liquid (53.7 g) that became a glass upon cooling to room temperature. The retained weight for this bismethacrylamide compound via TGA at 300° C. (TGA ramp rate=10° C./min., air purge) was 94.8%, and the decomposition onset was at 374° C. An FTIR was run on this monomer and it was found to have major absorptions at 2923, 1711, 1650, 1623, 1468, 1377, 1190, 805, and 725 wavenumbers.

Example 39

Synthesis of Compound 42

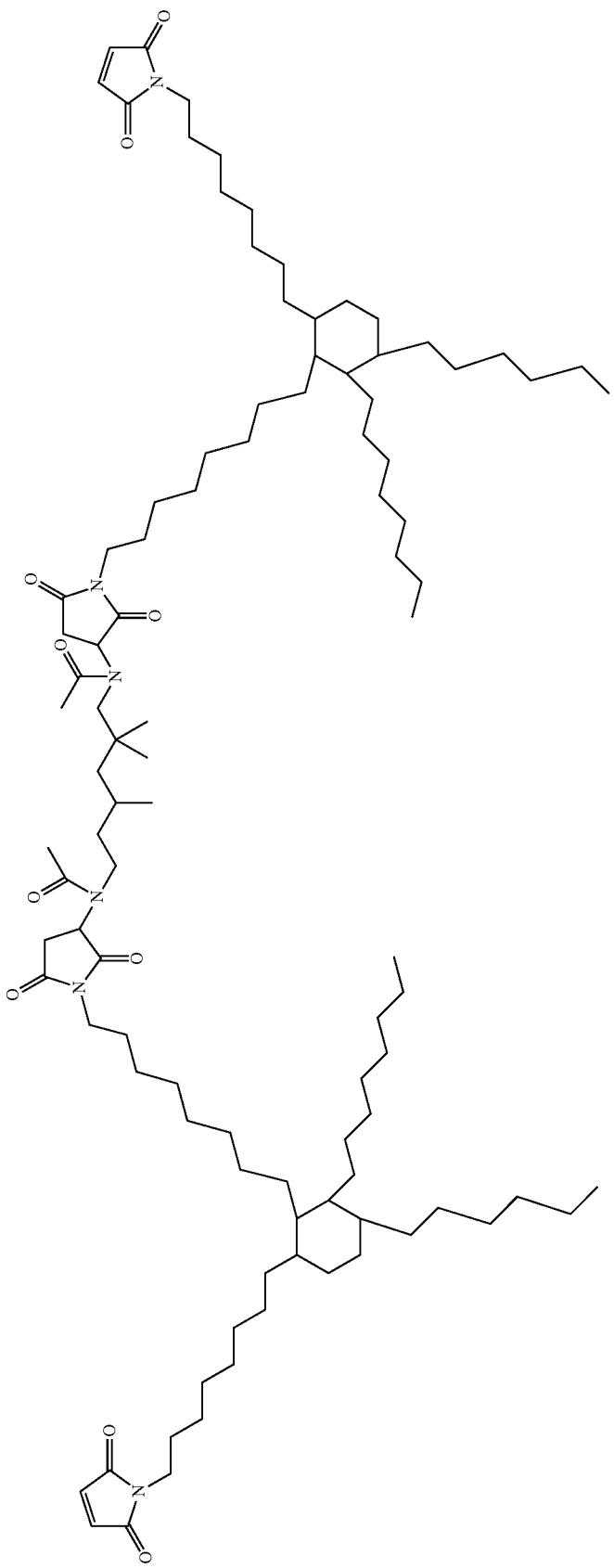

X-BMI (34.75 g, 50 mmol) and toluene (50 ml) was added to a 250 ml flask. Trimethylhexanediamine (TCI America, 3.96 g, 25 mmol) was dripped into this magnetically stirred solution. An exotherm was observed to occur, which resulted in a 6° C. increase in temperature of the solution. Once the amine was completely added, the mixture was rotated in a 65° C. H$_2$O bath for 2 hours. The mixture was allowed to cool and then acetic anhydride (5.1 g, 50 mmol) was dripped in. The flask was then rotated in a 65° C. water bath for another hour. The toluene and acetic acid were removed via rotary evaporation followed by air sparge. The product was a very viscous, clear, amber, liquid. The retained weight via TGA at 300° C. (TGA ramp rate=10° C./min., air purge) was 99.2%, and the decomposition onset was 431.2° C. A DSC was conducted (ramp rate=10° C./min., air purge) on a sample of this material catalyzed with 2% by weight dicumyl peroxide. A cure exotherm was observed to occur with an onset of 136.8° C., a cure maxima at 155.8° C. and a cure energy of 88.0 J/g. An FTIR was run on the final compound and it was found to have major absorptions at 2924, 2851, 1771, 1699, 1650, 1440, 1406, 1366, 1137, 827, and 696 wavenumbers.

Example 40

Synthesis of Compound 20

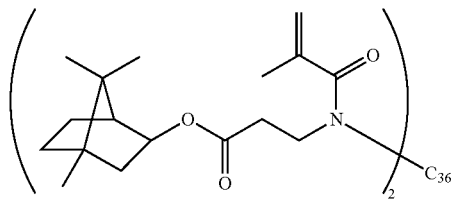

Versamine 552 (56.3 g, 100 mmol), toluene (100 ml), and isobornyl acrylate (41.7 g, 200 mmol) were stirred at 80° C. for 18 hours in a 500 ml flask. An FTIR run on this Michael addition intermediate showed that the absorbances at 1635 and 1619 cm$^{-1}$ had disappeared. Methacrylic anhydride (32.4 g, 210 mmol) was added, which resulted in a mild exotherm. The mixture was then heated and stirred for 1.5 hours at 65° C. The solution was treated with sodium bicarbonate (15 g, along with 3 g water), dried with MgSO$_4$ (10 g) and then passed over silica gel (20 g). The toluene was removed via rotary evaporation followed air sparge. The product was a clear, viscous, light orange liquid that weighed 105.6 g (97.0% of theory). The retained weight for this bismethacrylamide compound via TGA at 300° C. (ramp rate=10° C./min., air purge) was 95.29%, and the decomposition onset was 337.27° C. A DSC was conducted (ramp rate=10° C./min., air purge) on this material with 2% by weight dicumyl peroxide. A cure exotherm was observed to occur with an onset of 155.6° C., a cure maxima at 172.0° C. and a cure energy of 140.8 J/g. An FTIR was run on this monomer and it was found to have major absorptions at 2925, 2853, 1731, 1649, 1626, 1455, 1370, 1311, 1163, 1055, 906, and 723 wavenumbers.

Example 41

Synthesis of Compound 21

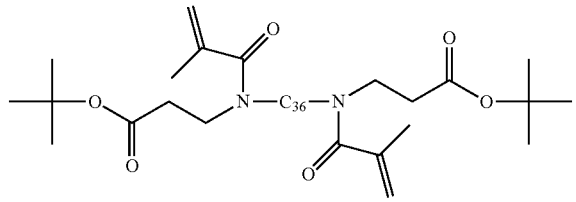

Versamine 552 (56.3 g, 100 mmol) and t-butyl acrylate (25.63 g, 200 mmol), and toluene (100 ml) were placed into a 500 ml flask. There was a mild exotherm that occurred when this mixture was stirred at room temperature. This mixture was then stirred at 80° C. for 4.5 hours. Methacrylic anhydride (30.8 g, 200 mmol) was then added and this new mixture was then heated and stirred for 2 hours at 65° C. The solution was neutralized with sodium bicarbonate (20 g, plus 3 g water). The mix was dried with 10 g MgSO$_4$ and then passed over 20 g SiO$_2$. The toluene was removed using rotary evaporation followed by an air sparge. The product was a light yellow, moderately viscous liquid that weighed 83.63 g. The retained weight for this bismethacrylamide compound via TGA at 200° C. (TGA ramp rate=10° C./min., air purge) was 99.1%, and the decomposition onset was 266.0° C. A DSC was conducted (ramp rate=10° C./min, air purge) on a sample of this material that was catalyzed with 2% by weight dicumyl peroxide. A cure exotherm was observed to occur with an onset of 157.9° C., a cure maxima at 171.2° C. and a cure energy of 114.0 J/g. An FTIR was run on this monomer and it was found to have major absorptions at 2923, 2854, 1729, 1649, 1626, 1456, 1367, 1150, 1055, and 847 wavenumbers.

Example 42

Synthesis of Compound 22

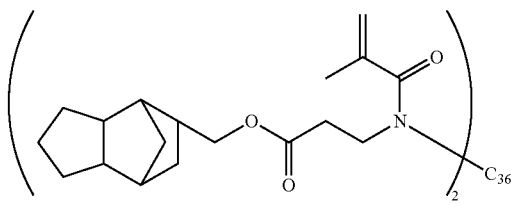

A two-neck, 500 ml flask was charged with TCD Alcohol M (49.87 g, 300 mmol; Celanese Chemicals, Calvert City, Ky.), acrylic acid (23.78 g, 330 mmol), 250 ml heptane, 3.0 g methanesulfonic acid, and 132 mg 4-methoxyphenol. The flask was equipped with a stir bar, Dean Stark trap, air inlet tube, and condenser. This mixture was refluxed under a mild air sparge for 65 minutes. A total of 5.3 ml water (theory=5.4) was collected in the trap. The reaction mixture was cooled, neutralized (45 g sodium bicarbonate plus 3 g water), dried with 10 g MgSO$_4$, and then passed over 20 g silica gel. The solvent was removed via rotary evaporation followed by an air sparge. The product was a clear, light yellow, low viscosity liquid. It weighed 64.3 g (97.3% of theory). An FTIR trace of this compound showed significant absorptions at 2945, 1714, 1638, 1452, 1294, 1161, 1012, 936, and 813 wavenumbers.

A solution of Versamine 552 (56.3 g, 100 mmol) and TCD acrylate (44.12 g, 200 mmol) in 100 ml toluene was stirred in a 500 ml flask at room temperature. A mild exotherm was observed. The mixture was then stirred at 80° C. for 6.0 hours. Methacrylic anhydride (30.8 g, 200 mmol) was added and the new mixture was then heated and stirred for 1.5 hours at 65° C. The solution was neutralized with sodium bicarbonate (15 g, plus 3 g H$_2$O), dried with MgSO$_4$ (10 g) and then passed over silica gel (20 g). The toluene was removed to yield 107.0 g (96.2% of theory) of a viscous, hazy, yellow liquid. The retained weight for this bismethacrylamide compound via TGA at 300° C. (TGA ramp rate=10° C./min., air purge) was 94.6%, and the decomposition onset was 400.4° C. A DSC was run (ramp rate=10° C./min., air purge) on a sample of this material catalyzed with 2% by weight dicumyl peroxide. A cure exotherm was observed to occur with an onset of 150.3° C., a cure maxima at 175.5° C. and a cure energy of 74.8 J/g. An FTIR was run on this monomer and it was found to have major absorptions at 2923, 2855, 1736, 1649, 1626, 1465, 1374, 1308, 1169, 1005, 905, and 722 wavenumbers.

Example 43

Synthesis of Compound 23

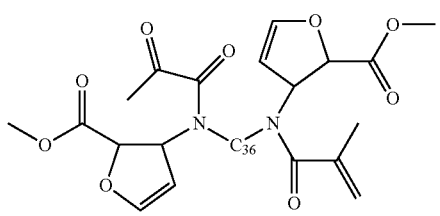

Versamine 552 (9.56 g, 17.8 mmol), methyl-2-furoate (4.51 g, 35.7 mmol), and toluene (50 ml) were stirred in a 125 ml flask. An exotherm was noted. The mixture was then refluxed for 3.0 hours. Methacrylic anhydride (30.8 g, 200 mmol) was added. The mixture was then refluxed for another 2.0 hours. The solution was neutralized with sodium bicarbonate (10 g, plus 4 g water), dried with MgSO$_4$ (10 g) and then passed over silica gel (15.5 g). The toluene was removed to yield 9.14 g (55.6% of theory) of a light yellow liquid. The retained weight for this bismethacrylamide compound via TGA at 300° C. (TGA ramp rate=10° C./min, air purge) was 95.8%, and the decomposition onset was 443.3° C. A DSC was conducted (ramp rate=10° C./min., air purge) on a sample of this material catalyzed with 2% by weight dicumyl peroxide. A cure exotherm was observed to have a cure maxima at 185.2° C. and a cure energy of 56.7 J/g. An FTIR trace run on this monomer revealed major absorptions at 3319, 2920, 2852, 1730, 1655, 1616, 1533, 1456, 1375, 1308, 1219, 1007, 921, and 747 wavenumbers.

Example 44

Synthesis of Compound 24

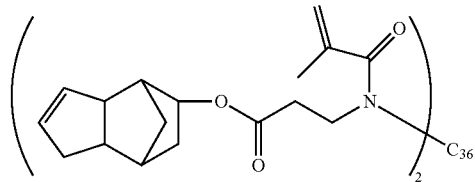

Versamine 552 (26.8 g, 50 mmol), dicyclopentadiene monoacrylate (20.4 g, 100 mmol; Bimax Chemicals, Glen Rock, Pa.), and toluene (100 ml) were stirred together in a 2-neck 500 ml flask. A slight exotherm was noted. This mixture was then stirred at 70° C. overnight. An FTIR spectrum the following morning indicated that the acrylate carbon-carbon double bond was no longer present. Methacrylic anhydride (30.8 g, 200 mmol) was then added, dropwise to the stirred solution. Another exotherm occurred, resulting in a temperature increase of approximately 10° C. The mixture was heated and stirred at 60° C. for 2.5 hours. The mixture was extracted with 5×25 ml of deionized water. The solution was washed with aqueous sodium bicarbonate, dried with MgSO$_4$ (22 g) and then passed over silica gel (20 g). Removal of toluene by rotary evaporation followed by air sparge resulted in the recovery of a clear amber viscous liquid. The product weighed 48.9 g (90.6% of theory). The retained weight for this bismethacrylamide compound via TGA at 300° C. (TGA ramp rate=10° C./min, air purge) was 96.9%, and the decomposition onset was 347.6° C. A DSC was conducted (ramp rate=10° C./min., air purge) on a sample of this material catalyzed with 2% by weight dicumyl peroxide. A cure exotherm was observed to occur with an onset of 154.5° C., a cure maxima at 181.3° C. and a cure energy of 105.0 J/g. An FTIR was run on this monomer and it was found to have major absorptions at 2923, 2853, 1729, 1627, 1463, 1377, 1303, 1178, 1056, 988, 905, 794, and 699 wavenumbers.

Example 45

Synthesis of Compound 25

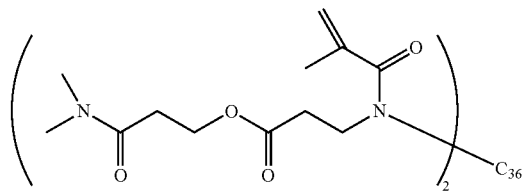

Versamine 552 (53.6 g, 100 mmol), N,N-dimethacryamide (20.0 g, 202 mmol), and toluene (50 ml) were stirred together in a 500 ml flask (again, there was a noticeable exotherm). The mixture was then stirred at 80° C. for 3 hours. Methacrylic anhydride (30.8 g, 200 mmol) was then dripped into this solution, over a span of 30 minutes. The new mixture was then stirred at 80° C. overnight. The mixture was extracted with 50 ml of deionized water and 3×25 ml of brine. The solution was washed with aqueous sodium bicarbonate, dried with MgSO₄ (10 g) and then passed over silica gel (20 g). The toluene was removed by rotary evaporation followed by an air sparge. The product was a clear brown liquid that weighed 76.35 g (87.8% of theory). The retained weight for this bis-methacrylamide compound via TGA at 300° C. (TGA ramp rate=10° C./min, air purge) was 96.5%, and the decomposition onset was 433.2° C. A DSC was run (ramp rate=10° C./min, air purge) on a sample of this material in the presence of 2% by weight dicumyl peroxide. A cure exotherm was observed to occur with an onset of 159.0° C., a cure maxima at 170.8° C. and a cure energy of 141.0 J/g. An FTIR was run on this monomer and it was found to have major absorptions at 2923, 2852, 1622, 1463, 1143, 905, and 723 wavenumbers.

Example 46

Synthesis of Compound 26

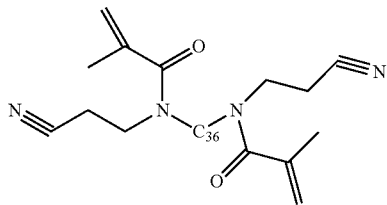

Acrylonitrile (10.61 g, 200 mmol) and Versamine 552 (53.6 g, 100 mmol) were stirred in a 250 ml flask. The mixture was stirred at room temperature. There was no immediate evidence of an exotherm. The flask was charged with 100 ml of toluene and the solution was refluxed for 90 minutes. Methacrylic anhydride (30.8 g, 200 mmol) was added to the mixture and reflux was continued for another hour. The solution was neutralized with sodium NaHCO₃ (20 g plus 8 g H₂O), dried with MgSO₄ (15 g) and then passed over silica gel (25 g). The toluene was removed to yield 67.8 g (87.2%) of a light yellow liquid. The retained weight via TGA at 300° C. for this bismethacrylamide compound (TGA ramp rate=10° C./min., air purge) was 96.9%, and the decomposition onset was 375° C. A DSC was run (ramp rate=10° C./min., air purge) on a sample of this material catalyzed with 2% by weight dicumyl peroxide. A cure exotherm was observed to occur with an onset of 156.2° C., a cure maxima at 182.8° C. and a cure energy of 59.0 J/g. An FTIR was run on this monomer and it was found to have major absorptions at 3369, 2922, 2853, 2248, 1730, 1649, 1622, 1532, 1464, 1375, 1176, 913, and 722 wavenumbers.

Example 47

Synthesis of Compound 27

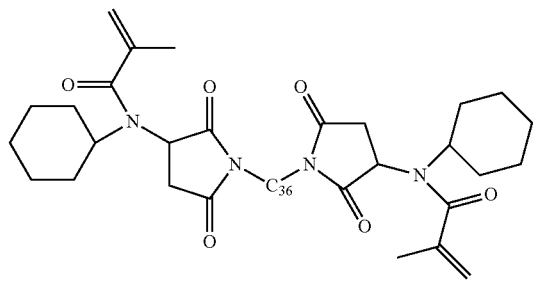

Cyclohexylamine (19.84 g, 200 mmol) and X-BMI (69.6 g, 100 mmol) were mixed in a 500 ml flask (an exotherm was observed). Next, 50 ml of toluene was added to the mix. This mixture stirred at 80° C. for 4.5 hours. Methacrylic anhydride (30.8 g, 200 mmol) was added. Again, a mild exotherm occurred. The mixture was stirred at 65° C. for another 3.5 hours. The solution was neutralized with sodium bicarbonate (20 g, plus 3 g water) and treated with MgSO₄ (10 g). During this time, some of the product foamed over and a portion of the product was lost. The remaining solution was passed over silica gel (20 g). The toluene was removed by rotary evaporation followed by sparging. The product was a viscous, light brown clear liquid. It weighed 84.7 g (82.0% of theory). The retained weight for this bismethacrylamide compound via TGA at 300° C. (TGA ramp rate=10° C./min, air purge) was 91.1%, and the decomposition onset was 479.67° C. A DSC was conducted (ramp rate=10° C./min., air purge) on a sample of this material catalyzed with 2% by weight dicumyl peroxide. A cure exotherm was observed to occur with an onset of 158.7° C., a cure maxima at 187.0° C. and a cure energy of 19.2 J/g. An FTIR was run on this monomer and it was found to have major absorptions at 2930, 2853, 1703, 1635, 1402, and 1132 wavenumbers.

Example 48

Synthesis of Compound 28

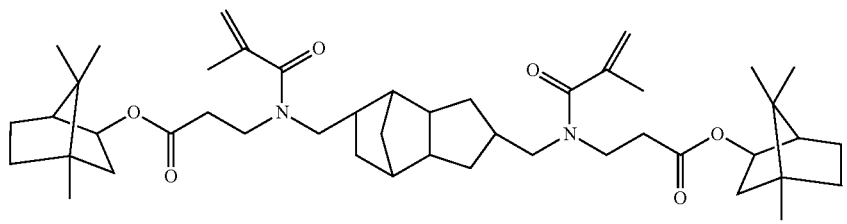 [SMILES: C=C(C)C(=O)N(CCC(=O)OC1CC2(C)CCC1C2(C)C)CC1CC2C3CC(CN(CCC(=O)OC4CC5(C)CCC4C5(C)C)C(=O)C(=C)C)C(C3)C2C1]

TCD diamine (19.4 g, 100 mmol, Celanese) and isobornyl acrylate (41.7 g, 200 mmol, SR506D, Sartomer) were mixed in a 250 ml flask which resulted in a mild exotherm. The mix was heated to 80° C. and maintained at this temperature for 17 hours. An FTIR spectrum on the intermediate showed the disappearance of absorbances at 1635 and 1619 cm$^{-1}$. 100 ml of toluene and methacrylic anhydride (32.4 g, 210 mmol) were then added and the new mixture was heated to 60° C. for 3 hours. The solution was neutralized with sodium bicarbonate (15 g, plus 3 g water), dried with MgSO$_4$ (10 g) and then passed over silica gel (20 g). The solvent was removed by rotary evaporation followed by sparging. The product was a very viscous liquid that became glassy solid as it cooled to room temperature. The retained weight for this bismethacrylamide compound via TGA at 300° C. (TGA ramp rate=10° C./min., air purge) was 94.2%, and the decomposition onset was 313.8° C. A DSC was conducted (ramp rate=10° C./min, air purge) on a sample of this material catalyzed with 2% by weight dicumyl peroxide. A cure exotherm was observed to occur with an onset of 145.4° C., a cure maxima at 161.5° C. and a cure energy of 171.3 J/g. An FTIR was run on this monomer and it was found to have major absorptions at 2947, 1728, 1645, 1623, 1454, 1370, 1164, 1055, 1010, 909, and 785 wavenumbers.

Example 49

Synthesis of Compound 29

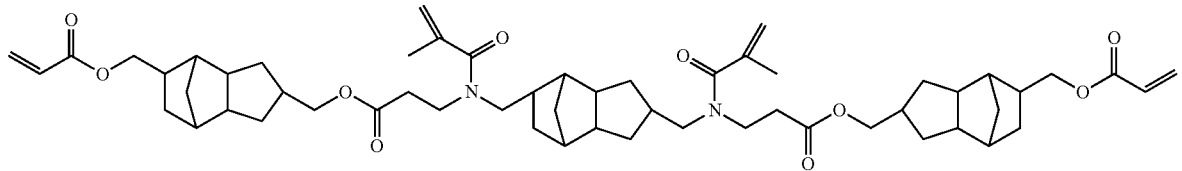 [SMILES: C=CC(=O)OCC1CC2CC1C1CC(COC(=O)CCN(CC3CC4C5CC(CN(CCC(=O)OCC6CC7C8CC(COC(=O)C=C)C(C8)C7C6)C(=O)C(=C)C)C(C5)C4C3)C(=O)C(=C)C)CC21]

SR-833S (60.9 g, 200 mmol, Sartomer) and TCD diamine (19.4 g, 100 mmol; Celanese Chemical) were mixed in a 500 ml flask at room temperature. There was an exotherm which caused the temperature to increase to approximately 40° C. Next, 100 ml of toluene was added and the solution was heated to and maintained at 80° C. for 2.75 hours. The mixture was then cooled and methacrylic anhydride (30.8 g, 200 mmol) was added (resulting in another exotherm). The mixture was then maintained at 65° C. for 16.5 hours. The solution was neutralized with NaHCO$_3$ (20 g, plus 5 g water), treated with MgSO$_4$ (15 g) and then passed over silica gel. The solvent was removed via rotary evaporation followed by sparging. The product was a very viscous, light yellow liquid that weighed 89.7 g (95.5% of theory). The retained weight for this compound via TGA at 300° C. (TGA ramp rate=10° C./min., air purge) was 99.6%, and the decomposition onset was 418.3° C. A DSC was run (ramp rate=10° C./min., air purge) on a sample of this material catalyzed with 2% by weight dicumyl peroxide. A cure exotherm was observed to occur with an onset of 129.6° C., a cure maxima at 137.1° C. and a cure energy of 164.8 J/g. A TMA (thermomechanical analysis) was run on a cured pellet of this monomer. The TMA revealed an $\alpha_1$ of 56.4 ppm per ° C., an $\alpha_2$ of 130.0 ppm per ° C., and a $T_g$ of 110.9° C. An FTIR was run on this monomer and it was found to have major absorptions at 2944, 1723, 1621, 1407, 1268, 1179, 1053, 982, and 810 wavenumbers.

Example 50

Synthesis of Compound 30

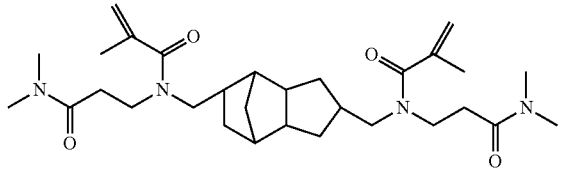

TCD-diamine (19.4 g, 100 mmol, Celanese), N,N-dimethacryamide (20.0 g, 202 mmol, Ciba), and toluene (100 ml) were stirred in a 1-neck 500 ml flask. There was no exotherm observed after 10 minutes of stirring at room temperature. The mixture was then heated to 80° C. for 3 hours. Methacrylic anhydride (30.8 g, 200 mmol) was added and the new mixture was then maintained at 80° C. for 1.33 hours. The mixture was extracted with 3×25 ml of brine. The solution was washed with aqueous sodium bicarbonate, dried with MgSO$_4$ (18 g) and then passed over silica gel (20 g). The solvent was then removed by rotary evaporation followed by air sparge. An extremely viscous amber liquid was recovered which weighed 48.67 g (92.1% of theory). The retained weight for this bismethacrylamide compound via TGA at 300° C. (TGA ramp rate=10° C./min, air purge) was 96.9%, and the decomposition onset was 317.2° C. A DSC was conducted (ramp rate=10° C./min., air purge) on a sample of this material catalyzed with 2% by weight dicumyl peroxide. A cure exotherm was observed to occur with an onset of 146.4° C., a cure maxima at 159.6° C. and a cure energy of 198.4 J/g. An FTIR was run on this monomer and it was found to have major absorptions at 2944, 2873, 1716, 1614, 1451, 1414, 1297, 1144, 1048, 912, and 787 wavenumbers.

Example 51

Synthesis of Compound 32

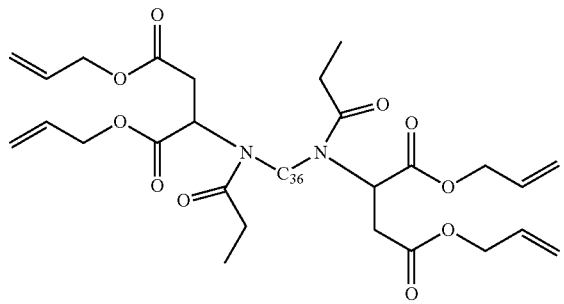

Example 52

Synthesis of Compound 33

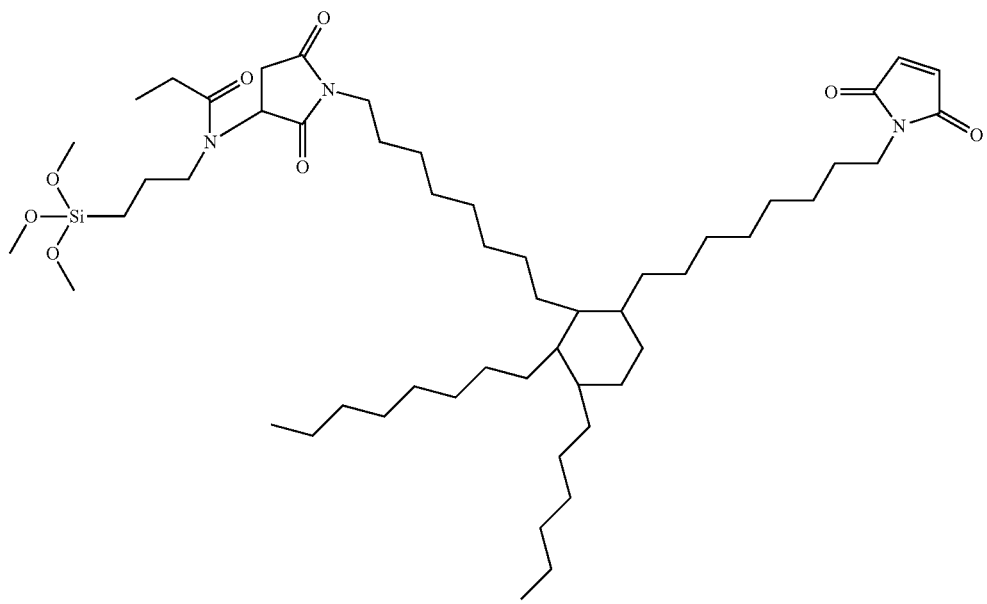 [SMILES: CCCCCCCCC1C(CCCCCC)CCC(CCCCCCCCN2C(=O)C=CC2=O)C1CCCCCCCCN1C(=O)CC(N(CCC[Si](OC)(OC)OC)C(=O)CC)C1=O]

Versamine 552 (26.75 g, 50 mmol, Cognis) and 25 ml of toluene were added to a 250 ml flask. The solution was stirred at room temperature. Diallyl maleate (19.64 g, 100 mmol; TCI America, Boston) and 25 ml of toluene were dripped in over a five-minute period. There was a mild exotherm. The mixture was stirred at room temperature for another 3.5 hours. Propionic anhydride (13.01 g, 100 mmol) was added (which produced another exotherm). The mixture was allowed to stir at room temperature overnight. The volatiles were then removed by rotary evaporation followed by an air sparge. The product was a clear light yellow liquid that weighed 46.9 g (90.2% of theory). The retained weight for this Tetraallyl-functional compound via TGA at 250° C. (TGA ramp rate=10° C./min., air purge) was 96.3%, and the decomposition onset was 325.1° C. A DSC was conducted (ramp rate=10° C./min., air purge) on a sample of this material catalyzed with 2% by weight dicumyl peroxide. A cure exotherm was observed to occur with an onset of 156.5° C., a cure maxima at 180.1° C. and a cure energy of 160.7 J/g. An FTIR was run on this monomer and it was found to have major absorptions at 2944, 2853, 1736, 1650, 1462, 1376, 1272, 1162, 987, 928, and 722 wavenumbers.

X-BMI (174.0 g, 500 meq) and 100 ml of toluene were placed in a 500 ml flask. Silquest A-1100 (8.96 g, 50 meq; OSi Specialties, Danbury Conn.) was dripped into stirred solution. The mixture was then stirred at room temperature overnight. Propionic anhydride (6.9 g, 53 meq) was added and the new mixture was stirred at room temperature for half an hour. The temperature was increased to 60° C. for 2 hours, followed by a reflux for 2.25 hours. The volatiles were removed by rotary evaporation followed by an air sparge. The product was a clear light yellow oily liquid that weighed 183.97 g (98.9% of theory). The retained weight for this modified bismaleimide compound via TGA at 300° C. (TGA ramp rate=10° C./min., air purge) was 99.6%, and the decomposition onset was 476.4° C. A DSC was run (ramp rate=10° C./min., air purge) on a sample of this material that was catalyzed with 2% by weight dicumyl peroxide. An FTIR was run on this monomer and it was found to have major absorptions at 2925, 1708, 1650, 1406, 1079, 956, 826, and 695 wavenumbers.

Example 53

Synthesis of Compound 37

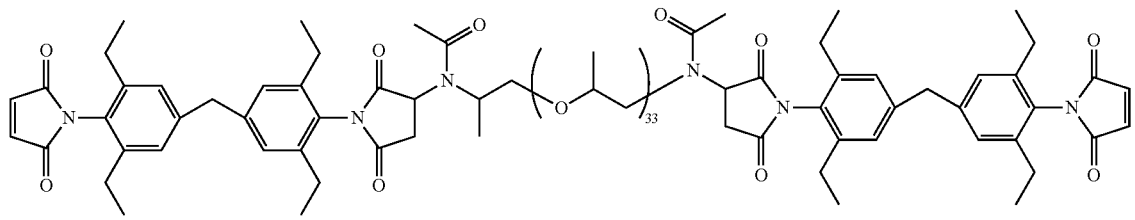

M-DEA BMI (28.24 g, 60 mmol, from EXAMPLE 1) was dissolved in 100 ml of warm toluene. Jeffamine D-2000 (29.76 g, 15 mmol) was dripped into this magnetically stirred solution over a 15-minute period. The mixture was then refluxed for one hour. Acetic anhydride (6.13 g, 60 mmol) was added and this new mixture was then also refluxed for one hour. The product was concentrated via rotary evaporation followed by air sparge to give a red viscous liquid that weighed 59.0 g. The retained weight for this amide extended bismaleimide compound via TGA at 300° C. (TGA ramp rate=10° C./min, air purge) was 99.52%. The decomposition onset temperature was 376.1° C. An FTIR was run on this monomer and it was found to have major absorptions at 2970, 1712, 1644, 1475, 1375, 1087, 830, and 692 wavenumbers.

Example 54

Synthesis of Compound 38

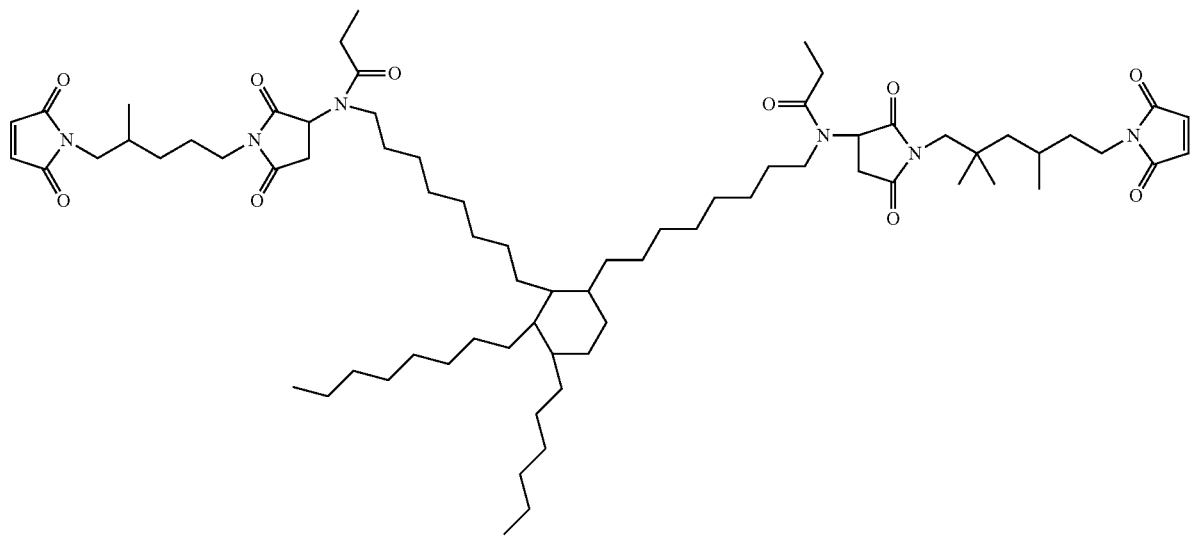 [SMILES: CCCCCCCCC1C(CCCCCC)CCC(CCCCCCCCN(C(=O)CC)C2CC(=O)N(CC(C)(C)CC(C)CCN3C(=O)C=CC3=O)C2=O)C1CCCCCCCCN(C(=O)CC)C1CC(=O)N(CCCC(C)CN2C(=O)C=CC2=O)C1=O]

The bismaleimide of 2-methyl-1,5-diaminopentane was prepared. Toluene (400 ml) and methanesulfonic acid (80 g) were added to a 1-liter flask. Triethylamine (64 g) was then dripped in over about ten minutes. Maleic anhydride (107.9 g, 1100 mmol) was dissolved into this mixture. The diamine, 2-methyldiaminopentane (58.1 g, 500 mmol) was then dripped into the stirred mixture (pot temperature was about 70° C.) over 30 minute period. A Dean Stark trap and condenser were attached. The solution was then refluxed for 63 hours and 16.5 ml water was collected in the trap. The solution was allowed to cool. Deionized water (50 ml) was added and the upper (toluene phase was removed and set aside. The bottom phase was then extracted with toluene (7×100 ml). The combined organic phase was washed with aqueous sodium bicarbonate, dried with MgSO$_4$ (25 g) and passed over silica gel (50 g). The toluene was removed via rotary evaporation followed by an air sparge. A light yellow liquid, which froze upon cooling to a yellow-white solid, was recovered which weighed 75.6 g (54.7% of theory). The BMI compound was subjected to thermogravimetric analysis (TGA). The retained weight at 300° C. (TGA ramp rate=10° C./min., air purge) was 97.9% and the decomposition onset was 485.4° C. The compound was found to have significant infrared absorptions at 3459, 3100, 2934, 1693, 1586, 1441, 1406, 1185, 1110, 825, and 695 wavenumbers. This BMI was designated "Part A".

The bismaleimide of trimethylhexamethylenediamine was prepared. Toluene (300 ml) and methanesulfonic acid (61 g) were added to a 1-liter flask. Triethylamine (45 g) was dripped in (a significant exotherm from salt formation was observed). Maleic anhydride (65.2 g, 664 mmol) was dissolved into this warm mixture with magnetic stirring. To this solution was added trimethylhexamethylenediamine (47.49 g, 300 mmol) at about 50° C. over 20 minute period. The solution was refluxed for 16.4 hours and 11.0 ml water was collected in a Dean-Stark trap. The solution was allowed to cool. Deionized water (30 ml) was added and the upper toluene phase was removed and set aside. An extraction was done on the lower phase using toluene (7×75 ml). The organic phase was washed with aqueous sodium bicarbonate, then treated with MgSO$_4$ (15 g) and passed over silica gel (30 g). The toluene was removed via rotary evaporation followed by an air sparge. The product was place in a 75° C. oven to dry the solid completely. The product was an almost white solid that weighed 75.67 g (79.2% of theoretical yield). The BMI compound was subjected to thermogravimetric analysis (TGA). The retained weight at 300° C. (TGA ramp rate=10° C./min., air purge) was 95.8% and the decomposition onset was 492.9° C. The compound was found to have significant infrared absorptions at 3461, 3101, 2960, 1703, 1587, 1440, 1407, 1370, 1138, 827, and 694 wavenumbers. This BMI was designated "Part B".

The two bismaleimides from above "Part A" (6.08 g, 22 mmol) and "Part B" (5.73 g, 18 mmol) above were dissolved in hot toluene (30 ml). Versamine 552 (10.7 g, 20 mmol) was then dissolved in about two times its own volume with toluene. The diluted Versamine 552 was added dropwise, over a five minute period to the mixed BMI solution. The mixture was then brought to a gentle reflux for one hour. Propionic anhydride (5.34 g, 41 mmol) was then added and the reflux was continued for an additional 30 minutes. Toluene and propionic acid were removed via rotary evaporation followed by air sparge at 80° C. The product was a clear, very viscous light yellow liquid that weighed 24.76 g (99.7% of theory). The retained weight via TGA at 300° C. (TGA ramp rate=10° C./min., air purge) was 98.7%, and the decomposition onset was 433.6° C. An FTIR was run on the final compound and it was found to have major absorptions at 3466, 3103, 2925, 2853, 1704, 1645, 1439, 1405, 1306, 1133, 1039, 827, and 695 wavenumbers.

Example 55

Synthesis of Compound 39 ylsiloxane PS510 (58.4 g, 20 mmol; United Chemical Technologies, Bristol, Pa.) was then dripped in over a 15 minute period, while the temperature of the first solution was kept at 60° C. The mixture was then stirred at this temperature for 4.5 hours. Acetic anhydride (4.08 g, 40 mmol) was then added. The new mixture was stirred overnight (14 hrs) at room temperature. The toluene and acetic acid was removed by rotary evaporation and air sparge. The product was a very viscous, clear, light yellow, tacky liquid. The retained weight via TGA at 300° C. (TGA ramp rate=10° C./min., air purge) was 99.2%, and the decomposition onset was 385.3° C. A DSC was conducted (ramp rate=10° C./min., air purge) on a sample of this material catalyzed with 2% by weight dicumyl peroxide. A cure exotherm was observed to occur with an onset of 132.9° C., a cure maxima at 155.9° C. and a cure energy of 51.1 J/g. An FTIR was run on the final compound and it was found to have major absorptions at 2964, 1713, 1651, 1476, 1377, 1258, 1075, 1021, 865, 797, and 692 wavenumbers.

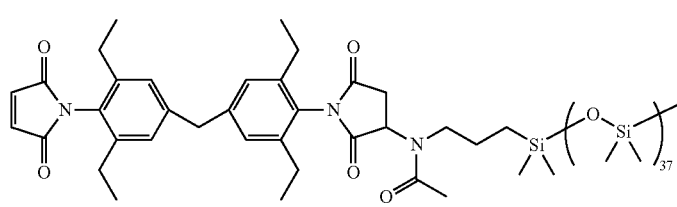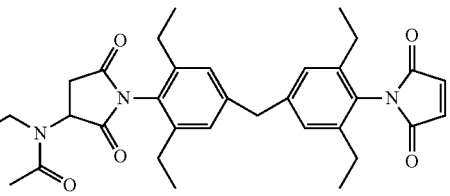

The bismaleimide from EXAMPLE 1 Part A (M-DEA BMI, 18.8 g, 40 mmol) was dissolved in 150 ml of hot toluene (~100° C.). The solution was allowed to cool to approximately 60° C. Aminopropyldimethyl terminated polydimeth- Example 56

Synthesis of Compound 40

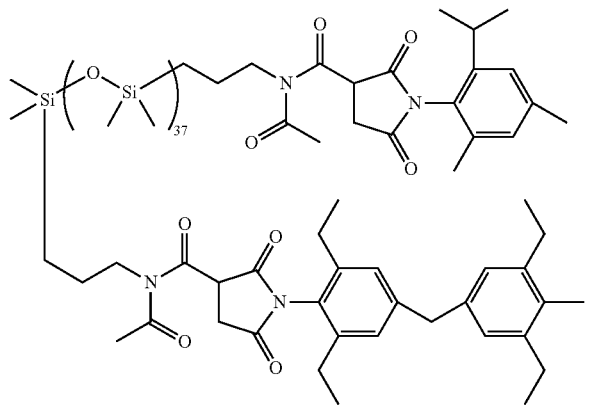

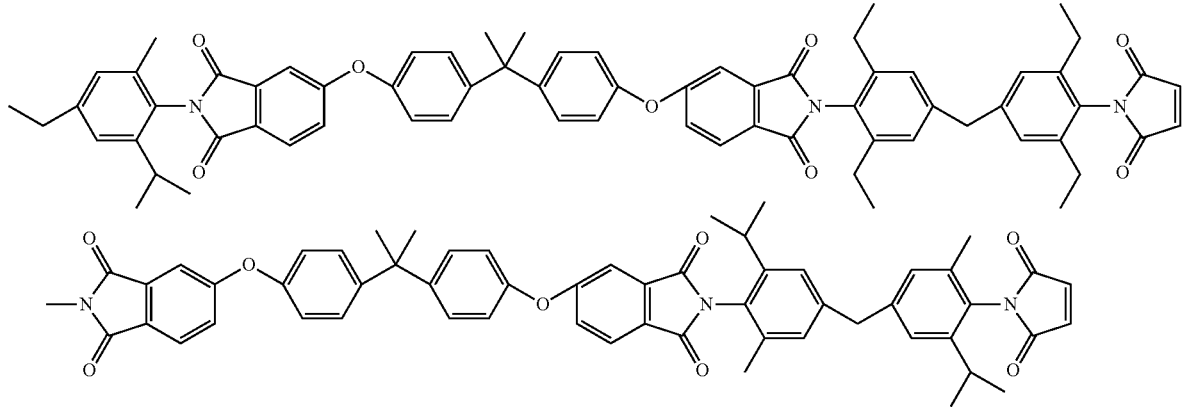

A short chain length imide-extended bismaleimide monomer was first prepared. Bisphenol A dianhydride (GE Plastics, 26.0 g, 50 mmol), maleic anhydride (9.8 g, 100 mmol) toluene (150 ml) were heated together in a 500 ml flask. The solids were stirred to give a solution/slurry. Methylene-bis(2,6-diethylaniline) (Lonza, 15.53 g, 50 mmol) and methylene-bis(2-isopropyl-6-methylaniline (Lonza, 15.53 g, 50 mmol) were dissolved into 50 ml of toluene and dripped into the solution containing the dissolved anhydride mixture. The addition of the mixed amines caused a purple phase (amic acid intermediate) to separate out. Methanesulfonic acid (2.0 g) was added and the solution was refluxed for 4 hrs. The purple phase went into solution as the reaction proceeded. A total of 3.6 ml of $H_2O$ (equivalent to theory) was collected by the end of the reflux period. The solution was neutralized with sodium bicarbonate (10 g) and then passed over silica gel (15 g). The toluene was removed via rotary evaporation followed by an air sparge. The mix became too thick to fully dry in the rotary evaporator, so it was transferred to a crystallizing dish and dried in an oven. The product was a clear, amber, glassy, amorphous solid. The BMI compound was subjected to thermogravimetric analysis (TGA). The decomposition onset was 501.5° C. (TGA ramp rate=10° C./min., air purge). The compound was found to have significant infrared absorptions at 2966, 1776, 1710, 1600, 1475, 1372, 1233, 1153, 1103, 829, and 691 wavenumbers. This compound was designated "Part A".

The imide-extended bismaleimide from Part A (50.6 g, 40 mmol) was dissolved in 100 ml of hot toluene (~80° C.). The mix was cooled to ~60° C. and aminopropyldimethyl terminated polydimethylsiloxane PS510 (United Chemical Technologies, 58.4 g, 20 mmol) was dripped in. This mixture was stirred for 4 hours at 50° C. The flask was then charged with acetic anhydride (4.08 g, 40 mmol). This new mixture was stirred overnight at room temperature. The toluene and acetic acid removed via rotary evaporation followed by an air sparge. It was then dried for 20 hours in a 100° C. oven. The product was a yellow-white, crumbly, rubbery solid. The retained weight via TGA at 300° C. (TGA ramp rate=10° C./min., air purge) was 98.5%, and the decomposition onset was 383.7° C. A DSC was conducted (ramp rate=10° C./min, air purge) on a sample of this material catalyzed with 2% by weight dicumyl peroxide. A cure exotherm was observed to occur with an onset of 142.8° C., a cure maxima at 187.0° C. and a cure energy of 28.3 J/g. A glass transition (inflection point) was also observed to occur at 116.14° C. An FTIR was run on the final compound and it was found to have major absorptions at 2965, 1716, 1711, 1652, 1599, 1476, 1370, 1261, 1094, 1012, 792, 752, and 692 wavenumbers.

Example 57

Synthesis of Compound 41

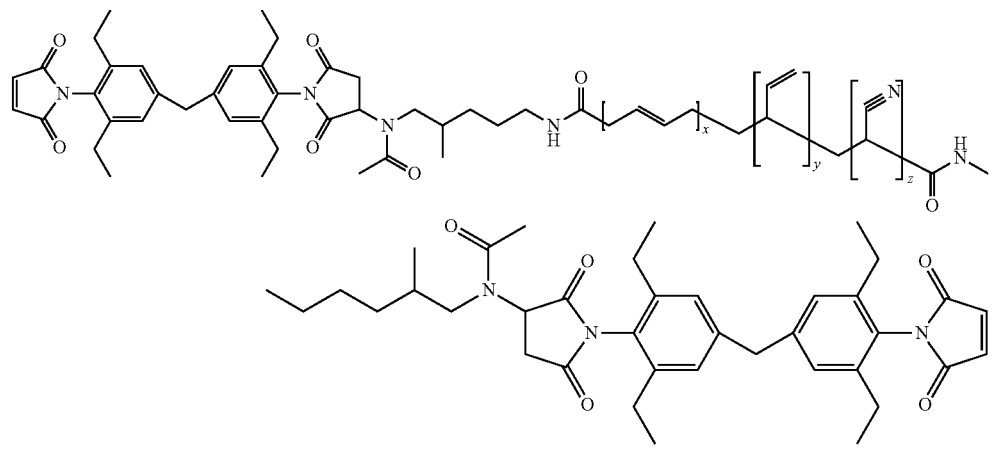

The methylene-bis(2,6-diethylaniline) BMI described in EXAMPLE 1 (18.8 g, 40 mmol) and 50 ml toluene were stirred and heated to 80° C. in a 500 ml, single-neck flask to obtain a homogeneous solution. The solution was then cooled to 70° C. and a solution of Hycar ATBN 1300X42 (Noveon, Inc., 18.1 g, 20 mmol) in 100 ml toluene was then dripped into the BMI solution over the course of twenty minutes. This mixture was stirred another hour at 70° C. and then acetic anhydride (4.08 g, 40 mmol) was added. This new solution was then stirred for another 3 hours at 65-70° C. The toluene and residual acetic acid were then removed to yield 38.57 g (100.0% of theory) of a clear, amber, glassy solid. This compound was a pliable, stretchable solid at 120° C. A TGA run on the neat compound revealed a retained weight of 99.1% at 300° C. and a decomposition onset of 449.55° C. An FTIR trace run on this solid revealed significant absorptions at 2935, 2236, 1711, 1649, 1471, 1374, 1263, 1187, 967, 827, and 692 wavenumbers.

Example 58

Performance of Amide Extended Bismaleimides

A comparative example compound (X-BMI) was prepared as described in the U.S. Pat. No. 5,973,166, the entire disclosure of which is incorporated herein by reference. X-BMI is a product which is described in U.S. Pat. No. 5,973,166, EXAMPLE 6, the fourth product in Table 3. As can be understood from the description provided in U.S. Pat. No. 5,973,166, X-BMI is a bismaleimide of Versamine® 552, prepared by using methanesulfonic acid and triethylamine.

All ratios of other reagents used were identical to those used to produce the test monomers. Test portions of the compounds indicated and X-BMI monomers were catalyzed with about 2% by weight of dicumyl peroxide. These mixtures were used to affix aluminum studs (with round flat contact areas measuring 0.177 inches in diameter) (parts numbered 1-10 in Table 3, below) to both alumina (14×14×19 mm) and steel (16×16×19 mm) slugs. These assemblies were cured in an oven at 185° C. for 1.5 hours. Room temperature tensile adhesion was then using a Sebastian III tensile tester. The results of these tests are summarized in Table 3.

TABLE 3

Tensile Adhesion (pounds force) Comparison of Compounds 5, 6, 7 and X-BMI

| | Compound 5 | | Compound 6 | | Compound 7 | | X-BMI | |
|---|---|---|---|---|---|---|---|---|
| Part No. | Alumina | Steel | Alumina | Steel | Alumina | Steel | Alumina | Steel |
| 1 | 51 | 65 | 87 | 23 | 40 | 51 | 5 | 45 |
| 2 | 78 | 79 | 13 | 81 | 31 | 63 | 4 | 49 |
| 3 | 57 | 74 | 53 | 105 | 14 | 63 | 0 | 14 |
| 4 | 21 | 86 | 32 | 106 | 14 | 35 | 0 | 27 |
| 5 | 51 | 56 | 72 | 47 | 2 | 52 | 1 | 62 |
| 6 | 31 | 65 | 51 | 108 | 33 | 61 | 10 | 39 |
| 7 | 56 | 85 | 77 | 85 | 12 | 37 | 6 | 39 |
| 8 | 39 | 73 | 24 | 90 | 4 | 63 | 9 | 35 |
| 9 | 71 | 74 | 46 | 129 | 4 | 80 | 15 | 43 |
| 10 | 52 | 49 | 5 | 67 | 2 | 86 | 11 | 39 |
| χ | 50.7 | 70.6 | 46 | 84.1 | 15.6 | 59.1 | 6.1 | 39.2 |
| σ | 17.1 | 12 | 27.6 | 31.5 | 14.1 | 16.3 | 5.1 | 12.8 |

The invention compounds 5, 6 and 7 had approximately a 1.8, 2.15, and 1.5 fold higher adhesion than the X-BMI control, respectively, on steel and an impressive 8.3, 7.5, 2.6 fold higher adhesion, respectively on alumina. The performance of the amide-extended bismaleimide compounds was therefore superior to an analogous compound based on the X-BMI.

Example 59

Performance of Invention Compounds Versus the X-Bismaleimide

Compounds 20, 13, and 25 were prepared and compared to X-BMI control as described above in EXAMPLE 36 except that the curing was carried out for 185° C. for 1.25 hours. The results of these tests are summarized in Table 4.

TABLE 4

Tensile Adhesion (pounds force) Comparison of Compounds 13, 20, 25 and X-BMI

| | Compound 20 | | Compound 13 | | Compound 25 | | X-BMI | |
|---|---|---|---|---|---|---|---|---|
| Part No. | Alumina | Steel | Alumina | Steel | Alumina | Steel | Alumina | Steel |
| 1 | 95 | 81 | 163 | 101 | 62 | 69 | 30 | 81 |
| 2 | 117 | 92 | 109 | 115 | 72 | 62 | 65 | 60 |
| 3 | 108 | 112 | 189 | 176 | 91 | 38 | 71 | 58 |
| 4 | 70 | 107 | 147 | 163 | 90 | 68 | 43 | 37 |
| 5 | 114 | 15* | 166 | 157 | 99 | 79 | 34 | 40 |
| 6 | 57 | 47 | 145 | 134 | 87 | 67 | 20 | 14 |
| 7 | 74 | 23* | 68 | 74 | 93 | 94 | 45 | 30 |
| 8 | 95 | 75 | 131 | 154 | 102 | 96 | 60 | 72 |
| 9 | 90 | 64 | 160 | 102 | 82 | 18 | 42 | 4 |
| 10 | 66 | 60 | 166 | 122 | 86 | 67 | 45 | 36 |
| χ | 88.6 | 79.5 | 144.4 | 129.8 | 86.4 | 65.8 | 45.5 | 43.4 |
| σ | 21 | 22.9 | 34.6 | 32.6 | 12 | 23.5 | 15.9 | 24.5 |

*Indicates an off center pull. Data not included in average

The invention compounds 20, 13 and 25 had approximately a 1.5 to 3 fold higher adhesion than the X-BMI control on both alumina and steel. Compounds 20 and 25 were bismethacrylamides. Compound 13 was a methacrylamide-extended diacrylate. The performance of these invention compounds were significantly superior to an analogous compound based on the X-BMI.

Example 60

Performance of Invention Compounds Versus X-Bismaleimide

Compounds 21, 22, and 38 were prepared and compared to an X-BMI control as described above in EXAMPLE 36 except that the curing was carried out at 185° C. for 1.25 hours. The results of these tests are summarized in Table 5.

TABLE 5

Tensile Adhesion (pounds force) Comparison of Compounds 21, 22, 38 and X-BMI

| | Compound 21 | | Compound 22 | | Compound 38 | | X-BMI | |
|---|---|---|---|---|---|---|---|---|
| Part No. | Alumina | Steel | Alumina | Steel | Alumina | Steel | Alumina | Steel |
| 1 | 14 | 48 | 69 | 54 | 166 | 123 | 11 | 42 |
| 2 | 79 | 25 | 80 | 51 | 195 | 181 | 52 | 51 |
| 3 | 11 | 12 | 48 | 51 | 194 | 126 | 55 | 55 |
| 4 | 83 | 18 | 68 | 55 | 161 | 122 | 16 | 83 |
| 5 | 91 | 68 | 52 | 52 | 165 | 163 | 17 | 58 |
| 6 | 22 | 31 | 37 | 53 | 141 | 172 | 13 | 55 |
| 7 | 14 | 68 | 92 | 51 | 165 | 178 | 0 | 66 |
| 8 | 76 | 8 | 81 | 72 | 183 | 167 | 1 | 45 |
| 9 | 22 | 70 | 23 | 56 | 174 | 128 | 46 | 52 |
| 10 | 47 | 74 | 67 | 57 | 181 | 177 | 55 | 68 |

TABLE 5-continued

Tensile Adhesion (pounds force) Comparison of Compounds 21, 22, 38 and X-BMI

| | Compound 21 | | Compound 22 | | Compound 38 | | X-BMI | |
|---|---|---|---|---|---|---|---|---|
| Part No. | Alumina | Steel | Alumina | Steel | Alumina | Steel | Alumina | Steel |
| $\chi$ | 45.9 | 42.2 | 61.7 | 55.2 | 172.5 | 153.7 | 22.6 | 57.5 |
| $\sigma$ | 33 | 26.3 | 21.4 | 6.3 | 16.4 | 25.5 | 22.7 | 12.1 |

Although invention compounds 21 and 22 showed approximately the same adhesion as the X-BMI control on steel, both showed greater than 2 fold higher adhesion on alumina Compound 38 showed greater adhesion on both alumina (7.3 fold greater) and steel (2.7 fold greater). Compounds 21 and 22 were both bismethacrylamides. Compound 38 was an amide-extended bismaleimide. The performance of the invention compounds was therefore superior to an analogous compound based on the X-BMI.

Example 61

Performance of Invention Compounds Versus X-Bismaleimide

Compounds 37, 11, and 28 were prepared and compared to the X-BMI control as described above in EXAMPLE 36 except that the curing was carried out for 185° C. for 1.25 hours. This time the room temperature tensile adhesion of aluminum studs (0.177 inch diameter circular contact area) was tested on steel 16×16×19 mm slugs. The results of these tests are summarized in Table 6.

TABLE 6

Tensile Adhesion (pounds force) Comparison of Compounds 37, 11, 28 and X-BMI

| Part No. | Compound 37 Steel | Compound 11 Steel | Compound 28 Steel | X-BMI Steel |
|---|---|---|---|---|
| 1 | 56 | 82 | 63 | 84 |
| 2 | 66 | 10 | 83 | 87 |
| 3 | 59 | 23 | 69 | 61 |
| 4 | 70 | 113 | 104 | 58 |
| 5 | 72 | 77 | 75 | 3 |
| 6 | 68 | 80 | 51 | 35 |
| 7 | 63 | 91 | 78 | 73 |
| 8 | 55 | 76 | 80 | 41 |
| 9 | 53 | 13 | 78 | 52 |
| 10 | 65 | 67 | 75 | 31 |
| $\chi$ | 62.7 | 63.2 | 75.6 | 52.5 |
| $\sigma$ | 6.6 | 35.3 | 13.7 | 25.9 |

All of the invention compounds had better adhesion to steel than the X-BMI control. Compounds 37, 11, and 28 had 19%, 20%, and 44% greater adhesion than the X-BMI, respectively. Compound 37 was a low modulus, poly(propylene oxide) bridged, amide-extended BMI. Compound 11 was an amide-extended diacrylate. Compound 28 was a bismethacrylamide monomer. The adhesion performance of all of these invention compounds was therefore found to be superior to an analogous test composition based on the X-BMI.

Example 62

Performance of Invention Compounds Versus X-Bismaleimide

Compounds 10, 29, and 39 were prepared and compared to the X-BMI control as described above in EXAMPLE 36 except that the curing was carried out for 200° C. for 1.25 hours. This time the room temperature tensile adhesion of aluminum studs (0.177 inch diameter circular contact area) was tested on steel 16×16×19 mm slugs. The results of these tests are summarized in Table 7.

TABLE 7

Tensile Adhesion (pounds force) Comparison of Compounds 10, 29, 39 and X-BMI

| Part No. | Compound 10 Steel | Compound 29 Steel | Compound 39 Steel | X-BMI Steel |
|---|---|---|---|---|
| 1 | 67 | 69 | 38 | 8 |
| 2 | 70 | 150 | 36 | 28 |
| 3 | 74 | 132 | 62 | 20 |
| 4 | 84 | 140 | 20 | 54 |
| 5 | 69 | 158 | 34 | 35 |
| 6 | 92 | 148 | 35 | 80 |
| 7 | 103 | 110 | 36 | 54 |
| 8 | 59 | 59 | 59 | 22 |
| 9 | 111 | 127 | 39 | 53 |
| 10 | 60 | 91 | 52 | 20 |
| $\chi$ | 78.9 | 118.4 | 41.4 | 34.7 |
| $\sigma$ | 18.0 | 34.9 | 12.8 | 22.1 |

All of the invention compounds had better adhesion to steel than the X-BMI control. Compounds 10, 29, and 39 had 127%, 241%, and 19% greater adhesion than the X-BMI, respectively. Compound 10 was a low modulus polyamide-extended BMI. Compound 29 was a bismethacylamide-extended diacrylate. Compound 39 was a low modulus, silicone bridged, amide-extended bismaleimide. The adhesion performance of all of these invention compounds was therefore found to be superior to an analogous test composition based on the X-BMI.

Example 63

Performance of Invention Compounds Versus Michael-Addition-Only Parent Compounds The Michael addition parent compounds of invention Compounds 5 and 42 were prepared according to an identical procedure outlined in EXAMPLES 5 and 17, respectively. The reactions were stopped and worked-up after the Michael addition reaction was complete. These secondary amine-extended bismaleimides were then evaluated by TGA (neat) and DSC (with 2% by weight dicumyl peroxide added). The TGA and DSC runs were conducted at the standard 10° C. per minute ramp rate and with an air purge. The results of those tests are summarized and compared to the N-acylated invention compounds in Table 8.

TABLE 8

TGA and DSC Comparison of Amine-Extended and Amide-Extended BMI Compounds

| | Compound 5 | Non-Acylated Compound 5 | Compound 42 | Non-Acylated Compound 42 |
|---|---|---|---|---|
| Residual Weight % @ 300° C. | 100.0 | 99.31 | 99.23 | 99.09 |
| Residual Weight % @ 400° C. | 98.72 | 96.42 | 96.69 | 94.22 |
| Cure Onset, | 136.4, | 136.8, | 136.8, | 149.8, |

TABLE 8-continued

TGA and DSC Comparison of Amine-Extended and Amide-Extended BMI Compounds

|  | Compound 5 | Non-Acylated Compound 5 | Compound 42 | Non-Acylated Compound 42 |
|---|---|---|---|---|
| Maxima (° C.) | 152.5 | 164.9 | 155.8 | 177.8 |
| Cure Energy (J/g) | 74.2 | 79.6 | 88.0 | 72.2 |
| Secondary Thermal Event? | No | Yes (300.0° C.) | No | Yes (330.9° C.) |

The weight loss at 300° C. for the amide and amine extended BMI compounds was substantially the same. The weight loss at 400° C. was 2.3% higher for the Michael-addition-only control versus Compound 5, and 2.47% higher the amine-extended control versus Compound 17. The cure peak maxima and/or cure onsets were retarded in the amine-extended BMI controls versus the invention compounds. Both of the amine-extended BMI controls had secondary exothermic events that were not present in the invention compounds. This secondary exotherm is presumably a consequence of the retro-Michael addition reaction and appears to be a harbinger of early thermal decomposition.

While this invention has been described with respect to these specific examples, it should be clear that other modifications and variations would be possible without departing from the spirit of this invention.

What is claimed is:

1. A compound having a structure selected from the group consisting of Compounds 1-42:

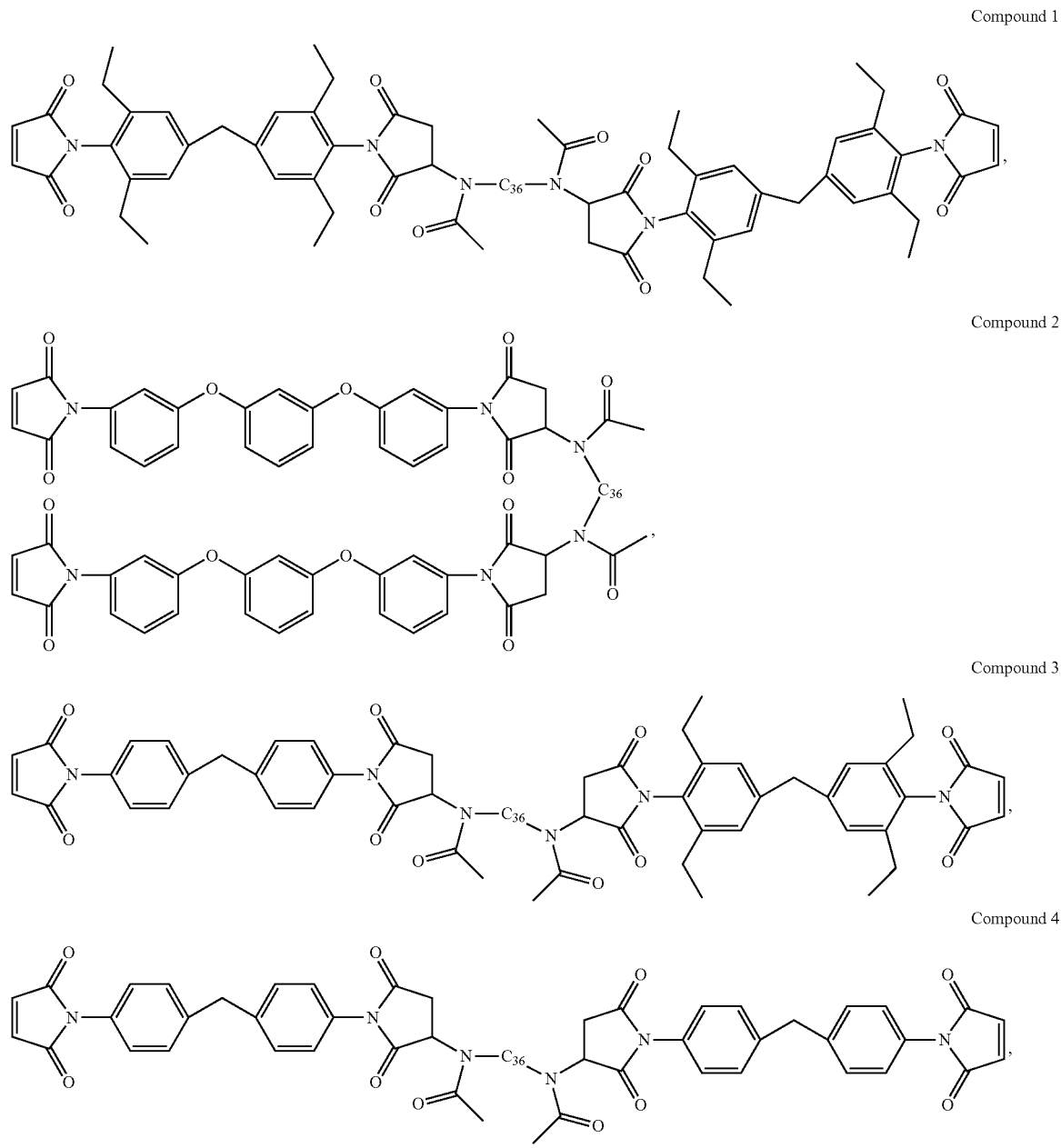

Compound 5
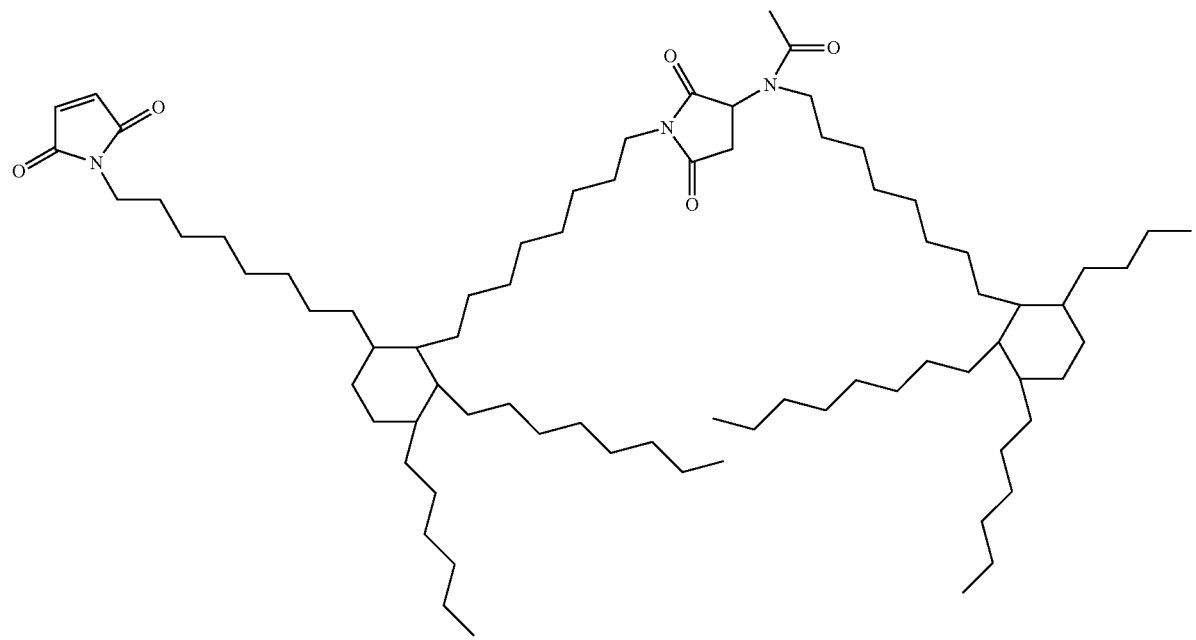
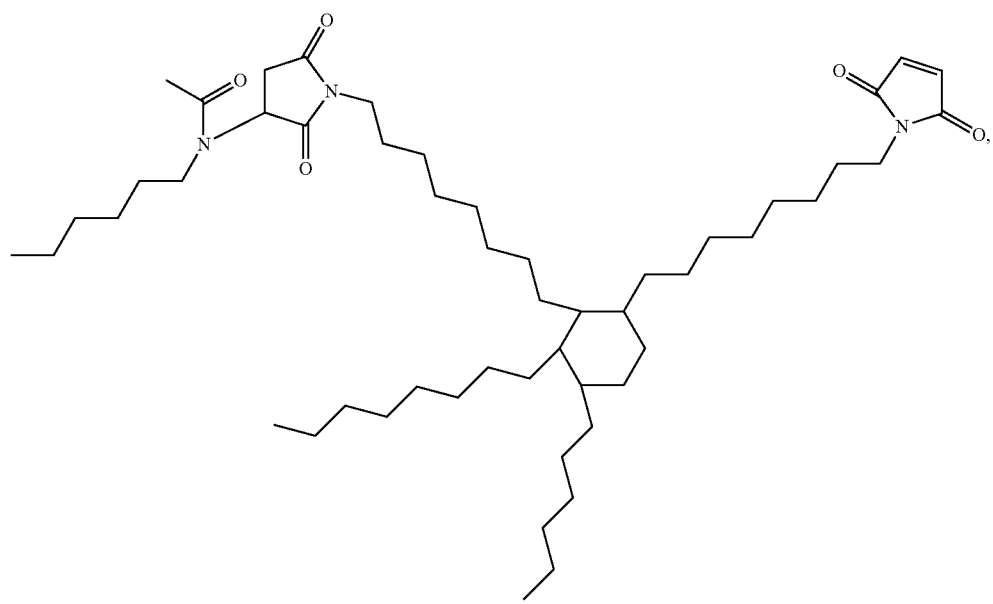

Compound 6
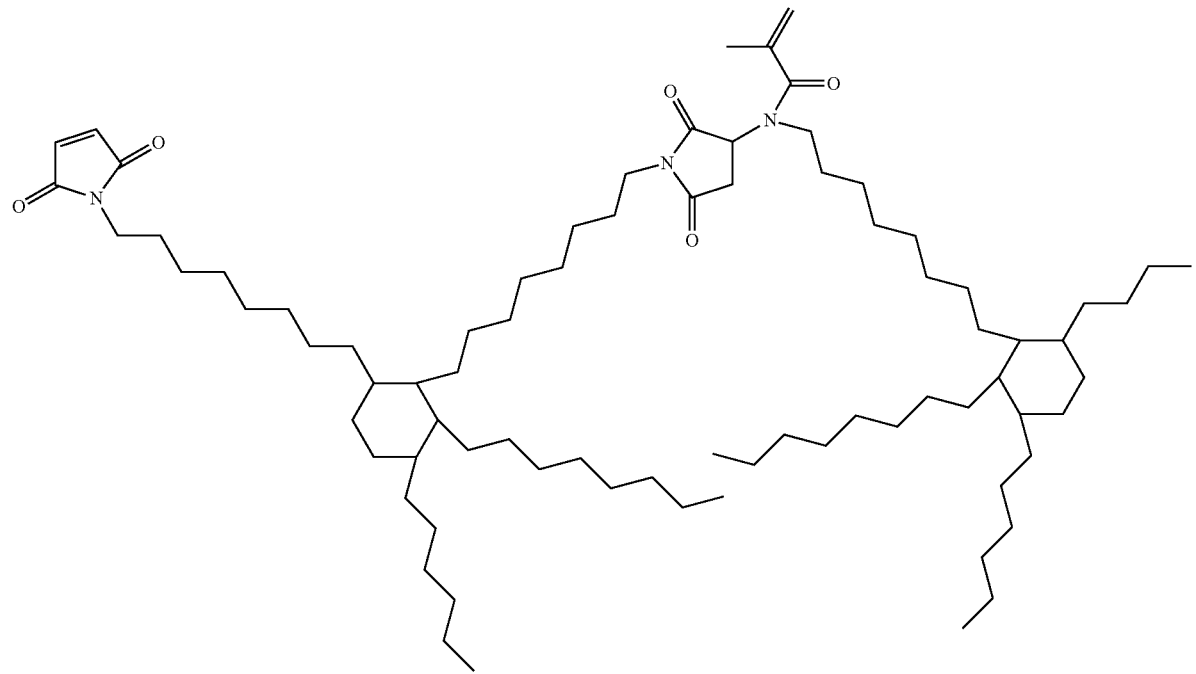
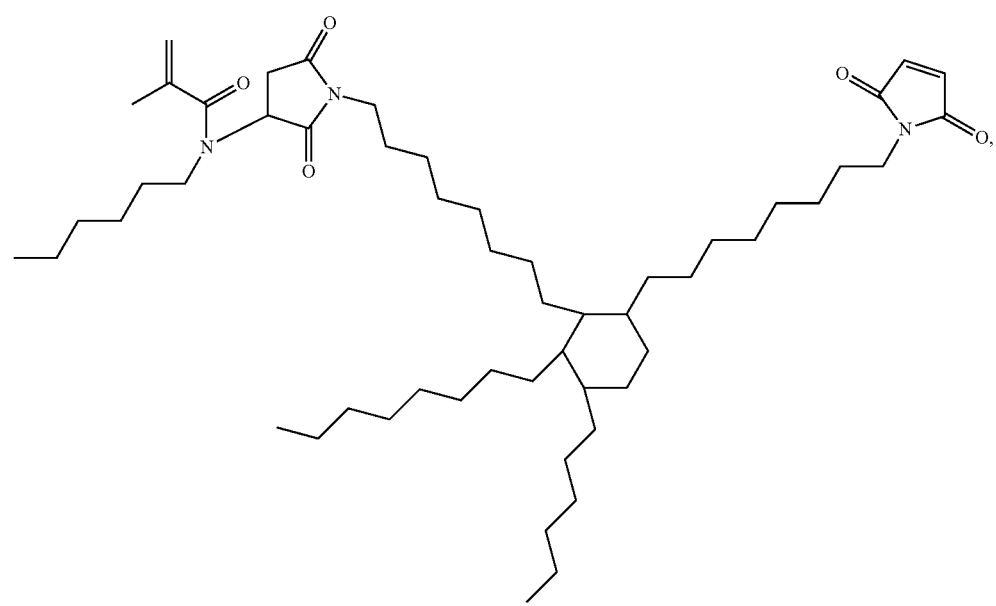

-continued
Compound 7
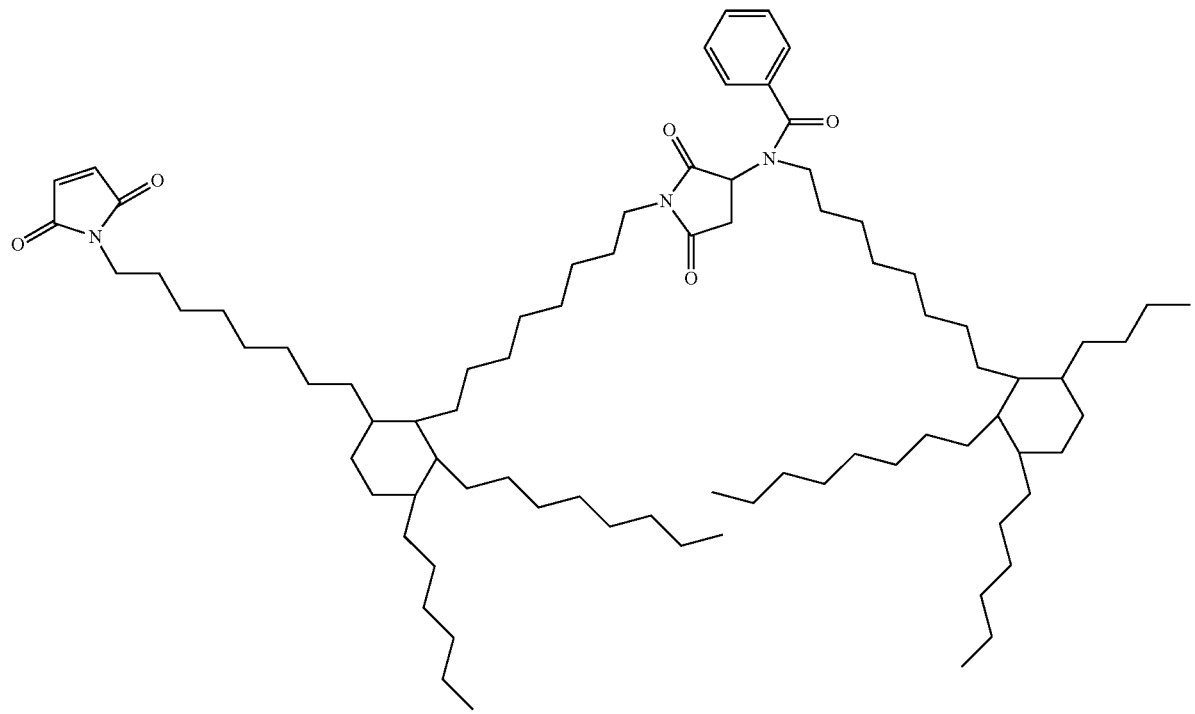
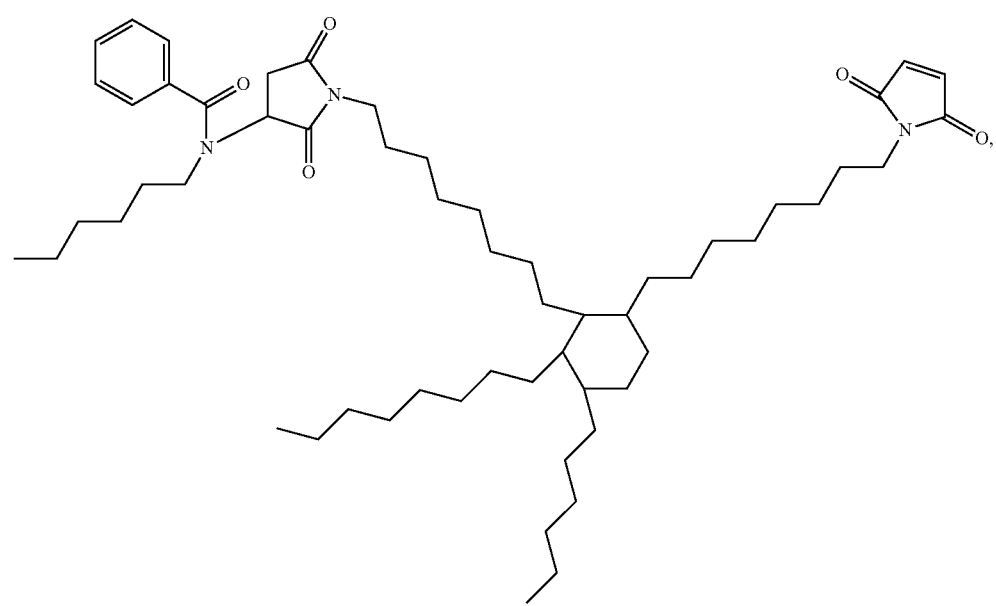

-continued
Compound 8
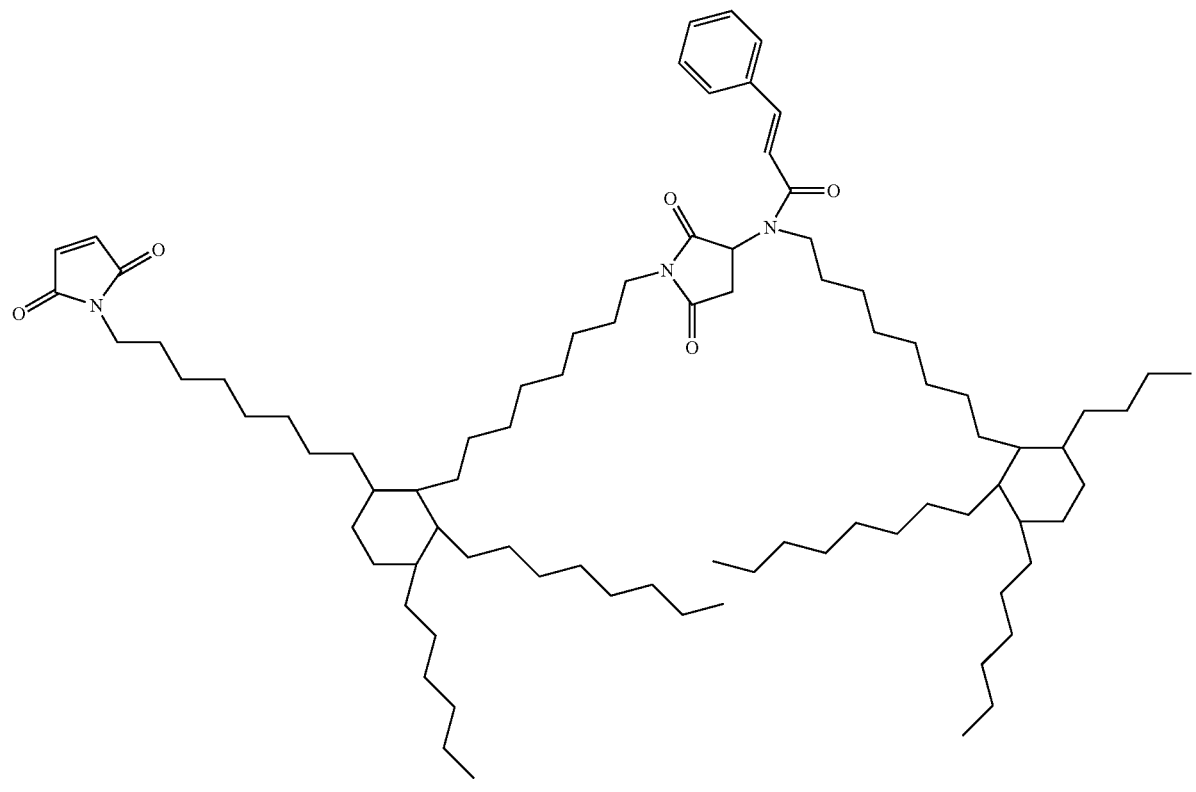
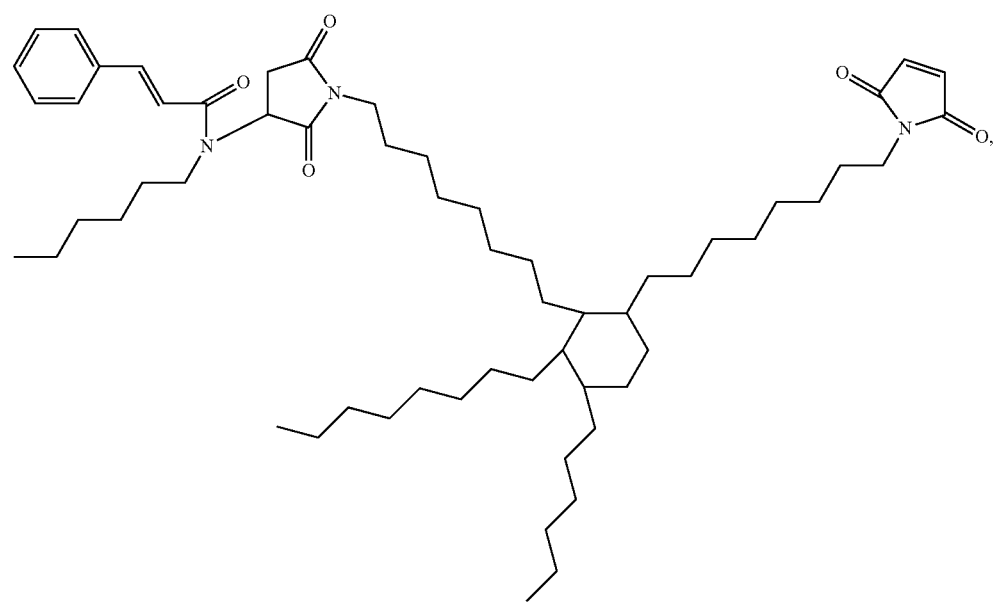
Compound 9
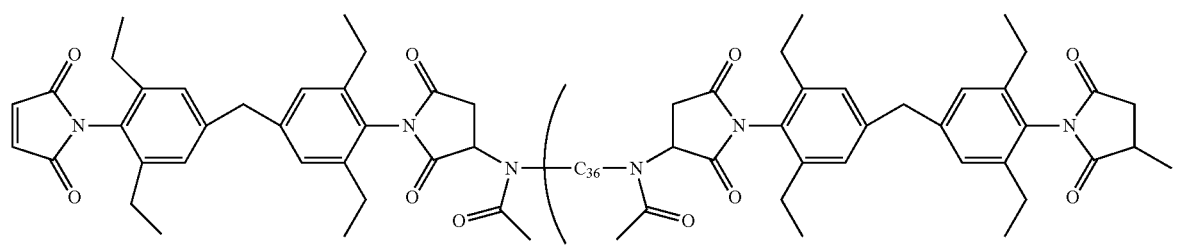

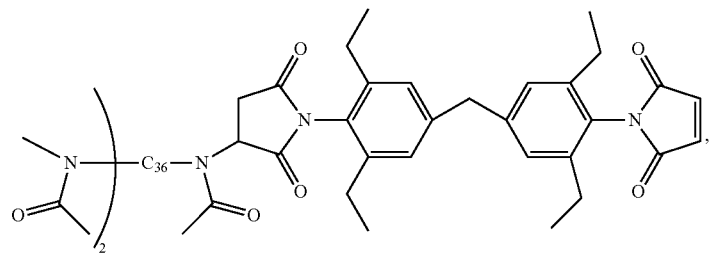
Compound 10
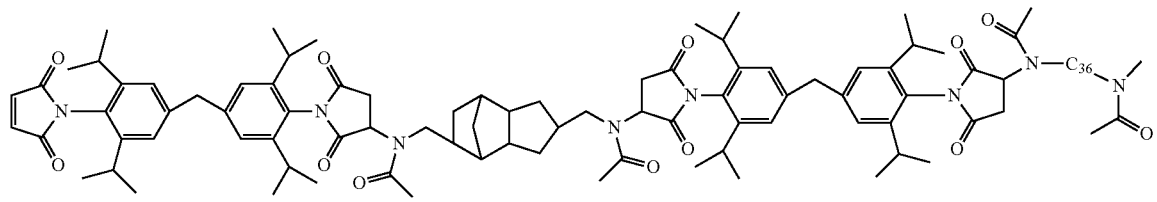
Compound 11
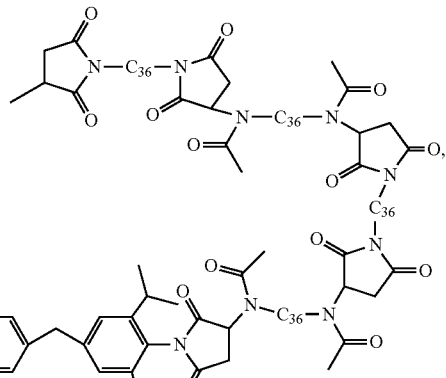
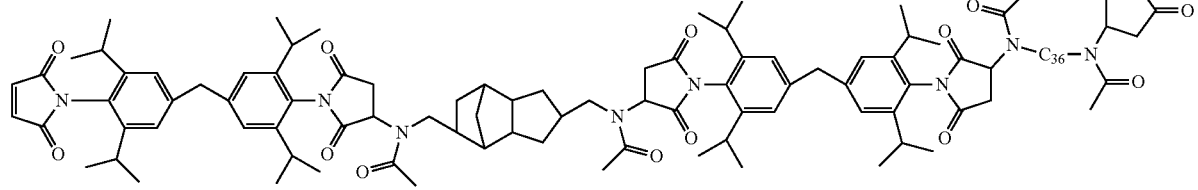
Compound 12
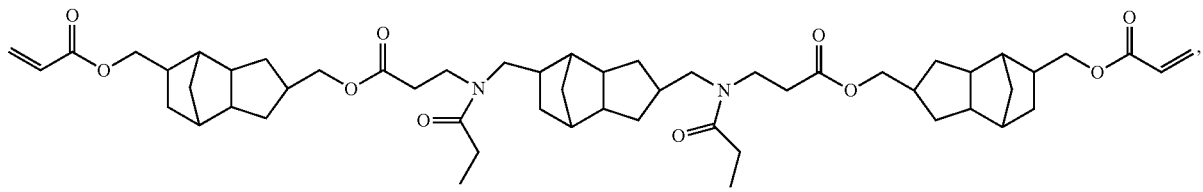
Compound 13
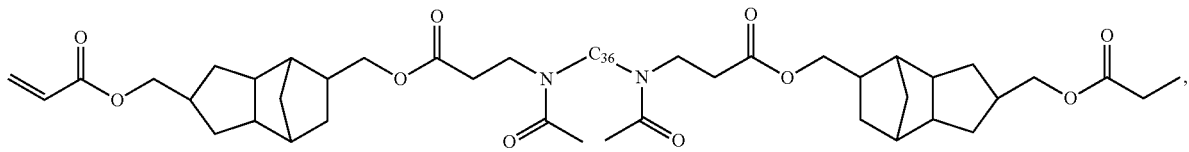
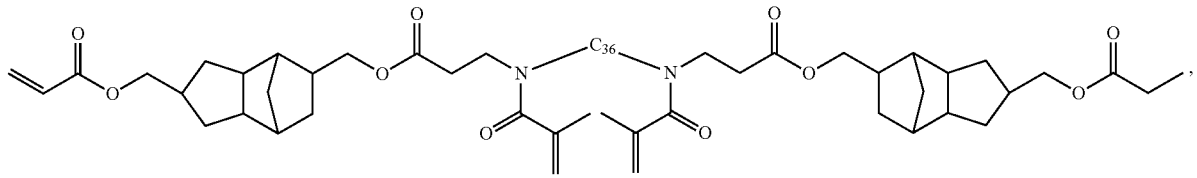

-continued
Compound 14
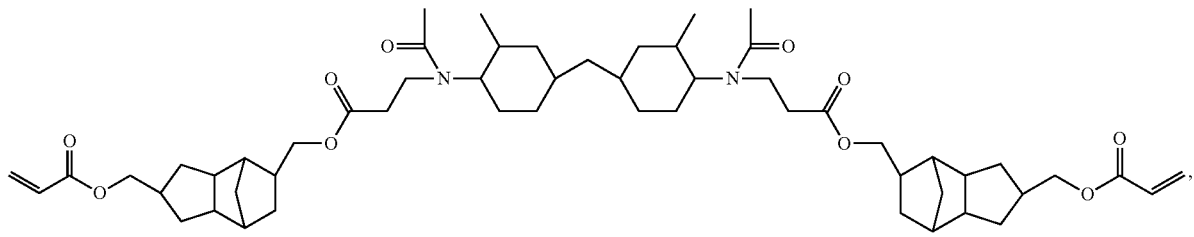
Compound 15
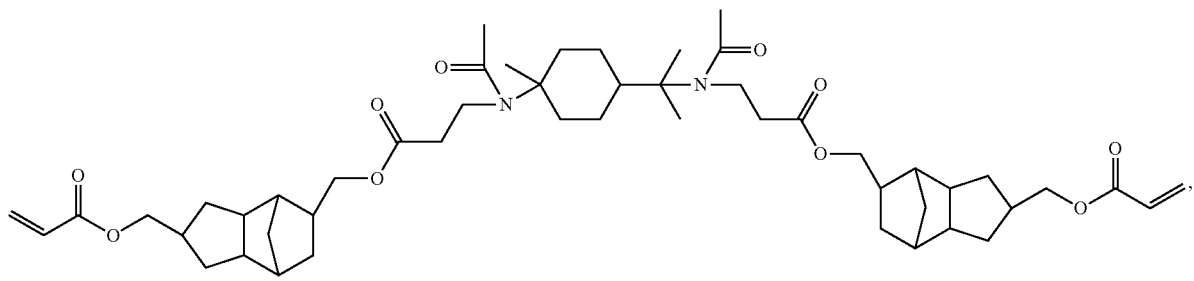
Compound 16
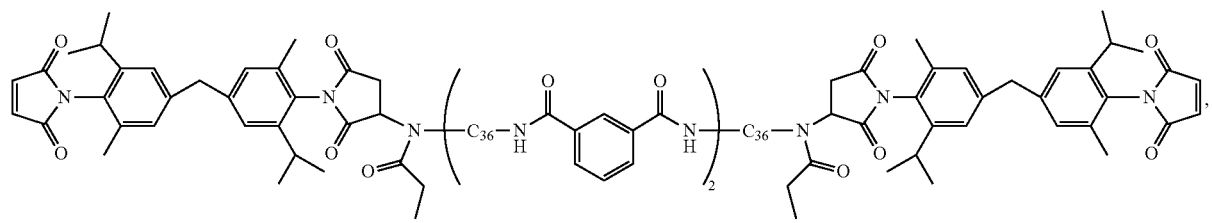
Compound 17
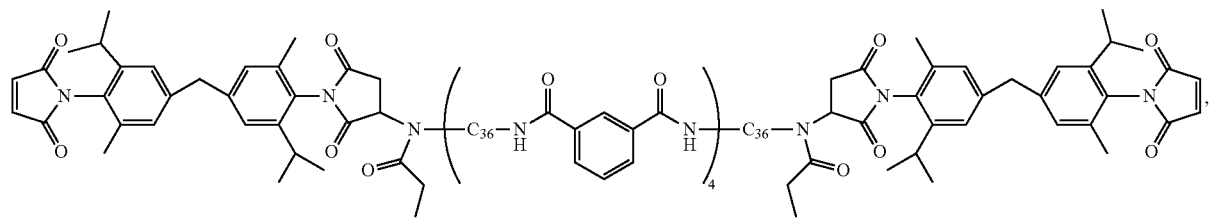
Compound 18                         Compound 19
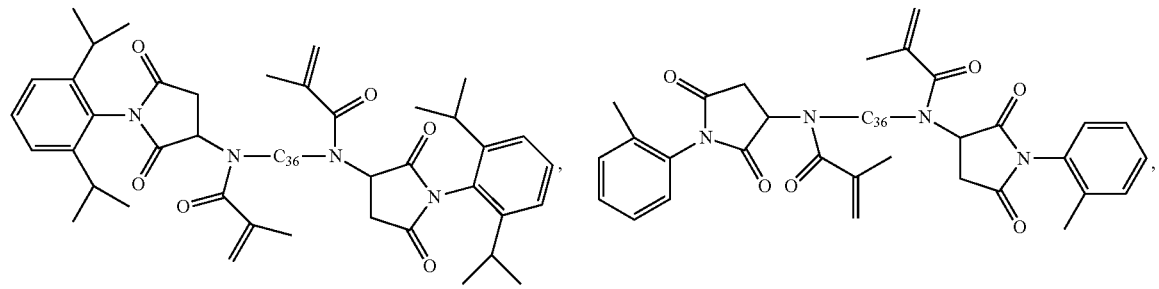
Compound 20                         Compound 21
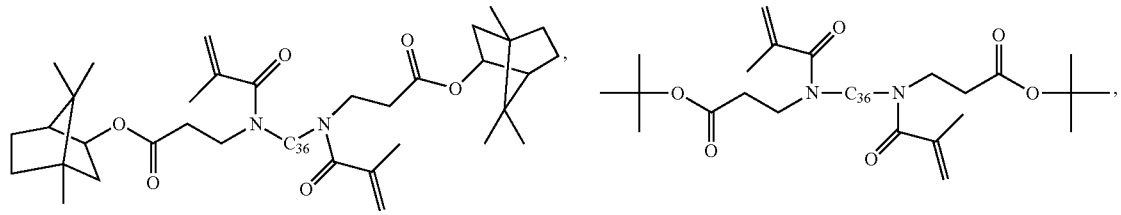

-continued
Compound 22
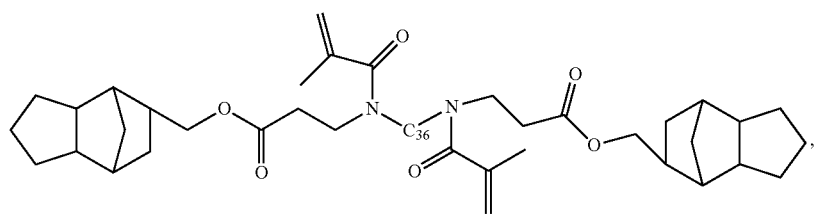
Compound 23
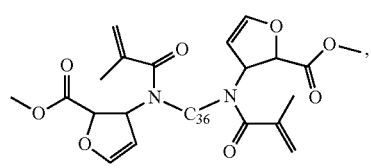
Compound 24
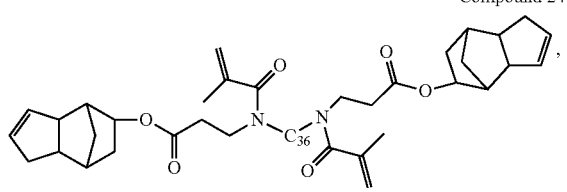
Compound 25
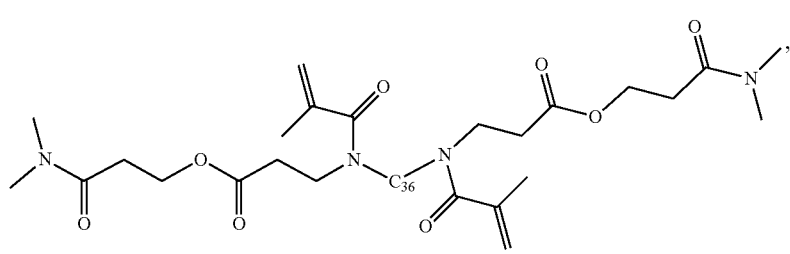
Compound 26
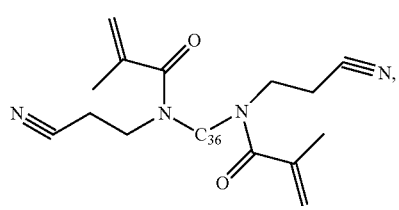
Compound 27
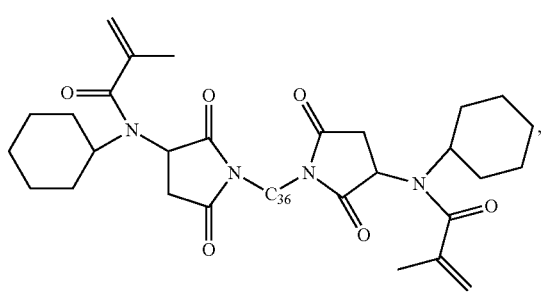
Compound 28
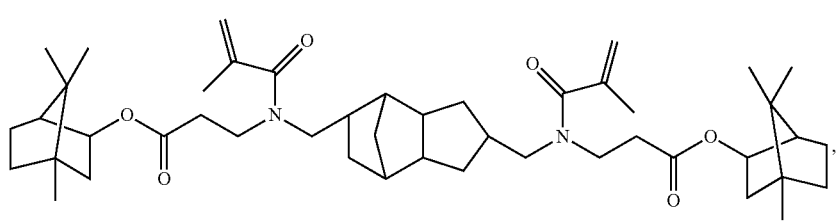
Compound 29
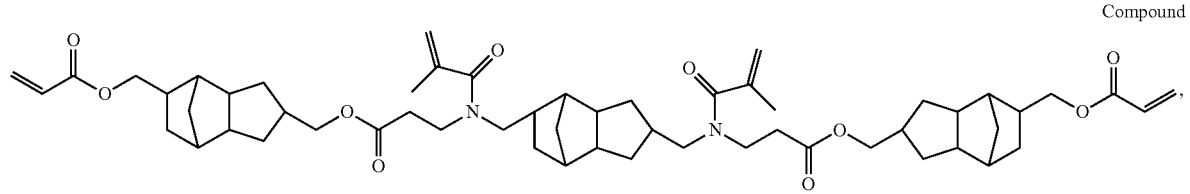
Compound 30
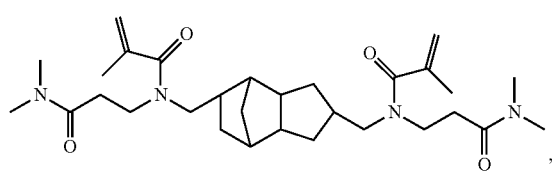
Compound 31
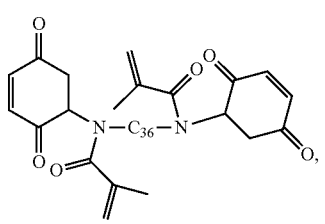

Compound 32
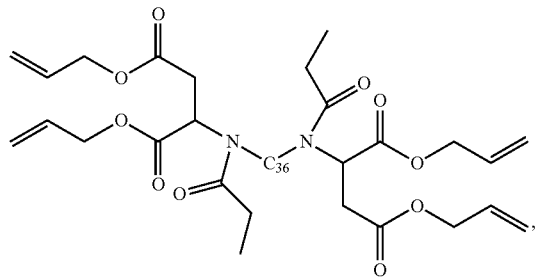
Compound 33
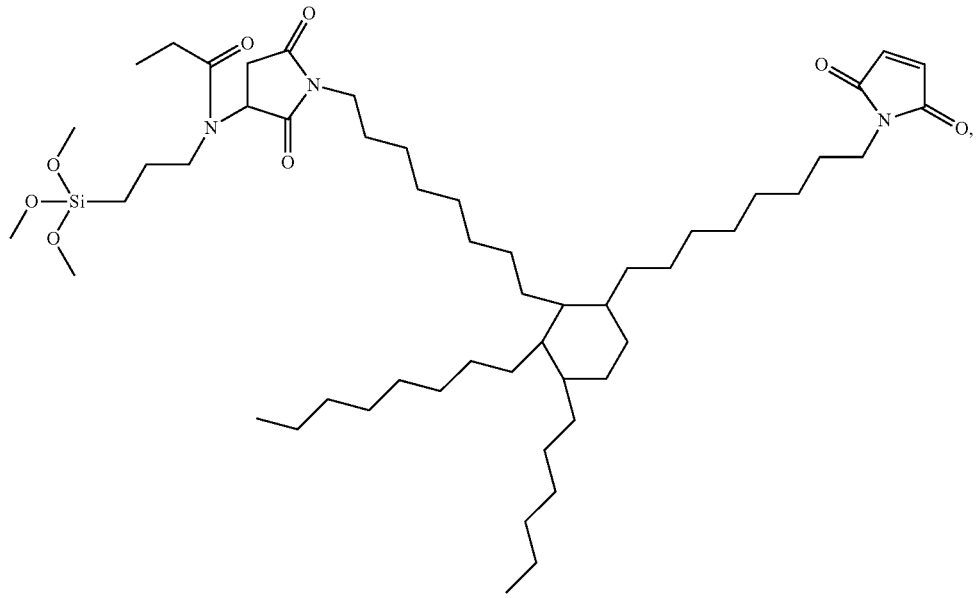
Compound 34
Compound 35
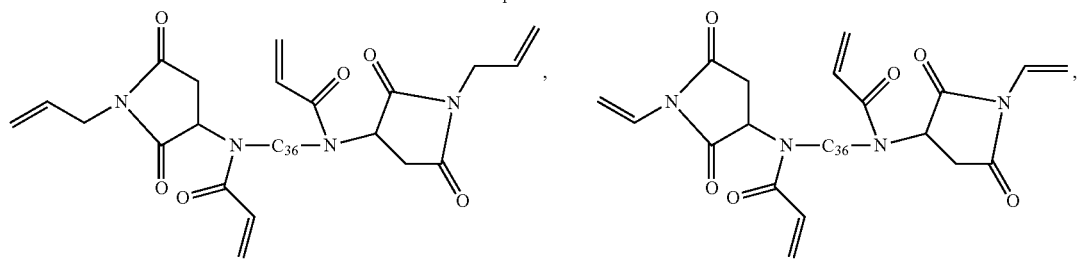
Compound 36
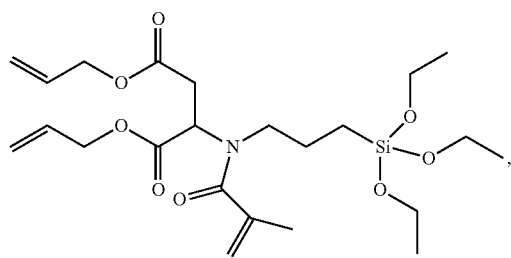

-continued
Compound 37
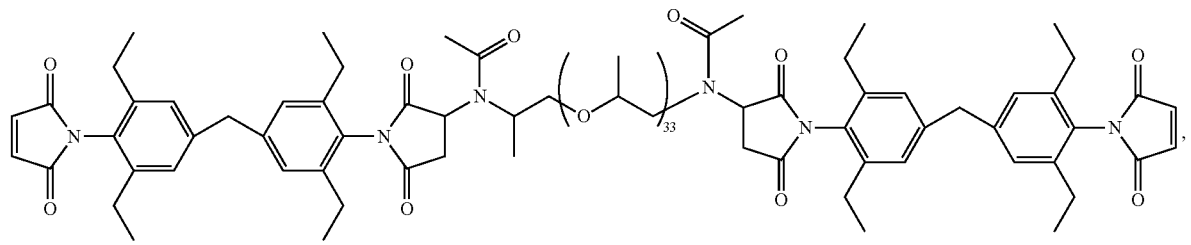
Compound 38
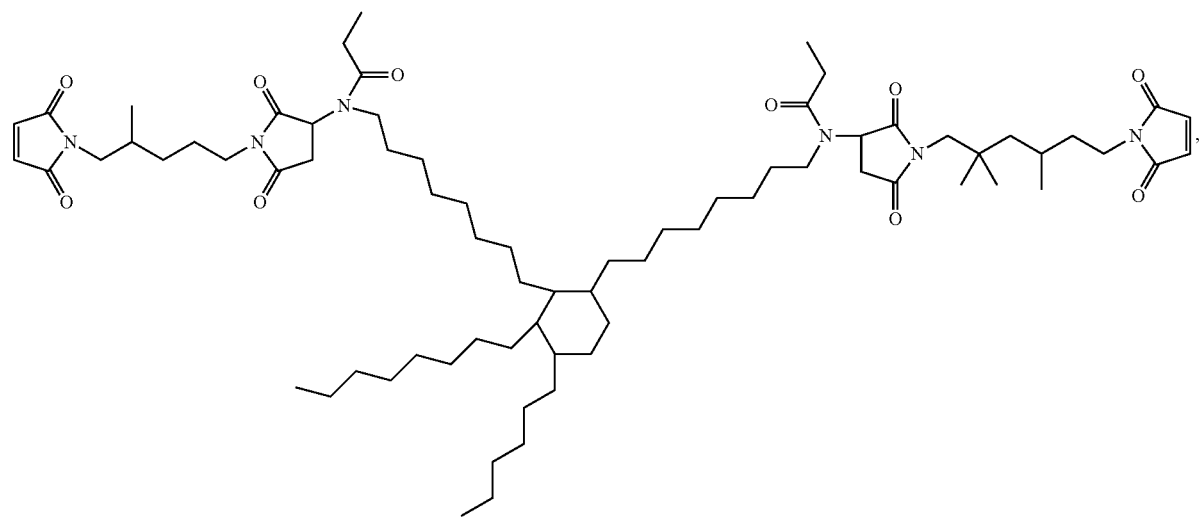
Compound 39
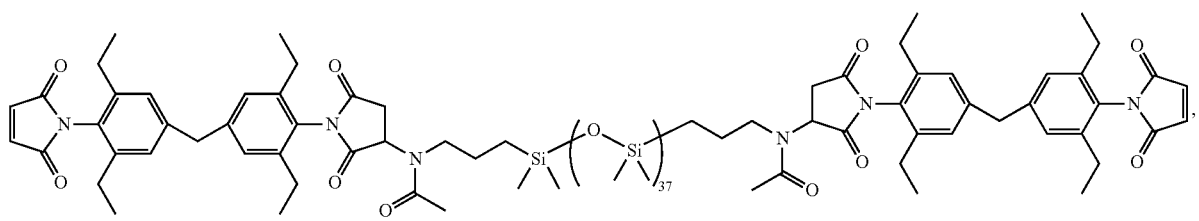
Compound 40
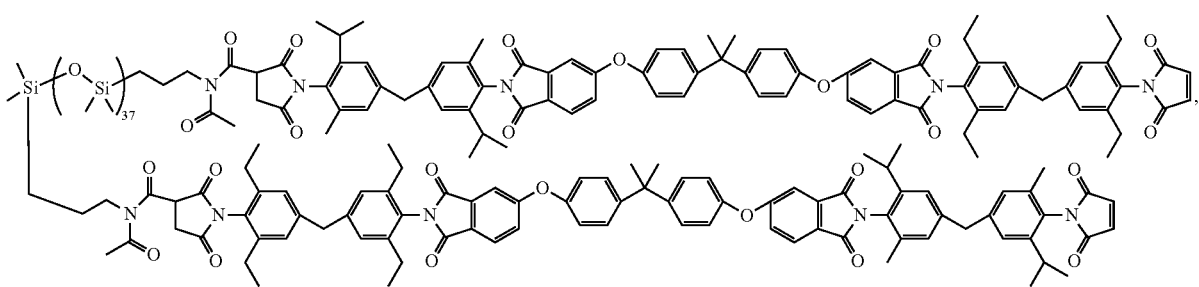
Compound 41
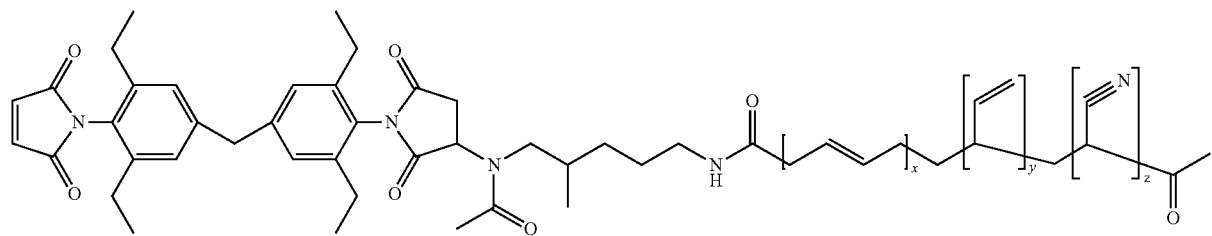

-continued
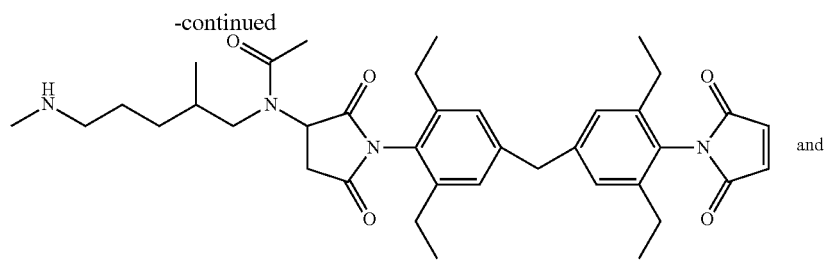
and
Compound 42
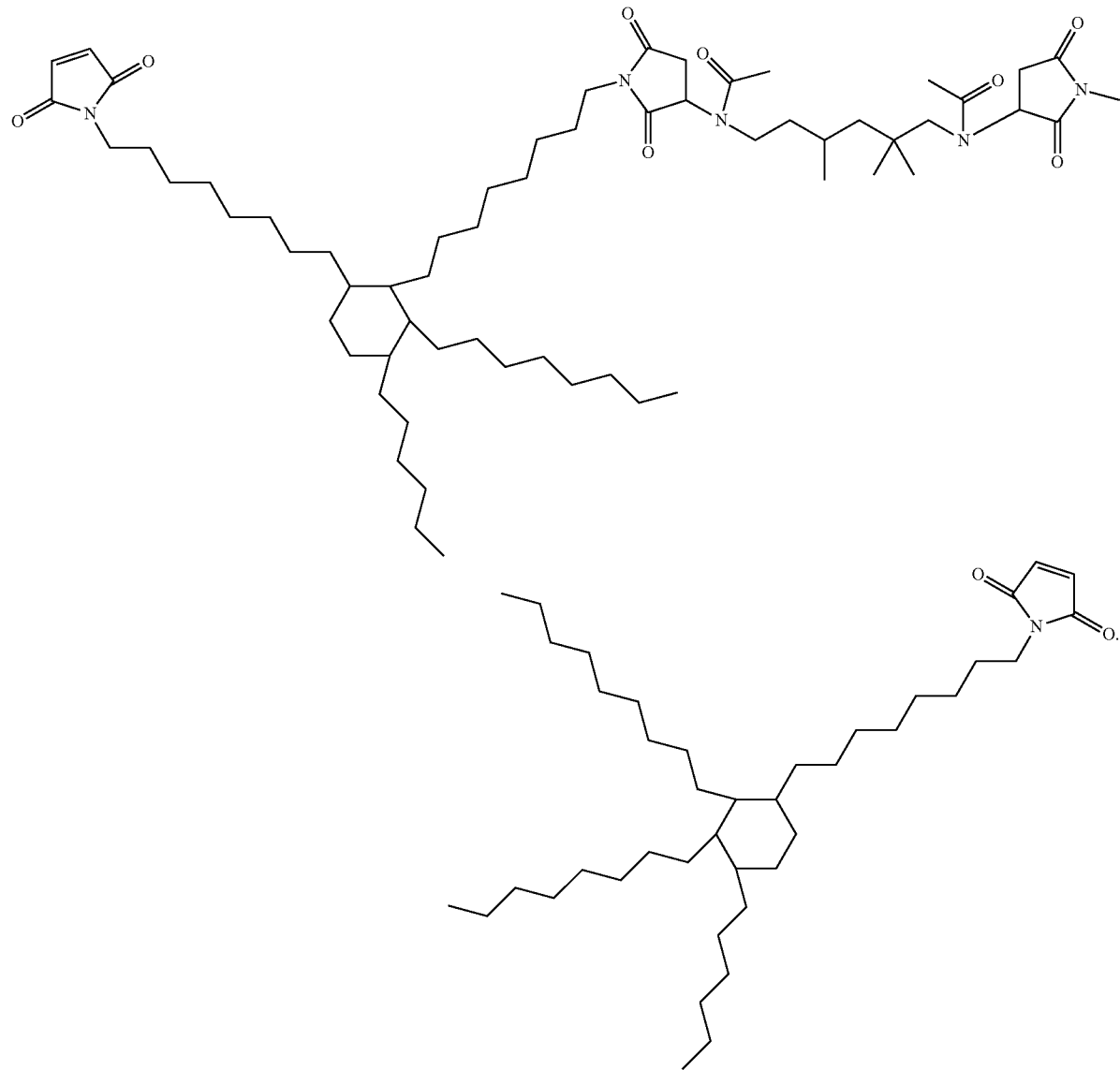
* * * * *